(12) United States Patent
Adachi et al.

(10) Patent No.: US 8,735,406 B2
(45) Date of Patent: May 27, 2014

(54) 8-OXODIHYDROPURINE DERIVATIVE

(75) Inventors: Keiji Adachi, Suita (JP); Yoko Nakai, Suita (JP); Tomoyuki Furuta, Suita (JP); Yuki Fujii, Suita (JP)

(73) Assignee: Dainippon Sumitomo Pharma Co., Ltd., Osaka (JP)

( * ) Notice: Subject to any disclaimer, the term of this patent is extended or adjusted under 35 U.S.C. 154(b) by 0 days.

(21) Appl. No.: 13/395,429

(22) PCT Filed: Sep. 8, 2010

(86) PCT No.: PCT/JP2010/065433
§ 371 (c)(1),
(2), (4) Date: Mar. 9, 2012

(87) PCT Pub. No.: WO2011/030798
PCT Pub. Date: Mar. 17, 2011

(65) Prior Publication Data
US 2012/0172347 A1   Jul. 5, 2012

(30) Foreign Application Priority Data
Sep. 9, 2009   (JP) ................................. 2009-207673

(51) Int. Cl.
*A61K 31/522* (2006.01)
*C07D 473/40* (2006.01)
(52) U.S. Cl.
USPC ....................................... 514/263.3; 544/265
(58) Field of Classification Search
USPC ....................................................... 544/265
See application file for complete search history.

(56) References Cited

U.S. PATENT DOCUMENTS

| 6,028,076 A | 2/2000 | Hirota et al. | |
| 6,372,740 B1 * | 4/2002 | Murata et al. | 514/234.2 |
| 2002/0128232 A1 * | 9/2002 | Henderson et al. | 514/79 |

FOREIGN PATENT DOCUMENTS

| JP | 2001048882 A | 2/2001 |
| WO | WO-98/01448 A1 | 1/1998 |
| WO | WO-9928320 A1 | 6/1999 |
| WO | WO-0230886 A2 | 4/2002 |
| WO | WO-2008032164 A2 | 3/2008 |
| WO | WO-2008145839 A1 | 12/2008 |
| WO | WO-2008145843 A1 | 12/2008 |

OTHER PUBLICATIONS

Mangieri, R.A. Pharmacological Research 56 (2007) 360-366.*
Extended EP Search Report for Application No. EP 10 81 5393.3, dated Jan. 28, 2013.
Chinese Office Action and Search Report for Chinese Application No. 201080050320.8, dated Dec. 4, 2013, with an English translation.

* cited by examiner

Primary Examiner — Golam M M Shameem
Assistant Examiner — Laura Daniel
(74) Attorney, Agent, or Firm — Birch Stewart Kolasch & Birch, LLP

(57) ABSTRACT

The present invention provides a compound represented by the formula (1) or a pharmaceutically acceptable salt thereof (wherein W represents a hydrogen atom, a halogen atom, or the others; A represents an alkyl group optionally substituted by aryl group or the others, an aryl group, or the others; and one of X and Y represents a di-substituted alkylaminocarbonyl group, or the others, and the other represents a hydrogen atom, an alkyl group, an alkylcarbonyl group, or the others); a medicament or a pharmaceutical composition for treatment or prophylaxis of FAAH-related diseases such as depression, anxiety disorder or pains, comprising the compound or the like as an active ingredient; a use of the compound or the like; and a method for treatment or prophylaxis using the compound or the like.

(1)

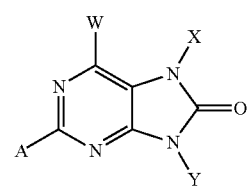

16 Claims, No Drawings

8-OXODIHYDROPURINE DERIVATIVE

This application is the National Stage under 35 USC §371 of International Application No. PCT/JP2010/065433 filed on Sep. 8, 2010, which claims priority under 35 USC §119 (a)-(d) of Application No. 2009-207673 filed on Sep. 9, 2009 in Japan.

TECHNICAL FIELD

The present invention relates to a novel 8-oxodihydropurine derivative showing an inhibitory effect on fatty acid amide hydrolase (Fatty Acid Amide Hydrolase; hereinafter sometimes referred to as "FAAH") and a pharmaceutically acceptable salt thereof as well as a medicament for treatment or prophylaxis of depression, anxiety disorder or pains comprising the compound as an active ingredient.

BACKGROUND ART

It has been known for many years that cannabis shows a variety of psychotropic actions or analgesic actions and it was shown clearly in the 1960s that such actions are caused by a series of compounds (cannabinoid) centering on e-tetrahydrocannabinol ($\Delta^9$-THC). At the beginning of the 1990s, two kinds of cannabinoid receptors (CB1 and CB2) were found out as a receptor to which $\Delta^9$-THC binds, and also at 1992, N-arachidonoyl ethanolamine (anandamide; AEA) as an endogenous cannabinoid was found from a brain of pig. Anandamide is known to be metabolized mainly by FAAH. Also it has been known that in addition to anandamide, fatty acid amides such as palmitoylethanolamide (PEA), oleylethanolamide (OEA) and oleamide, 2-arachidonoylglycerol (2-AG) and the others are hydrolyzed by FAAH. It has been shown clearly that amounts of these fatty acid amides including anandamide are increased in FAAH knockout mouse, but interestingly it hasn't been acknowledged side effects that are observed in the case of CB1 receptor agonist such as catalepsy, hypothermia, hypomotility and overeating (for example, see Non-Patent Literature-1). Also since the above-mentioned side effects are not observed even at administrating of a FAAH inhibitor, the FAAH inhibitor is expected to be a therapeutic medicament with few side effects compared with CB1 receptor agonist. In fact, it has been reported that the FAAH inhibitor shows an efficacy on pains (neuropathic pain, inflammatory pain, nociceptive pain), anxiety disorder and depression in animal models (for example, see Non-Patent Literature-2). In addition, it has been known that FAAH and fatty acid amides as a substrate are related to various diseases. For example, it has been known that FAAH is increased in a brain of Alzheimer's patient, OEA is related to a feeding regulation, and oleamide is related to an induction of sleeping (for example, see Non-Patent Literature-3), and it has also been reported that the FAAH inhibitor shows a cerebro- and neuro-protective effect as well as a therapeutic effect on thamuria and urinary incontinence, and a therapeutic effect on over active bladder.

A low-molecular compound showing the FAAH inhibitory activity has been reported for example, 4,5-diphenyl imidazole derivatives (for example, see Patent Literature-1), dioxane-2-alkylcarbamic acid derivatives (for example, see Patent Literature-2), O-aryl-N-alkyl carbamic acid aryl ester derivatives (for example, see Patent Literature-3), α-ketoheterocycle derivatives (for example, see Patent Literature-4), biarylether urea derivatives (for example, see Patent Literature-5), triazolopyridine (or pyrimidine)carboxamide derivatives (for example, see Patent Literatures-6, 7) and a low-molecular compound showing the CB1 receptor-binding activity has been also reported for example, benzimidazolone carboxamide derivatives (for example, see Patent Literature-8). But there is neither a description of the present compound having 8-oxodihydropurine structure represented by the below-mentioned formula (1) nor a suggestion of the present compound in these related art documents.

RELATED ART DOCUMENTS

Patent Documents

[Patent Literature-1]: WO 02/087569 pamphlet
[Patent Literature-2]: WO 04/020430 pamphlet
[Patent Literature-3]: WO 04/033422 pamphlet
[Patent Literature-4]: WO 04/033652 pamphlet
[Patent Literature-5]: WO 08/047,229 pamphlet
[Patent Literature-6]: WO 08/145,839 pamphlet
[Patent Literature-7]: WO 08/145,843 pamphlet
[Patent Literature-8]: WO 08/032,164 pamphlet

Non-Patent Documents

[Non-Patent Literature-1]: Cravatt B. F. et al: Proc. Natl. Acad. Sci., 98, 9371 (2001)
[Non-Patent Literature-2]: Kathuria, S. et al: Nature Med., 9, 76 (2003)
[Non-Patent Literature-3]: Benito C. et al: J. Neurosci., 23, 11136 (2003)

DISCLOSURE OF INVENTION

Problems to be Solved by Invention

An object of the present invention is to provide a novel 8-oxodihydropurine derivative and a pharmaceutically acceptable salt thereof as well as a fatty acid amide hydrolase (FAAH) inhibitor comprising the same as an active ingredient and a medicament or a pharmaceutical composition useful for treatment or prophylaxis of depression, anxiety disorder or pains, and a use thereof and a method for treatment or prophylaxis using the same.

Means to Solve Problems

The present inventors have intensively studied and as a result, they have found out that 8-oxodihydropurine derivative having an urea structure at 7- or 9-position, that is, the compound represented by the below-mentioned formula (1) has a strong FAAH inhibitory activity and is thus useful as a medicament for treatment or prophylaxis of depression, anxiety disorder or pains, and have therefore completed the present invention. That is, the present invention provides:
[1] A compound represented by the below-mentioned formula (1):

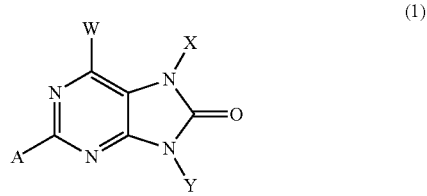

[wherein

W represents a hydrogen atom, a halogen atom, a $C_{1-6}$ alkyl group optionally substituted with halogen atom or a $C_{1-6}$ alkyloxy group optionally substituted with halogen atom;

A represents a hydrogen atom, a $C_{1-6}$ alkyl group, a $C_{2-6}$ alkenyl group, a $C_{2-6}$ alkynyl group [[said $C_{1-6}$ alkyl group, $C_{2-6}$ alkenyl group and $C_{2-6}$ alkynyl group each may be optionally substituted at an optional substitutable position with one or two or more substituents selected from the group consisting of halogen atom, optionally substituted $C_{3-8}$ cycloalkyl group, optionally substituted $C_{4-10}$ cycloalkenyl group, optionally substituted 3 to 10 membered heterocycloalkyl group, optionally substituted 4 to 10 membered heterocycloalkenyl group, optionally substituted $C_{6-10}$ aryl group, optionally substituted 5 to 10 membered heteroaryl group, hydroxy group, optionally substituted amino group, optionally substituted $C_{1-6}$ alkyloxy group, optionally substituted $C_{3-8}$ cycloalkyloxy group, optionally substituted 3 to 10 membered heterocycloalkyloxy group, optionally substituted $C_{6-10}$ aryloxy group, optionally substituted 5 to 10 membered heteroaryloxy group, substituted $C_{3-8}$ cycloalkyl ($C_{1-6}$ alkyl)oxy group, substituted 3 to 10 membered heterocycloalkyl ($C_{1-6}$ alkyl)oxy group, substituted $C_{6-10}$ aryl($C_{1-6}$ alkyl)oxy group, substituted 5 to 10 membered heteroaryl($C_{1-6}$ alkyl)oxy group and optionally substituted $C_{1-6}$ alkyloxycarbonyl group]], an optionally substituted $C_{3-8}$ cycloalkyl group, an optionally substituted $C_{4-10}$ cycloalkenyl group, an optionally substituted $C_{6-10}$ aryl group, an optionally substituted 5 to 10 membered heteroaryl group, an optionally substituted 3 to 10 membered heterocycloalkyl group or an optionally substituted 4 to 10 membered heterocycloalkenyl group (provided that said optionally substituted 5 to 10 membered heteroaryl group, optionally substituted 3 to 10 membered heterocycloalkyl group and optionally substituted 4 to 10 membered heterocycloalkenyl group each binds at the carbon atom on each ring to a pyrimidine ring of the compound represented by the above-mentioned formula (1));

one of X and Y represents a group represented by the formula [Q]: —$CONR^1R^2$ and the other represents a hydrogen atom, an optionally substituted $C_{1-6}$ alkylcarbonyl group, a $C_{1-6}$ alkyl group (said $C_{1-6}$ alkyl group may be optionally substituted at an optional substitutable position with one or two or more substituents selected from the group consisting of halogen atom, hydroxy group, optionally substituted $C_{3-8}$ cycloalkyl group, optionally substituted $C_{1-6}$ alkyloxy group, optionally substituted $C_{6-10}$ aryl group, optionally substituted 5 to 10 membered heteroaryl group and optionally substituted amino group) or an optionally substituted $C_{3-8}$ cycloalkyl group;

$R^1$ represents a $C_{1-6}$ alkyl group [[said $C_{1-6}$ alkyl group may be optionally substituted at an optional substitutable position with one or two or more substituents selected from the group consisting of halogen atom, optionally substituted $C_{3-8}$ cycloalkyl group, optionally substituted $C_{4-10}$ cycloalkenyl group, optionally substituted 3 to 10 membered heterocycloalkyl group, optionally substituted 4 to 10 membered heterocycloalkenyl group, optionally substituted $C_{6-10}$ aryl group, optionally substituted 5 to 10 membered heteroaryl group, hydroxy group, optionally substituted $C_{1-6}$ alkyloxy group, optionally substituted $C_{3-8}$ cycloalkyloxy group, optionally substituted $C_{6-10}$ aryloxy group, optionally substituted 5 to 10 membered heteroaryloxy group, substituted $C_{6-10}$ aryl ($C_{1-6}$ alkyl) oxy group, substituted 5 to 10 membered heteroaryl($C_{1-6}$ alkyl)oxy group, optionally substituted amino group, optionally substituted $C_{1-6}$ alkyloxycarbonyl group and optionally substituted aminocarbonyl group]], an optionally substituted $C_{3-8}$ cycloalkyl group, an optionally substituted $C_{6-10}$ aryl group, an optionally substituted 5 to 10 membered heteroaryl group, an optionally substituted 3 to 10 membered heterocycloalkyl group or an optionally substituted 4 to 10 membered heterocycloalkenyl group;

$R^2$ represents a $C_{1-6}$ alkyl group (said $C_{1-6}$ alkyl group may be optionally substituted at an optional substitutable position with one or two or more substituents selected from the group consisting of halogen atom, hydroxy group and optionally substituted $C_{1-6}$ alkyloxy group) or an optionally substituted $C_{3-8}$ cycloalkyl group, or alternatively $R^1$ and $R^2$ combine together with the nitrogen atom to which $R^1$ and $R^2$ both bind to represent a cyclic group represented by the below-mentioned formula (2):

(2)

[[wherein G represents —$CH_2$—, —CH=CH—, —$NR^5$—, —C(=$CHR^6$)—, an oxygen atom or a single bond (provided when G represents —$CH_2$— or —CH=CH—, then $R^3$ and $R^4$ can bind to the optional carbon atom of the —$CH_2$— or —CH=CH— instead of a hydrogen atom), n and m are the same as or different from each other and represent 2 or 3 when G is —$NR^5$— or an oxygen atom, and are the same as or different from each other and represent an integer of 1 to 3 when G is —$CH_2$—, —CH=CH— or —C(=$CHR^6$)—, and represent both 1 when G is a single bond;

$R^3$ and $R^4$ bind to the carbon atom on the cyclic group represented by the above-mentioned formula (2), and are the same as or different from each other and represent a hydrogen atom, a halogen atom, an optionally substituted $C_{3-8}$ cycloalkyl group, an optionally substituted $C_{4-10}$ cycloalkenyl group, a hydroxy group, an optionally substituted $C_{1-6}$ alkyloxy group, an optionally substituted $C_{3-8}$ cycloalkyloxy group, an optionally substituted $C_{1-6}$ alkyloxycarbonyl group, an optionally substituted aminocarbonyl group, an optionally substituted $C_{6-10}$ aryl group, an optionally substituted 5 to 10 membered heteroaryl group, an optionally substituted $C_{6-10}$ aryloxy group, an optionally substituted 5 to 10 membered heteroaryloxy group, a $C_{1-6}$ alkyl group [[said $C_{1-6}$ alkyl group may be optionally substituted at an optional substitutable position with one or two or more substituents selected from the group consisting of halogen atom, optionally substituted $C_{3-8}$ cycloalkyl group, hydroxy group, optionally substituted $C_{1-6}$ alkyloxy group, optionally substituted $C_{3-8}$ cycloalkyloxy group, optionally substituted $C_{1-6}$ alkyloxycarbonyl group, optionally substituted aminocarbonyl group, optionally substituted $C_{6-10}$ aryl group, optionally substituted 5 to 10 membered heteroaryl group, optionally substituted $C_{6-10}$ aryloxy group, optionally substituted 5 to 10 membered heteroaryloxy group, substituted $C_{6-10}$ aryl ($C_{1-6}$ alkyl)oxy group, substituted 5 to 10 membered heteroaryl ($C_{1-6}$ alkyl)oxy group, optionally substituted 3 to 10 membered heterocycloalkyl group and optionally substituted 3 to 10 membered heterocycloalkyloxy group]], a $C_{2-6}$ alkenyl group, a $C_{2-6}$ alkynyl group (said $C_{2-6}$ alkenyl group and $C_{2-6}$ alkynyl group may be optionally substituted at an optional substitutable position with one or two or more substituents selected from the group consisting of optionally substituted $C_{6-10}$ aryl group and optionally substituted 5 to 10 membered heteroaryl group), an optionally substituted 3 to 10 membered heterocycloalkyl group or an optionally substituted 4 to 10 membered heterocycloalkenyl group, or alternatively $R^3$ and $R^4$ combine to form an oxo group, or $R^3$ and $R^4$ bind to the same carbon atom on the cyclic group represented by the above-mentioned formula (2) and combine together with the carbon atom to which they bind to form a Spiro ring consisting of an optionally substituted $C_{3-8}$ saturated aliphatic carbocycle, an optionally substituted $C_{4-10}$ unsaturated aliphatic carbocycle, an optionally substituted 3 to 10 membered saturated aliphatic heterocycle or an optionally substituted 4 to 10 membered unsaturated aliphatic heterocycle, or $R^3$ and $R^4$ each binds to the neighboring carbon atom on the cyclic group represented by the above-mentioned formula (2) and combine together with the carbon atom to which they bind to form a fused ring selected from the group consisting of an optionally substituted $C_{3-8}$ saturated aliphatic carbocycle, an optionally substituted $C_{4-10}$ unsaturated aliphatic carbocycle, an optionally substituted 3 to 10 membered saturated aliphatic heterocycle, an optionally substituted 4 to 10 membered unsaturated aliphatic heterocycle, an optionally substituted $C_{6-10}$ aromatic ring or an optionally substituted 5 to 10 membered aromatic heterocycle, or alternatively $R^3$ and $R^4$ each binds to a non-neighboring different carbon atom on the cyclic group represented by the above-mentioned formula (2) and combine to represent a methylene group, an ethylene group, a propylene group, a butylene group and then may form a bridged ring;

$R^5$ represents a $C_{1-6}$ alkyl group (said $C_{1-6}$ alkyl group may be optionally substituted at an optional substitutable position with one or two or more substituents selected from the group consisting of halogen atom, optionally substituted $C_{3-8}$ cycloalkyl group, optionally substituted $C_{6-10}$ aryl group and optionally substituted 5 to 10 membered heteroaryl group), an optionally substituted $C_{3-8}$ cycloalkyl group, an optionally substituted $C_{6-10}$ aryl group or an optionally substituted 5 to 10 membered heteroaryl group;

$R^6$ represents an optionally substituted $C_{6-10}$ aryl group or an optionally substituted 5 to 10 membered heteroaryl group]]], or a pharmaceutically acceptable salt thereof;

[2] The compound of the above [1] or a pharmaceutically acceptable salt thereof wherein one of X or Y represents an optionally substituted $C_{1-6}$ alkylcarbonyl group, a $C_{1-6}$ alkyl group (said $C_{1-6}$ alkyl group may be optionally substituted at an optional substitutable position with one or two or more substituents selected from the group consisting of halogen atom, hydroxy group, optionally substituted $C_{3-8}$ cycloalkyl group, optionally substituted $C_{1-6}$ alkyloxy group, optionally substituted $C_{6-10}$ aryl group, optionally substituted 5 to 10 membered heteroaryl group and optionally substituted amino group) or an optionally substituted $C_{3-8}$ cycloalkyl group;

[3] The compound of the above [2] or a pharmaceutically acceptable salt thereof wherein one of X or Y represents a $C_{1-6}$ alkyl group (said $C_{1-6}$ alkyl group may be optionally substituted at an optional substitutable position with one or two or more substituents selected from the group consisting of halogen atom, hydroxy group, optionally substituted $C_{3-8}$ cycloalkyl group and optionally substituted $C_{1-6}$ alkyloxy group);

[4] The compound of any one of the above [1] to [3] or a pharmaceutically acceptable salt thereof wherein A represents a $C_{1-6}$ alkyl group, a $C_{2-6}$ alkenyl group (said $C_{1-6}$ alkyl group and $C_{2-6}$ alkenyl group may be optionally substituted at an optional substitutable position with one or two or more substituents selected from the group consisting of halogen atom, optionally substituted $C_{3-8}$ cycloalkyl group, optionally substituted $C_{4-10}$ cycloalkenyl group, optionally substituted 3 to 10 membered heterocycloalkyl group, optionally substituted $C_{6-10}$ aryl group, optionally substituted 5 to 10 membered heteroaryl group, hydroxy group, optionally substituted amino group and optionally substituted $C_{1-6}$ alkyloxy group), an optionally substituted $C_{3-8}$ cycloalkyl group, an optionally substituted $C_{6-10}$ aryl group, an optionally substituted 5 to 10 membered heteroaryl group or an optionally substituted 3 to 10 membered heterocycloalkyl group;

[5] The compound of the above [4] or a pharmaceutically acceptable salt thereof wherein A represents a $C_{1-6}$ alkyl group, a $C_{2-6}$ alkenyl group (said $C_{1-6}$ alkyl group and $C_{2-6}$ alkenyl group may be optionally substituted at an optional substitutable position with one or two or more substituents selected from the group consisting of optionally substituted $C_{6-10}$ aryl group, optionally substituted amino group and optionally substituted $C_{1-6}$ alkyloxy group), an optionally substituted $C_{3-8}$ cycloalkyl group, an optionally substituted $C_{6-10}$ aryl group or an optionally substituted 5 to 10 membered heteroaryl group;

[6] The compound of any one of the above [1] to [5] or a pharmaceutically acceptable salt thereof wherein represents a $C_{1-6}$ alkyl group [[said $C_{1-6}$ alkyl group may be optionally substituted at an optional substitutable position with one or two or more substituents selected from the group consisting of halogen atom, optionally substituted $C_{3-8}$ cycloalkyl group, optionally substituted $C_{4-10}$ cycloalkenyl group, optionally substituted $C_{6-10}$ aryl group, optionally substituted 5 to 10 membered heteroaryl group, hydroxy group, optionally substituted $C_{1-6}$ alkyloxy group, optionally substituted $C_{3-8}$ cycloalkyloxy group, optionally substituted $C_{6-10}$ aryloxy group, optionally substituted 5 to 10 membered heteroaryloxy group, substituted $C_{6-10}$ aryl($C_{1-6}$ alkyl)oxy group and substituted 5 to 10 membered heteroaryl($C_{1-6}$ alkyl)oxy group]], an optionally substituted $C_{6-10}$ aryl group or an optionally substituted 5 to 10 membered heteroaryl group;

[7] The compound of the above [6] or a pharmaceutically acceptable salt thereof wherein $R^1$ represents a $C_{1-6}$ alkyl group (said $C_{1-6}$ alkyl group may be optionally substituted at an optional substitutable position with one or two or more substituents selected from the group consisting of halogen atom, optionally substituted $C_{3-8}$ cycloalkyl group, optionally substituted $C_{4-10}$ cycloalkenyl group, optionally substituted $C_{6-10}$ aryl group, optionally substituted $C_{1-6}$ alkyloxy group and optionally substituted $C_{6-10}$ aryloxy group);

[8] The compound of any one of the above [1] to [5] represented by the below-mentioned formula (1-2a) or (1-2b):

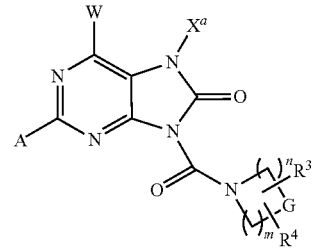

(1-2a)

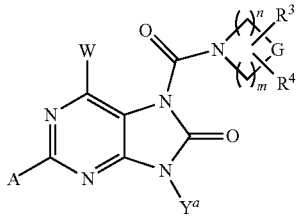

(1-2b)

or a pharmaceutically acceptable salt thereof,

[[wherein $X^a$ and $Y^a$ represent an optionally substituted $C_{1-6}$ alkylcarbonyl group, a $C_{1-6}$ alkyl group (said $C_{1-6}$ alkyl group may be optionally substituted at an optional substitutable position with one or two or more substituents selected from the group consisting of halogen atom, hydroxy group, optionally substituted $C_{3-8}$ cycloalkyl group, optionally substituted $C_{1-6}$ alkyloxy group, optionally substituted $C_{6-10}$ aryl group, optionally substituted 5 to 10 membered heteroaryl group and optionally substituted amino group) or an optionally substituted $C_{3-8}$ cycloalkyl group, and A, W, n, m, G, $R^3$ and $R^4$ are the same as defined in the above-mentioned [1]]];

[9] The compound of the above [8] or a pharmaceutically acceptable salt thereof wherein $R^3$ and $R^4$ are the same as or different from each other and represent a hydrogen atom, a halogen atom, a optionally substituted $C_{6-10}$ aryl group, an optionally substituted 5 to 10 membered heteroaryl group, a $C_{1-6}$ alkyl group [[said $C_{1-6}$ alkyl group may be optionally substituted at an optional substitutable position with one or two or more substituents selected from the group consisting of halogen atom, optionally substituted $C_{3-8}$ cycloalkyl group, optionally substituted $C_{1-6}$ alkyloxy group, optionally substituted $C_{3-8}$ cycloalkyloxy group, optionally substituted $C_{6-10}$ aryl group, optionally substituted 5 to 10 membered heteroaryl group, optionally substituted $C_{6-10}$ aryloxy group, optionally substituted 5 to 10 membered heteroaryloxy group, substituted $C_{6-10}$ aryl ($C_{1-6}$ alkyl)oxy group and substituted 5 to 10 membered heteroaryl($C_{1-6}$ alkyl)oxy group]];

[10] The compound of the above [9] or a pharmaceutically acceptable salt thereof wherein $R^3$ and $R^4$ are the same as or different from each other and represent a hydrogen atom, a halogen atom, an optionally substituted $C_{6-10}$ aryl group, a $C_{1-6}$ alkyl group (said $C_{1-6}$ alkyl group may be optionally substituted at an optional substitutable position with one or two or more substituents selected from the group consisting of optionally substituted $C_{6-10}$ aryl group, optionally substituted 5 to 10 membered heteroaryl group, optionally substituted $C_{6-10}$ aryloxy group and optionally substituted 5 to 10 membered heteroaryloxy group);

[11] The compound of any one of the above [8] to [10] or a pharmaceutically acceptable salt thereof wherein G represents —$CH_2$— and then n and m are the same as or different from each other and represent 1 or 2, or alternatively G is —$NR^5$— and $R^5$ represents a $C_{1-6}$ alkyl group (said $C_{1-6}$ alkyl group may be optionally substituted at an optional substitutable position with one or two or more substituents selected from the group consisting of halogen atom, optionally substituted $C_{6-10}$ aryl group and optionally substituted 5 to 10 membered heteroaryl group) or an optionally substituted $C_{6-10}$ aryl group, and then n and m are the same as or different from each other and represent 2 or 3;

[12] The compound of any one of the above [1] to [11] or a pharmaceutically acceptable salt thereof wherein W represents a hydrogen atom;

[13] The compound of the above [1] selected from any one of the following compounds or a pharmaceutically acceptable salt thereof:

N,9-Dimethyl-8-oxo-2-phenyl-N-(4-phenylbutyl)-8,9-dihydro-7H-purine-7-carboxamide (Example No. 36);

N-Ethyl-2-(3-methoxyphenyl)-N,9-dimethyl-8-oxo-8,9-dihydro-7H-purine-7-carboxamide (Example No. 60);

2-(3-Methoxyphenyl)-N,9-dimethyl-8-oxo-N-(2-phenylethyl)-8,9-dihydro-7H-purine-7-carboxamide (Example No. 64);

2-(3-Methoxyphenyl)-N,9-dimethyl-8-oxo-N-(2-phenoxyethyl)-8,9-dihydro-7H-purine-7-carboxamide (Example No. 65);

7-({4-[2-(4-Chlorophenyl)ethyl]piperidin-1-yl}carbonyl)-2-(3-methoxyphenyl)-9-methyl-7,9-dihydro-8H-purine-8-one (Example No. 68);

N-[2-(4-Chlorophenyl)ethyl]-2-(3-methoxyphenyl)-N,9-dimethyl-8-oxo-8,9-dihydro-7H-purine-7-carboxamide (Example No. 69);

N-(4-Fluorobenzyl)-2-(3-methoxyphenyl)-N,9-dimethyl-8-oxo-8,9-dihydro-7H-purine-7-carboxamide (Example No. 71);

N-[2-(4-Fluorophenyl)ethyl]-2-(3-methoxyphenyl)-N,9-dimethyl-8-oxo-8,9-dihydro-7H-purine-7-carboxamide (Example No. 74);

N-[2-(3-Fluorophenyl)ethyl]-2-(3-methoxyphenyl)-N,9-dimethyl-8-oxo-8,9-dihydro-7H-purine-7-carboxamide (Example No. 75);

N-[2-(3-Chlorophenyl)ethyl]-2-(3-methoxyphenyl)-N,9-dimethyl-8-oxo-8,9-dihydro-7H-purine-7-carboxamide (Example No. 76);

N-[2-(4-Chlorophenoxy)ethyl]-2-(3-methoxyphenyl)-N,9-dimethyl-8-oxo-8,9-dihydro-7H-purine-7-carboxamide (Example No. 77);

N-(4-Chlorobenzyl)-2-(3-methoxyphenyl)-N,9-dimethyl-8-oxo-8,9-dihydro-7H-purine-7-carboxamide (Example No. 78);

2-(3-Methoxyphenyl)-N,9-dimethyl-8-oxo-N-[4-(trifluoromethyl)benzyl]-8,9-dihydro-7H-purine-7-carboxamide (Example No. 81);

2-(3-Methoxyphenyl)-N,9-dimethyl-8-oxo-N-[4-(trifluoromethoxy)benzyl]-8,9-dihydro-7H-purine-7-carboxamide (Example No. 83);

N-[2-(3-Chlorophenoxy)ethyl]-2-(3-methoxyphenyl)-N,9-dimethyl-8-oxo-8,9-dihydro-7H-purine-7-carboxamide (Example No. 90);

N-[2-(4-Fluorophenoxy)ethyl]-2-(3-methoxyphenyl)-N,9-dimethyl-8-oxo-8,9-dihydro-7H-purine-7-carboxamide (Example No. 91);

2-(3-Methoxyphenyl)-N,9-dimethyl-8-oxo-N-{2-[4-(trifluoromethyl)phenyl]ethyl}-8,9-dihydro-7H-purine-7-carboxamide (Example No. 92);

2-(3-Methoxyphenyl)-N-[2-(4-methoxyphenyl)ethyl]-N,9-dimethyl-8-oxo-8,9-dihydro-7H-purine-7-carboxamide (Example No. 93);

7-({4-[(E)-2-(4-Chlorophenyl)ethenyl]-3,6-dihydropyridin-1(2H)-yl}carbonyl)-2-(3-methoxyphenyl)-9-methyl-7,9-dihydro-8H-purine-8-one (Example No. 94);

7-({4-[(E)-2-(4-Fluorophenyl)ethenyl]-3,6-dihydropyridin-1(2H)-yl}carbonyl)-2-(3-methoxyphenyl)-9-methyl-7,9-dihydro-8H-purine-8-one (Example No. 95);

7-({4-[2-(4-Fluorophenyl)ethyl]piperidin-1-yl}carbonyl)-2-(3-methoxyphenyl)-9-methyl-7,9-dihydro-8H-purine 8-one (Example No. 96);

2-(3-Methoxyphenyl)-N,9-dimethyl-8-oxo-N-[2-(3-phenyl-1,2,4-oxadiazol-5-yl)ethyl]-8,9-dihydro-7H-purine-7-carboxamide (Example No. 104);

N-[2-(3,4-Dichlorophenyl)ethyl]-2-(3-methoxyphenyl)-N,9-dimethyl-8-oxo-8,9-dihydro-7H-purine-7-carboxamide (Example No. 105);

N-[2-(Cyclohex-1-en-1-yl)ethyl]-2-(3-methoxyphenyl)-N,9-dimethyl-8-oxo-8,9-dihydro-7H-purine-7-carboxamide (Example No. 106);

N-(2-Cyclohexylethyl)-2-(3-methoxyphenyl)-N,9-dimethyl-8-oxo-8,9-dihydro-7H-purine-7-carboxamide (Example No. 109);

N-[2-(2,4-Dichlorophenyl)ethyl]-2-(3-methoxyphenyl)-N,9-dimethyl-8-oxo-8,9-dihydro-7H-purine-7-carboxamide (Example No. 110);

7-({4-[(E)-2-(4-Chlorophenyl)ethenyl]piperidin-1-yl}carbonyl)-2-(3-methoxyphenyl)-9-methyl-7,9-dihydro-8H-purine-8-one (Example No. 112);

N-{2-[4-(Dimethylamino)phenyl]ethyl}-2-(3-methoxyphenyl)-N,9-dimethyl-8-oxo-8,9-dihydro-7H-purine-7-carboxamide (Example No. 113);

N-[2-(Cyclopropylmethoxy)ethyl]-2-(3-methoxyphenyl)-N,9-dimethyl-8-oxo-8,9-dihydro-7H-purine-7-carboxamide (Example No. 116);

2-(3-Methoxyphenyl)-7-({4-[2-(4-methoxyphenyl)ethyl]piperidin-1-yl}carbonyl)-9-methyl-7,9-dihydro-8H-purine-8-one (Example No. 118);

7-{[4-(4-Methoxyphenyl)piperazin-1-yl]carbonyl}-9-methyl-2-phenyl-7,9-dihydro-8H-purine-8-one (Example No. 135);

7-{[4-(4-Ethoxyphenyl)piperazin-1-yl]carbonyl}-2-(3-methoxyphenyl)-9-methyl-7,9-dihydro-8H-purine-8-one (Example No. 141);

7-{[4-(4-Chlorophenyl)piperazin-1-yl]carbonyl}-2-(3-methoxyphenyl)-9-methyl-7,9-dihydro-8H-purine-8-one (Example No. 142);

7-{[4-(4-Ethoxyphenyl)piperazin-1-yl]carbonyl}-9-methyl-2-(pyridin-3-yl)-7,9-dihydro-8H-purine-8-one (Example No. 144);

N-[2-(4-Chlorophenyl)ethyl]-N,9-dimethyl-8-oxo-2-(pyridin-3-yl)-8,9-dihydro-7H-purine-7-carboxamide (Example No. 145);

N-[2-(4-Chlorophenoxy)ethyl]-N,9-dimethyl-8-oxo-2-(pyridin-3-yl)-8,9-dihydro-7H-purine-7-carboxamide (Example No. 146);

7-({4-[2-(4-Chlorophenyl)ethyl]piperidin-1-yl}carbonyl)-9-methyl-2-(pyridin-3-yl)-7,9-dihydro-8H-purine-8-one (Example No. 147);

N,N,9-Trimethyl-8-oxo-2-(pyridin-4-yl)-8,9-dihydro-7H-purine-7-carboxamide (Example No. 148);

7-{[4-(4-Ethoxyphenyl)piperazin-1-yl]carbonyl}-9-methyl-2-(pyridin-4-yl)-7,9-dihydro-8H-purine-8-one (Example No. 149);

N-[2-(4-Chlorophenyl)ethyl]-N,9-dimethyl-8-oxo-2-(pyridin-4-yl)-8,9-dihydro-7H-purine-7-carboxamide (Example No. 150);

N-[2-(4-Chlorophenoxy)ethyl]-N,9-dimethyl-8-oxo-2-(pyridin-4-yl)-8,9-dihydro-7H-purine-7-carboxamide (Example No. 151);

7-({4-[2-(4-Chlorophenyl)ethyl]piperidin-1-yl}carbonyl)-9-methyl-2-(pyridin-4-yl)-7,9-dihydro-8H-purine-8-one (Example No. 152);

N-[2-(4-Chlorophenyl)ethyl]-N,9-dimethyl-8-oxo-2-propyl-8,9-dihydro-7H-purine-7-carboxamide (Example No. 154);

2-Butyl-N-[2-(4-chlorophenyl)ethyl]-N,9-dimethyl-8-oxo-8,9-dihydro-7H-purine-7-carboxamide (Example No. 155);

2-Benzyl-N-[2-(4-chlorophenyl)ethyl]-N,9-dimethyl-8-oxo-8,9-dihydro-7H-purine-7-carboxamide (Example No. 158);

9-(Azetidin-1-ylcarbonyl)-2-[2-(3-fluorophenyl)ethyl]-7-methyl-7,9-dihydro-8H-purine-8-one (Example No. 164);

2-[2-(3-Fluorophenyl)ethyl]-N,N,7-trimethyl-8-oxo-7,8-dihydro-9H-purine-9-carboxamide (Example No. 165);

2-(2-Fluoropyridin-4-yl)-9-methyl-7-(pyrrolidin-1-ylcarbonyl)-7,9-dihydro-8H-purine-8-one (Example No. 215);

N-Ethyl-N,9-dimethyl-8-oxo-2-(pyridin-4-yl)-8,9-dihydro-7H-purine-7-carboxamide (Example No. 220);

N-Ethyl-2-(2-fluoropyridin-4-yl)-N,9-dimethyl-8-oxo-8,9-dihydro-7H-purine-7-carboxamide (Example No. 221);

N-[2-(4-Chlorophenyl)ethyl]-2-(2-fluoropyridin-4-yl)-N,9-dimethyl-8-oxo-8,9-dihydro-7H-purine-7-carboxamide (Example No. 222);

N-(2-Cyclohexylethyl)-N,9-dimethyl-8-oxo-2-(pyridin-4-yl)-8,9-dihydro-7H-purine-7-carboxamide (Example No. 223);

N-Ethyl-2-(3-methoxybenzyl)-N,9-dimethyl-8-oxo-8,9-dihydro-7H-purine-7-carboxamide (Example No. 277);

7-Methyl-9-(pyrrolidin-1-ylcarbonyl)-2-{2-[4-(trifluoromethyl)phenyl]ethyl}-7,9-dihydro-8H-purine-8-one (Example No. 312);

7-Methyl-9-(pyrrolidin-1-ylcarbonyl)-2-{2-[3-(trifluoromethyl)phenyl]ethyl}-7,9-dihydro-8H-purine-8-one (Example No. 313);

N,N,7-Trimethyl-8-oxo-2-[4-(trifluoromethyl)phenyl]-7,8-dihydro-9H-purine-9-carboxamide (Example No. 326);

2-[2-Fluoro-4-(trifluoromethyl)phenyl]-N,N,7-trimethyl-8-oxo-7,8-dihydro-9H-purine-9-carboxamide (Example No. 338); 2-[2-Chloro-4-(trifluoromethyl)phenyl]-N,N,7-trimethyl-8-oxo-7,8-dihydro-9H-purine-9-carboxamide (Example No. 339);

9-(Azetidin-1-ylcarbonyl)-2-[3-(4-fluorophenoxy)propyl]-7-methyl-7,9-dihydro-8H-purine-8-one (Example No. 401);

2-(Methoxymethyl)-9-methyl-7-[(3-phenylazetidin-1-yl)carbonyl]-7,9-dihydro-8H-purine-8-one (Example No. 438);

7-{[3-(4-Fluorophenyl)azetidin-1-yl]carbonyl}-2-(methoxymethyl)-9-methyl-7,9-dihydro-8H-purine-8-one (Example No. 439);

7-{[3-(3-Fluorophenyl)azetidin-1-yl]carbonyl}-2-(methoxymethyl)-9-methyl-7,9-dihydro-8H-purine-8-one (Example No. 440);

7-{[3-(2-Fluorophenyl)azetidin-1-yl]carbonyl}-2-(methoxymethyl)-9-methyl-7,9-dihydro-8H-purine-8-one (Example No. 441);

2-(Methoxymethyl)-9-methyl-7-({[3-(3-trifluoromethyl)phenyl]azetidin-1-yl}carbonyl)-7,9-dihydro-8H-purine-8-one (Example No. 443);

7-{[3-(2-Chlorophenyl)azetidin-1-yl]carbonyl}-2-(methoxymethyl)-9-methyl-7,9-dihydro-8H-purine-8-one (Example No. 453);

7-({3-[4-(Benzyloxy)phenyl]azetidin-1-yl}carbonyl)-2-(methoxymethyl)-9-methyl-7,9-dihydro-8H-purine-8-one (Example No. 456);

2-(Methoxymethyl)-9-methyl-7-({3-[4-(trifluoromethoxy)phenyl]azetidin-1-yl}carbonyl)-7,9-dihydro-8H-purine-8-one (Example No. 458);

7-{[(3R)-3-(4-Fluorophenoxy)pyrrolidin-1-yl]carbonyl}-2-(methoxymethyl)-9-methyl-7,9-dihydro-8H-purine-8-one (Example No. 480);

7-{[(3S)-3-(3-Fluorophenoxy)pyrrolidin-1-yl]carbonyl}-2-(methoxymethyl)-9-methyl-7,9-dihydro-8H-purine-8-one (Example No. 482);

7-{[(3S)-3-(2-Fluorophenoxy)pyrrolidin-1-yl]carbonyl}-2-(methoxymethyl)-9-methyl-7,9-dihydro-8H-purine-8-one (Example No. 483);

2-(Methoxymethyl)-9-methyl-7-{[(3S)-3-(4-methylphenoxy)pyrrolidin-1-yl]carbonyl}-7,9-dihydro-8H-purine-8-one (Example No. 484);

2-(Methoxymethyl)-9-methyl-7-{[(3S)-3-(3-methylphenoxy)pyrrolidin-1-yl]carbonyl}-7,9-dihydro-8H-purine-8-one (Example No. 485);

2-(Methoxymethyl)-9-methyl-7-{[(3S)-3-(2-methylphenoxy)pyrrolidin-1-yl]carbonyl}-7,9-dihydro-8H-purine-8-one (Example No. 486);

7-{[(3R)-3-(3-Chlorophenoxy)pyrrolidin-1-yl]carbonyl}-2-(methoxymethyl)-9-methyl-7,9-dihydro-8H-purine-8-one (Example No. 487);

7-{[(3S)-3-(4-Chlorophenoxy)pyrrolidin-1-yl]carbonyl}-2-(methoxymethyl)-9-methyl-7,9-dihydro-8H-purine-8-one (Example No. 489);

7-{[(3S)-3-(3-Chlorophenoxy)pyrrolidin-1-yl]carbonyl}-2-(methoxymethyl)-9-methyl-7,9-dihydro-8H-purine-8-one (Example No. 490);

7-{[(3S)-3-(2-Chlorophenoxy)pyrrolidin-1-yl]carbonyl}-2-(methoxymethyl)-9-methyl-7,9-dihydro-8H-purine-8-one (Example No. 491);

2-[2-(3,5-Difluorophenyl)ethyl]-N,N,7-trimethyl-8-oxo-7,8-dihydro-9H-purine-9-carboxamide (Example No. 497);

2-[2-(4-Fluorophenyl)ethyl]-N,N,7-trimethyl-8-oxo-7,8-dihydro-9H-purine-9-carboxamide (Example No. 533);

2-{2-[4-(2,2-Difluoroethoxy)phenyl]ethyl}-N,N,7-trimethyl-8-oxo-7,8-dihydro-9H-purine-9-carboxamide (Example No. 538);

9-(Azetidin-1-ylcarbonyl)-2-[2-(4-fluorophenyl)ethyl]-7-methyl-7,9-dihydro-8H-purine-8-one (Example No. 587);

2-[2-(3-Chlorophenoxy)ethyl]-N,N,7-trimethyl-8-oxo-7,8-dihydro-9H-purine-9-carboxamide (Example No. 641);

7-Ethyl-2-[2-(3-fluorophenyl)ethyl]-N,N-dimethyl-8-oxo-7,8-dihydro-9H-purine-9-carboxamide (Example No. 644);

7-Ethyl-2-[2-(4-fluorophenyl)ethyl]-N,N-dimethyl-8-oxo-7,8-dihydro-9H-purine-9-carboxamide (Example No. 645);

2-[2-(2-Fluorophenyl)ethyl]-N,N-dimethyl-8-oxo-7-propyl-7,8-dihydro-9H-purine-9-carboxamide (Example No. 646);

2-[2-(3-Fluorophenyl)ethyl]-N,N-dimethyl-8-oxo-7-propyl-7,8-dihydro-9H-purine-9-carboxamide (Example No. 647);

2-[2-(4-Fluorophenyl)ethyl]-N,N-dimethyl-8-oxo-7-propyl-7,8-dihydro-9H-purine-9-carboxamide (Example No. 648);

7-{[3-(3-Fluorophenyl)azetidin-1-yl]carbonyl}-2-(methoxymethyl)-9-propyl-7,9-dihydro-8H-purine-8-one (Example No. 660); and 2-(Methoxymethyl)-9-propyl-7-({3-[3-(trifluoromethyl)phenyl]azetidin-1-yl}carbonyl)-7,9-dihydro-8H-purine-8-one (Example No. 662);

[14] The compound of the above [1] selected from any one of the following compounds or a pharmaceutically acceptable salt thereof:

N,9-Dimethyl-8-oxo-2-phenyl-N-(4-phenylbutyl)-8,9-dihydro-7H-purine-7-carboxamide (Example No. 36);

2-(3-Methoxyphenyl)-N,9-dimethyl-8-oxo-N-(2-phenylethyl)-8,9-dihydro-7H-purine-7-carboxamide (Example No. 64);

2-(3-Methoxyphenyl)-N,9-dimethyl-8-oxo-N-(2-phenoxyethyl)-8,9-dihydro-7H-purine-7-carboxamide (Example No. 65);

7-({4-[2-(4-Chlorophenyl)ethyl]piperidin-1-yl}carbonyl)-2-(3-methoxyphenyl)-9-methyl-7,9-dihydro-8H-purine-8-one (Example No. 68);

N-[2-(4-Chlorophenyl)ethyl]-2-(3-methoxyphenyl)-N,9-dimethyl-8-oxo-8,9-dihydro-7H-purine-7-carboxamide (Example No. 69);

N-[2-(4-Fluorophenyl)ethyl]-2-(3-methoxyphenyl)-N,9-dimethyl-8-oxo-8,9-dihydro-7H-purine-7-carboxamide (Example No. 74);

N-[2-(3-Fluorophenyl)ethyl]-2-(3-methoxyphenyl)-N,9-dimethyl-8-oxo-8,9-dihydro-7H-purine-7-carboxamide (Example No. 75);

N-[2-(3-Chlorophenyl)ethyl]-2-(3-methoxyphenyl)-N,9-dimethyl-8-oxo-8,9-dihydro-7H-purine-7-carboxamide (Example No. 76);

N-[2-(4-Chlorophenoxy)ethyl]-2-(3-methoxyphenyl)-N,9-dimethyl-8-oxo-8,9-dihydro-7H-purine-7-carboxamide (Example No. 77);

N-(4-Chlorobenzyl)-2-(3-methoxyphenyl)-N,9-dimethyl-8-oxo-8,9-dihydro-7H-purine-7-carboxamide (Example No. 78);

2-(3-Methoxyphenyl)-N,9-dimethyl-8-oxo-N-[4-(trifluoromethoxy)benzyl]-8,9-dihydro-7H-purine-7-carboxamide (Example No. 83);

N-[2-(3-Chlorophenoxy)ethyl]-2-(3-methoxyphenyl)-N,9-dimethyl-8-oxo-8,9-dihydro-7H-purine-7-carboxamide (Example No. 90);

N-[2-(4-Fluorophenoxy)ethyl]-2-(3-methoxyphenyl)-N,9-dimethyl-8-oxo-8,9-dihydro-7H-purine-7-carboxamide (Example No. 91);

2-(3-Methoxyphenyl)-N,9-dimethyl-8-oxo-N-{2-[4-(trifluoromethyl)phenyl]ethyl}-8,9-dihydro-7H-purine-7-carboxamide (Example No. 92);

2-(3-Methoxyphenyl)-N-[2-(4-methoxyphenyl)ethyl]-N,9-dimethyl-8-oxo-8,9-dihydro-7H-purine-7-carboxamide (Example No. 93);

7-({4-[(E)-2-(4-Chlorophenyl)ethenyl]-3,6-dihydropyridin-1(2H)-yl}carbonyl)-2-(3-methoxyphenyl)-9-methyl-7,9-dihydro-8H-purine-8-one (Example No. 94);

7-({4-[(E)-2-(4-Fluorophenyl)ethenyl]-3,6-dihydropyridin-1(2H)-yl}carbonyl)-2-(3-methoxyphenyl)-9-methyl-7,9-dihydro-8H-purine-8-one (Example No. 95);

2-(3-Methoxyphenyl)-N,9-dimethyl-8-oxo-N-[2-(3-phenyl-1,2,4-oxadiazol-5-yl)ethyl]-8,9-dihydro-7H-purine-7-carboxamide (Example No. 104);

N-[2-(3,4-Dichlorophenyl)ethyl]-2-(3-methoxyphenyl)-N,9-dimethyl-8-oxo-8,9-dihydro-7H-purine-7-carboxamide (Example No. 105);

N-[2-(Cyclohex-1-en-1-yl)ethyl]-2-(3-methoxyphenyl)-N,9-dimethyl-8-oxo-8,9-dihydro-7H-purine-7-carboxamide (Example No. 106);

N-(2-Cyclohexylethyl)-2-(3-methoxyphenyl)-N,9-dimethyl-8-oxo-8,9-dihydro-7H-purine-7-carboxamide (Example No. 109);

N-[2-(2,4-Dichlorophenyl)ethyl]-2-(3-methoxyphenyl)-N,9-dimethyl-8-oxo-8,9-dihydro-7H-purine-7-carboxamide (Example No. 110);

7-({4-[(E)-2-(4-Chlorophenyl)ethenyl]piperidin-1-yl}carbonyl)-2-(3-methoxyphenyl)-9-methyl-7,9-dihydro-8H-purine-8-one (Example No. 112);

N-{2-[4-(Dimethylamino)phenyl]ethyl}-2-(3-methoxyphenyl)-N,9-dimethyl-8-oxo-8,9-dihydro-7H-purine-7-carboxamide (Example No. 113);

N-[2-(Cyclopropylmethoxy)ethyl]-2-(3-methoxyphenyl)-N,9-dimethyl-8-oxo-8,9-dihydro-7H-purine-7-carboxamide (Example No. 116);

2-(3-Methoxyphenyl)-7-({4-[2-(4-methoxyphenyl)ethyl]piperidin-1-yl}carbonyl)-9-methyl-7,9-dihydro-8H-purine-8-one (Example No. 118);

7-{[4-(4-Ethoxyphenyl)piperazin-1-yl]carbonyl}-9-methyl-2-(pyridine-3-yl)-7,9-dihydro-8H-purine-8-one (Example No. 144);

N-[2-(4-Chlorophenyl)ethyl]-N,9-dimethyl-8-oxo-2-(pyridin-3-yl)-8,9-dihydro-7H-purine-7-carboxamide (Example No. 145);

N-[2-(4-Chlorophenoxy)ethyl]-N,9-dimethyl-8-oxo-2-(pyridin-3-yl)-8,9-dihydro-7H-purine-7-carboxamide (Example No. 146);

7-({4-[2-(4-Chlorophenyl)ethyl]piperidin-1-yl}carbonyl)-9-methyl-2-(pyridin-3-yl)-7,9-dihydro-8H-purine-8-one (Example No. 147);

N-[2-(4-Chlorophenyl)ethyl]-N,9-dimethyl-8-oxo-2-(pyridin-4-yl)-8,9-dihydro-7H-purine-7-carboxamide (Example No. 150);

N-[2-(4-Chlorophenoxy)ethyl]-N,9-dimethyl-8-oxo-2-(pyridin-4-yl)-8,9-dihydro-7H-purine-7-carboxamide (Example No. 151);

7-({4-[2-(4-Chlorophenyl)ethyl]piperidin-1-yl}carbonyl)-9-methyl-2-(pyridin-4-yl)-7,9-dihydro-8H-purine-8-one (Example No. 152);

2-Butyl-N-[2-(4-chlorophenyl)ethyl]-N,9-dimethyl-8-oxo-8,9-dihydro-7H-purine-7-carboxamide (Example No. 155);

2-Benzyl-N-[2-(4-chlorophenyl)ethyl]-N,9-dimethyl-8-oxo-8,9-dihydro-7H-purine-7-carboxamide (Example No. 158);

2-[2-(3-Fluorophenyl)ethyl]-N,N,7-trimethyl-8-oxo-7,8-dihydro-9H-purine-9-carboxamide (Example No. 165);

N-Ethyl-N,9-dimethyl-8-oxo-2-(pyridin-4-yl)-8,9-dihydro-7H-purine-7-carboxamide (Example No. 220);

N-Ethyl-2-(2-fluoropyridin-4-yl)-N,9-dimethyl-8-oxo-8,9-dihydro-7H-purine-7-carboxamide (Example No. 221);

N-[2-(4-Chlorophenyl)ethyl]-2-(2-fluoropyridin-4-yl)-N,9-dimethyl-8-oxo-8,9-dihydro-7H-purine-7-carboxamide (Example No. 222);

N-(2-Cyclohexylethyl)-N,9-dimethyl-8-oxo-2-(pyridin-4-yl)-8,9-dihydro-7H-purine-7-carboxamide (Example No. 223);

N,N,7-Trimethyl-8-oxo-2-[4-(trifluoromethyl)phenyl]-7,8-dihydro-9H-purine-9-carboxamide (Example No. 326);

2-[2-Fluoro-4-(trifluoromethyl)phenyl]-N,N,7-trimethyl-8-oxo-7,8-dihydro-9H-purine-9-carboxamide (Example No. 338);

2-[2-Chloro-4-(trifluoromethyl)phenyl]-N,N,7-trimethyl-8-oxo-7,8-dihydro-9H-purine-9-carboxamide (Example No. 339);

9-(Azetidin-1-ylcarbonyl)-2-[3-(4-fluorophenoxy)propyl]-7-methyl-7,9-dihydro-8H-purine-8-one (Example No. 401);

2-(Methoxymethyl)-9-methyl-7-[(3-phenylazetidin-1-yl)carbonyl]-7,9-dihydro-8H-purine-8-one (Example No. 438);

7-{[3-(4-Fluorophenyl)azetidin-1-yl]carbonyl}-2-(methoxymethyl)-9-methyl-7,9-dihydro-8H-purine-8-one (Example No. 439);

7-{[3-(3-Fluorophenyl)azetidin-1-yl]carbonyl}-2-(methoxymethyl)-9-methyl-7,9-dihydro-8H-purine-8-one (Example No. 440);

7-{[3-(2-Fluorophenyl)azetidin-1-yl]carbonyl}-2-(methoxymethyl)-9-methyl-7,9-dihydro-8H-purine-8-one (Example No. 441);

2-(Methoxymethyl)-9-methyl-7-({[3-(3-trifluoromethyl)phenyl]azetidin-1-yl}carbonyl)-7,9-dihydro-8H-purine-8-one (Example No. 443);

7-{[3-(2-Chlorophenyl)azetidin-1-yl]carbonyl}-2-(methoxymethyl)-9-methyl-7,9-dihydro-8H-purine-8-one (Example No. 453);

7-({3-[4-(Benzyloxy)phenyl]azetidin-1-yl}carbonyl)-2-(methoxymethyl)-9-methyl-7,9-dihydro-8H-purine-8-one (Example No. 456);

2-(Methoxymethyl)-9-methyl-7-({3-[4-(trifluoromethoxy)phenyl]azetidin-1-yl}carbonyl)-7,9-dihydro-8H-purine-8-one (Example No. 458);

7-{[(3R)-3-(4-Fluorophenoxy)pyrrolidin-1-yl]carbonyl}-2-(methoxymethyl)-9-methyl-7,9-dihydro-8H-purine-8-one (Example No. 480);

7-{[(3S)-3-(3-Fluorophenoxy)pyrrolidin-1-yl]carbonyl}-2-(methoxymethyl)-9-methyl-7,9-dihydro-8H-purine-8-one (Example No. 482);

7-{[(3S)-3-(2-Fluorophenoxy)pyrrolidin-1-yl]carbonyl}-2-(methoxymethyl)-9-methyl-7,9-dihydro-8H-purine-8-one (Example No. 483);

2-(Methoxymethyl)-9-methyl-7-{[(3S)-3-(4-methylphenoxy)pyrrolidin-1-yl]carbonyl}-7,9-dihydro-8H-purine-8-one (Example No. 484);

2-(Methoxymethyl)-9-methyl-7-{[(3S)-3-(3-methylphenoxy)pyrrolidin-1-yl]carbonyl}-7,9-dihydro-8H-purine-8-one (Example No. 485);

2-(Methoxymethyl)-9-methyl-7-{[(3S)-3-(2-methylphenoxy)pyrrolidin-1-yl]carbonyl}-7,9-dihydro-8H-purine-8-one (Example No. 486);

7-{[(3R)-3-(3-Chlorophenoxy)pyrrolidin-1-yl]carbonyl}-2-(methoxymethyl)-9-methyl-7,9-dihydro-8H-purine-8-one (Example No. 487);

7-{[(3S)-3-(4-Chlorophenoxy)pyrrolidin-1-yl]carbonyl}-2-(methoxymethyl)-9-methyl-7,9-dihydro-8H-purine-8-one (Example No. 489);

7-{[(3S)-3-(3-Chlorophenoxy)pyrrolidin-1-yl]carbonyl}-2-(methoxymethyl)-9-methyl-7,9-dihydro-8H-purine-8-one (Example No. 490);

7-{[(3S)-3-(2-Chlorophenoxy)pyrrolidin-1-yl]carbonyl}-2-(methoxymethyl)-9-methyl-7,9-dihydro-8H-purine-8-one (Example No. 491);

2-[2-(3,5-Difluorophenyl)ethyl]-N,N,7-trimethyl-8-oxo-7,8-dihydro-9H-purine-9-carboxamide (Example No. 497);

2-[2-(4-Fluorophenyl)ethyl]-N,N,7-trimethyl-8-oxo-7,8-dihydro-9H-purine-9-carboxamide (Example No. 533);

2-{2-[4-(2,2-Difluoroethoxy)phenyl]ethyl}-N,N,7-trimethyl-8-oxo-7,8-dihydro-9H-purine-9-carboxamide (Example No. 538);

9-(Azetidin-1-ylcarbonyl)-2-[2-(4-fluorophenyl)ethyl]-7-methyl-7,9-dihydro-8H-purine-8-one (Example No. 587);

2-[2-(3-Chlorophenoxy)ethyl]-N,N,7-trimethyl-8-oxo-7,8-dihydro-9H-purine-9-carboxamide (Example No. 641);

7-Ethyl-2-[2-(3-fluorophenyl)ethyl]-N,N-dimethyl-8-oxo-7,8-dihydro-9H-purine-9-carboxamide (Example No. 644);

7-Ethyl-2-[2-(4-fluorophenyl)ethyl]-N,N-dimethyl-8-oxo-7,8-dihydro-9H-purine-9-carboxamide (Example No. 645);

2-[2-(2-Fluorophenyl)ethyl]-N,N-dimethyl-8-oxo-7-propyl-7,8-dihydro-9H-purine-9-carboxamide (Example No. 646);

2-[2-(3-Fluorophenyl)ethyl]-N,N-dimethyl-8-oxo-7-propyl-7,8-dihydro-9H-purine-9-carboxamide (Example No. 647);

2-[2-(4-Fluorophenyl)ethyl]-N,N-dimethyl-8-oxo-7-propyl-7,8-dihydro-9H-purine-9-carboxamide (Example No. 648);

7-{[3-(3-Fluorophenyl)azetidin-1-yl]carbonyl}-2-(methoxymethyl)-9-propyl-7,9-dihydro-8H-purine-8-one (Example No. 660); and 2-(Methoxymethyl)-9-propyl-7-({3-[3-(trifluoromethyl)phenyl]azetidin-1-yl}carbonyl)-7,9-dihydro-8H-purine-8-one (Example No. 662);

[15] A medicament comprising as an active ingredient the compound of any one of the above [1] to [14] or a pharmaceutically acceptable salt thereof;

[16] The medicament of the above [15] for treatment or prophylaxis of depression, anxiety disorder or pains;

[17] The medicament of the above [16] for treatment or prophylaxis of pains;

[18] A fatty acid amide hydrolase (FAAH) inhibitor comprising as an active ingredient the compound of any one of the above [1] to [14] or a pharmaceutically acceptable salt thereof;

[19] A pharmaceutical composition comprising as an active ingredient the compound of any one of the above [1] to [14] or a pharmaceutically acceptable salt thereof and a pharmaceutically acceptable carrier;

[20] The pharmaceutical composition of the above [19] for treatment or prophylaxis of depression, anxiety disorder or pains;

[21] A use of the compound of any one of the above [1] to [14] or a pharmaceutically acceptable salt thereof in a preparation of a medicament for treatment or prophylaxis of depression, anxiety disorder or pains;

[22] The compound of any one of the above [1] to [14] or a pharmaceutically acceptable salt thereof or a pharmaceutical composition comprising the same as an active ingredient for treatment or prophylaxis of depression, anxiety disorder or pains; and

[23] A method for treatment or prophylaxis of depression, anxiety disorder or pains comprising administering a therapeutically effective amount of the compound of any one of the above [1] to [14] or a pharmaceutically acceptable salt thereof to a patient in need thereof.

Effect of Invention

The present invention provides a fatty acid amide hydrolase (FAAH) inhibitor comprising 8-oxodihydropurine derivative or a pharmaceutically acceptable salt thereof as an active ingredient. The FAAH inhibitor of the present invention is useful as a medicament for treatment or prophylaxis of depression, anxiety disorder or pains.

MODE FOR CARRYING OUT THE INVENTION

A term "a halogen atom" to be used herein includes fluorine atom, chlorine atom, bromine atom or iodine atom.

The term "alkyl group" to be used herein means a straight chain or branched chain saturated aliphatic hydrocarbon group, and specifically includes for example, methyl group, ethyl group, propyl group, isopropyl group, butyl group, sec-butyl group, isobutyl group, tert-butyl group, pentyl group and hexyl group. The alkyl group includes usually an alkyl group having 1 to 6 carbon atom(s), and preferably an alkyl group having 1 to 4 carbon atom(s). Herein, for example, $C_{1-6}$ represents a carbon number of 1 to 6, $C_{1-4}$ represents a carbon number of 1 to 4, and $C_6$ represents a carbon number of 6. In the case of the other numbers, they can be read similarly.

The term "an alkyl group optionally substituted with halogen atom" means in addition to the above-mentioned alkyl group, a straight chain or branched chain alkyl group substituted with the same or different one to five halogen atom(s), and specifically includes in addition to the specific examples of the above-mentioned alkyl group, for example, a haloalkyl group such as difluoromethyl group, trifluoromethyl group, 2,2-difluoroethyl group, 2,2,2-trifluoroethyl group, 2-chloroethyl group, pentafluoroethyl group and 3,3,3-trifluoropropyl group. The haloalkyl group includes usually a haloalkyl group having 1 to 6 carbon atom(s), and preferably a haloalkyl group having 1 to 4 carbon atom(s).

The term "alkenyl group" to be used herein means a straight chain or branched chain unsaturated aliphatic hydrocarbon group having one or two or more double bond(s), and specifically includes for example, vinyl group, 1-propenyl group, 2-propenyl group, 1-methylvinyl group, 1-butenyl group, 1-ethylvinyl group, 1-methyl-2-propenyl group, 2-butenyl group, 3-butenyl group, 2-methyl-1-propenyl group, 2-methyl-2-propenyl group, 1-pentenyl group and 1-hexenyl group. The alkenyl group includes usually an alkenyl group having 2 to 6 carbon atoms, and preferably an alkenyl group having 2 to 4 carbon atoms.

The term "alkynyl group" to be used herein means a straight chain or branched chain unsaturated aliphatic hydrocarbon group having one or two or more triple bond(s), and specifically includes for example, ethynyl group, 1-propynyl group, 2-propynyl group, 1-butynyl group, 1-methyl-2-propynyl group, 3-butynyl group, 1-pentynyl group and 1-hexynyl group. The alkynyl group includes usually an alkynyl group having 2 to 6 carbon atoms, and preferably an alkynyl group having 2 to 4 carbon atoms.

The term "alkyloxy group" to be used herein means an oxy group substituted with the above-mentioned alkyl group, and specifically includes for example, methoxy group, ethoxy group, propoxy group, 1-methylethoxy group, butoxy group, 1-methylpropoxy group, 2-methylpropoxy group, 1,1-dimethylethoxy group, pentyloxy group and hexyloxy group. The alkyl moiety of the alkyloxy group includes usually an alkyl group having 1 to 6 carbon atom(s), and preferably an alkyl group having 1 to 4 carbon atom(s).

The term "alkyloxy group optionally substituted with halogen atom" means in addition to the above-mentioned alkyloxy group, a straight chain or branched chain haloalkyloxy group substituted with the same or different one to five halogen atom(s), and specifically includes in addition to the specific examples of the above-mentioned alkyloxy group, for example, haloalkyloxy group such as difluoromethoxy group, trifluoromethoxy group, 2,2-difluoroethoxy group, 2,2,2-trifluoroethoxy group, 2-chloroethoxy group, pentafluoroethoxy group and 3,3,3-trifluoropropoxy group. The haloalkyl moiety of the haloalkyloxy group includes usually a haloakyl group having to 6 carbon atom(s), and preferably a haloalkyl group having 1 to 4 carbon atom(s).

The term "cycloalkyl group" to be used herein means a monocyclic saturated aliphatic carbocyclic group or a bicyclic saturated aliphatic carbocyclic group where saturated aliphatic carbocycle, unsaturated aliphatic carbocycle, saturated aliphatic heterocycle, unsaturated aliphatic heterocycle, aromatic ring or aromatic heterocycle is fused to the monocyclic saturated aliphatic carbocyclic group, and specifically includes for example, cyclopropyl group, cyclobutyl group, cyclopentyl group, cyclohexyl group, cycloheptyl group, cyclooctyl group and bicyclo[3.2.0]heptyl group. The cycloalkyl group includes usually a $C_{3-8}$ cycloalkyl group, and preferably a $C_{3-6}$ cycloalkyl group.

The term "cycloalkyloxy group" to be used herein means an oxy group substituted with the above-mentioned cycloalkyl group, and specifically includes for example, cyclopropyloxy group, cyclobutyloxy group, cyclopentyloxy group, cyclohexyloxy group, cycloheptyloxy group and cyclooctyloxy group. The cycloalkyloxy group includes usually a $C_{3-8}$ cycloalkyloxy group, and preferably a $C_{3-6}$ cycloalkyloxy group.

The term "cycloalkyl(alkyl)oxy group" to be used herein means an alkyloxy group substituted with the above-mentioned "cycloalkyl group", and specifically includes for example, cyclohexylmethyloxy group, cyclopentylmethyloxy group, cyclobutylmethyloxy group, cyclohexylethyloxy group, cyclohexylpropyloxy group, cyclopentylethyloxy group and cyclopentylpropyloxy group. The cycloalkyl (alkyl)oxy group includes usually a $C_{1-6}$ alkyloxy group substituted with $C_{3-8}$ cycloalkyl group, and preferably a $C_{1-6}$ alkyloxy group substituted with $C_{3-6}$ cycloalkyl group. The substituted cycloalkyl(alkyl)oxy group means a cycloalkyl (alkyl)oxy group where cycloalkyl moiety of the cycloalkyl (alkyl)oxy group is substituted with one or the same or different two or more substituent(s) selected from the group of the below-mentioned Substituent (β).

The term "cycloalkenyl group" to be used herein means a monocyclic unsaturated aliphatic carbocyclic group having one or two or more double bond(s) on the ring or a bicyclic unsaturated aliphatic carbocyclic group where saturated aliphatic carbocycle, unsaturated aliphatic carbocycle, saturated aliphatic heterocycle, unsaturated aliphatic heterocycle, aromatic ring or aromatic heterocycle is fused to the monocyclic unsaturated aliphatic carbocyclic group (provided that the position of the double bond is not particularly limited as long as the resulting compound is chemically stable), and specifically includes for example, cyclobutenyl group, cyclopentenyl group, cyclohexenyl group, cycloheptenyl group and cyclooctenyl group. The cycloalkenyl group includes usually a 4 to 10 membered cycloalkenyl group, preferably a 4 to 6 membered cycloalkenyl group, and more preferably a 5 or 6 membered cycloalkenyl group.

The term "heterocycloalkyl group" to be used herein means a monocyclic saturated aliphatic heterocyclic group containing 1 to 3 heteroatom(s) selected from nitrogen atom, oxygen atom or sulfur atom or a bicyclic saturated aliphatic heterocyclic group where saturated aliphatic carbocycle, unsaturated aliphatic carbocycle, saturated aliphatic heterocycle, unsaturated aliphatic heterocycle, aromatic ring or aromatic heterocycle is fused to the monocyclic saturated aliphatic heterocyclic group (provided that the position of the heteroatom on the ring is not particularly limited as long as the resulting compound is chemically stable), and specifically includes for example, azetidinyl group, pyrrolidinyl group, piperidyl group, piperidino group, piperazinyl group, perhydroazepinyl group, perhydroazocinyl group, perhydroazoninyl group, perhydroazecinyl group, tetrahydrofuryl group, tetrahydrothienyl group, tetrahydropyranyl group, morpholinyl group, morpholino group, thiomorpholinyl group and 1,4-dioxanyl group. The heterocycloalkyl group includes usually a 3 to 10 membered heterocycloalkyl group and preferably a 4 to 8 membered heterocycloalkyl group (such as azetidinyl group, pyrrolidinyl group, piperidyl group, piperidino group, piperazinyl group, perhydroazepinyl group, perhydroazocinyl group, tetrahydrofuryl group, tetrahydrothienyl group, tetrahydropyranyl group, morpholinyl group, morpholino group, thiomorpholinyl group, 1,4-dioxanyl group), and more preferably a 4 to 6 membered heterocycloalkyl group (such as azetidinyl group, pyrrolidinyl group, piperidyl group, piperidino group, piperazinyl group, tetrahydrofuryl group, tetrahydrothienyl group, tetrahydropyranyl group, morpholinyl group, morpholino group, thiomorpholinyl group, 1,4-dioxanyl group).

The term "heterocycloalkyloxy group" to be used herein means an oxy group substituted with the above-mentioned "heterocycloalkyl group", and specifically includes for example, 3-pyrrolidinyloxy group and 3- or 4-piperidyloxy group. The heterocycloalkyloxy group includes usually an oxy group substituted with 3 to 10 membered heterocycloalkyl group, and preferably an oxy group substituted with 4 to 8 membered heterocycloalkyl group.

The term "heterocycloalkyl(alkyl)oxy group" to be used herein means an alkyloxy group substituted with the above-mentioned "heterocycloalkyl group", and specifically includes for example, 3-pyrrolidinylmethyloxy group, 3- or 4-piperidylmethyloxy group, piperidinomethyloxy group, N-piperazinylethyloxy group, 1-, 2- or 3-pyrrolidinylethyloxy group and 1-, 2- or 3-pyrrolidinylpropyloxy group. The heterocycloalkyl(alkyl)oxy group includes usually a $C_{1-6}$ alkyloxy group substituted with 3 to 10 membered heterocycloalkyl group, and preferably a $C_{1-6}$ alkyloxy group substituted with 4 to 8 membered heterocycloalkyl group. The substituted heterocycloalkyl(alkyl)oxy group means a heterocycloalkyl(alkyl)oxy group where the heterocycloalkyl moiety of the heterocycloalkyl(alkyl)oxy group is substituted with one or the same or different two or more substituent(s) selected from the group of the below-mentioned Substituent (β).

The term "heterocycloalkenyl group" to be used herein means a monocyclic unsaturated aliphatic heterocyclic group containing 1 to 3 heteroatom(s) selected from nitrogen atom, oxygen atom or sulfur atom and having 1 to 3 double bond(s) or a bicyclic unsaturated aliphatic heterocyclic group where saturated aliphatic carbocycle, unsaturated aliphatic carbocycle, saturated aliphatic heterocycle, unsaturated aliphatic heterocycle, aromatic ring or aromatic heterocycle is fused to the monocyclic unsaturated aliphatic heterocyclic group (provided that the position of the heteroatom and the double bond on the ring are not particularly limited as long as the resulting compound is chemically stable), and specifically includes for example, pyrrolinyl group, tetrahydropyridyl group, imidazolinyl group and tetrahydroisoquinolyl group and preferably 3-pyrrolinyl group, 3-tetrahydropyridyl group and 2-imidazolinyl group. The heterocycloalkenyl group includes usually a 4 to 10 membered heterocycloalkenyl group, preferably a 5 to 8 membered heterocycloalkenyl group, and more preferably a 5 or 6 membered heterocycloalkenyl group.

The term "aryl group" to be used herein means a monocyclic aromatic ring group or a bicyclic aromatic ring group where saturated aliphatic carbocycle, unsaturated aliphatic carbocycle, saturated aliphatic heterocycle, unsaturated aliphatic heterocycle or aromatic ring is fused to the monocyclic aromatic ring, and includes specifically for example, phenyl group, 1-naphthyl group and 2-naphthyl group. The aryl group includes usually a $C_{6-10}$ aryl group and preferably a $C_6$ or $C_{10}$ aryl group.

The term "heteroaryl group" to be used herein means a monocyclic aromatic heterocyclic group containing 1 to 4 heteroatom(s) selected from nitrogen atom, oxygen atom and sulfur atom or a bicyclic aromatic heterocyclic group where saturated aliphatic carbocycle, unsaturated aliphatic carbocycle, saturated aliphatic heterocycle, unsaturated aliphatic heterocycle, aromatic ring or aromatic heterocycle is fused to the monocyclic aromatic heterocyclic group (provided that the position of the heteroatom on the ring is not particularly limited as long as the resulting compound is chemically stable), and specifically includes for example, furyl group, thienyl group, pyrrolyl group, oxazolyl group, isooxazolyl group, thiazolyl group, isothiazolyl group, imidazolyl group, pyrazolyl group, furazanyl group, oxadiazolyl group, triazolyl group, pyridyl group, pyrimidinyl group, pyrazinyl group, indolyl group, quinolyl group, isoquinolyl group, quinazolinyl group, imidazo[2,1-b][1,3]thiazolyl group, benzofuranyl group, indolizinyl group and indazolyl group. The heteroaryl group includes usually a 5 to 10 membered heteroaryl group and preferably a 5 or 6 membered monocyclic heteroaryl group or a 9 or 10 membered bicyclic heteroaryl group.

The term "alkylcarbonyl group" to be used herein means a carbonyl group substituted with the above-mentioned "alkyl group" and includes specifically for example, acetyl group, propionyl group and butyryl group. The alkylcarbonyl group includes usually a carbonyl group substituted with alkyl group having 1 to 6 carbon atom(s), and preferably a carbonyl group substituted with alkyl group having 1 to 4 carbon atom(s). Herein, for example, a $C_{1-6}$ alkylcarbonyl group or a $C_{1-4}$ alkylcarbonyl group means a carbonyl group substituted with alkyl group having 1 to 6 carbon atom(s) or a carbonyl group substituted with alkyl group having 1 to 4 carbon atom(s) respectively.

The term "alkyloxycarbonyl group" to be used herein means a carbonyl group substituted with the above-mentioned "alkyloxy group" and includes specifically for example, methoxycarbonyl group, ethoxycarbonyl group, propoxycarbonyl group and butoxycarbonyl group. The alkyloxycarbonyl group includes usually an oxycarbonyl group substituted with alkyl group having 1 to 6 carbon atom(s) and preferably an oxycarbonyl group substituted with alkyl group having 1 to 4 carbon atom(s). Herein, for example a $C_{1-6}$ alkyloxycarbonyl group or a $C_{1-4}$ alkyloxycarbonyl group means an oxycarbonyl group substituted with alkyl group having 1 to 6 carbon atom(s) or an oxycarbonyl group substituted with alkyl group having 1 to 4 carbon atom(s) respectively.

The term "arylcarbonyl group" to be used herein means a carbonyl group substituted with the above-mentioned "aryl group" and includes specifically for example, benzoyl group, 4-methylbenzoyl group, 1-naphthoyl group and 2-naphthoyl group. The arylcarbonyl group includes usually a $C_{6-10}$ arylcarbonyl group and preferably a $C_6$ or $C_{10}$ arylcarbonyl group. Herein, for example, a $C_{6-10}$ arylcarbonyl group means a carbonyl group substituted with an aryl group having 6 to 10 carbon atoms.

The term "aryloxy group" to be used herein means an oxy group substituted with the above-mentioned "aryl group" and specifically includes for example, phenyloxy group, 1-napthyloxy group and 2-napthyloxy group. The aryloxy group includes usually a $C_{6-10}$ aryloxy group and preferably a $C_6$ or $C_{10}$ aryloxy group.

The term "aryl(alkyl)oxy group" to be used herein means an alkyloxy group substituted with the above-mentioned "aryl group" and specifically includes for example, benzyloxy group. The aryl(alkyl)oxy group includes usually a $C_{1-6}$ alkyloxy group substituted with $C_{6-10}$ monocyclic or bicyclic aryl group and preferably a $C_{1-6}$ alkyloxy group substituted with $C_6$ monocyclic aryl group or $C_{10}$ bicyclic aryl group. The substituted aryl(alkyl)oxy group means an aryl(alkyl)oxy group where an aryl moiety in the aryl(alkyl)oxy group is substituted with one or the same or different two or more substituent(s) selected from the group of the below-mentioned Substituent (β).

The term "heteroaryloxy group" to be used herein means an oxy group substituted with the above-mentioned "heteroaryl group" and specifically includes for example, thiazolyloxy group, imidazolyloxy group, pyrazolyloxy group, pyridyloxy group, pyrimidinyloxy group and indolyloxy group. The heteroaryloxy group includes usually a 5 to 10 membered monocyclic or bicyclic heteroaryloxy group and preferably a 5 or 6 membered monocyclic heteroaryloxy group or a 9 or 10 membered bicyclic heteroaryloxy group.

The term "heteroaryl(alkyl)oxy group" to be used herein means an alkyloxy group substituted with the above-mentioned "heteroaryl group", and specifically includes for example, 2-, 3- or 4-pyridylmethyloxy group. The heteroaryl (alkyl)oxy group includes usually a $C_{1-6}$ alkyloxy group substituted with 5 to 10 membered monocyclic or bicyclic heteroaryl group, and preferably a $C_{1-6}$ alkyloxy group substituted with 5 or 6 membered monocyclic heteroaryl group or 9 or 10 membered bicyclic heteroaryl group. The substituted heteroaryl(alkyl)oxy group means a heteroaryl (alkyl)oxy group where a heteroaryl moiety in the heteroaryl (alkyl)oxy group is substituted with one or the same or different two or more substituent(s) selected from the group of the below-mentioned Substituent (β).

The term "alkylthio group" to be used herein means a thio group substituted with the above-mentioned "alkyl group" and specifically includes for example, methylthio group, ethylthio group, propylthio group, 1-methylethylthio group, butylthio group, 1-methylpropylthio group, 2-methylpropylthio group, 1,1-dimethylethylthio group, pentylthio group and hexylthio group. The alkylthio group includes usually an alkylthio group having 1 to 6 carbon atom(s) and preferably an alkylthio group having 1 to 4 carbon atom(s).

The term "alkylsulfonyl group" to be used herein means a sulfonyl group substituted with the above-mentioned "alkyl group" and specifically includes for example, methylsulfonyl group, ethylsulfonyl group, propylsulfonyl group, 1-methylethylsulfonyl group, butylsulfonyl group, 1-methylpropylsulfonyl group, 2-methylpropylsulfonyl group, 1,1-dimethylethylsulfonyl group, pentylsulfonyl group and hexylsulfonyl group. The alkylsulfonyl group includes usually an alkylsulfonyl group having 1 to 6 carbon atom(s) and preferably an alkylsulfonyl group having 1 to 4 carbon atom(s).

The term "arylsulfonyl group" to be used herein means a sulfonyl group substituted with the above-mentioned "aryl group" and specifically includes for example, phenylsulfonyl group, 4-methylphenylsulfonyl group, 1-naphthylsulfonyl group and 2-naphthylsulfonyl group. The arylsulfonyl group includes usually a $C_{6-10}$ arylsulfonyl group and preferably a $C_6$ or $C_{10}$ arylsulfonyl group.

When the "alkyl", "alkenly" or "alkynyl" group or moiety is substituted, the substituent includes one or the same or different two or more substituent(s) selected from the group of the below-mentioned Substituent (α) unless otherwise specifically noted:

Substituent (α)

halogen atom, $C_{3-8}$ cycloalkyl group, $C_{4-10}$ cycloalkenyl group, 3 to 10 membered heterocycloalkyl group, 4 to 10 membered heterocycloalkenyl group, $C_{6-10}$ aryl group, 5 to 10 membered heteroaryl group, hydroxy group, $C_{1-6}$ alkyloxy group optionally substituted with one or two or more halogen atom(s), $C_{3-8}$ cycloalkyloxy group, 3 to 10 membered heterocycloalkyloxy group, $C_{6-10}$ aryloxy group, 5 to 10 membered heteroaryloxy group, $C_{3-8}$ cycloalkyl($C_{1-6}$ alkyl)oxy group, 3 to 10 membered heterocycloalkyl($C_{1-6}$ alkyl)oxy group, $C_{6-10}$ aryl($C_{1-6}$ alkyl)oxy group, 5 to 10 membered heteroaryl ($C_{1-6}$ alkyl)oxy group, amino group (said amino group may be optionally substituted with one or two or more substituent(s) selected from the group consisting of $C_{1-6}$ alkyl group optionally substituted with one or two or more halogen atom(s), $C_{3-8}$ cycloalkyl group, $C_{6-10}$ aryl group and 5 to 10 membered heteroaryl group, or alternatively two substituent(s) on the amino group combine together with a nitrogen atom to which they bind to form 5 to 10 membered saturated or unsaturated aliphatic cyclic amino group), $C_{1-6}$ alkyloxycarbonyl group, aminocarbonyl group (the amino moiety of said aminocarbonyl group may be optionally substituted with one or two or more substituent(s) selected from the group consisting of $C_{1-6}$ alkyl group optionally substituted with one or two or more halogen atom(s), $C_{3-8}$ cycloalkyl group, $C_{6-10}$ aryl group and 5 to 10 membered heteroaryl group, or alternatively two substituent(s) on the amino group combine together with a nitrogen atom to which they bind to form 5 to 10 membered saturated or unsaturated aliphatic cyclic amino group).

Preferably, one or the same or different two or more substituent(s) selected from the group of the below-mentioned Substituent (α') is included:

Substituent (α')

halogen atom, $C_{3-8}$ cycloalkyl group, $C_{4-10}$ cycloalkenyl group, 3 to 10 membered heterocycloalkyl group, $C_{6-10}$ aryl group, 5 to 10 membered heteroaryl group, hydroxy group, $C_{1-6}$ alkyloxy group optionally substituted with one or two or more halogen atom(s), amino group (said amino group may be optionally substituted with one or two or more substituent(s) selected from the group consisting of $C_{1-6}$ alkyl group optionally substituted with one or two or more halogen atom(s), $C_{3-8}$ cycloalkyl group, $C_{6-10}$ aryl group and 5 to 10 membered heteroaryl group, or alternatively two substituent(s) on the amino group combine together with a nitrogen atom to which they bind to form 5 to 10 membered saturated or unsaturated aliphatic cyclic amino group).

When the "cycloalkyl", "cycloalkenyl", "heterocycloalkyl", "heterocycloalkenyl" group or moiety, or "saturated aliphatic carbocycle", "unsaturated aliphatic carbocycle", "saturated aliphatic heterocycle" and "unsaturated aliphatic heterocycle" is substituted, the substituent includes one or the same or different two or more substituent(s) selected from the group of the below-mentioned Substituent (β) unless otherwise specifically noted:

Substituent (β)

$C_{1-6}$ alkyl group optionally substituted with one or two or more halogen atom(s), halogen atom, $C_{3-8}$ cycloalkyl group, $C_{4-10}$ cycloalkenyl group, $C_{6-10}$ aryl group, 5 to 10 membered heteroaryl group, hydroxy group, $C_{1-6}$ alkyloxy group substituted with one or two or more halogen atom(s), $C_{3-8}$ cycloalkyloxy group, $C_{6-10}$ aryloxy group, 5 to 10 membered heteroaryloxy group, $C_{6-10}$ aryl($C_{2-6}$ alkyl)oxy group and 5 to membered heteroaryl ($C_{1-6}$ alkyl)oxy group, amino group (said amino group may be optionally substituted with one or two or more substituent(s) selected from the group consisting of $C_{1-6}$ alkyl group optionally substituted with one or two or more halogen atom(s), $C_{3-8}$ cycloalkyl group, $C_{6-10}$ aryl group and 5 to 10 membered heteroaryl group, or alternatively two substituent(s) on the amino group combine together with a nitrogen atom to which they bind to form 5 to 10 membered saturated or unsaturated aliphatic cyclic amino group), carboxyl group, cyano group, nitro group, carbamoyl group, $C_{1-6}$ alkylcarbonyl group, $C_{1-6}$ alkylcarbonyloxy group, $C_{1-6}$ alkyloxycarbonyl, $C_{1-6}$ alkylthio group, $C_{1-6}$ alkylsulfonyl group, $C_{6-10}$ arylcarbonyl group, $C_{6-10}$ arylsulfonyl group, cycloalkyl(alkyl)oxy group.

When the "aryl" or "heteroaryl" group or moiety in the "aryl group", "heteroaryl group", "aryloxy group", "heteroaryloxy group", "arylalkyloxy group" and "heteroarylalkyloxy group", or "aromatic ring" or "aromatic heterocycle" is substituted, the substituent includes the same or different one to five substituent(s) selected from the above-mentioned Substituent (β) unless otherwise specifically noted:

The term "optionally substituted amino group" to be used herein means an unsubstituted amino group, a mono- or di-substituted amino group substituted with one or the same or different two substituent(s) selected from the group of the below-mentioned Substituent (Y), or a 5 to 10 membered saturated or unsaturated aliphatic cyclic amino group which two substituents on the amino group combine together with a nitrogen atom to which they bind to form, and specifically includes for example, methylamino group, ethylamino group, propylamino group, dimethylamino group, diethylamino group, ethyl-methyl amino group, pyrrolidinyl group, piperidyl group and piperazinyl group.

Substituent (Y)

$C_{1-6}$ alkyl group optionally substituted with halogen atom, $C_{3-8}$ cycloalkyl group, $C_{6-10}$ aryl group, 5 to 10 membered heteroaryl group;

provided that the "optionally substituted amino group" is substituted on the "alkyl group", "alkenyl group", "alkynyl group", "cycloalkyl group", "cycloalkenyl group", "heterocycloalkyl group" or "heterocycloalkenyl group", any other heteroatom doesn't bind to the carbon atom to which the amino group binds.

The term "optionally substituted aminocarbony group" to be used herein means a carbonyl group substituted with the above-mentioned "optionally substituted amino group" and specifically includes for example, methylaminocarbonyl group, ethylaminocarbonyl group, propylaminocarbonyl group, dimethylaminocarbonyl group, diethylaminocarbonyl group, dipropylaminocarbonyl group, ethylmethylaminocarbonyl group, benzylmethylaminocarbonyl group, pyrrolidinylcarbonyl group, piperidylcarbonyl group and piperazinylcarbonyl group.

The term "saturated aliphatic carbocycle" to be used herein means a monocyclic or bicyclic saturated aliphatic carbocycle, and specifically includes for example, cyclopropane, cyclobutane, cyclopentane, cyclohexane, cycloheptane, cyclooctane and bicyclo[3.2.0]heptane. The saturated aliphatic carbocycle includes usually a 3 to 8 membered saturated aliphatic carbocycle and preferably a 3 to 6 membered saturated aliphatic carbocycle.

The term "unsaturated aliphatic carbocycle" to be used herein means a monocyclic or bicyclic unsaturated aliphatic carbocycle containing one or two or more double bond(s) on the ring (provided that the position of the double bond is not particularly limited as long as the resulting compound is chemically stable), and specifically includes for example, cyclobuten, cyclopentene, cyclohexene, cycloheptene and cyclooctene. The unsaturated aliphatic carbocycle includes usually a 4 to 10 membered unsaturated aliphatic carbocycle, preferably a 4 to 6 membered unsaturated aliphatic carbocycle and more preferably a 5 or 6 membered unsaturated aliphatic carbocycle.

The term "saturated aliphatic heterocycle" to be used herein means a monocyclic or bicyclic saturated aliphatic heterocycle containing 1 to 3 heteroatom(s) selected from nitrogen atom, oxygen atom or sulfur atom (provided that the position of the heteroatom is not particularly limited as long as the resulting compound is chemically stable), and specifically includes for example, azetidine, pyrrolidine, piperidine, piperazine, perhydroazepine, perhydroazocine, perhydroazonine, perhydroazecine, tetrahydrofuran, tetrahydrothiophene, tetrahydropyrane, morpholine, thiomorpholine and 1,4-dioxane. The saturated aliphatic heterocycle includes usually a 3 to 10 membered saturated aliphatic heterocycle, preferably a 4 to 8 membered saturated aliphatic heterocycle (such as azetidine, pyrrolidine, piperidine, piperazine, perhydroazepine, perhydroazocine, tetrahydrofuran, tetrahydrothiophene, tetrahydropyrane, morpholine, thiomorpholine, 1,4-dioxane), and more preferably a 4 to 6 membered saturated aliphatic heterocycle (such as azetidine, pyrrolidine, piperidine, piperazine, tetrahydrofuran, tetrahydrothiophene, tetrahydropyrane, morpholine, thiomorpholine, 1,4-dioxane).

The term "unsaturated aliphatic heterocycle" to be used herein means a monocyclic or bicyclic unsaturated aliphatic heterocycle containing 1 to 3 heteroatom(s) selected from nitrogen atom, oxygen atom or sulfur atom and having one to three double bond(s) (provided that each position of the heteroatom and the double bond is not particularly limited as long as the resulting compound is chemically stable), and specifically includes for example, pyrroline, tetrahydropyridine, imidazoline and tetrahydroisoquinoline, and preferably 3-pyrroline, 3-tetrahydropyridine and 2-imidazoline. The unsaturated aliphatic heterocycle includes usually a 4 to 10 membered unsaturated aliphatic heterocycle, preferably a 5 to 8 membered unsaturated aliphatic heterocycle and more preferably a 5 to 6 membered unsaturated aliphatic heterocycle.

The "aromatic ring" to be used herein means a monocyclic or bicyclic aromatic carbocycle and specifically includes for example, benzene and naphthalene. The aromatic ring includes usually a $C_{6-10}$ aromatic ring and preferably a $C_6$ or $C_{10}$ aromatic ring.

The term "aromatic heterocycle" to be used herein means a monocyclic or bicyclic aromatic heterocycle containing 1 to 4 heteroatom(s) selected from nitrogen atom, oxygen atom or sulfur atom (provided that the position of the heteroatom is not particularly limited as long as the resulting compound is chemically stable), and specifically includes for example, furan, thiophene, pyrrole, oxazole, isooxazole, thiazole, isothiazole, imidazole, pyrazole, furazan, oxadiazole, triazole, pyridine, pyrimidine, pyrazine, indole, quinoline, isoquinoline, quinazoline, imidazo[2,1-b][1,3]thiazole, benzofuran, indolizine and indazole. The aromatic heterocycle includes usually a 5 to 10 membered aromatic heterocycle and preferably a 5 or 6 membered monocyclic aromatic heterocycle or a 9 or 10 membered bicyclic aromatic heterocycle.

In the present compound represented by the general formula (1), the preferred substituent is as follows:

W represents a hydrogen atom, a halogen atom, a $C_{1-6}$ alkyl group optionally substituted with halogen atom or a $C_{1-6}$ alkyloxy group optionally substituted with halogen atom,
preferably a hydrogen atom or a halogen atom, and
more preferably a hydrogen atom.

Specific examples of W include hydrogen atom, fluorine atom, chlorine atom, methyl group, ethyl group, propyl group, difluoromethyl group, trifluoromethyl group, methoxy group, ethoxy group, difluoromethoxy group, trifluoromethoxy group and the others.

A represents a hydrogen atom, a $C_{1-6}$ alkyl group, a $C_{2-6}$ alkenyl group, a $C_{2-6}$ alkynyl group [[said $C_{1-6}$ alkyl group, $C_{2-6}$ alkenyl group and $C_{2-6}$ alkynyl group may be optionally substituted at an optional substitutable position with one or two or more substituent(s) selected from the group consisting of halogen atom, optionally substituted $C_{3-8}$ cycloalkyl group, optionally substituted $C_{4-10}$ cycloalkenyl group, optionally substituted 3 to 10 membered heterocycloalkyl group, optionally substituted 4 to 10 membered heterocycloalkenyl group, optionally substituted $C_{6-10}$ aryl group, optionally substituted 5 to 10 membered heteroaryl group, hydroxy group, optionally substituted amino group, optionally substituted $C_{1-6}$ alkyloxy group, optionally substituted $C_{3-8}$ cycloalkyloxy group, optionally substituted 3 to 10 membered heterocycloalkyloxy group, optionally substituted $C_{6-10}$ aryloxy group, optionally substituted 5 to 10 membered heteroaryloxy group, substituted $C_{3-8}$ cycloalkyl($C_{1-6}$ alkyl)oxy group, substituted 3 to 10 membered heterocycloalkyl ($C_{1-6}$ alkyl)oxy group, substituted $C_{6-10}$ aryl($C_{1-6}$ alkyl)oxy group, substituted 5 to 10 membered heteroaryl($C_{1-6}$ alkyl) oxy group and optionally substituted $C_{1-6}$ alkyloxycarbonyl group]], an optionally substituted $C_{3-8}$ cycloalkyl group, an optionally substituted $C_{4-10}$ cycloalkenyl group, an optionally substituted $C_{6-10}$ aryl group, an optionally substituted 5 to 10 membered heteroaryl group, an optionally substituted 3 to 10 membered heterocycloalkyl group or an optionally substituted 4 to 10 membered heterocycloalkenyl group (provided that said optionally substituted 5 to 10 membered heteroaryl group, optionally substituted 3 to 10 membered heterocycloalkyl group and optionally substituted 4 to 10 membered heterocycloalkenyl group each binds at any carbon atom on each ring to the pyrimidine ring in the compound represented by the above-mentioned formula (1)).

Preferably A represents a $C_{1-6}$ alkyl group, a $C_{2-6}$ alkenyl group (said $C_{1-6}$ alkyl group and $C_{2-6}$ alkenyl group may be optionally substituted at an optional substitutable position with one or two or more substituent(s) selected from the group consisting of halogen atom, optionally substituted $C_{3-8}$ cycloalkyl group, optionally substituted $C_{4-10}$ cycloalkenyl group, optionally substituted 3 to 10 membered heterocycloalkyl group, optionally substituted $C_{6-10}$ aryl group, optionally substituted 5 to 10 membered heteroaryl group, hydroxy group, optionally substituted amino group and optionally substituted $C_{1-6}$ alkyloxy group), an optionally substituted $C_{3-8}$ cycloalkyl group, an optionally substituted $C_{6-10}$ aryl group, an optionally substituted 5 to 10 membered heteroaryl group or an optionally substituted 3 to 10 membered heterocycloalkyl group.

More preferably A represents a $C_{1-6}$ alkyl group, a $C_{2-6}$ alkenyl group (said $C_{1-6}$ alkyl group and $C_{2-6}$ alkenyl group may be optionally substituted at an optional substitutable position with one or two or more substituent(s) selected from the group consisting of optionally substituted $C_{6-10}$ aryl group, optionally substituted amino group and optionally substituted $C_{1-6}$ alkyloxy group), an optionally substituted $C_{3-8}$ cycloalkyl group, an optionally substituted $C_{6-10}$ aryl group and an optionally substituted 5 to 10 membered heteroaryl group.

Specific examples of A include methyl group, ethyl group, propyl group, phenyl group, benzyl group, phenylethyl group, phenylethenyl group, 2-, 3- or 4-methoxyphenyl group, 2-, 3- or 4-trifluoromethylphenyl group, pyridyl group, furyl group, thienyl group, pyrimidinyl group, pyrazinyl group, cyclohexyl group, 2-, 3- or 4-chlorophenylethyl group, 2-, 3- or 4-fluorophenylethyl group, 2-, 3- or 4-chlorophenylethenyl group, 2-, 3- or 4-fluorophenylethenyl group, 3,4-dichlorophenylethyl group, methoxymethyl group, ethoxymethyl group, 2-, 3- or 4-fluoropyridyl group, 2-, 3- or 4-methoxybenzyl group, 2-, 3- or 4-trifluoromethylphenylethyl group, 3,5-difluorophenylethyl group, 2,2-difluoroethoxyphenylethyl group and the others.

The compound represented by the below-mentioned formula (1-1a) or (1-1b):

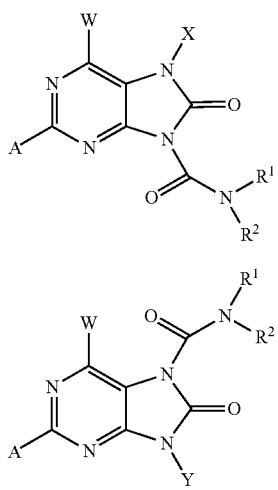

(1-1a)

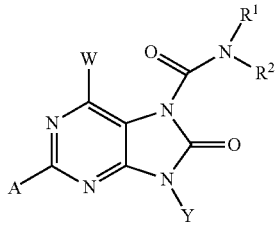

(1-1b)

wherein one of X and Y represent a group represented by the formula [Q]: —CONR$^1$R$^2$ and X, Y, A, W, R$^1$ and R$^2$ are the same as defined in the above-mentioned [1], or a pharmaceutically acceptable salt thereof is encompassed in the present invention.

Among X and Y, the other of X (which is sometimes referred to as X$^a$) or Y (which is sometimes referred to as Y$^a$) both being not [Q]: —CONR$^1$R$^2$ represents a hydrogen atom, an optionally substituted $C_{1-6}$ alkylcarbonyl group, a $C_{1-6}$ alkyl group (said $C_{1-6}$ alkyl group may be optionally substituted at an optional substitutable position with one or two or more substituent(s) selected from the group consisting of halogen atom, hydroxy group, optionally substituted $C_{3-8}$ cycloalkyl group, optionally substituted $C_{1-6}$ alkyloxy group, optionally substituted $C_{6-10}$ aryl group, optionally substituted 5 to 10 membered heteroaryl group and optionally substituted amino group) or an optionally substituted $C_{3-8}$ cycloalkyl group, preferably an optionally substituted $C_{1-6}$ alkylcarbonyl group, a $C_{1-6}$ alkyl group (said $C_{1-6}$ alkyl group may be optionally substituted at an optional substitutable position with one or two or more substituent(s) selected from the group consisting of halogen atom, hydroxy group, optionally substituted $C_{3-8}$ cycloalkyl group, optionally substituted $C_{1-6}$ alkyloxy group, optionally substituted $C_{6-10}$ aryl group, optionally substituted 5 to 10 membered heteroaryl group and optionally substituted amino group) or an optionally substituted $C_{3-8}$ cycloalkyl group, and more preferably a $C_{1-6}$ alkyl group (said $C_{1-6}$ alkyl group may be optionally substituted at an optional substitutable position with one or two or more substituent(s) selected from the group consisting of halogen atom, hydroxy group, optionally substituted $C_{3-8}$ cycloalkyl group and optionally substituted $C_{1-6}$ alkyloxy group).

Specific examples include hydrogen atom, acetyl group, methyl group, ethyl group, propyl group, cyclopropyl group and the others.

In the above-mentioned formula [Q],

R$^1$ represents a $C_{1-6}$ alkyl group [[said $C_{1-6}$ alkyl group may be optionally substituted at an optional substitutable position with one or two or more substituent(s) selected from the group consisting of halogen atom, optionally substituted $C_{3-8}$ cycloalkyl group, optionally substituted $C_{4-10}$ cycloalkenyl group, optionally substituted 3 to 10 membered heterocycloalkyl group, optionally substituted 4 to 10 membered heterocycloalkenyl group, optionally substituted $C_{6-10}$ aryl group, optionally substituted 5 to 10 membered heteroaryl group, hydroxy group, optionally substituted $C_{1-6}$ alkyloxy group, optionally substituted $C_{3-8}$ cycloalkyloxy group, optionally substituted $C_{6-10}$ aryloxy group, optionally substituted 5 to 10 membered heteroaryloxy group, substituted $C_{6-10}$ aryl($C_{1-6}$ alkyl)oxy group, substituted 5 to 10 membered heteroaryl($C_{1-6}$ alkyl)oxy group, optionally substituted amino group, optionally substituted $C_{1-6}$ alkyloxycarbonyl group and optionally substituted aminocarbony group (provided that in said $C_{1-6}$ alkyl group, the carbon atom adjacent to the nitrogen atom of the amide group that is included in the above-mentioned formula [Q] isn't substituted with hydroxy group, optionally substituted $C_{1-6}$ alkyloxy group, optionally substituted $C_{3-8}$ cycloalkyloxy group, optionally substituted $C_{6-10}$ aryloxy group, optionally substituted 5 to 10 membered heteroaryloxy group, substituted $C_{6-10}$ aryl($C_{1-6}$ alkyl)oxy group, substituted 5 to 10 membered heteroaryl($C_{1-6}$ alkyl)oxy group and optionally substituted amino group)]], an optionally substituted $C_{3-8}$ cycloalkyl group, an optionally substituted $C_{6-10}$ aryl group, an optionally substituted 5 to 10 membered heteroaryl group, an optionally substituted 3 to 10 membered heterocycloalkyl group or an optionally substituted 4 to 10 membered heterocycloalkenyl group (provided that said optionally substituted 5 to 10 membered heteroaryl group, optionally substituted 3 to 10 membered heterocycloalkyl group and optionally substituted 4 to 10 membered heterocycloalkenyl group each binds at any carbon atom on each ring to the nitrogen atom in the amide group that is included in the above-mentioned formula [Q]).

Preferably R$^1$ represents a $C_{1-6}$ alkyl group [[said $C_{1-6}$ alkyl group may be optionally substituted at an optional substitutable position with one or two or more substituent(s) selected from the group consisting of halogen atom, optionally substituted $C_{3-8}$ cycloalkyl group, optionally substituted $C_{4-10}$ cycloalkenyl group, optionally substituted $C_{6-10}$ aryl group, optionally substituted 5 to 10 membered heteroaryl group, hydroxy group, optionally substituted $C_{1-6}$ alkyloxy group, optionally substituted $C_{3-8}$ cycloalkyloxy group, optionally substituted $C_{6-10}$ aryloxy group, optionally substituted 5 to 10 membered heteroaryloxy group, substituted $C_{6-10}$ aryl($C_{1-6}$ alkyl)oxy group and substituted 5 to 10 membered heteroaryl ($C_{1-6}$ alkyl)oxy group]], an optionally substituted $C_{6-10}$ aryl group or an optionally substituted 5 to 10 membered heteroaryl group.

More preferably R$^1$ represents a $C_{1-6}$ alkyl group (said $C_{1-6}$ alkyl group may be optionally substituted at an optional substitutable position with one or two or more substituent(s) selected from the group consisting of halogen atom, optionally substituted $C_{3-8}$ cycloalkyl group, optionally substituted $C_{4-10}$ cycloalkenyl group, optionally substituted $C_{6-10}$ aryl group, optionally substituted $C_{1-6}$ alkyloxy group and optionally substituted $C_{6-10}$ aryloxy group).

Specific examples of R$^1$ include methyl group, ethyl group, propyl group, phenyl group, benzyl group, phenylethyl group, pyridyl group, furyl group, thienyl group, pyrimidinyl group, pyrazinyl group, cyclohexyl group, hydroxyethyl group, methoxyethyl group and the others.

R$^2$ represents a $C_{1-6}$ alkyl group [[said $C_{1-6}$ alkyl group may be optionally substituted at an optional substitutable position with one or two or more substituent(s) selected from the group consisting of halogen atom, hydroxy group and optionally substituted $C_{1-6}$ alkyloxy group (provided that the carbon atom adjacent to the amide group that is included in the above-mentioned formula [Q] isn't substituted with hydroxy group and optionally substituted $C_{1-6}$ alkyloxy group)]], or an optionally substituted $C_{3-8}$ cycloalkyl group, preferably a $C_{1-6}$ alkyl group optionally substituted with halogen atom, and more preferably a $C_{1-4}$ alkyl group.

Specific examples of $R^2$ include methyl group, ethyl group, propyl group, cyclopropyl group, methoxyethyl group and the others.

Also $R^1$ and $R^2$ may combine together with a nitrogen atom to which they bind to form a cyclic group represented by the below-mentioned formula (2):

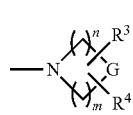

(2)

In the above-mentioned formula (2), G represents $-CH_2-$, $-CH=CH-$, $-NR^5-$, $-C(=CHR^6)-$, an oxygen atom or a single bond, preferably $-CH_2-$, $-NR^5-$ or a single bond, and more preferably $-CH_2-$ or $-NR^5-$ (provided that when G is $-CH_2-$ or $-CH=CH-$, then $R^3$ and $R^4$ may bind to an optional carbon atom of $-CH_2-$ or $-CH=CH-$ as G instead of a hydrogen atom).

When G represents $-NR^5-$ or an oxygen atom, then n and m are the same as or different from each other and represent 2 or 3, and when G represents $-CH_2-$, $-CH=CH-$ or $-C(=CHR^6)-$, then n and m are the same as or different from each other and represent an integer of 1 to 3 and preferably 1 or 2, and when G represents a single bond, then n and m are both 1.

$R^3$ and $R^4$ bind to the carbon atom on the cyclic group represented by the above-mentioned formula (2) and are the same as or different from each other and represent a hydrogen atom, a halogen atom, an optionally substituted $C_{3-8}$ cycloalkyl group, an optionally substituted $C_{4-10}$ cycloalkenyl group, a hydroxy group, an optionally substituted $C_{1-6}$ alkyloxy group, an optionally substituted $C_{3-8}$ cycloalkyloxy group, an optionally substituted $C_{1-6}$ alkyloxycarbonyl group, an optionally substituted aminocarbonyl group, an optionally substituted $C_{6-10}$ aryl group, an optionally substituted 5 to 10 membered heteroaryl group, an optionally substituted $C_{6-10}$ aryloxy group, an optionally substituted $C_{6-10}$ aryloxy group, an optionally substituted 5 to 10 membered heteroaryloxy group, a $C_{1-6}$ alkyl group [[said $C_{1-6}$ alkyl group may be optionally substituted at an optional substitutable position with one or two or more substituent(s) selected from the group consisting of halogen atom, optionally substituted $C_{3-8}$ cycloalkyl group, hydroxy group, optionally substituted $C_{1-6}$ alkyloxy group, optionally substituted $C_{3-8}$ cycloalkyloxy group, optionally substituted $C_{1-6}$ alkyloxycarbonyl group, optionally substituted aminocarbonyl group, optionally substituted $C_{6-10}$ aryl group, optionally substituted 5 to 10 membered heteroaryl group, optionally substituted $C_{6-10}$ aryloxy group, optionally substituted 5 to 10 membered heteroaryloxy group, substituted $C_{6-10}$ aryl ($C_{1-6}$ alkyl)oxy group, substituted 5 to 10 membered heteroaryl($C_{1-6}$ alkyl) oxy group, optionally substituted 3 to 10 membered heterocycloalkyl group (said optionally substituted 3 to 10 membered heterocycloalkyl group may be substituted at any carbon atom on the ring of the optionally substituted 3 to 10 membered heterocycloalkyl group or at a nitrogen atom on the ring of the optionally substituted 3 to 10 membered heterocycloalkyl group when said optionally substituted 3 to 10 membered heterocycloalkyl group contains a nitrogen atom) and optionally substituted 3 to 10 membered heterocycloalkyloxy group]], a $C_{2-6}$ alkenyl group, a $C_{2-6}$ alkynyl group (said $C_{2-6}$ alkenyl group and $C_{2-6}$ alkynyl group may be optionally substituted at an optional substitutable position with one or two or more substituent(s) selected from the group consisting of optionally substituted $C_{6-10}$ aryl group and optionally substituted 5 to 10 membered heteroaryl group), an optionally substituted 3 to 10 membered heterocycloalkyl group or an optionally substituted 4 to 10 membered heterocycloalkenyl group (said optionally substituted 3 to 10 membered heterocycloalkyl group and optionally substituted 4 to 10 membered heterocycloalkenyl group may be substituted at any carbon atom on each ring, or at a nitrogen atom on the ring of the optionally substituted 3 to 10 membered heterocycloalkyl group and the optionally substituted 4 to 10 membered heterocycloalkenyl group when said optionally substituted 3 to 10 membered heterocycloalkyl group and optionally substituted 4 to 10 membered heterocycloalkenyl group contain a nitrogen atom); or alternatively $R^3$ and $R^4$ combine together to form an oxo group (in this case, G represents preferably $-CH_2-$), or $R^3$ and $R^4$ bind to the same carbon atom on the cyclic group represented by the above-mentioned formula (2), and combine together with the carbon atom to form a spiro ring selected from the group consisting of optionally substituted $C_{3-8}$ saturated aliphatic carbocycle, optionally substituted $C_{4-10}$ unsaturated aliphatic carbocycle, optionally substituted 3 to 10 membered saturated aliphatic heterocycle and optionally substituted 4 to 10 membered unsaturated aliphatic heterocycle, or alternatively $R^3$ and $R^4$ each binds to the neighboring carbon atom on the cyclic group represented by the above-mentioned formula (2) and combine together with the carbon atoms to form a fused ring selected from the group consisting of optionally substituted $C_{3-8}$ saturated aliphatic carbocycle, optionally substituted $C_{4-10}$ unsaturated aliphatic carbocycle, optionally substituted 3 to 10 membered saturated aliphatic heterocycle, optionally substituted 4 to 10 membered unsaturated aliphatic heterocycle, optionally substituted $C_{6-10}$ aromatic ring and optionally substituted 5 to 10 membered aromatic heterocycle, or alternatively $R^3$ and $R^4$ each binds to the different non-neighboring carbon atom on the cyclic group represented by the above-mentioned formula (2), and combine together with the carbon atoms to represent a methylene group, an ethylene group, a propylene group, a butylene group and then may form a bridged ring.

Preferably $R^3$ and $R^4$ are the same as or different from each other and represent a hydrogen atom, a halogen atom, an optionally substituted $C_{6-10}$ aryl group, an optionally substituted 5 to 10 membered heteroaryl group, an optionally substituted $C_{6-10}$ aryloxy group, a $C_{1-6}$ alkyl group [[said $C_{1-6}$ alkyl group may be optionally substituted at an optional substitutable position with one or two or more substituent(s) selected from the group consisting of halogen atom, optionally substituted $C_{3-8}$ cycloalkyl group, optionally substituted $C_{1-6}$ alkyloxy group, optionally substituted $C_{3-8}$ cycloalkyloxy group, optionally substituted $C_{6-10}$ aryl group, optionally substituted 5 to 10 membered heteroaryl group, optionally substituted $C_{6-10}$ aryloxy group, optionally substituted 5 to 10 membered heteroaryloxy group, substituted $C_{6-10}$ aryl ($C_{1-6}$ alkyl)oxy group and substituted 5 to 10 membered heteroaryl ($C_{1-6}$ alkyl) oxy group]].

More preferably $R^3$ and $R^4$ are the same as or different from each other and represent a hydrogen atom, a halogen atom, an optionally substituted $C_{6-10}$ aryl group, a $C_{1-6}$ alkyl group (said $C_{1-6}$ alkyl group may be optionally substituted at an optional substitutable position with one or two or more substituent(s) selected from the group consisting of optionally substituted $C_{6-10}$ aryl group, optionally substituted 5 to 10 membered heteroaryl group, optionally substituted $C_{6-10}$ aryloxy group and optionally substituted 5 to 10 membered heteroaryloxy group).

Specific examples of $R^3$ and $R^4$ include hydrogen atom, fluorine atom, chlorine atom, benzyl group, methyl group, ethyl group, propyl group, pyridyl group, furyl group, thienyl group, pyrimidinyl group, pyrazinyl group, phenyl group, methoxymethyl group, phenylethylgroup, fluorophenylethyl group, chlorophenylethyl group, methoxyphenylethyl group, 2-, 3- or 4-fluorophenoxymethyl group, 2-, 3- or 4-fluorophenoxy group, 2-, 3- or 4-methoxyphenoxy group, 2-, 3- or 4-fluorophenyl group and the others.

$R^5$ represents a $C_{1-6}$ alkyl group (said $C_{1-6}$ alkyl group may be optionally substituted at an optional substitutable position with one or two or more substituent(s) selected from the group consisting of halogen atom, optionally substituted $C_{3-8}$ cycloalkyl group, optionally substituted $C_{6-10}$ aryl group and optionally substituted 5 to 10 membered heteroaryl group), an optionally substituted $C_{3-8}$ cycloalkyl group, an optionally substituted $C_{6-10}$ aryl group or an optionally substituted 5 to 10 membered heteroaryl group, preferably a $C_{1-6}$ alkyl group (said $C_{1-6}$ alkyl group may be optionally substituted at an optional substitutable position with one or two or more optionally substituted $C_{6-10}$ aryl group) or an optionally substituted $C_{6-10}$ aryl group, and more preferably an optionally substituted $C_{6-10}$ aryl group.

Specific examples of $R^5$ include benzyl group, methyl group, ethyl group, propyl group, phenyl group, fluorophenyl group, phenylethyl group and the others.

$R^6$ represents an optionally substituted $C_{6-10}$ aryl group or an optionally substituted 5 to 10 membered heteroaryl group, and preferably an optionally substituted $C_{6-10}$ aryl group.

Specific examples of $R^6$ include phenyl group, 2-, 3- or 4-fluorophenyl group and the others.

Specific examples of the cyclic group represented by the above-mentioned formula (2) include azetidinyl group, pyrrolidinyl group, piperidyl group, piperazinyl group, morpholinyl group, difluoroazetidinyl group, 2- or 3-methylpyrrolidinyl group, 3-phenylpyrrolidinyl group, 4-methylpiperidyl group, 4-phenylpiperidyl group, 4-phenylazetidinyl group, 4-phenoxyazetidinyl group, 3-phenoxypyrrolidinyl group and the others.

In these cases, the compound represented by the below-mentioned formula (1-2a) or (1-2b):

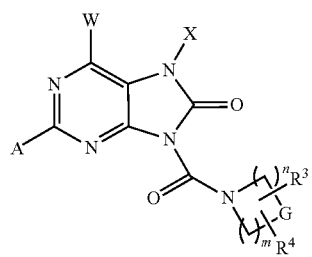

(1-2a)

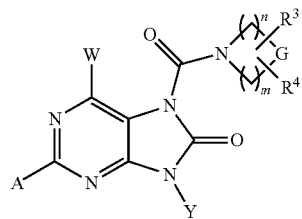

(1-2b)

wherein X, Y, A, W, n, m, G, $R^3$ and $R^4$ are the same as defined in the above-mentioned [1], or a pharmaceutically acceptable salt thereof is encompassed in the present invention.

Specific examples of the above-mentioned formula [Q] include dimethylaminocarbonyl group, diethylaminocarbonyl group, dipropylaminocarbonyl group, ethylmethylaminocarbonyl group, benzylmethylaminocarbonyl group, methyl(2-phenyl)ethylaminocarbonyl group, azetidinocarbonyl group, pyrrolidinocarbonyl group, piperidinocarbonyl group and the others.

Among the present compound represented by the general formula (1), the preferred compound includes the below-mentioned compound or a pharmaceutically acceptable salt thereof.

The compound wherein

A represents a $C_{1-6}$ alkyl group, a $C_{2-6}$ alkenyl group (said $C_{1-6}$ alkyl group and $C_{2-6}$ alkenyl group may be optionally substituted at an optional substitutable position with one or two or more substituent(s) selected from the group consisting of halogen atom, optionally substituted $C_{3-8}$ cycloalkyl group, optionally substituted $C_{4-10}$ cycloalkenyl group, optionally substituted 3 to 10 membered heterocycloalkyl group, optionally substituted $C_{6-10}$ aryl group, optionally substituted 5 to 10 membered heteroaryl group, hydroxy group, optionally substituted amino group and optionally substituted $C_{1-6}$ alkyloxy group), an optionally substituted $C_{3-8}$ cycloalkyl group, an optionally substituted $C_{6-10}$ aryl group, an optionally substituted 5 to 10 membered heteroaryl group or an optionally substituted 3 to 10 membered heterocycloalkyl group, one of X and Y represents a group represented by the formula [Q]: —CONR$^1$R$^2$ and the other represents an optionally substituted $C_{1-6}$ alkylcarbonyl group, a $C_{1-6}$ alkyl group (said $C_{1-6}$ alkyl group may be optionally substituted at an optional substitutable position with one or two or more substituent(s) selected from the group consisting of halogen atom, hydroxy group, optionally substituted $C_{3-8}$ cycloalkyl group, optionally substituted $C_{1-6}$ alkyloxy group, optionally substituted $C_{6-10}$ aryl group, optionally substituted 5 to 10 membered heteroaryl group and optionally substituted amino group) or an optionally substituted $C_{3-8}$ cycloalkyl group, $R^1$ represents a $C_{1-6}$ alkyl group [[said $C_{1-6}$ alkyl group may be optionally substituted at an optional substitutable position with one or two or more substituent(s) selected from the group consisting of halogen atom, optionally substituted $C_{3-8}$ cycloalkyl group, optionally substituted $C_{4-10}$ cycloalkenyl group, optionally substituted $C_{6-10}$ aryl group, optionally substituted 5 to 10 membered heteroaryl group, hydroxy group, optionally substituted $C_{1-6}$ alkyloxy group, optionally substituted $C_{3-8}$ cycloalkyloxy group, optionally substituted $C_{6-10}$ aryloxy group, optionally substituted 5 to 10 membered heteroaryloxy group, substituted $C_{6-10}$ aryl ($C_{1-6}$ alkyl)oxy group and substituted 5 to 10 membered heteroaryl($C_{1-6}$ alkyl) oxy group]], an optionally substituted $C_{6-10}$ aryl group or an optionally substituted 5 to 10 membered heteroaryl group, or alternatively $R^1$ and $R^2$ combine together with a nitrogen atom to which they bind to form the cyclic group represented by the above-mentioned formula (2), and W, $R^2$, G, $R^3$, $R^4$, n, m, $R^5$ and $R^6$ are the same as defined in the above-mentioned [1].

Preferably the compound wherein

A represents a $C_{1-6}$ alkyl group, a $C_{2-6}$ alkenyl group (said $C_{1-6}$ alkyl group and $C_{2-6}$ alkenyl group may be optionally substituted at an optional substitutable position with one or two or more substituent(s) selected from the group consisting of optionally substituted $C_{6-10}$ aryl group, optionally substituted amino group and optionally substituted $C_{1-6}$ alkyloxy group), an optionally substituted $C_{3-8}$ cycloalkyl group, an optionally substituted $C_{6-10}$ aryl group or an optionally substituted 5 to 10 membered heteroaryl group, one of X and Y represents the group represented by the formula [Q]: —$CONR^1R^2$ and the other represents a $C_{1-6}$ alkyl group (said $C_{1-6}$ alkyl group may be optionally substituted at an optional substitutable position with one or two or more substituent(s) selected from the group consisting of halogen atom, hydroxy group, optionally substituted $C_{3-8}$ cycloalkyl group and optionally substituted $C_{1-6}$ alkyloxy group), $R^1$ represents a $C_{1-6}$ alkyl group (said $C_{1-6}$ alkyl group may be optionally substituted at an optional substitutable position with one or two or more substituent(s) selected from the group consisting of halogen atom, optionally substituted $C_{3-8}$ cycloalkyl group, optionally substituted $C_{4-10}$ cycloalkenyl group, optionally substituted $C_{6-10}$ aryl group, optionally substituted $C_{1-6}$ alkyloxy group and optionally substituted $C_{6-10}$ aryloxy group), or alternatively $R^1$ and $R^2$ combine together with a nitrogen atom to which they bind to form the cyclic group represented by the above-mentioned formula (2), and W, $R^2$, G, $R^3$, n, m, $R^5$ and $R^6$ are the same as defined in the above-mentioned [1];

More preferably the compound wherein

A represents a $C_{1-6}$ alkyl group, a $C_{2-6}$ alkenyl group (said $C_{1-6}$ alkyl group and $C_{2-6}$ alkenyl group may be optionally substituted at an optional substitutable position with one or two or more substituent(s) selected from the group consisting of optionally substituted $C_{6-10}$ aryl group, optionally substituted amino group and optionally substituted $C_{1-6}$ alkyloxy group), an optionally substituted $C_{3-8}$ cycloalkyl group, an optionally substituted $C_{6-10}$ aryl group or an optionally substituted 5 to 10 membered heteroaryl group, one of X and Y represents the group represented by the formula [Q]: —$CONR^1R^2$ and the other represents a $C_{1-6}$ alkyl group (said $C_{1-6}$ alkyl group may be optionally substituted at an optional substitutable position with one or two or more substituent(s) selected from the group consisting of halogen atom, hydroxy group, optionally substituted $C_{3-8}$ cycloalkyl group and optionally substituted $C_{1-6}$ alkyloxy group), $R^1$ represents a $C_{1-6}$ alkyl group (said $C_{1-6}$ alkyl group may be optionally substituted at an optional substitutable position with one or two or more substituent(s) selected from the group consisting of halogen atom, optionally substituted $C_{3-8}$ cycloalkyl group, optionally substituted $C_{4-10}$ cycloalkenyl group, optionally substituted $C_{6-10}$ aryl group, optionally substituted $C_{1-6}$ alkyloxy group and optionally substituted $C_{6-10}$ aryloxy group), or alternatively $R^1$ and $R^2$ combine together with a nitrogen atom to which they bind to form the cyclic group represented by the above-mentioned formula (2), W represents a hydrogen atom, and $R^2$, G, $R^3$, $R^4$, n, m, $R^5$ and $R^6$ are the same as defined in the above-mentioned [1].

Among the cyclic group represented by the above-mentioned formula (2), the preferred cyclic group includes the below-mentioned cyclic group.

The cyclic group represented by the above-mentioned formula (2) wherein $R^3$ and $R^4$ are the same as or different from each other and represent a hydrogen atom, a halogen atom, an optionally substituted $C_{6-10}$ aryl group, an optionally substituted 5 to 10 membered heteroaryl group, an optionally substituted $C_{6-10}$ aryloxy group, a $C_{1-6}$ alkyl group [[said $C_{1-6}$ alkyl group may be optionally substituted at an optional substitutable position with one or two or more substituent(s) selected from the group consisting of halogen atom, optionally substituted $C_{3-8}$ cycloalkyl group, optionally substituted $C_{1-6}$ alkyloxy group, optionally substituted $C_{3-8}$ cycloalkyloxy group, optionally substituted $C_{6-10}$ aryl group, optionally substituted 5 to 10 membered heteroaryl group, optionally substituted $C_{6-10}$ aryloxy group, optionally substituted 5 to 10 membered heteroaryloxy group, substituted $C_{6-10}$ aryl ($C_{1-6}$ alkyl)oxy group and substituted 5 to 10 membered heteroaryl ($C_{1-6}$ alkyl)oxy group]], G represents —$CH_2$—, n and m are the same as or different from each other and represent 1 or 2, or G represents —$NR^5$— and $R^5$ represents a $C_{1-6}$ alkyl group (said $C_{1-6}$ alkyl group may be optionally substituted at an optional substitutable position with one or two or more substituent(s) selected from the group consisting of halogen atom, optionally substituted $C_{6-10}$ aryl group and optionally substituted 5 to 10 membered heteroaryl group) or an optionally substituted $C_{6-10}$ aryl group, and n and m are the same as or different from each other and represent 2 or 3.

Preferably the cyclic group represented by the above-mentioned formula (2) wherein $R^3$ and $R^4$ are the same as or different from each other and represent a hydrogen atom, a halogen atom, an optionally substituted $C_{6-10}$ aryl group, an optionally substituted $C_{6-10}$ aryloxy group, a $C_{1-6}$ alkyl group (said $C_{1-6}$ alkyl group may be optionally substituted at an optional substitutable position with one or two or more optionally substituted $C_{6-10}$ aryl group, optionally substituted 5 to 10 membered heteroaryl group, optionally substituted $C_{6-10}$ aryloxy group and optionally substituted 5 to 10 membered heteroaryloxy group), G represents —$CH_2$—, n and m are the same as or different from each other and represent 1 or 2, or G represents —$NR^5$—, $R^5$ represents a $C_{1-6}$ alkyl group (said $C_{1-6}$ alkyl group may be optionally substituted at an optional substitutable position with one or two or more substituent(s) selected from the group consisting of halogen atom, optionally substituted $C_{6-10}$ aryl group and optionally substituted 5 to 10 membered heteroaryl group) or an optionally substituted $C_{6-10}$ aryl group, n and m are the same as or different from each other and represent 2 or 3.

Specific examples of the present compound include the compounds described in the below-mentioned Examples or a pharmaceutically acceptable salt thereof and particularly a preferred compounds include the compounds described in the below-mentioned Compounds Groups (A) to (C) and (A') to (C'). More preferred compounds include the compounds described in the below-mentioned Compound Group (B') or Compound Group (C') and furthermore preferred compounds include the compounds described in the below-mentioned Compound Group (C').

Compound Group (A)

2-[(E)-2-(4-Chlorophenyl)ethenyl]-9-methyl-7-(pyrrolidin-1-ylcarbonyl)-7,9-dihydro-8H-purine-8-one (Example No. 8);

9-Methyl-2-[(E)-2-(4-methylphenyl)ethenyl]-7-(pyrrolidin-1-ylcarbonyl)-7,9-dihydro-8H-purine-8-one (Example No. 9);

9-Methyl-2-(2-phenylethyl)-7-(pyrrolidin-1-ylcarbonyl)-7,9-dihydro-8H-purine-8-one (Example No. 11);

2-[2-(4-Methoxyphenyl)ethyl]-9-methyl-7-(pyrrolidin-1-ylcarbonyl)-7,9-dihydro-8H-purine-8-one (Example No. 12);

2-(4-Chlorobenzyl)-9-methyl-7-(pyrrolidin-1-ylcarbonyl)-7,9-dihydro-8H-purine-8-one (Example No. 20);

9-Methyl-2-phenyl-7-[(4-phenylpiperidin-1-yl)carbonyl]-7,9-dihydro-8H-purine-8-one (Example No. 33);

Ethyl N-methyl-N-[(9-methyl-8-oxo-2-phenyl-8,9-dihydro-7H-purin-7-yl)carbonyl]glycinate (Example No. 37);

N-(2-Methoxyethyl)-N,9-dimethyl-8-oxo-2-phenyl-8,9-dihydro-7H-purine-7-carboxamide (Example No. 39);

9-Methyl-2-phenyl-7-({4-[5-(trifluoromethyl)-pyridin-2-yl]piperazin-1-yl}carbonyl)-7,9-dihydro-8H-purine-8-one (Example No. 50);

2-(3-Methoxyphenyl)-9-methyl-7-[(4-phenylpiperidin-1-yl)carbonyl]-7,9-dihydro-8H-purine-8-one (Example No. 61);

7-[(4-Benzylpiperidin-1-yl)carbonyl]-2-(3-methoxyphenyl)-9-methyl-7,9-dihydro-8H-purine-8-one (Example No. 66);

N-(3-Methoxybenzyl)-2-(3-methoxyphenyl)-N,9-dimethyl-8-oxo-8,9-dihydro-7H-purine-7-carboxamide (Example No. 73);

N-(3-Chlorobenzyl)-2-(3-methoxyphenyl)-N,9-dimethyl-8-oxo-8,9-dihydro-7H-purine-7-carboxamide (Example No. 79);

N-(4-Methoxybenzyl)-2-(3-methoxyphenyl)-N,9-dimethyl-8-oxo-8,9-dihydro-7H-purine-7-carboxamide (Example No. 80);

2-(3-Methoxyphenyl)-N,9-dimethyl-8-oxo-N-[3-(trifluoromethyl)benzyl]-8,9-dihydro-7H-purine-7-carboxamide (Example No. 82);

7-{[4-(3-Fluorobenzyl)piperazin-1-yl]carbonyl}-2-(3-methoxyphenyl)-9-methyl-7,9-dihydro-8H-purine-8-one (Example No. 85);

N-Benzyl-2-(3-methoxyphenyl)-N,9-dimethyl-8-oxo-8,9-dihydro-7H-purine-7-carboxamide (Example No. 88);

2-(3-Methoxyphenyl)-9-methyl-7-({4-[4-(trifluoromethyl)benzyl]piperazin-1-yl}carbonyl)-7,9-dihydro-8H-purine-8-one (Example No. 89);

7-[(4-Cyclohexylpiperazin-1-yl)carbonyl]-2-(3-methoxyphenyl)-9-methyl-7,9-dihydro-8H-purine-8-one (Example No. 97);

7-[(4-Cyclopentylpiperazin-1-yl)carbonyl]-2-(3-methoxyphenyl)-9-methyl-7,9-dihydro-8H-purine-8-one (Example No. 98);

2-(3-Methoxyphenyl)-N,9-dimethyl-8-oxo-N-propyl-8,9-dihydro-7H-purine-7-carboxamide (Example No. 107);

2-(3-Methoxyphenyl)-N,9-dimethyl-N-(2-methylpropyl)-8-oxo-8,9-dihydro-7H-purine-7-carboxamide (Example No. 108);

2-(3-Methoxyphenyl)-N,9-dimethyl-8-oxo-N-[2-(pyridin-2-yl)ethyl]-8,9-dihydro-7H-purine-7-carboxamide (Example No. 114);

2-(3-Methoxyphenyl)-N,9-dimethyl-8-oxo-N-[2-(pyridin-4-yl)ethyl]-8,9-dihydro-7H-purine-7-carboxamide (Example No. 115);

7-{[4-(2-Methoxyethyl)piperidin-1-yl]carbonyl}-2-(3-methoxyphenyl)-9-methyl-7,9-dihydro-8H-purine-8-one (Example No. 119);

7-{[4-(3-Methoxyphenyl)piperazin-1-yl]carbonyl}-9-methyl-2-phenyl-7,9-dihydro-8H-purine-8-one (Example No. 121);

7-{[4-(2-Methoxyphenyl)piperazin-1-yl]carbonyl}-9-methyl-2-phenyl-7,9-dihydro-8H-purine-8-one (Example No. 122);

7-{[4-(2-Fluorophenyl)piperazin-1-yl]carbonyl}-9-methyl-2-phenyl-7,9-dihydro-8H-purine-8-one (Example No. 125);

7-{[4-(2-Chlorophenyl)piperazin-1-yl]carbonyl}-9-methyl-2-phenyl-7,9-dihydro-8H-purine-8-one (Example No. 127);

9-Methyl-7-{[4-(2-methylphenyl)piperazin-1-yl]carbonyl}-2-phenyl-7,9-dihydro-8H-purine-8-one (Example No. 130);

N-[2-(4-Chlorophenyl)ethyl]-N,2,9-trimethyl-8-oxo-8,9-dihydro-7H-purine-7-carboxamide (Example No. 157);

2-(2,2-Dimethylpropyl)-N-ethyl-N,9-dimethyl-8-oxo-8,9-dihydro-7H-purine-7-carboxamide (Example No. 160);

2-Butyl-N-ethyl-N,9-dimethyl-8-oxo-8,9-dihydro-7H-purine-7-carboxamide (Example No. 161);

2-Cyclohexyl-N-ethyl-N,9-dimethyl-8-oxo-8,9-dihydro-7H-purine-7-carboxamide (Example No. 162);

2-(3-Fluorophenyl)-9-methyl-7-(pyrrolidin-1-ylcarbonyl)-7,9-dihydro-8H-purine-8-one (Example No. 167);

9-Methyl-2-(3-methylphenyl)-7-(pyrrolidin-1-ylcarbonyl)-7,9-dihydro-8H-purine-8-one (Example No. 170);

7-Methyl-2-phenyl-9-(pyrrolidin-1-ylcarbonyl)-7,9-dihydro-8H-purine-8-one (Example No. 224);

2-(4-Fluorophenyl)-7-methyl-9-(pyrrolidin-1-ylcarbonyl)-7,9-dihydro-8H-purine-8-one (Example No. 227);

7-Methyl-2-(3-methylphenyl)-9-(pyrrolidin-1-ylcarbonyl)-7,9-dihydro-8H-purine-8-one (Example No. 228);

7-Methyl-2-(4-methylphenyl)-9-(pyrrolidin-1-ylcarbonyl)-7,9-dihydro-8H-purine-8-one (Example No. 229);

2-(3-Methoxyphenyl)-7-methyl-9-(pyrrolidin-1-ylcarbonyl)-7,9-dihydro-8H-purine-8-one (Example No. 230);

2-(4-Methoxyphenyl)-7-methyl-9-(pyrrolidin-1-ylcarbonyl)-7,9-dihydro-8H-purine-8-one (Example No. 231);

2-(4-Ethoxyphenyl)-7-methyl-9-(pyrrolidin-1-ylcarbonyl)-7,9-dihydro-8H-purine-8-one (Example No. 233);

7-Methyl-9-(pyrrolidin-1-ylcarbonyl)-2-[4-(trifluoromethyl)phenyl]-7,9-dihydro-8H-purine-8-one (Example No. 235);

7-Methyl-9-(pyrrolidin-1-ylcarbonyl)-2-[4-(trifluoromethoxy)phenyl]-7,9-dihydro-8H-purine-8-one (Example No. 237);

2-(3-Acetylphenyl)-7-methyl-9-(pyrrolidin-1-ylcarbonyl)-7,9-dihydro-8H-purine-8-one (Example No. 238);

2-(Biphenyl-4-yl)-7-methyl-9-(pyrrolidin-1-ylcarbonyl)-7,9-dihydro-8H-purine-8-one (Example No. 239);

7-Methyl-2-[(E)-2-phenylethenyl]-9-(pyrrolidin-1-ylcarbonyl)-7,9-dihydro-8H-purine-8-one (Example No. 241);

2-[(E)-2-(4-Fluorophenyl)ethenyl]-7-methyl-9-(pyrrolidin-1-ylcarbonyl)-7,9-dihydro-8H-purine-8-one (Example No. 245);

2-[(E)-2-(3-Methoxyphenyl)ethenyl]-7-methyl-9-(pyrrolidin-1-ylcarbonyl)-7,9-dihydro-8H-purine-8-one (Example No. 247);

2-(6-Methoxypyridin-3-yl)-7-methyl-9-(pyrrolidin-1-ylcarbonyl)-7,9-dihydro-8H-purine-8-one (Example No. 250);

2-(2-Fluorobenzyl)-9-methyl-7-(pyrrolidin-1-ylcarbonyl)-7,9-dihydro-8H-purine-8-one (Example No. 254);

9-Methyl-2-(2-methylbenzyl)-7-(pyrrolidin-1-ylcarbonyl)-7,9-dihydro-8H-purine-8-one (Example No. 257);

9-Methyl-2-(3-methylbenzyl)-7-(pyrrolidin-1-ylcarbonyl)-7,9-dihydro-8H-purine-8-one (Example No. 258);

2-(2,4-Difluorobenzyl)-9-methyl-7-(pyrrolidin-1-ylcarbonyl)-7,9-dihydro-8H-purine-8-one (Example No. 266);
2-(2,6-Difluorobenzyl)-9-methyl-7-(pyrrolidin-1-ylcarbonyl)-7,9-dihydro-8H-purine-8-one (Example No. 268);
2-(3,5-Difluorobenzyl)-9-methyl-7-(pyrrolidin-1-ylcarbonyl)-7,9-dihydro-8H-purine-8-one (Example No. 270);
2-Benzyl-N-ethyl-N,9-dimethyl-8-oxo-8,9-dihydro-7H-purine-7-carboxamide (Example No. 278);
N-Ethyl-2-(4-fluorobenzyl)-N,9-dimethyl-8-oxo-8,9-dihydro-7H-purine-7-carboxamide (Example No. 279);
N-Ethyl-2-(4-methoxybenzyl)-N,9-dimethyl-8-oxo-8,9-dihydro-7H-purine-7-carboxamide (Example No. 280);
N-Ethyl-N,9-dimethyl-2-(4-methylbenzyl)-8-oxo-8,9-dihydro-7H-purine-7-carboxamide (Example No. 281);
N-Ethyl-N,9-dimethyl-2-(3-methylbenzyl)-8-oxo-8,9-dihydro-7H-purine-7-carboxamide (Example No. 282);
2-(3-Fluorobenzyl)-7-methyl-9-(pyrrolidin-1-ylcarbonyl)-7,9-dihydro-8H-purine-8-one (Example No. 286);
2-(3-Methoxybenzyl)-7-methyl-9-(pyrrolidin-1-ylcarbonyl)-7,9-dihydro-8H-purine-8-one (Example No. 288);
7-Methyl-2-(2-phenylethyl)-9-(pyrrolidin-1-ylcarbonyl)-7,9-dihydro-8H-purine-8-one (Example No. 290);
7-Methyl-2-(3-methylbenzyl)-9-(pyrrolidin-1-ylcarbonyl)-7,9-dihydro-8H-purine-8-one (Example No. 294);
2-(4-Fluorobenzyl)-7-methyl-9-(pyrrolidin-1-ylcarbonyl)-7,9-dihydro-8H-purine-8-one (Example No. 295);
2-(2,4-Difluorobenzyl)-7-methyl-9-(pyrrolidin-1-ylcarbonyl)-7,9-dihydro-8H-purine-8-one (Example No. 296);
2-(2,5-Difluorobenzyl)-7-methyl-9-(pyrrolidin-1-ylcarbonyl)-7,9-dihydro-8H-purine-8-one (Example No. 297);
2-(2,6-Difluorobenzyl)-7-methyl-9-(pyrrolidin-1-ylcarbonyl)-7,9-dihydro-8H-purine-8-one (Example No. 298);
2-(3,5-Difluorobenzyl)-7-methyl-9-(pyrrolidin-1-ylcarbonyl)-7,9-dihydro-8H-purine-8-one (Example No. 299);
2-(2-Fluorobenzyl)-7-methyl-9-(pyrrolidin-1-ylcarbonyl)-7,9-dihydro-8H-purine-8-one (Example No. 300);
9-Butyl-2-phenyl-7-(pyrrolidin-1-ylcarbonyl)-7,9-dihydro-8H-purine-8-one (Example No. 306);
2-[2-(4-Fluorophenyl)ethyl]-7-methyl-9-(pyrrolidin-1-ylcarbonyl)-7,9-dihydro-8H-purine-8-one (Example No. 314);
2-Cyclohexyl-9-methyl-7-(pyrrolidin-1-ylcarbonyl)-7,9-dihydro-8H-purine-8-one (Example No. 316); and
2-(3-Aminophenyl)-9-methyl-7-(pyrrolidin-1-ylcarbonyl)-7,9-dihydro-8H-purine-8-one (Example No. 317).
Compound Group (B)
9-Methyl-2-[(E)-2-phenylethenyl]-7-(pyrrolidin-1-ylcarbonyl)-7,9-dihydro-8H-purine-8-one (Example No. 1);
N-Ethyl-N,9-dimethyl-8-oxo-2-phenyl-8,9-dihydro-7H-purine-7-carboxamide (Example No. 2);
2-[(E)-2-(4-Methoxyphenyl)ethenyl]-9-methyl-7-(pyrrolidin-1-ylcarbonyl)-7,9-dihydro-8H-purine-8-one (Example No. 4);
2-[(E)-2-(4-Fluorophenyl)ethenyl]-9-methyl-7-(pyrrolidin-1-ylcarbonyl)-7,9-dihydro-8H-purine-8-one (Example No. 5);
9-Methyl-2-phenyl-7-(pyrrolidin-1-ylcarbonyl)-7,9-dihydro-8H-purine-8-one (Example No. 16);
2-(3-Chlorobenzyl)-9-methyl-7-(pyrrolidin-1-ylcarbonyl)-7,9-dihydro-8H-purine-8-one (Example No. 19);
7-(Azetidin-1-ylcarbonyl)-9-methyl-2-phenyl-7,9-dihydro-8H-purine-8-one (Example No. 23);
9-Methyl-2-phenyl-7-(piperidin-1-ylcarbonyl)-7,9-dihydro-8H-purine-8-one (Example No. 24);
N-Benzyl-N,9-dimethyl-8-oxo-2-phenyl-8,9-dihydro-7H-purine-7-carboxamide (Example No. 34);
N,9-Dimethyl-8-oxo-2-phenyl-N-(3-phenylpropyl)-8,9-dihydro-7H-purine-7-carboxamide (Example No. 35);
2-(3-Methoxyphenyl)-N,N,9-trimethyl-8-oxo-8,9-dihydro-7H-purine-7-carboxamide (Example No. 48);
2-(3-Methoxyphenyl)-9-methyl-7-(piperidin-1-ylcarbonyl)-7,9-dihydro-8H-purine-8-one (Example No. 49);
9-Methyl-2-phenyl-7-{[4-(pyrimidin-2-yl)piperazin-1-yl]carbonyl}-7,9-dihydro-8H-purine-8-one (Example No. 51);
9-Methyl-2-phenyl-7-{[4-(pyridin-2-yl)piperazin-1-yl]carbonyl}-7,9-dihydro-8H-purine-8-one (Example No. 52);
9-Methyl-7-{[4-(6-methylpyridin-2-yl)piperazin-1-yl]carbonyl}-2-phenyl-7,9-dihydro-8H-purine-8-one (Example No. 53);
7-{[4-(6-Methoxypyridin-2-yl)piperazine-1-yl]carbonyl}-9-methyl-2-phenyl-7,9-dihydro-8H-purine-8-one (Example No. 54);
9-Methyl-2-phenyl-7-{[4-(1,3-thiazol-2-yl)piperazin-1-yl]carbonyl}-7,9-dihydro-8H-purine-8-one (Example No. 55);
9-Methyl-7-{[4-(5-methylpyridin-2-yl)piperazin-1-yl]carbonyl}-2-phenyl-7,9-dihydro-8H-purine-8-one (Example No. 56);
7-(Azetidin-1-ylcarbonyl)-2-(3-methoxyphenyl)-9-methyl-7,9-dihydro-8H-purine-8-one (Example No. 57);
N-(2-Methoxyethyl)-2-(3-methoxyphenyl)-N,9-dimethyl-8-oxo-8,9-dihydro-7H-purine-7-carboxamide (Example No. 59);
7-{[(3R)-3-Fluoropyrrolidin-1-yl]carbonyl}-2-(3-methoxyphenyl)-9-methyl-7,9-dihydro-8H-purine-8-one (Example No. 62);
7-{[(3S)-3-Fluoropyrrolidin-1-yl]carbonyl}-2-(3-methoxyphenyl)-9-methyl-7,9-dihydro-8H-purine-8-one (Example No. 63);
2-(3-Methoxyphenyl)-9-methyl-7-{[4-(2-phenylethyl-) piperazin-1-yl]carbonyl}-7,9-dihydro-8H-purine-8-one (Example No. 67);
N-(3-Fluorobenzyl)-2-(3-methoxyphenyl)-N,9-dimethyl-8-oxo-8,9-dihydro-7H-purine-7-carboxamide (Example No. 72);
7-{[4-(4-Fluorobenzyl)piperazin-1-yl]carbonyl}-2-(3-methoxyphenyl)-9-methyl-7,9-dihydro-8H-purine-8-one (Example No. 84);
7-{[4-(4-Chlorobenzyl)piperazin-1-yl]carbonyl}-2-(3-methoxyphenyl)-9-methyl-7,9-dihydro-8H-purine-8-one (Example No. 86);
7-{[4-(3-Chlorobenzyl)piperazin-1-yl]carbonyl}-2-(3-methoxyphenyl)-9-methyl-7,9-dihydro-8H-purine-8-one (Example No. 87);
2-(3-Methoxyphenyl)-9-methyl-7-{[4-(2,2,2-trifluoroethyl)piperazin-1-yl]carbonyl}-7,9-dihydro-8H-purine-8-one (Example No. 99);
7-{[4-(2-Cyclohexylethyl)piperazin-1-yl]carbonyl}-2-(3-methoxyphenyl)-9-methyl-7,9-dihydro-8H-purine-8-one (Example No. 100);
2-(3-Methoxyphenyl)-9-methyl-7-{[4-(phenoxymethyl)piperidin-1-yl]carbonyl}-7,9-dihydro-8H-purine-8-one (Example No. 101);
7-{[4-(4-Chlorobenzylidene)piperidin-1-yl]carbonyl}-2-(3-methoxyphenyl)-9-methyl-7,9-dihydro-8H-purine-8-one (Example No. 102);
N-(2-Chloroethyl)-2-(3-methoxyphenyl)-N,9-dimethyl-8-oxo-8,9-dihydro-7H-purine-7-carboxamide (Example No. 103);
2-(3-Methoxyphenyl)-N,9-dimethyl-8-oxo-N-[2-(tetrahydro-2H-pyran-4-yl)ethyl]-8,9-dihydro-7H-purine-7-carboxamide (Example No. 117);

9-Methyl-2-phenyl-7-[(4-phenylpiperazin-1-yl)carbonyl]-7,9-dihydro-8H-purine-8-one (Example No. 120);

7-{[4-(4-Fluorophenyl)piperazin-1-yl]carbonyl}-9-methyl-2-phenyl-7,9-dihydro-8H-purine-8-one (Example No. 123);

7-{[4-(3-Fluorophenyl)piperazin-1-yl]carbonyl}-9-methyl-2-phenyl-7,9-dihydro-8H-purine-8-one (Example No. 124);

7-{[4-(4-Chlorophenyl)piperazin-1-yl]carbonyl}-9-methyl-2-phenyl-7,9-dihydro-8H-purine-8-one (Example No. 126);

9-Methyl-7-{[4-(4-methylphenyl)piperazin-1-yl]carbonyl}-2-phenyl-7,9-dihydro-8H-purine-8-one (Example No. 128);

9-Methyl-7-{[4-(3-methylphenyl)piperazin-1-yl]carbonyl}-2-phenyl-7,9-dihydro-8H-purine-8-one (Example No. 129);

7-{[4-(4-Ethoxyphenyl)piperazin-1-yl]carbonyl}-9-methyl-2-phenyl-7,9-dihydro-8H-purine-8-one (Example No. 131);

4-{4-[(9-Methyl-8-oxo-2-phenyl-8,9-dihydro-7H-purine-7-yl)carbonyl]piperazin-1-yl}benzonitrile (Example No. 132);

7-{[4-(4-Acetylphenyl)piperazin-1-yl]carbonyl}-9-methyl-2-phenyl-7,9-dihydro-8H-purine-8-one (Example No. 133);

9-Methyl-2-phenyl-7-({4-[4-(trifluoromethyl)phenyl]piperazin-1-yl}carbonyl)-7,9-dihydro-8H-purine-8-one (Example No. 134);

7-{[4-(4-Fluorophenyl)piperazin-1-yl]carbonyl}-2-(3-methoxyphenyl)-9-methyl-7,9-dihydro-8H-purine-8-one (Example No. 136);

7-{[4-(3-Fluorophenyl)piperazin-1-yl]carbonyl}-2-(3-methoxyphenyl)-9-methyl-7,9-dihydro-8H-purine-8-one (Example No. 137);

2-(3-Methoxyphenyl)-9-methyl-7-{[4-(4-methylphenyl)piperazin-1-yl]carbonyl}-7,9-dihydro-8H-purine-8-one (Example No. 138);

2-(3-Methoxyphenyl)-9-methyl-7-{[4-(3-methylphenyl)piperazin-1-yl]carbonyl}-7,9-dihydro-8H-purine-8-one (Example No. 139);

2-(3-Methoxyphenyl)-9-methyl-7-[(4-phenylpiperazin-1-yl)carbonyl]-7,9-dihydro-8H-purine-8-one (Example No. 140);

N,N,9-Trimethyl-8-oxo-2-(pyridin-3-yl)-8,9-dihydro-7H-purine-7-carboxamide (Example No. 143);

N-[2-(4-Chlorophenyl)ethyl]-2-cyclopropyl-N,9-dimethyl-8-oxo-8,9-dihydro-7H-purine-7-carboxamide (Example No. 153);

N-[2-(4-Chlorophenyl)ethyl]-2-cyclohexyl-N,9-dimethyl-8-oxo-8,9-dihydro-7H-purine-7-carboxamide (Example No. 156);

2-(2-Fluorophenyl)-9-methyl-7-(pyrrolidin-1-ylcarbonyl)-7,9-dihydro-8H-purine-8-one (Example No. 166);

2-(4-Fluorophenyl)-9-methyl-7-(pyrrolidin-1-ylcarbonyl)-7,9-dihydro-8H-purine-8-one (Example No. 168);

9-Methyl-2-(4-methylphenyl)-7-(pyrrolidin-1-ylcarbonyl)-7,9-dihydro-8H-purine-8-one (Example No. 171);

2-(3-Methoxyphenyl)-9-methyl-7-(pyrrolidin-1-ylcarbonyl)-7,9-dihydro-8H-purine-8-one (Example No. 173);

2-[4-(Dimethylamino)phenyl]-9-methyl-7-(pyrrolidin-1-ylcarbonyl)-7,9-dihydro-8H-purine-8-one (Example No. 182);

9-Methyl-2-[4-(methylsulfanyl)phenyl]-7-(pyrrolidin-1-ylcarbonyl)-7,9-dihydro-8H-purine-8-one (Example No. 183);

2-(2,3-Difluorophenyl)-9-methyl-7-(pyrrolidin-1-ylcarbonyl)-7,9-dihydro-8H-purine-8-one (Example No. 187);

2-(2,5-Difluorophenyl)-9-methyl-7-(pyrrolidin-1-ylcarbonyl)-7,9-dihydro-8H-purine-8-one (Example No. 189);

2-(2-Fluoro-3-methoxyphenyl)-9-methyl-7-(pyrrolidin-1-ylcarbonyl)-7,9-dihydro-8H-purine-8-one (Example No. 196);

2-(2-Fluoro-5-methoxyphenyl)-9-methyl-7-(pyrrolidin-1-ylcarbonyl)-7,9-dihydro-8H-purine-8-one (Example No. 200);

2-(3-Fluoro-5-methylphenyl)-9-methyl-7-(pyrrolidin-1-ylcarbonyl)-7,9-dihydro-8H-purine-8-one (Example No. 201);

9-Methyl-2-(3-nitrophenyl)-7-(pyrrolidin-1-ylcarbonyl)-7,9-dihydro-8H-purine-8-one (Example No. 203);

9-Methyl-2-(pyridin-3-yl)-7-(pyrrolidin-1-ylcarbonyl)-7,9-dihydro-8H-purine-8-one (Example No. 205);

2-(6-Methoxypyridin-3-yl)-9-methyl-7-(pyrrolidin-1-ylcarbonyl)-7,9-dihydro-8H-purine-8-one (Example No. 206);

2-(6-Fluoropyridine-3-yl)-9-methyl-7-(pyrrolidin-1-ylcarbonyl)-7,9-dihydro-8H-purine-8-one (Example No. 207);

9-Methyl-2-(pyridin-4-yl)-7-(pyrrolidin-1-ylcarbonyl)-7,9-dihydro-8H-purine-8-one (Example No. 213);

2-(2-Chloropyridin-4-yl)-9-methyl-7-(pyrrolidin-1-ylcarbonyl)-7,9-dihydro-8H-purine-8-one (Example No. 214);

N-Ethyl-N,9-dimethyl-8-oxo-2-(pyridin-3-yl)-8,9-dihydro-7H-purine-7-carboxamide (Example No. 219);

2-(3-Fluorophenyl)-7-methyl-9-(pyrrolidin-1-ylcarbonyl)-7,9-dihydro-8H-purine-8-one (Example No. 226);

2-(3-ethoxyphenyl)-7-methyl-9-(pyrrolidin-1-ylcarbonyl)-7,9-dihydro-8H-purine-8-one (Example No. 232);

7-Methyl-9-(pyrrolidin-1-ylcarbonyl)-2-[3-(trifluoromethyl)phenyl]-7,9-dihydro-8H-purine-8-one (Example No. 234);

7-Methyl-9-(pyrrolidin-1-ylcarbonyl)-2-[3-(trifluoromethoxy)phenyl]-7,9-dihydro-8H-purine-8-one (Example No. 236);

7-Methyl-9-(pyrrolidin-1-ylcarbonyl)-2-{(E)-2-[3-(trifluoromethyl)phenyl]ethenyl}-7,9-dihydro-8H-purine-8-one (Example No. 244);

2-[(E)-2-(3-Fluorophenyl)ethenyl]-7-methyl-9-(pyrrolidin-1-ylcarbonyl)-7,9-dihydro-8H-purine-8-one (Example No. 246);

2-Benzyl-9-methyl-7-(pyrrolidin-1-ylcarbonyl)-7,9-dihydro-8H-purine-8-one (Example No. 253);

2-(3-Fluorobenzyl)-9-methyl-7-(pyrrolidin-1-ylcarbonyl)-7,9-dihydro-8H-purine-8-one (Example No. 255);

2-(4-Fluorobenzyl)-9-methyl-7-(pyrrolidin-1-ylcarbonyl)-7,9-dihydro-8H-purine-8-one (Example No. 256);

2-(3-Methoxybenzyl)-9-methyl-7-(pyrrolidin-1-ylcarbonyl)-7,9-dihydro-8H-purine-8-one (Example No. 261);

2-(4-Methoxybenzyl)-9-methyl-7-(pyrrolidin-1-ylcarbonyl)-7,9-dihydro-8H-purine-8-one (Example No. 262);

2-(Biphenyl-4-ylmethyl)-9-methyl-7-(pyrrolidin-1-ylcarbonyl)-7,9-dihydro-8H-purine-8-one (Example No. 265);

2-(2,5-Difluorobenzyl)-9-methyl-7-(pyrrolidin-1-ylcarbonyl)-7,9-dihydro-8H-purine-8-one (Example No. 267);

2-Butyl-9-methyl-7-(pyrrolidin-1-ylcarbonyl)-7,9-dihydro-8H-purine-8-one (Example No. 274);

N-Ethyl-2-(3-fluorobenzyl)-N,9-dimethyl-8-oxo-8,9-dihydro-7H-purine-7-carboxamide (Example No. 284);

2-(4-Methoxybenzyl)-7-methyl-9-(pyrrolidin-1-ylcarbonyl)-7,9-dihydro-8H-purine-8-one (Example No. 287);

7-Methyl-2-(4-methylbenzyl)-9-(pyrrolidin-1-ylcarbonyl)-7,9-dihydro-8H-purine-8-one (Example No. 289);

2-(3,4-Difluorobenzyl)-7-methyl-9-(pyrrolidin-1-ylcarbonyl)-7,9-dihydro-8H-purine-8-one (Example No. 293);

2-Phenyl-9-propyl-7-(pyrrolidin-1-ylcarbonyl)-7,9-dihydro-8H-purine-8-one (Example No. 304);
2-[2-(3-Fluorophenyl)ethyl]-7-methyl-9-(pyrrolidin-1-ylcarbonyl)-7,9-dihydro-8H-purine-8-one (Example No. 315);
2-(3-Methoxyphenyl)-N,N,7-trimethyl-8-oxo-7,8-dihydro-9H-purine-9-carboxamide (Example No. 322);
2-[4-(Difluoromethyl)phenyl]-N,N,7-trimethyl-8-oxo-7,8-dihydro-9H-purine-9-carboxamide (Example No. 330);
2-[3-(Difluoromethoxy)phenyl]-N,N,7-trimethyl-8-oxo-7,8-dihydro-9H-purine-9-carboxamide (Example No. 331);
2-[3-(Difluoromethyl)phenyl]-N,N,7-trimethyl-8-oxo-7,8-dihydro-9H-purine-9-carboxamide (Example No. 332);
N,N,7-Trimethyl-8-oxo-2-[4-(2,2,2-trifluoroethoxy)phenyl]-7,8-dihydro-9H-purine-9-carboxamide (Example No. 334);
2-[3-(2,2-Difluoroethoxy)phenyl]-N,N,7-trimethyl-8-oxo-7,8-dihydro-9H-purine-9-carboxamide (Example No. 335);
N,N,7-Trimethyl-8-oxo-2-[3-(2,2,2-trifluoroethoxy)phenyl)]-7,8-dihydro-9H-purine-9-carboxamide (Example No. 336);
2-[4-(Difluoromethoxy)phenyl]-N,N,7-trimethyl-8-oxo-7,8-dihydro-9H-purine-9-carboxamide (Example No. 337);
9-(Azetidin-1-ylcarbonyl)-2-(4-methoxyphenyl)-7-methyl-7,9-dihydro-8H-purine-8-one (Example No. 356);
7-(Azetidin-1-ylcarbonyl)-2-(3-methoxybenzyl)-9-methyl-7,9-dihydro-8H-purine-8-one (Example No. 375);
7-(Azetidin-1-ylcarbonyl)-9-methyl-2-[3-(trifluoromethyl)benzyl]-7,9-dihydro-8H-purine-8-one (Example No. 379);
7-(Azetidin-1-ylcarbonyl)-2-[(3-methoxyphenoxy)methyl]-9-methyl-7,9-dihydro-8H-purine-8-one (Example No. 404);
7-{[3-(2,4-Difluorophenyl)azetidin-1-yl]carbonyl}-2-(methoxymethyl)-9-methyl-7,9-dihydro-8H-purine-8-one (Example No. 454);
7-{[3-(4-Fluoro-3-methyl-phenyl)azetidin-1-yl]carbonyl}-2-(methoxymethyl)-9-methyl-7,9-dihydro-8H-purine-8-one (Example No. 455);
2-(Methoxymethyl)-7-{[3-(3-methoxyphenyl)azetidin-1-yl]carbonyl}-9-methyl-7,9-dihydro-8H-purine-8-one (Example No. 459);
2-(Ethoxymethyl)-9-methyl-7-[(3-phenylazetidin-1-yl)carbonyl]-7,9-dihydro-8H-purine-8-one (Example No. 460);
2-(Ethoxy ethyl)-7-{[3-(3-fluorophenyl)azetidin-1-yl]carbonyl}-9-methyl-7,9-dihydro-8H-purine-8-one (Example No. 462);
2-(Ethoxymethyl)-7-{[3-(4-ethoxyphenyl)azetidin-1-yl]carbonyl}-9-methyl-7,9-dihydro-8H-purine-8-one (Example No. 463);
2-(Ethoxymethyl)-7-{[3-(2-fluorophenyl)azetidin-1-yl]carbonyl}-9-methyl-7,9-dihydro-8H-purine-8-one (Example No. 465);
7-{[3-(2-Fluorophenoxy)azetidin-1-yl]carbonyl}-2-(methoxymethyl)-9-methyl-7,9-dihydro-8H-purine-8-one (Example No. 479);
2-(Methoxymethyl)-9-methyl-7-{[(3R)-3-phenoxypyrrolidin-1-yl]carbonyl}-7,9-dihydro-8H-purine-8-one (Example No. 488);
7-({3-[(4-Fluorophenoxy)methyl]azetidin-1-yl}carbonyl)-2-(methoxymethyl)-9-methyl-7,9-dihydro-8H-purine-8-one (Example No. 492);
N,N,7-Trimethyl-2-[2-(4-methylphenyl)ethyl]-8-oxo-7,8-dihydro-9H-purine-9-carboxamide (Example No. 494);
2-[2-(2,4-Difluorophenyl)ethyl]-N,N,7-trimethyl-8-oxo-7,8-dihydro-9H-purine-9-carboxamide (Example No. 506);
2-{2-[3-(2,2-Difluoroethoxy)phenyl]ethyl}-N,N,7-trimethyl-8-oxo-7,8-dihydro-9H-purine-9-carboxamide (Example No. 530);
N,N,7-Trimethyl-8-oxo-2-{2-[4-(trifluoromethyl)phenyl]ethyl}-7,8-dihydro-9H-purine-9-carboxamide (Example No. 540);
N,N,7-Trimethyl-8-oxo-2-{2-[3-(2,2,2-trifluoroethoxy)phenyl]ethyl}-7,8-dihydro-9H-purine-9-carboxamide (Example No. 552);
N,N,7-Trimethyl-8-oxo-2-{2-[4-(2,2,2-trifluoroethoxy)phenyl]ethyl}-7,8-dihydro-9H-purine-9-carboxamide (Example No. 553);
9-(Azetidin-1-ylcarbonyl)-2-{2-[4-(difluoromethyl)phenyl]ethyl}-7-methyl-7,9-dihydro-8H-purine-8-one (Example No. 576);
9-(Azetidin-1-ylcarbonyl)-2-[2-(3,5-difluorophenyl)ethyl]-7-methyl-7,9-dihydro-8H-purine-8-one (Example No. 580);
9-(Azetidin-1-ylcarbonyl)-2-[2-(2-fluorophenyl)ethyl]-7-methyl-7,9-dihydro-8H-purine-8-one (Example No. 583);
9-(Azetidin-1-ylcarbonyl)-2-{2-[4-(2,2-difluoroethoxy)phenyl]ethyl}-7-methyl-7,9-dihydro-8H-purine-8-one (Example No. 593);
9-(Azetidin-1-ylcarbonyl)-7-methyl-2-{2-[3-(2,2,2-trifluoroethoxy)phenyl]ethyl}-7,9-dihydro-8H-purine-8-one (Example No. 612);
9-(Azetidin-1-ylcarbonyl)-7-methyl-2-{2-[4-(2,2,2-trifluoroethoxy)phenyl]ethyl}-7,9-dihydro-8H-purine-8-one (Example No. 613);
7-Methyl-9-[3-phenylazetidin-1-yl)carbonyl]-2-propyl-7,9-dihydro-8H-purine-8-one (Example No. 637);
9-(Azetidin-1-ylcarbonyl)-7-ethyl-2-[2-(2-fluorophenyl)ethyl]-7,9-dihydro-8H-purine-8-one (Example No. 649);
9-(Azetidin-1-ylcarbonyl)-7-ethyl-2-[2-(3-fluorophenyl)ethyl]-7,9-dihydro-8H-purine-8-one (Example No. 650);
9-(Azetidin-1-ylcarbonyl)-7-ethyl-2-[2-(4-fluorophenyl)ethyl]-7,9-dihydro-8H-purine-8-one (Example No. 651);
N,N,7-Trimethyl-8-oxo-2-[3-(trifluoromethyl)benzyl]-7,8-dihydro-9H-purine-9-carboxamide (Example No. 654);
9-Ethyl-2-(methoxymethyl)-7-[(3-phenylazetidin-1-yl)carbonyl]-7,9-dihydro-8H-purine-8-one (Example No. 655);
9-Ethyl-7-{[3-(4-fluorophenyl)azetidin-1-yl]carbonyl}-2-(methoxymethyl)-7,9-dihydro-8H-purine-8-one (Example No. 656);
9-Ethyl-7-{[3-(3-fluorophenyl)azetidin-1-yl]carbonyl}-2-(methoxymethyl)-7,9-dihydro-8H-purine-8-one (Example No. 657);
2-(Methoxymethyl)-7-[(3-phenylazetidin-1-yl)carbonyl]-9-propyl-7,9-dihydro-8H-purine-8-one (Example No. 658);
7-{[3-(4-Fluorophenyl)azetidin-1-yl]carbonyl}-2-(methoxymethyl)-9-propyl-7,9-dihydro-8H-purine-8-one (Example No. 659); and
7-{[3-(2-Fluorophenyl)azetidin-1-yl]carbonyl}-2-(methoxymethyl)-9-propyl-7,9-dihydro-8H-purine-8-one (Example No. 661).

Compound Group (C)
N,9-Dimethyl-8-oxo-2-phenyl-N-(4-phenylbutyl)-8,9-dihydro-7H-purine-7-carboxamide (Example No. 36);
N-Ethyl-2-(3-methoxyphenyl)-N,9-dimethyl-8-oxo-8,9-dihydro-7H-purine-7-carboxamide (Example No. 60);
2-(3-Methoxyphenyl)-N,9-dimethyl-8-oxo-N-(2-phenylethyl)-8,9-dihydro-7H-purine-7-carboxamide (Example No. 64);
2-(3-Methoxyphenyl)-N,9-dimethyl-8-oxo-N-(2-phenoxyethyl)-8,9-dihydro-7H-purine-7-carboxamide (Example No. 65);

7-({4-[2-(4-Chlorophenyl)ethyl]piperidin-1-yl}carbonyl)-2-(3-methoxyphenyl)-9-methyl-7,9-dihydro-8H-purine-8-one (Example No. 68);

N-[2-(4-Chlorophenyl)ethyl]-2-(3-methoxyphenyl)-N,9-dimethyl-8-oxo-8,9-dihydro-7H-purine-7-carboxamide (Example No. 69);

N-(4-Fluorobenzyl)-2-(3-methoxyphenyl)-N,9-dimethyl-8-oxo-8,9-dihydro-7H-purine-7-carboxamide (Example No. 71);

N-[2-(4-Fluorophenyl)ethyl]-2-(3-methoxyphenyl)-N,9-dimethyl-8-oxo-8,9-dihydro-7H-purine-7-carboxamide (Example No. 74);

N-[2-(3-Fluorophenyl)ethyl]-2-(3-methoxyphenyl)-N,9-dimethyl-8-oxo-8,9-dihydro-7H-purine-7-carboxamide (Example No. 75);

N-[2-(3-Chlorophenyl)ethyl]-2-(3-methoxyphenyl)-N,9-dimethyl-8-oxo-8,9-dihydro-7H-purine-7-carboxamide (Example No. 76);

N-[2-(4-Chlorophenoxy)ethyl]-2-(3-methoxyphenyl)-N,9-dimethyl-8-oxo-8,9-dihydro-7H-purine-7-carboxamide (Example No. 77);

N-(4-Chlorobenzyl)-2-(3-methoxyphenyl)-N,9-dimethyl-8-oxo-8,9-dihydro-7H-purine-7-carboxamide (Example No. 78);

2-(3-Methoxyphenyl)-N,9-dimethyl-8-oxo-N-[4-(trifluoromethyl)benzyl]-8,9-dihydro-7H-purine-7-carboxamide (Example No. 81);

2-(3-Methoxyphenyl)-N,9-dimethyl-8-oxo-N-[4-(trifluoromethoxy)benzyl]-8,9-dihydro-7H-purine-7-carboxamide (Example No. 83);

N-[2-(3-Chlorophenoxy)ethyl]-2-(3-methoxyphenyl)-N,9-dimethyl-8-oxo-8,9-dihydro-7H-purine-7-carboxamide (Example No. 90);

N-[2-(4-Fluorophenoxy)ethyl]-2-(3-methoxyphenyl)-N,9-dimethyl-8-oxo-8,9-dihydro-7H-purine-7-carboxamide (Example No. 91);

2-(3-Methoxyphenyl)-N,9-dimethyl-8-oxo-N-{2-[4-(trifluoromethyl)phenyl]ethyl}-8,9-dihydro-7H-purine-7-carboxamide (Example No. 92);

2-(3-Methoxyphenyl)-N-[2-(4-methoxyphenyl)ethyl]-N,9-dimethyl-8-oxo-8,9-dihydro-7H-purine-7-carboxamide (Example No. 93);

7-({4-[(E)-2-(4-Chlorophenyl)ethenyl]-3,6-dihydropyridin-1(2H)-yl}carbonyl)-2-(3-methoxyphenyl)-9-methyl-7,9-dihydro-8H-purine-8-one (Example No. 94);

7-({4-[(E)-2-(4-Fluorophenyl)ethenyl]-3,6-dihydropyridin-1(2H)-yl}carbonyl)-2-(3-methoxyphenyl)-9-methyl-7,9-dihydro-8H-purine-8-one (Example No. 95);

7-({4-[2-(4-Fluorophenyl)ethyl]piperidin-1-yl}carbonyl)-2-(3-methoxyphenyl)-9-methyl-7,9-dihydro-8H-purine-8-one (Example No. 96);

2-(3-Methoxyphenyl)-N,9-dimethyl-8-oxo-N-[2-(3-phenyl-1,2,4-oxadiazol-5-yl)ethyl]-8,9-dihydro-7H-purine-7-carboxamide (Example No. 104);

N-[2-(3,4-Dichlorophenyl)ethyl]-2-(3-methoxyphenyl)-N,9-dimethyl-8-oxo-8,9-dihydro-7H-purine-7-carboxamide (Example No. 105);

N-[2-(Cyclohex-1-en-1-yl)ethyl]-2-(3-methoxyphenyl)-N,9-dimethyl-8-oxo-8,9-dihydro-7H-purine-7-carboxamide (Example No. 106);

N-(2-Cyclohexylethyl)-2-(3-methoxyphenyl)-N,9-dimethyl-8-oxo-8,9-dihydro-7H-purine-7-carboxamide (Example No. 109);

N-[2-(2,4-Dichlorophenyl)ethyl]-2-(3-methoxyphenyl)-N,9-dimethyl-8-oxo-8,9-dihydro-7H-purine-7-carboxamide (Example No. 110);

7-({4-[(E)-2-(4-Chlorophenyl)ethenyl]piperidin-1-yl}carbonyl)-2-(3-methoxyphenyl)-9-methyl-7,9-dihydro-8H-purine-8-one (Example No. 112);

N-{2-[4-(Dimethylamino)phenyl]ethyl}-2-(3-methoxyphenyl)-N,9-dimethyl-8-oxo-8,9-dihydro-7H-purine-7-carboxamide (Example No. 113);

N-[2-(Cyclopropylmethoxy)ethyl]-2-(3-methoxyphenyl)-N,9-dimethyl-8-oxo-8,9-dihydro-7H-purine-7-carboxamide (Example No. 116);

2-(3-Methoxyphenyl)-7-({4-[2-(4-methoxyphenyl)ethyl]piperidin-1-yl}carbonyl)-9-methyl-7,9-dihydro-8H-purine-8-one (Example No. 118);

7-{[4-(4-Methoxyphenyl)piperazin-1-yl]carbonyl}-9-methyl-2-phenyl-7,9-dihydro-8H-purine-8-one (Example No. 135);

7-{[4-(4-Ethoxyphenyl)piperazin-1-yl]carbonyl}-2-(3-methoxyphenyl)-9-methyl-7,9-dihydro-8H-purine-8-one (Example No. 141);

7-{[4-(4-Chlorophenyl)piperazin-1-yl]carbonyl}-2-(3-methoxyphenyl)-9-methyl-7,9-dihydro-8H-purine-8-one (Example No. 142);

7-{[4-(4-Ethoxyphenyl)piperazin-1-yl]carbonyl}-9-methyl-2-(pyridin-3-yl)-7,9-dihydro-8H-purine-8-one (Example No. 144);

N-[2-(4-Chlorophenyl)ethyl]-N,9-dimethyl-8-oxo-2-(pyridin-3-yl)-8,9-dihydro-7H-purine-7-carboxamide (Example No. 145);

N-[2-(4-Chlorophenoxy)ethyl]-N,9-dimethyl-8-oxo-2-(pyridin-3-yl)-8,9-dihydro-7H-purine-7-carboxamide (Example No. 146);

7-({4-[2-(4-Chlorophenyl)ethyl]piperidin-1-yl}carbonyl)-9-methyl-2-(pyridin-3-yl)-7,9-dihydro-8H-purine-8-one (Example No. 147);

N,N,9-Trimethyl-8-oxo-2-(pyridin-4-yl)-8,9-dihydro-7H-purine-7-carboxamide (Example No. 148);

7-{[4-(4-Ethoxyphenyl)piperazin-1-yl]carbonyl}-9-methyl-2-(pyridin-4-yl)-7,9-dihydro-8H-purine-8-one (Example No. 149);

N-[2-(4-Chlorophenyl)ethyl]-N,9-dimethyl-8-oxo-2-(pyridin-4-yl)-8,9-dihydro-7H-purine-7-carboxamide (Example No. 150);

N-[2-(4-Chlorophenoxy)ethyl]-N,9-dimethyl-8-oxo-2-(pyridin-4-yl)-8,9-dihydro-7H-purine-7-carboxamide (Example No. 151);

7-({4-[2-(4-Chlorophenyl)ethyl]piperidin-1-yl}carbonyl)-9-methyl-2-(pyridin-4-yl)-7,9-dihydro-8H-purine-8-one (Example No. 152);

N-[2-(4-Chlorophenyl)ethyl]-N,9-dimethyl-8-oxo-2-propyl- (Example No. 154);

2-Butyl-N-[2-(4-chlorophenyl)ethyl]-N,9-dimethyl-8-oxo-8,9-dihydro-7H-purine-7-carboxamide (Example No. 155);

2-Benzyl-N-[2-(4-chlorophenyl)ethyl]-N,9-dimethyl-8-oxo-8,9-dihydro-7H-purine-7-carboxamide (Example No. 158);

9-(Azetidin-1-ylcarbonyl)-2-[2-(3-fluorophenyl)ethyl]-7-methyl-7,9-dihydro-8H-purine-8-one (Example No. 164);

2-[2-(3-Fluorophenyl)ethyl]-N,N,7-trimethyl-8-oxo-7,8-dihydro-9H-purine-9-carboxamide (Example No. 165);

2-(2-Fluoropyridin-4-yl)-9-methyl-7-(pyrrolidin-1-ylcarbonyl)-7,9-dihydro-8H-purine-8-one (Example No. 215);

N-Ethyl-N,9-dimethyl-8-oxo-2-(pyridin-4-yl)-8,9-dihydro-7H-purine-7-carboxamide (Example No. 220);

N-Ethyl-2-(2-fluoropyridin-4-yl)-N,9-dimethyl-8-oxo-8,9-dihydro-7H-purine-7-carboxamide (Example No. 221);

N-[2-(4-Chlorophenyl)ethyl]-2-(2-fluoropyridin-4-yl)-N,9-dimethyl-8-oxo-8,9-dihydro-7H-purine-7-carboxamide (Example No. 222);

N-(2-Cyclohexylethyl)-N,9-dimethyl-8-oxo-2-(pyridin-4-yl)-8,9-dihydro-7H-purine-7-carboxamide (Example No. 223);

N-Ethyl-2-(3-methoxybenzyl)-N,9-dimethyl-8-oxo-8,9-dihydro-7H-purine-7-carboxamide (Example No. 277);

7-Methyl-9-(pyrrolidin-1-ylcarbonyl)-2-{2-[4-(trifluoromethyl)phenyl]ethyl}-7,9-dihydro-8H-purine-8-one (Example No. 312);

7-Methyl-9-(pyrrolidin-1-ylcarbonyl)-2-{2-[3-(trifluoromethyl)phenyl]ethyl}-7,9-dihydro-8H-purine-8-one (Example No. 313);

N,N,7-Trimethyl-8-oxo-2-[4-(trifluoromethyl)phenyl]-7,8-dihydro-9H-purine-9-carboxamide (Example No. 326);

2-[2-Fluoro-4-(trifluoromethyl)phenyl]-N,N,7-trimethyl-8-oxo-7,8-dihydro-9H-purine-9-carboxamide (Example No. 338);

2-[2-Chloro-4-(trifluoromethyl)phenyl]-N,N,7-trimethyl-8-oxo-7,8-dihydro-9H-purine-9-carboxamide (Example No. 339);

9-(Azetidin-1-ylcarbonyl)-2-[3-(4-fluorophenoxy)propyl]-7-methyl-7,9-dihydro-8H-purine-8-one (Example No. 401);

2-(Methoxymethyl)-9-methyl-7-[(3-phenylazetidin-1-yl)carbonyl]-7,9-dihydro-8H-purine-8-one (Example No. 438);

7-{[3-(4-Fluorophenyl)azetidin-1-yl]carbonyl}-2-(methoxymethyl)-9-methyl-7,9-dihydro-8H-purine-8-one (Example No. 439);

7-{[3-(3-Fluorophenyl)azetidin-1-yl]carbonyl}-2-(methoxymethyl)-9-methyl-7,9-dihydro-8H-purine-8-one (Example No. 440);

7-{[3-(2-Fluorophenyl)azetidin-1-yl]carbonyl}-2-(methoxymethyl)-9-methyl-7,9-dihydro-8H-purine-8-one (Example No. 441);

2-(Methoxymethyl)-9-methyl-7-({[3-(3-trifluoromethyl)phenyl]azetidin-1-yl}carbonyl)-7,9-dihydro-8H-purine-8-one (Example No. 443);

7-{[3-(2-Chlorophenyl)azetidin-1-yl]carbonyl}-2-(methoxymethyl)-9-methyl-7,9-dihydro-8H-purine-8-one (Example No. 453);

7-({3-[4-(Benzyloxy)phenyl]azetidie-1-yl}carbonyl)-2-(methoxymethyl)-9-methyl-7,9-dihydro-8H-purine-8-one (Example No. 456);

2-(Methoxymethyl)-9-methyl-7-({3-[4-(trifluoromethoxy)phenyl]azetidin-1-yl}carbonyl)-7,9-dihydro-8H-purine-8-one (Example No. 458);

7-{[(3R)-3-(4-Fluorophenoxy)pyrrolidin-1-yl]carbonyl}-2-(methoxymethyl)-9-methyl-7,9-dihydro-8H-purine-8-one (Example No. 480);

7-{[(3S)-3-(3-Fluorophenoxy)pyrrolidin-1-yl]carbonyl}-2-(methoxymethyl)-9-methyl-7,9-dihydro-8H-purine-8-one (Example No. 482);

7-{[(3S)-3-(2-Fluorophenoxy)pyrrolidin-1-yl]carbonyl}-2-(methoxymethyl)-9-methyl-7,9-dihydro-8H-purine-8-one (Example No. 483);

2-(Methoxymethyl)-9-methyl-7-{[(3S)-3-(4-methylphenoxy)pyrrolidin-1-yl]carbonyl}-7,9-dihydro-8H-purine-8-one (Example No. 484);

2-(Methoxymethyl)-9-methyl-7-{[(3S)-3-(3-methylphenoxy)pyrrolidin-1-yl]carbonyl}-7,9-dihydro-8H-purine-8-one (Example No. 485);

2-(Methoxymethyl)-9-methyl-7-{[(3S)-3-(2-methylphenoxy)pyrrolidin-1-yl]carbonyl}-7,9-dihydro-8H-purine-8-one (Example No. 486);

7-{[(3R)-3-(3-Chlorophenoxy)pyrrolidin-1-yl]carbonyl}-2-(methoxymethyl)-9-methyl-7,9-dihydro-8H-purine-8-one (Example No. 487);

7-{[(33)-3-(4-Chlorophenoxy)pyrrolidin-1-yl]carbonyl}-2-(methoxymethyl)-9-methyl-7,9-dihydro-8H-purine-8-one (Example No. 489);

7-{[(3S)-3-(3-Chlorophenoxy)pyrrolidin-1-yl]carbonyl}-2-(methoxymethyl)-9-methyl-7,9-dihydro-8H-purine-8-one (Example No. 490); 7-{[(3S)-3-(2-Chlorophenoxy)pyrrolidin-1-yl]carbonyl}-2-(methoxymethyl)-9-methyl-7,9-dihydro-8H-purine-8-one (Example No. 491);

2-[2-(3,5-Difluorophenyl)ethyl]-N,N,7-trimethyl-8-oxo-7,8-dihydro-9H-purine-9-carboxamide (Example No. 497);

2-[2-(4-Fluorophenyl)ethyl]-N,N,7-trimethyl-8-oxo-7,8-dihydro-9H-purine-9-carboxamide (Example No. 533);

2-{2-[4-(2,2-Difluoroethoxy)phenyl]ethyl}-N,N,7-trimethyl-8-oxo-7,8-dihydro-9H-purine-9-carboxamide (Example No. 538);

9-(Azetidin-1-ylcarbonyl)-2-[2-(4-fluorophenyl)ethyl]-7-methyl-7,9-dihydro-8H-purine-8-one (Example No. 587);

2-[2-(3-Chlorophenoxy)ethyl]-N,N,7-trimethyl-8-oxo-7,8-dihydro-9H-purine-9-carboxamide (Example No. 641);

7-Ethyl-2-[2-(3-fluorophenyl)ethyl]-N,N-dimethyl-8-oxo-7,8-dihydro-9H-purine-9-carboxamide (Example No. 644);

7-Ethyl-2-[2-(4-fluorophenyl)ethyl]-N,N-dimethyl-8-oxo-7,8-dihydro-9H-purine-9-carboxamide (Example No. 645);

2-[2-(2-Fluorophenyl)ethyl]-N,N-dimethyl-8-oxo-7-propyl-7,8-dihydro-9H-purine-9-carboxamide (Example No. 646);

2-[2-(3-Fluorophenyl)ethyl]-N,N-dimethyl-8-oxo-7-propyl-7,8-dihydro-9H-purine-9-carboxamide (Example No. 647);

2-[2-(4-Fluorophenyl)ethyl]-N,N-dimethyl-8-oxo-7-propyl-7,8-dihydro-9H-purine-9-carboxamide (Example No. 648);

7-{[3-(3-Fluorophenyl)azetidin-1-yl]carbonyl}-2-(methoxymethyl)-9-propyl-7,9-dihydro-8H-purine-8-one (Example No. 660); and 2-(Methoxymethyl)-9-propyl-7-({3-[3-(trifluoromethyl)phenyl]azetidin-1-yl}carbonyl)-7,9-dihydro-8H-purine-8-one (Example No. 662).

Compound Group (A')

9-Methyl-2-phenyl-7-({4-[5-(trifluoromethyl)pyridin-2-yl]piperazin-1-yl}carbonyl)-7,9-dihydro-8H-purine-8-one (Example No. 50);

2-(3-Methoxyphenyl)-N,9-dimethyl-8-oxo-N-propyl-8,9-dihydro-7H-purine-7-carboxamide (Example No. 107);

2-(3-Methoxyphenyl)-N,9-dimethyl-N-(2-methylpropyl)-8-oxo-8,9-dihydro-7H-purine-7-carboxamide (Example No. 108);

2-(3-Methoxyphenyl)-N,9-dimethyl-8-oxo-N-[2-(pyridin-2-yl)ethyl]-8,9-dihydro-7H-purine-7-carboxamide (Example No. 114);

2-(3-Methoxyphenyl)-N,9-dimethyl-8-oxo-N-[2-(pyridin-4-yl)ethyl]-8,9-dihydro-7H-purine-7-carboxamide (Example No. 115);

7-{[4-(2-Methoxyethyl)piperidin-1-yl]carbonyl}-2-(3-methoxyphenyl)-9-methyl-7,9-dihydro-8H-purine-8-one (Example No. 119);

N-[2-(4-Chlorophenyl)ethyl]-N,2,9-trimethyl-8-oxo-8,9-dihydro-7H-purine-7-carboxamide (Example No. 157);

2-(2,2-Dimethylpropyl)-N-ethyl-N,9-dimethyl-8-oxo-8,9-dihydro-7H-purine-7-carboxamide (Example No. 160);

2-Butyl-N-ethyl-N,9-dimethyl-8-oxo-8,9-dihydro-7H-purine-7-carboxamide (Example No. 161);

2-(3-Fluorophenyl)-9-methyl-7-(pyrrolidin-1-ylcarbonyl)-7,9-dihydro-8H-purine-8-one (Example No. 167);

9-Methyl-2-(3-methylphenyl)-7-(pyrrolidin-1-ylcarbonyl)-7,9-dihydro-8H-purine-8-one (Example No. 170);

2-Benzyl-N-ethyl-N,9-dimethyl-8-oxo-8,9-dihydro-7H-purine-7-carboxamide (Example No. 278);

N-Ethyl-2-(4-fluorobenzyl)-N,9-dimethyl-8-oxo-8,9-dihydro-7H-purine-7-carboxamide (Example No. 279);

N-Ethyl-2-(4-methoxybenzyl)-N,9-dimethyl-8-oxo-8,9-dihydro-7H-purine-7-carboxamide (Example No. 280);

N-Ethyl-N,9-dimethyl-2-(4-methylbenzyl)-8-oxo-8,9-dihydro-7H-purine-7-carboxamide (Example No. 281);

N-Ethyl-N,9-dimethyl-2-(3-methylbenzyl)-8-oxo-8,9-dihydro-7H-purine-7-carboxamide (Example No. 282);

9-Butyl-2-phenyl-7-(pyrrolidin-1-ylcarbonyl)-7,9-dihydro-8H-purine-8-one (Example No. 306); and 2-(3-Aminophenyl)-9-methyl-7-(pyrrolidin-1-ylcarbonyl)-7,9-dihydro-8H-purine-8-one (Example No. 317).

Compound Group (B')

2-(3-Chlorobenzyl)-9-methyl-7-(pyrrolidin-1-ylcarbonyl)-7,9-dihydro-8H-purine-8-one (Example No. 19);

2-(3-Methoxyphenyl)-N,N,9-trimethyl-8-oxo-8,9-dihydro-7H-purine-7-carboxamide (Example No. 48);

N-(2-Methoxyethyl)-2-(3-methoxyphenyl)-N,9-dimethyl-8-oxo-8,9-dihydro-7H-purine-7-carboxamide (Example No. 59);

2-(3-Methoxyphenyl)-9-methyl-7-{[4-(2-phenylethyl-) piperazin-1-yl]carbonyl}-7,9-dihydro-8H-purine-8-one (Example No. 67);

N-(3-Fluorobenzyl)-2-(3-methoxyphenyl)-N,9-dimethyl-8-oxo-8,9-dihydro-7H-purine-7-carboxamide (Example No. 72);

7-{[4-(3-Chlorobenzyl)piperazin-1-yl]carbonyl}-2-(3-methoxyphenyl)-9-methyl-7,9-dihydro-8H-purine-8-one (Example No. 87);

2-(3-Methoxyphenyl)-9-methyl-7-{[4-(phenoxymethyl)piperidin-1-yl]carbonyl}-7,9-dihydro-8H-purine-8-one (Example No. 101);

N-(2-Chloroethyl)-2-(3-methoxyphenyl)-N,9-dimethyl-8-oxo-8,9-dihydro-7H-purine-7-carboxamide (Example No. 103);

7-{[4-(4-Chlorophenyl)piperazin-1-yl]carbonyl}-9-methyl-2-phenyl-7,9-dihydro-8H-purine-8-one (Example No. 126);

7-{[4-(4-Ethoxyphenyl)piperazin-1-yl]carbonyl}-9-methyl-2-phenyl-7,9-dihydro-8H-purine-8-one (Example No. 131);

7-{[4-(4-Fluorophenyl)piperazin-1-yl]carbonyl}-2-(3-methoxyphenyl)-9-methyl-7,9-dihydro-8H-purine-8-one (Example No. 136);

N-[2-(4-Chlorophenyl)ethyl]-2-cyclohexyl-N,9-dimethyl-8-oxo-8,9-dihydro-7H-purine-7-carboxamide (Example No. 156);

2-(3-Methoxyphenyl)-9-methyl-7-(pyrrolidin-1-ylcarbonyl)-7,9-dihydro-8H-purine-8-one (Example No. 173);

N-Ethyl-N,9-dimethyl-8-oxo-2-(pyridin-3-yl)-8,9-dihydro-7H-purine-7-carboxamide (Example No. 219);

7-Methyl-9-(pyrrolidin-1-ylcarbonyl)-2-[3-(trifluoromethoxy)phenyl]-7,9-dihydro-8H-purine-8-one (Example No. 236);

2-Benzyl-9-methyl-7-(pyrrolidin-1-ylcarbonyl)-7,9-dihydro-8H-purine-8-one (Example No. 253);

N-Ethyl-2-(3-fluorobenzyl)-N,9-dimethyl-8-oxo-8,9-dihydro-7H-purine-7-carboxamide (Example No. 284);

2-[2-(3-Fluorophenyl)ethyl]-7-methyl-9-(pyrrolidin-1-ylcarbonyl)-7,9-dihydro-8H-purine-8-one (Example No. 315);

2-(3-Methoxyphenyl)-N,N,7-trimethyl-8-oxo-7,8-dihydro-9H-purine-9-carboxamide (Example No. 322);

2-[4-(Difluoromethyl)phenyl]-N,N,7-trimethyl-8-oxo-7,8-dihydro-9H-purine-9-carboxamide (Example No. 330);

2-[3-(Difluoromethoxy)phenyl]-N,N,7-trimethyl-8-oxo-7,8-dihydro-9H-purine-9-carboxamide (Example No. 331);

2-[3-(Difluoromethyl)phenyl]-N,N,7-trimethyl-8-oxo-7,8-dihydro-9H-purine-9-carboxamide (Example No. 332);

N,N,7-Trimethyl-8-oxo-2-[4-(2,2,2-trifluoroethoxy)phenyl]-7,8-dihydro-9H-purine-9-carboxamide (Example No. 334);

2-[3-(2,2-Difluoroethoxy)phenyl]-N,N,7-trimethyl-8-oxo-7,8-dihydro-9H-purine-9-carboxamide (Example No. 335);

N,N,7-Trimethyl-8-oxo-2-[3-(2,2,2-trifluoroethoxy)phenyl)]-7,8-dihydro-9H-purine-9-carboxamide (Example No. 336);

2-[4-(Difluoromethoxy)phenyl]-N,N,7-trimethyl-8-oxo-7,8-dihydro-9H-purine-9-carboxamide (Example No. 337);

9-(Azetidin-1-ylcarbonyl)-2-(4-methoxyphenyl)-7-methyl-7,9-dihydro-8H-purine-8-one (Example No. 356);

7-(Azetidin-1-ylcarbonyl)-2-(3-methoxybenzyl)-9-methyl-7,9-dihydro-8H-purine-8-one (Example No. 375);

7-(Azetidin-1-ylcarbonyl)-9-methyl-2-[3-(trifluoromethyl)benzyl]-7,9-dihydro-8H-purine-8-one (Example No. 379);

7-(Azetidin-1-ylcarbonyl)-2-[(3-methoxyphenoxy)methyl]-9-methyl-7,9-dihydro-8H-purine-8-one (Example No. 404);

7-{[3-(2,4-Difluorophenyl)azetidin-1-yl]carbonyl}-2-(methoxymethyl)-9-methyl-7,9-dihydro-8H-purine-8-one (Example No. 454);

7-{[3-(4-Fluoro-3-methylphenyl)azetidin-1-yl]carbonyl}-2-(methoxymethyl)-9-methyl-7,9-dihydro-8H-purine-8-one (Example No. 455);

2-(Methoxymethyl)-7-{[3-(3-methoxyphenyl)azetidin-1-yl]carbonyl}-9-methyl-7,9-dihydro-8H-purine-8-one (Example No. 459);

2-(Ethoxymethyl)-9-methyl-7-[(3-phenylazetidin-1-yl)carbonyl]-7,9-dihydro-8H-purine-8-one (Example No. 460);

2-(Ethoxymethyl)-7-{[3-(3-fluorophenyl)azetidin-1-yl]carbonyl}-9-methyl-7,9-dihydro-8H-purine-8-one (Example No. 462);

2-(Ethoxymethyl)-7-{[3-(4-ethoxyphenyl)azetidin-1-yl]carbonyl}-9-methyl-7,9-dihydro-8H-purine-8-one (Example No. 463);

2-(Ethoxymethyl)-7-{[3-(2-fluorophenyl)azetidin-1-yl]carbonyl}-9-methyl-7,9-dihydro-8H-purine-8-one (Example No. 465);

7-{[3-(2-Fluorophenoxy)azetidin-1-yl]carbonyl}-2-(methoxymethyl)-9-methyl-7,9-dihydro-8H-purine-8-one (Example No. 479);

2-(Methoxymethyl)-9-methyl-7-{[(3R)-3-phenoxypyrrolidin-1-yl]carbonyl}-7,9-dihydro-8H-purine-8-one (Example No. 488);

7-({3-[(4-Fluorophenoxy)methyl]azetidin-1-yl}carbonyl)-2-(methoxymethyl)-9-methyl-7,9-dihydro-8H-purine-8-one (Example No. 492);

N,N,7-Trimethyl-2-[2-(4-methylphenyl)ethyl]-8-oxo-7,8-dihydro-9H-purine-9-carboxamide (Example No. 494);

2-[2-(2,4-Difluorophenyl)ethyl]-N,N,7-trimethyl-8-oxo-7,8-dihydro-9H-purine-9-carboxamide (Example No. 506);

2-{2-[3-(2,2-Difluoroethoxy)phenyl]ethyl}-N,N,7-trimethyl-8-oxo-7,8-dihydro-9H-purine-9-carboxamide (Example No. 530);

N,N,7-Trimethyl-8-oxo-2-{2-[4-(trifluoromethyl)phenyl]ethyl}-7,8-dihydro-9H-purine-9-carboxamide (Example No. 540);

N,N,7-Trimethyl-8-oxo-2-{2-[3-(2,2,2-trifluoroethoxy)phenyl]ethyl}-7,8-dihydro-9H-purine-9-carboxamide (Example No. 552);

N,N,7-Trimethyl-8-oxo-2-{2-[4-(2,2,2-trifluoroethoxy)phenyl]ethyl}-7,8-dihydro-9H-purine-9-carboxamide (Example No. 553);

9-(Azetidin-1-ylcarbonyl)-2-{2-[4-(difluoromethyl)phenyl]ethyl}-7-methyl-7,9-dihydro-8H-purine-8-one (Example No. 576);

9-(Azetidin-1-ylcarbonyl)-2-[2-(3,5-difluorophenyl)ethyl]-7-methyl-7,9-dihydro-8H-purine-8-one (Example No. 580);

9-(Azetidin-1-ylcarbonyl)-2-[2-(2-fluorophenyl)ethyl]-7-methyl-7,9-dihydro-8H-purine-8-one (Example No. 583);

9-(Azetidin-1-ylcarbonyl)-2-{2-[4-(2,2-difluoroethoxy)phenyl]ethyl}-7-methyl-7,9-dihydro-8H-purine-8-one (Example No. 593);

9-(Azetidin-1-ylcarbonyl)-7-methyl-2-{2-[3-(2,2,2-trifluoroethoxy)phenyl]ethyl}-7,9-dihydro-8H-purine-8-one (Example No. 612);

9-(Azetidin-1-ylcarbonyl)-7-methyl-2-{2-[4-(2,2,2-trifluoroethoxy)phenyl]ethyl}-7,9-dihydro-8H-purine-8-one (Example No. 613);

7-Methyl-9-[3-phenylazetidin-1-yl)carbonyl]-2-propyl-7,9-dihydro-8H-purine-8-one (Example No. 637);

9-(Azetidin-1-ylcarbonyl)-7-ethyl-2-[2-(2-fluorophenyl)ethyl]-7,9-dihydro-8H-purine-8-one (Example No. 649);

9-(Azetidin-1-ylcarbonyl)-7-ethyl-2-[2-(3-fluorophenyl)ethyl]-7,9-dihydro-8H-purine-8-one (Example No. 650);

9-(Azetidin-1-ylcarbonyl)-7-ethyl-2-[2-(4-fluorophenyl)ethyl]-7,9-dihydro-8H-purine-8-one (Example No. 651);

N,N,7-Trimethyl-8-oxo-2-[3-(trifluoromethyl)benzyl]-7,8-dihydro-9H-purine-9-carboxamide (Example No. 654);

9-Ethyl-2-(methoxymethyl)-7-[(3-phenylazetidin-1-yl)carbonyl]-7,9-dihydro-8H-purine-8-one (Example No. 655);

9-Ethyl-7-{[3-(4-fluorophenyl)azetidin-1-yl]carbonyl}-2-(methoxymethyl)-7,9-dihydro-8H-purine-8-one (Example No. 656);

9-Ethyl-7-{[3-(3-fluorophenyl)azetidin-1-yl]carbonyl}-2-(methoxymethyl)-7,9-dihydro-8H-purine-8-one (Example No. 657);

2-(Methoxymethyl)-7-[(3-phenylazetidin-1-yl)carbonyl]-9-propyl-7,9-dihydro-8H-purine-8-one (Example No. 658);

7-{[3-(4-Fluorophenyl)azetidin-1-yl]carbonyl}-2-(methoxymethyl)-9-propyl-7,9-dihydro-8H-purine-8-one (Example No. 659); and 7-{[3-(2-Fluorophenyl)azetidin-1-yl]carbonyl}-2-(methoxymethyl)-9-propyl-7,9-dihydro-8H-purine-8-one (Example No. 661).

Compound Group (C')

N,9-Dimethyl-8-oxo-2-phenyl-N-(4-phenylbutyl)-8,9-dihydro-7H-purine-7-carboxamide (Example No. 36);

2-(3-Methoxyphenyl)-N,9-dimethyl-8-oxo-N-(2-phenylethyl)-8,9-dihydro-7H-purine-7-carboxamide (Example No. 64);

2-(3-Methoxyphenyl)-N,9-dimethyl-8-oxo-N-(2-phenoxyethyl)-8,9-dihydro-7H-purine-7-carboxamide (Example No. 65);

7-({4-[2-(4-Chlorophenyl)ethyl]piperidin-1-yl}carbonyl)-2-(3-methoxyphenyl)-9-methyl-7,9-dihydro-8H-purine-8-one (Example No. 68);

N-[2-(4-Chlorophenyl)ethyl]-2-(3-methoxyphenyl)-N,9-dimethyl-8-oxo-8,9-dihydro-7H-purine-7-carboxamide (Example No. 69);

N-[2-(4-Fluorophenyl)ethyl]-2-(3-methoxyphenyl)-N,9-dimethyl-8-oxo-8,9-dihydro-7H-purine-7-carboxamide (Example No. 74);

N-[2-(3-Fluorophenyl)ethyl]-2-(3-methoxyphenyl)-N,9-dimethyl-8-oxo-8,9-dihydro-7H-purine-7-carboxamide (Example No. 75);

N-[2-(3-Chlorophenyl)ethyl]-2-(3-ethoxyphenyl)-N,9-dimethyl-8-oxo-8,9-dihydro-7H-purine-7-carboxamide (Example No. 76);

N-[2-(4-Chlorophenoxy)ethyl]-2-(3-methoxyphenyl)-N,9-dimethyl-8-oxo-8,9-dihydro-7H-purine-7-carboxamide (Example No. 77);

N-(4-Chlorobenzyl)-2-(3-methoxyphenyl)-N,9-dimethyl-8-oxo-8,9-dihydro-7H-purine-7-carboxamide (Example No. 78);

2-(3-Methoxyphenyl)-N,9-dimethyl-8-oxo-N-[4-(trifluoromethoxy)benzyl]-8,9-dihydro-7H-purine-7-carboxamide (Example No. 83);

N-[2-(3-Chlorophenoxy)ethyl]-2-(3-methoxyphenyl)-N,9-dimethyl-8-oxo-8,9-dihydro-7H-purine-7-carboxamide (Example No. 90);

N-[2-(4-Fluorophenoxy)ethyl]-2-(3-methoxyphenyl)-N,9-dimethyl-8-oxo-8,9-dihydro-7H-purine-7-carboxamide (Example No. 91);

2-(3-Methoxyphenyl)-N,9-dimethyl-8-oxo-N-{2-[4-(trifluoromethyl)phenyl]ethyl}-8,9-dihydro-7H-purine-7-carboxamide (Example No. 92);

2-(3-Methoxyphenyl)-N-[2-(4-methoxyphenyl)ethyl]-N,9-dimethyl-8-oxo-8,9-dihydro-7H-purine-7-carboxamide (Example No. 93);

7-({4-[(E)-2-(4-Chlorophenyl)ethenyl]-3,6-dihydropyridin-1(2H)-yl}carbonyl)-2-(3-methoxyphenyl)-9-methyl-7,9-dihydro-8H-purine-8-one (Example No. 94);

7-({4-[(E)-2-(4-Fluorophenyl)ethenyl]-3,6-dihydropyridin-1(2H)-yl}carbonyl)-2-(3-methoxyphenyl)-9-methyl-7,9-dihydro-8H-purine-8-one (Example No. 95);

2-(3-Methoxyphenyl)-N,9-dimethyl-8-oxo-N-[2-(3-phenyl-1,2,4-oxadiazol-5-yl)ethyl]-8,9-dihydro-7H-purine-7-carboxamide (Example No. 104);

N-[2-(3,4-Dichlorophenyl)ethyl]-2-(3-methoxyphenyl)-N,9-dimethyl-8-oxo-8,9-dihydro-7H-purine-7-carboxamide (Example No. 105);

N-[2-(Cyclohex-1-en-1-yl)ethyl]-2-(3-methoxyphenyl)-N,9-dimethyl-8-oxo-8,9-dihydro-7H-purine-7-carboxamide (Example No. 106);

N-(2-Cyclohexylethyl)-2-(3-methoxyphenyl)-N,9-dimethyl-8-oxo-8,9-dihydro-7H-purine-7-carboxamide (Example No. 109);

N-[2-(2,4-Dichlorophenyl)ethyl]-2-(3-methoxyphenyl)-N,9-dimethyl-8-oxo-8,9-dihydro-7H-purine-7-carboxamide (Example No. 110);

7-({4-[(E)-2-(4-Chlorophenyl)ethenyl]piperidin-1-yl}carbonyl)-2-(3-methoxyphenyl)-9-methyl-7,9-dihydro-8H-purine-8-one (Example No. 112);

N-{2-[4-(Dimethylamino)phenyl]ethyl}-2-(3-methoxyphenyl)-N,9-dimethyl-8-oxo-8,9-dihydro-7H-purine-7-carboxamide (Example No. 113);

N-[2-(Cyclopropylmethoxy)ethyl]-2-(3-methoxyphenyl)-N,9-dimethyl-8-oxo-8,9-dihydro-7H-purine-7-carboxamide (Example No. 116);

2-(3-Methoxyphenyl)-7-({4-[2-(4-methoxyphenyl)ethyl]piperidin-1-yl}carbonyl)-9-methyl-7,9-dihydro-8H-purine-8-one (Example No. 118);

7-{[4-(4-Ethoxyphenyl)piperazin-1-yl]carbonyl}-9-methyl-2-(pyridine-3-yl)-7,9-dihydro-8H-purine-8-one (Example No. 144);

N-[2-(4-Chlorophenyl)ethyl]-N,9-dimethyl-8-oxo-2-(pyridin-3-yl)-8,9-dihydro-7H-purine-7-carboxamide (Example No. 145);

N-[2-(4-Chlorophenoxy)ethyl]-N,9-dimethyl-8-oxo-2-(pyridin-3-yl)-8,9-dihydro-7H-purine-7-carboxamide (Example No. 146);

7-({4-[2-(4-Chlorophenyl)ethyl]piperidin-1-yl}carbonyl)-9-methyl-2-(pyridin-3-yl)-7,9-dihydro-8H-purine-8-one (Example No. 147);

N-[2-(4-Chlorophenyl)ethyl]-N,9-dimethyl-8-oxo-2-(pyridin-4-yl)-8,9-dihydro-7H-purine-7-carboxamide (Example No. 150);

N-[2-(4-Chlorophenoxy)ethyl]-N,9-dimethyl-8-oxo-2-(pyridin-4-yl)-8,9-dihydro-7H-purine-7-carboxamide (Example No. 151);

7-({4-[2-(4-Chlorophenyl)ethyl]piperidin-1-yl}carbonyl)-9-methyl-2-(pyridin-4-yl)-7,9-dihydro-8H-purine-8-one (Example No. 152);

2-Butyl-N-[2-(4-chlorophenyl)ethyl]-N,9-dimethyl-8-oxo-8,9-dihydro-7H-purine-7-carboxamide (Example No. 155);

2-Benzyl-N-[2-(4-chlorophenyl)ethyl]-N,9-dimethyl-8-oxo-8,9-dihydro-7H-purine-7-carboxamide (Example No. 158);

2-[2-(3-Fluorophenyl)ethyl]-N,N,7-trimethyl-8-oxo-7,8-dihydro-9H-purine-9-carboxamide (Example No. 165);

N-Ethyl-N,9-dimethyl-8-oxo-2-(pyridine-4-yl)-8,9-dihydro-7H-purine-7-carboxamide (Example No. 220);

N-Ethyl-2-(2-fluoropyridin-4-yl)-N,9-dimethyl-8-oxo-8,9-dihydro-7H-purine-7-carboxamide (Example No. 221);

N-[2-(4-Chlorophenyl)ethyl]-2-(2-fluoropyridin-4-yl)-N,9-dimethyl-8-oxo-8,9-dihydro-7H-purine-7-carboxamide (Example No. 222);

N-(2-Cyclohexylethyl)-N,9-dimethyl-8-oxo-2-(pyridin-4-yl)-8,9-dihydro-7H-purine-7-carboxamide (Example No. 223);

N,N,7-Trimethyl-8-oxo-2-[4-(trifluoromethyl)phenyl]-7,8-dihydro-9H-purine-9-carboxamide (Example No. 326);

2-[2-Fluoro-4-(trifluoromethyl)phenyl]-N,N,7-trimethyl-8-oxo-7,8-dihydro-9H-purine-9-carboxamide (Example No. 338);

2-[2-Chloro-4-(trifluoromethyl)phenyl]-N,N,7-trimethyl-8-oxo-7,8-dihydro-9H-purine-9-carboxamide (Example No. 339);

9-(Azetidin-1-ylcarbonyl)-2-[3-(4-fluorophenoxy)propyl]-7-methyl-7,9-dihydro-8H-purine-8-one (Example No. 401);

2-(Methoxymethyl)-9-methyl-7-[(3-phenylazetidin-1-yl)carbonyl]-7,9-dihydro-8H-purine-8-one (Example No. 438);

7-{[3-(4-Fluorophenyl)azetidin-1-yl]carbonyl}-2-(methoxymethyl)-9-methyl-7,9-dihydro-8H-purine-8-one (Example No. 439);

7-{[3-(3-fluorophenyl)azetidine-1-yl]carbonyl}-2-(methoxymethyl)-9-methyl-7,9-dihydro-8H-purine-8-one (Example No. 440);

7-{[3-(2-Fluorophenyl)azetidin-1-yl]carbonyl}-2-(methoxymethyl)-9-methyl-7,9-dihydro-8H-purine-8-one (Example No. 441);

2-(Methoxymethyl)-9-methyl-7-({[3-(3-trifluoromethyl)phenyl]azetidin-1-yl}carbonyl)-7,9-dihydro-8H-purine-8-one (Example No. 443);

7-{[3-(2-Chlorophenyl)azetidin-1-yl]carbonyl}-2-(methoxymethyl)-9-methyl-7,9-dihydro-8H-purine-8-one (Example No. 453);

7-({3-[4-(Benzyloxy)phenyl]azetidin-1-yl}carbonyl)-2-(methoxymethyl)-9-methyl-7,9-dihydro-8H-purine-8-one (Example No. 456);

2-(Methoxymethyl)-9-methyl-7-({3-[4-(trifluoromethoxy)phenyl]azetidin-1-yl}carbonyl)-7,9-dihydro-8H-purine-8-one (Example No. 458);

7-{[(3R)-3-(4-Fluorophenoxy)pyrrolidin-1-yl]carbonyl}-2-(methoxymethyl)-9-methyl-7,9-dihydro-8H-purine-8-one (Example No. 480);

7-{[(3S)-3-(3-Fluorophenoxy)pyrrolidin-1-yl]carbonyl}-2-(methoxymethyl)-9-methyl-7,9-dihydro-8H-purine-8-one (Example No. 482);

7-{[(3S)-3-(2-Fluorophenoxy)pyrrolidin-1-yl]carbonyl}-2-(methoxymethyl)-9-methyl-7,9-dihydro-8H-purine-8-one (Example No. 483);

2-(Methoxymethyl)-9-methyl-7-{[(3S)-3-(4-methylphenoxy)pyrrolidin-1-yl]carbonyl}-7,9-dihydro-8H-purine-8-one (Example No. 484);

2-(Methoxymethyl)-9-methyl-7-{[(3S)-3-(3-methylphenoxy)pyrrolidin-1-yl]carbonyl}-7,9-dihydro-8H-purine-8-one (Example No. 485);

2-(Methoxymethyl)-9-methyl-7-{[(3S)-3-(2-methylphenoxy)pyrrolidin-1-yl]carbonyl}-7,9-dihydro-8H-purine-8-one (Example No. 486);

7-{[(3R)-3-(3-Chlorophenoxy)pyrrolidin-1-yl]carbonyl}-2-(methoxymethyl)-9-methyl-7,9-dihydro-8H-purine-8-one (Example No. 487);

7-{[(3S)-3-(4-Chlorophenoxy)pyrrolidin-1-yl]carbonyl}-2-(methoxymethyl)-9-methyl-7,9-dihydro-8H-purine-8-one (Example No. 489);

7-{[(3S)-3-(3-Chlorophenoxy)pyrrolidin-1-yl]carbonyl}-2-(methoxymethyl)-9-methyl-7,9-dihydro-8H-purine-8-one (Example No. 490);

7-{[(3S)-3-(2-Cychlorophenoxy)pyrrolidin-1-yl]carbonyl}-2-(methoxymethyl)-9-methyl-7,9-dihydro-8H-purine-8-one (Example No. 491);

2-[2-(3,5-Difluorophenyl)ethyl]-N,N,7-trimethyl-8-oxo-7,8-dihydro-9H-purine-9-carboxamide (Example No. 497);

2-[2-(4-Fluorophenyl)ethyl]-N,N,7-trimethyl-8-oxo-7,8-dihydro-9H-purine-9-carboxamide (Example No. 533);

2-{2-[4-(2,2-Difluoroethoxy)phenyl]ethyl}-N,N,7-trimethyl-8-oxo-7,8-dihydro-9H-purine-9-carboxamide (Example No. 538);

9-(Azetidin-1-ylcarbonyl)-2-[2-(4-fluorophenyl)ethyl]-7-methyl-7,9-dihydro-8H-purine-8-one (Example No. 587);

2-[2-(3-Chlorophenoxy)ethyl]-N,N,7-trimethyl-8-oxo-7,8-dihydro-9H-purine-9-carboxamide (Example No. 641);

7-Ethyl-2-[2-(3-fluorophenyl)ethyl]-N,N-dimethyl-8-oxo-7,8-dihydro-9H-purine-9-carboxamide (Example No. 644);

7-Ethyl-2-[2-(4-fluorophenyl)ethyl]-N,N-dimethyl-8-oxo-7,8-dihydro-9H-purine-9-carboxamide (Example No. 645);

2-[2-(2-Fluorophenyl)ethyl]-N,N-dimethyl-8-oxo-7-propyl-7,8-dihydro-9H-purine-9-carboxamide (Example No. 646);

2-[2-(3-Fluorophenyl)ethyl]-N,N-dimethyl-8-oxo-7-propyl-7,8-dihydro-9H-purine-9-carboxamide (Example No. 647);

2-[2-(4-Fluorophenyl)ethyl]-N,N-dimethyl-8-oxo-7-propyl-7,8-dihydro-9H-purine-9-carboxamide (Example No. 648);

7-{[3-(3-Fluorophenyl)azetidin-1-yl]carbonyl}-2-(methoxymethyl)-9-propyl-7,9-dihydro-8H-purine-8-one (Example No. 660); and 2-(Methoxymethyl)-9-propyl-7-({3-[3-(trifluoromethyl)phenyl]azetidin-1-yl}carbonyl)-7,9-dihydro-8H-purine-8-one (Example No. 662).

Also, the compound represented by the general formula (1), (1-2a) or (1-2b) may be labeled with one or more isotope(s) (such as $^{3}H$, $^{14}C$ and $^{35}S$). The deuterium exchange product wherein any one or two or more of $^{1}H$ is/are exchanged to $^{2}H$ (D) in the compounds represented by these general formulae (1), (1-2a) and (1-2b) are also emcompassed in the compounds represented by these general formulae respectively.

When the compound represented by the general formula (1) contains a group being capable of forming a salt in the structure, the compound can be if necessary, an acid addition salt with a pharmaceutically acceptable inorganic or organic acid or an alkali addition salt. The pharmaceutically acceptable salt includes for example, in the case of acid addition salt, a salt with an inorganic acid such as hydrochloride, hydrobromide, sulfate and phosphate, a salt with an organic carboxylic acid such as formate, acetate, fumarate, maleate, oxalate, citrate, malate, tartrate, aspartate and glutamate, and a salt with a sulfonic acid such as methanesulfonate, benzenesulfonate, p-toluenesulfonate, hydroxybenzenesulfonate and dihydroxybenzenesulfonate, and includes in the case of alkali addition salt ammonium salt, lithium salt, sodium salt, potassium salt, calcium salt, magnesium salt and the others.

Also the present invention emcompasses a hydrate or a solvate such as ethanol solvate of the compound represented by the general formula (1) or a pharmaceutically acceptable salt thereof. Further the present invention emcompasses a stereoisomer such as any tautomer and optical isomer and any crystal form. These compounds can be optionally isolated by using a well known method to those skilled in the art such as silica gel column chromatography, HPLC, ion-exchange chromatography, recrystallization and the others.

To obtain the above-mentioned optical isomer purely, a well known optical resolution method to those skilled in the art can be used. Specifically, when the compound of the present invention or its intermediate contains a basic functional group, such compound, etc. can be separated by forming a salt thereof with an optical active acid (such as monocarboxylic acids such as mandelic acid, N-benzyloxy alanine, lactic acid, dicarboxylic acids such as tartalic acid, o-diisopropylidene tartalic acid and malic acid, and sulfonic acids such as camphorsulfonic acid and bromocamphorsulfonic acid) in an inert solvent and then by performing a recrystallization and the others. Also when the compound of the present invention or its intermediate contains an acidic functional group, such compounds, etc. can be separated by forming a salt thereof with an optical active amine (such as organic amines such as α-phenethylamine, kinin, quinidine, cinchonidine, cinchonine, strychnine and the others) and then by performing a recrystallization and the others. The temperature at forming the salt includes for example, a range of room temperature to a boiling point of the solvent used.

The novel compound having 8-oxodihydropurine of the present invention or a pharmaceutically acceptable salt thereof shows a FAAH inhibitory activity and can be thus used as a medicament for treatment or prophylaxis of depression, anxiety disorder or pains. The depression to be used herein includes for example, major depression and bipolar depression. The anxiety disorder to be used herein includes for example, generalized anxiety disorder, social anxiety disorder, panic disorder and posttraumatic stress disorder. The pains to be used herein include for example, neuropathic pain, inflammatory pain and cancer pain.

Also the present compound or a pharmaceutically acceptable salt thereof can be used as a medicament for treatment or prophylaxis of the other diseases related to FAAH or endogenous cannabinoid, such as Alzheimer's disease, cognition disorder, schizophrenia, Parkinson's disease, attention deficit hyperactivity disorder (ADHD), sleep disorder, glaucoma, multiple sclerosis, fibromyalgia, inflammation, colon cancer, rectum cancer, prostatic cancer, cancer-related anorexia, nausea, vomiting.

A variety of ingredients for formulation such as common pharmaceutically acceptable carriers, binders, stabilizers, excipients, diluents, pH buffering agents, disintegrants, solubilizers, solubilizing agents, tonicity agents and the others can be added into the medicament for treatment or prophylaxis of depression, anxiety disorder or pains of the present invention. Also these medicaments for treatment or prophylaxis can be administered orally or parenterally. Here when administered orally, the medicaments can be administered orally in usual dosage form such as tablets, pills, powdered drug, powders, granules, capsules, syrups, emulsions, suspensions and the other formulations. When administered parenterally, the medicaments can be formulated into the dosage form such as intravenous injections (drops), intramuscular injections, subcutaneous injections, paints, eye-drops, ointments, suppositories, creams, lotions, cataplasms, gells, tapes, solutions, inhalations, aerosols and the others.

The solid preparations such as tablets are prepared by mixing the active ingredient with common pharmaceutically acceptable carriers or excipients such as lactose, sucrose and corn starch, binders such as crystalline cellulose, hydroxypropyl cellulose, polyvinylpyrrolidone, hydroxypropylmethyl cellulose and the others, disintegrants such as sodium carboxymethyl cellulose and sodium carboxymethyl starch, lubricants such as stearic acid and magnesium stearate, preservatives or the others.

When administered parenterally, the active ingredient is dissolved or suspended in a pharmaceutically acceptable carrier such as water, physiological saline, oil and aqueous glucose solution, and if necessary, emulsifiers, stabilizers, salts for osmotic adjustment or buffers can be added thereto as additive.

The formulation of the present compound can be prepared according to a conventional method, and for example, in the case of tablets, the compound of the Example 1 20 mg, lactose 100 mg, crystalline cellulose 25 mg and magnesium stearate 1 mg are mixed and the resulting mixtures are compressed to prepare the desired formulations.

The dose and frequency of administration may vary depending on the administration method, and the ages, weights and conditions of the patients, but a local administration to the diseased sites is preferred. Also it is preferred to administer the pharmaceutical formulation to the patient once or twice or more per day. When administered twice or more, it is desirable to administer the pharmaceutical formulation daily or repeatedly at a suitable interval.

The dose is usually 10 μg to 2 g as an active ingredient per one adult patient, preferably 100 μg to 1 g, and more preferably 1 mg to 200 mg, and can be administered once daily or in devided doses. When administered parenterally, the dose is usually 0.1 mg to 100 mg per one adult patient, preferably 0.3 mg to 50 mg, and can be administered once daily or in devided doses. A sustained-release formulation also can be used to decrease the frequency of administration.

Also the medicament for treatment or prophylaxis of depression, anxiety disorder or pains can be applied as an animal medicament.

Process of Present Compound

The present compound or a pharmaceutically acceptable salt thereof is a novel compound and can be prepared for example, according to the below-mentioned method. Also the present compound can be prepared according to the equivalent process to the well known method.

The compound to be used in the below-mentioned process may form a salt thereof similar to those of the compound represented by the formula (1) within the range which doesn't interfere with the reaction.

Also, in each below-mentioned reaction, if the structure of the starting material contains the functional group which may be involved in a reaction, such as amino group, carboxyl group, hydroxy group and carbonyl group, these groups may be protected by introducing a common protecting group, and also in that case, if necessary, may be removed the protecting group to obtain the desired compound.

The protecting group to be used for an amino group includes for example, alkylcarbonyl group (such as acetyl group and propionyl group), formyl group, phenylcarbonyl group, alkyloxycarbonyl group (such as methoxycarbonyl group, ethoxycarbonyl group and tert-butoxycarbonyl group), phenyloxycarbonyl group, arylalkyloxycarbonyl group (such as benzyloxycarbonyl group), trityl group, phthaloyl group, tosyl group and benzyl group.

The protecting group to be used for a carboxyl group includes for example, alkyl group (such as methyl group, ethyl group, propyl group, isopropyl group, butyl group and tert-butyl group), phenyl group, benzyl group, trityl group and silyl group (such as trimethylsilyl group and tert-butyl-dimethylsilyl group).

The protecting group to be used for a hydroxy group includes for example, methyl group, tert-butyl group, allyl group, substituted methyl group (such as methoxymethyl group and methoxyethoxymethyl group), ethoxyethyl group, tetrahydropyranyl group, tetrahydrofuranyl group, trityl group, arylalkyl group (such as benzyl group), alkylcarbonyl group (such as acetyl group and propionyl group), formyl group, benzoyl group, arylalkyloxycarbonyl group (such as benzyloxycarbonyl group), silyl group (such as trimethylsilyl group and tert-butyl-dimethylsilyl group).

The protection of a carbonyl group is carried out by converting a carbonyl group into an acyclic ketal (such as dimethylketal and diethylketal) or a cyclic ketal (such as 1,3-dioxolane and 1,3-dioxane).

Procedure A

In the formula (1), the compound represented by the below-mentioned formula (3) wherein X represents the group represented by the formula [Q] can be prepared by reacting the compound of the below-mentioned formula (A) and the compound of the below-mentioned formula (B).

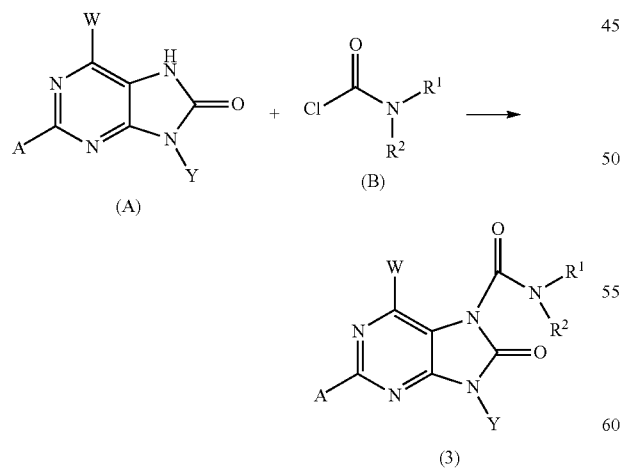

wherein A, W, Y, $R^1$ and $R^2$ are the same as defined in the above-mentioned [1].

The reaction between the compound of the formula (A) and the compound of the formula (B) can be usually carried out in a solvent-free or an appropriate solvent in the presence of a base under an atmospheric pressure condition or a pressured condition. The solvent used should be selected depending on the kind of starting materials and the others and includes for example, toluene, tetrahydrofuran, dioxane, ethyleneglycol dimethylether, methylene chloride, ethyl acetate, acetone, acetonitrile, N,N-dimethylformamide, 1-ethylpyrrolidin-2-one. These solvents may be used alone respectively or as a mixture of two or more of them. The base used includes for example, sodium hydride, triethylamine, 1,4-diazabicyclo[2.2.2]octane, potassium carbonate and sodium carbonate. The reaction temperature may be varied depending on the kind of starting materials used and the others and includes usually about −30° C. to about 150° C. and preferably about −10° C. to about 70° C.

The compound of the formula (B) to be used herein is commercially available, or may be prepared according to a well known method, for example, as those described in J. Am. Chem. Soc., 72, 1888 (1950); Tetrahedron Lett., 30, 3229 (1989).

The compound of the formula (A) to be used herein may be a well known product or may be prepared according to the equivalent process to those for the well known compound. The representative process is provided as below.

Process 1 of Compound of Formula (A)

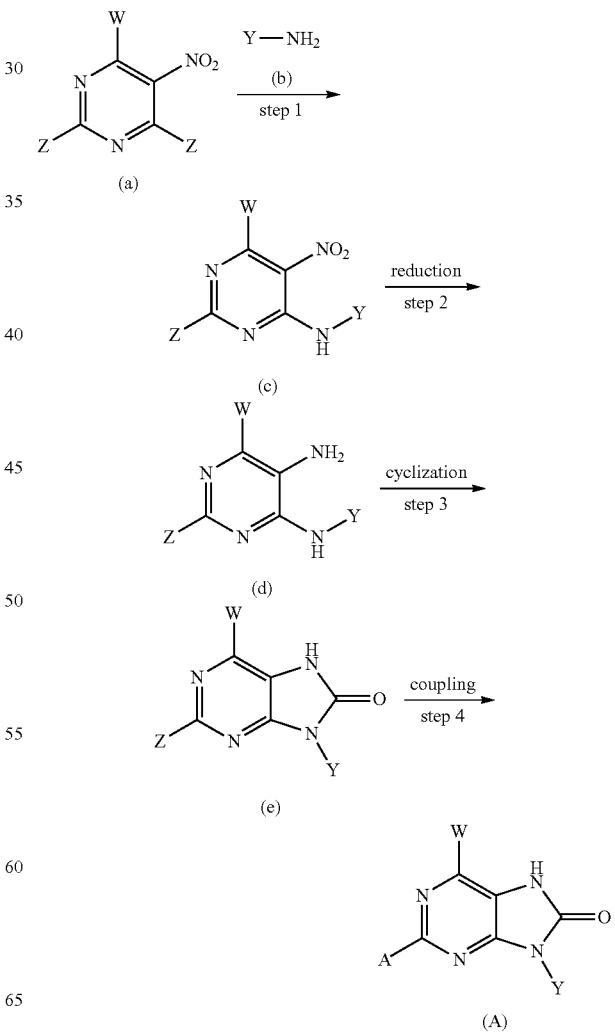

wherein Z represents a leaving group such as a halogen atom such as chlorine, bromine and iodine; a lower alkylsulfonyloxy group such as methanesulfonyloxy; trihalogenomethanesulfonyloxy group such as trifluoromethanesulfonyloxy; an arylsulfonyloxy group such as benzenesulfonyloxy and p-toluenesulfonyloxy; and the others, and in the compound of the formula (a), two Z are the same as or different from each other, and A, W and Y are the same as defined in the above-mentioned [1].

Step 1: Substitution Reaction

The reaction between the compound of the formula (a) and the compound of the formula (b) can be carried out in a solvent-free or an appropriate solvent under an atmospheric pressure condition or a pressured condition.

The solvent used should be selected depending on the kind of starting materials used and the others and includes for example, aromatic hydrocarbons such as benzene, toluene and xylene; ethers such as diethylether, tetrahydrofuran, cyclopentylmethylether and dioxane; halogenated hydrocarbons such as methylene chloride and chloroform; alcohols such as ethanol, isopropanol and ethylene glycol; ketones such as acetone and methyl ethyl ketone; ethyl acetate, acetonitrile, N,N-dimethylformamide, 1-methylpyrrolidin-2-one and dimethylsulfoxide. These solvents may be used alone respectively or as a mixture of two or more of them.

This reaction is carried out if necessary, in the presence of a base. Specific examples of the base include alkali hydroxides such as sodium hydroxide and potassium hydroxide; alkali carbonate such as sodium carbonate and potassium carbonate; alkali bicarbonate such as sodium bicarbonate and potassium bicarbonate; organic bases such as triethylamine, tributylamine, diisopropylethylamine and N-methylmorpholine; and the others, but excess amounts of the compound of the formula (b) can be replaced instead of the base. The compound of the formula (b) may be used in the form of acid addition salts such as those formed with hydrochloric acid and then may be formed a free base in the reaction system. The reaction temperature may be varied depending on the kind of starting materials and the others and includes usually about −10° C. to about 100 C.° and preferably about 0° C. to about 70° C.

The compound of the formula (a) to be used herein is commercially available, or may be prepared according to a well known method, for example, as those described in Chem. Ber., 39, 252 (1906) or the equivalent methods to them.

The compound of the formula (b) to be used herein is commercially available or may be prepared according to the well known method, for example, as those described in Ber., 50, 819 (1917) or the equivalent methods to them.

Step 2: Reduction Reaction

This reduction reaction can be carried out by a conventional method, for example, by reacting the compound of formula (c) with hydrogen in the presence of a catalyst such as palladium carbon, Raney nickel, platinum oxide and the others in an appropriate solvent. Also this reaction can be carried out by using a combination of a metal (such as tin, zinc and iron) or a metallic salt (such as stannous chloride) and an acid (such as hydrochloric acid and acetic acid) or iron or stannous chloride alone. The solvents to be used in these reactions include for example, alcohols such as ethanol and methanol, water, acetic acid, dioxane, tetrahydrofuran, N,N-dimethylformamide and the others. These solvents are used alone respectively or as a mixture of two or more of them. The reaction temperature may be varied depending on the kind of starting materials and the others and includes usually about 0° C. to about 80° C. and the reaction is carried out under an atmospheric pressure condition or a pressured condition.

Step 3: Cyclization Reaction

This cyclization reaction can be carried out by reacting the compound of the formula (d) with urea, carbonyl diimidazole, diethyl carbonate or phosgene or its equivalents (such as diphosgene, triphosgene and 4-nitrophenylchloro formate).

This reaction may be carried out in a solvent-free or an appropriate solvent under an atmospheric pressure condition or a pressured condition. The solvents include for example, tetrahydrofuran, dioxane, toluene, N,N-dimethylformamide and 1-methylpyrrolidin-2-one.

This reaction is carried out if necessary, in the presence of a base, and specific examples of the base include triethylamine, tributylamine, diisopropyl ethylamine and the others. The reaction temperature may be varied depending on the kind of starting materials and the others and includes usually about 20° C. to about 250° C. and preferably about 50° C. to about 220° C.

Step 4: Coupling Reaction

This coupling reaction may be carried out according to the methods described in for example, Tetrahedron Lett., 20, 3437 (1979); J. Org. Chem., 42, 1821 (1977); Bull. Chem. Soc. Jpn., 49, 1958 (1976); Angew. Chem. Int. Ed. Engl., 25, 508 (1986); J. Org. Chem., 37, 2320 (1972); Tetrahedron Lett., 50, 4467 (1975).

Specifically, the reaction is carried out for example, by reacting the compound of the formula (e) with an organic boron compound, an organic zinc compound, an organic magnesium compound, an organic tin compound, an alkene compound or an alkyne compound in the presence of an appropriate catalyst (such as palladium catalyst and nickel catalyst). This reaction is carried out if necessary, in the presence of the base, and specific examples of the base include sodium carbonate, potassium carbonate, cesium carbonate, triethylamine, tributylamine, diisopropylethylamine and the others. The reaction temperature may be varied depending on the kind of starting materials and the others and includes usually about 0° C. to about 250° C. and preferably about 20° C. to about 200° C.

Process 2 of Compound of Formula (A)

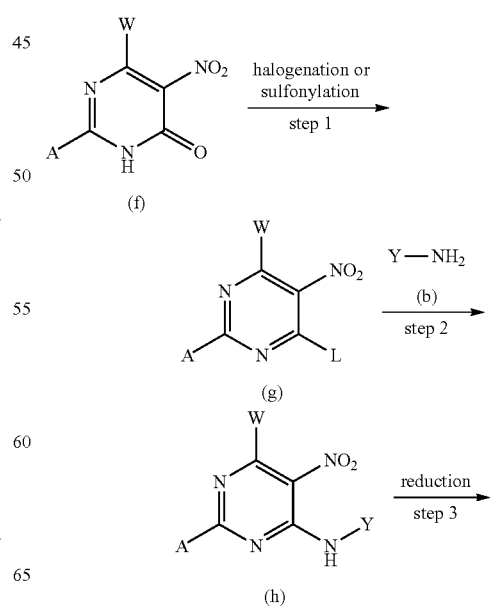

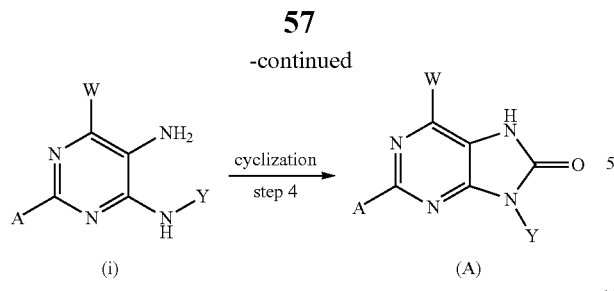

wherein L represents a leaving group (such as a halogen atom such as chlorine and bromine, a lower alkylsulfonyloxy group such as methanesulfonyloxy, a trihalogenomethanesulfonyloxy group such as trifluoromethanesulfonyloxy, and an arylsulfonyloxy group such as benzenesulfonyloxy and p-toluenesulfonyloxy), and A, W and Y are the same as defined in the above-mentioned [1].

Step 1: Halogenation or Sulfonylation Reaction

The halogenation reaction may be carried out for example, by reacting the compound of the formula (f) with a halogenating agent (such as phosphorus oxychloride and phosphorus tribromide). The sulfonylation reaction may be carried out for example, by reacting the compound of the formula (f) with a sulfonylating agent (such as methanesulfonyl chloride, p-toluenesulfonyl chloride and trifluoromethanesulfonyl chloride).

The compound of the formula (f) to be used herein is commercially available, or may be prepared according to a well known method, for example, as those described in *Angew. Chem.*, 76, 860 (1964); J. Med. Chem., 43, 4288 (2000) or the equivalent methods to them.

Step 2: Substitution Reaction

This reaction can be carried out by using the compound of the formula (g) according to the similar method to those described in the above-mentioned "Process 1 of Compound of Formula (A) (Step 1)".

Step 3: Reduction Reaction

This reaction may be carried out by using the compound of the formula (h) according to the similar method to those described in the above-mentioned "Process 1 of Compound of Formula (A) (Step 2)".

Step 4: Cyclization Reaction

This reaction may be carried out by using the compound of the formula (i) according to the similar method to those described in the above-mentioned "Process 1 of Compound of Formula (A) (Step 3)".

Process 3 of Compound of Formula (A)

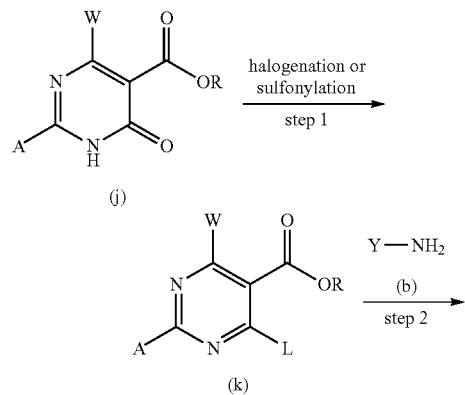

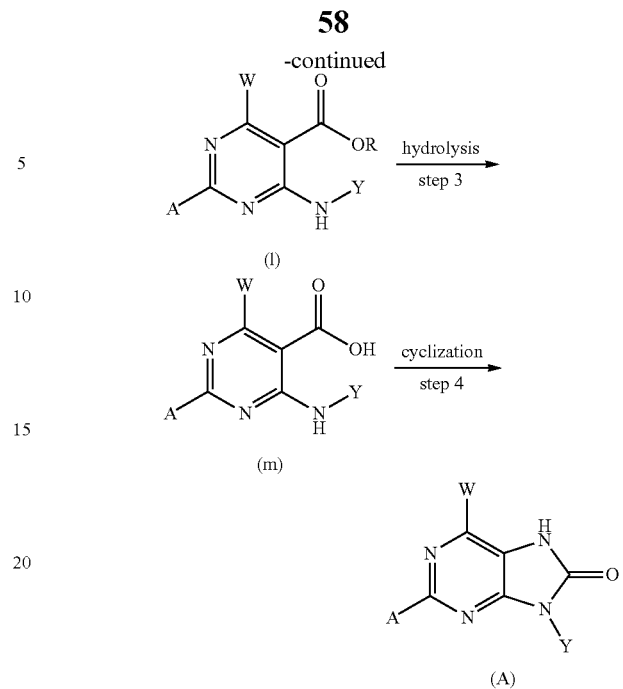

wherein R represents a $C_{1-6}$ alkyl group, and A, W and Y are the same as defined in the above-mentioned [1], and L is the same as defined in the above-mentioned "Process 2 of Compound of Formula (A)".

Step 1: Halogenation or Sulfonylation Reaction

This reaction may be carried out by using the compound of formula (j) according to the similar method to those described in the above-mentioned "Process 2 of Compound of Formula (A) (Step 1)".

The compound of the formula (j) to be used herein is commercially available, or may be prepared according to a well known method, for example, as those described in J. Med. Chem., 35, 4751 (1992); J. Org. Chem., 58, 4490 (1993) or the equivalent methods to them.

Step 2: Substitution Reaction

This reaction may be carried out by using the compound of the formula (k) according to the similar method to those described in the above-mentioned "Process 1 of Compound of Formula (A) (Step 1)" or the above-mentioned "Process 2 of Compound of Formula (A) (Step 2)".

Step 3: Hydrolysis Reaction

This hydrolysis reaction can be carried out by using the compound of formula (1) according to a conventional method, for example, by contacting the compound of formula (1) with water in an appropriate solvent under an acidic or basic condition using an acid or a base. The solvent used includes for example, alcohols such as methanol, ethanol, isopropanol and the others, tetrahydrofuran, dioxane, water and the others, and these solvents can be used alone respectively or as a mixture of two or more of them.

Specific examples of the acid include a mineral acid such as hydrochloric acid and sulfuric acid and the others, and an organic acid such as formic acid, acetic acid, propionic acid and oxalic acid. Specific examples of the base include alkali hydroxides such as sodium hydroxide and potassium hydroxide, and alkali carbonate such as sodium carbonate and potassium carbonate, and the others. The reaction temperature may be varied depending on the kind of starting materials and the others and includes usually about 0° C. to about 100° C.

Step 4: Cyclization Reaction

This cyclization reaction may be carried out by reacting the compound of the formula (m) with an azide compound. The azide compound used includes for example, diphenylphosphoryl azide and sodium azide.

This reaction may be carried out in a solvent-free or an appropriate solvent in the presence of a base under an atmospheric pressure condition or a pressured condition. The solvent includes for example, toluene, dimethoxyethane, acetone, methylethylketone, tetrahydrofuran, dioxane, ethyl acetate, N,N-dimethylformamide, 1-methylpyrrolidin-2-one and dimethylsulfoxide. The base includes for example, triethylamine, potassium carbonate and sodium carbonate. The reaction temperature may be varied depending on the kind of starting materials and the others and includes usually about 10° C. to about 150° C. and preferably about 30° C. to about 120° C.

Process 4 of Compound of Formula (A)

When in the above-mentioned process 1, process 2 or process 3, the substituent A in the compound of the formula (A) contains an unsaturated bond such as alkenyl group, a reduction treatment can produce the compound of the formula (A) wherein the substituent A is a group not containing an unsaturated bond such as alkyl group.

Process 5 of Compound of Formula (A)

When in the above-mentioned process 1, process 2 or process 3, the substituent A in the compound of formula (A) contains an alkenyl group, an ozonolysis treatment can produce an aldehyde compound. Also, reduction of the aldehyde group can produce an alcohol compound, which can be either further used in Mitsunobu reaction to produce an ester compound or can be further alkylated to produce an ether compound.

Process B

The below-mentioned compound of the formula (3) wherein X represents a group represented by the formula [Q] in the formula (1) can be prepared by reacting the below-mentioned compound of the formula (A), phosgene or its equivalent compound (such as diphosgene, triphosgene and 4-nitrophenyl chloroformate) and the below-mentioned compound of the formula (C).

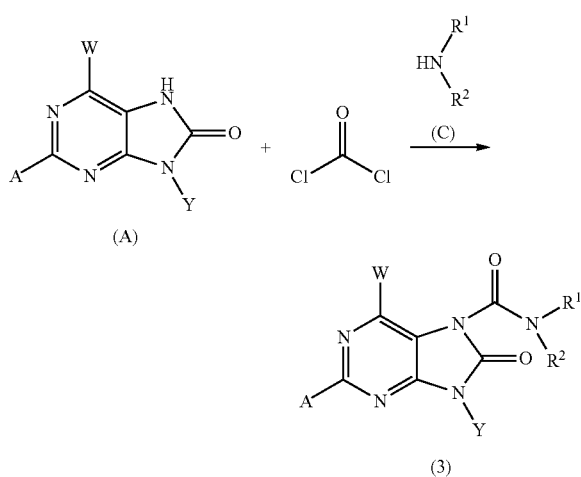

wherein A, W, Y, $R^1$ and $R^2$ are the same as defined in the above-mentioned [1].

This reaction is usually carried out in a solvent-free or an appropriate solvent in the presence of a base under an atmospheric pressure condition or a pressured condition. The compound of the formula (C) may be used in the form of acid addition salts such as those formed with hydrochloric acid and then may be formed a free base in the reaction system. The solvent used should be selected depending on the kind of starting materials and the others and includes for example, toluene, tetrahydrofuran, dioxane, ethyleneglycol dimethylether, methylene chloride, ethyl acetate, acetone, acetonitrile, N,N-dimethylformamide and 1-methylpyrrolidin-2-one. These solvents may be used alone respectively or as a mixture of two or more of them. The base includes for example, sodium hydride, triethylamine, diisopropylethylamine, 1,4-diazabicyclo[2.2.2]octane, potassium carbonate and sodium carbonate. The reaction temperature may be varied depending on the kind of starting materials and the others and includes usually about −30° C. to about 150° C. and preferably about −10° C. to about 70° C.

The compound of the formula (C) is commercially available, or may be prepared according to a well known method, for example, as those described in Arch. Pharm., 318, 727 (1985); Eur. J. Org. Chem., 12, 2582 (2004).

Process C

The compound of the formula (1) can be prepared by reacting the below-mentioned compound of the formula (D) with an organic boron compound, an organic zinc compound, an organic magnesium compound, an organic tin compound, an alkene compound or an alkyne compound.

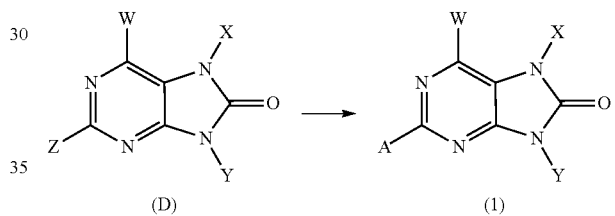

wherein wherein A, W, X and Y are the same as defined in the above-mentioned [1], and Z is the same as defined in the above-mentioned "Process 1 of Compound of Formula (A)".

This reaction can be carried out according to the similar method to those described in the above-mentioned "Process 1 of Compound of Formula (A) (Step 4)".

The compound of the formula (D) may be a well known product or may be prepared according to the equivalent process to those for the well known compound. The representative process is provided as below.

Process 1 of Compound of Formula (D)

The compound of the formula (D) wherein X represents a group represented by the formula [Q] can be prepared by reacting the above-mentioned compound of the formula (e) with the above-mentioned compound of the formula (B), or alternatively may be prepared by reacting the above-mentioned compound of the formula (e), the above-mentioned compound of the formula (C) and a phosgene or its equivalent compound (such as diphosgene, triphosgene and 4-nitrophenyl chloroformate).

This reaction can be carried out according to the similar method to those described in the above-mentioned "Process A" or "Process B".

Process 2 of Compound of Formula (D)

The compound of the formula (D) wherein Y represents a group represented by the formula [Q] can be prepared from the compound of the formula (n) according to the below-mentioned method.

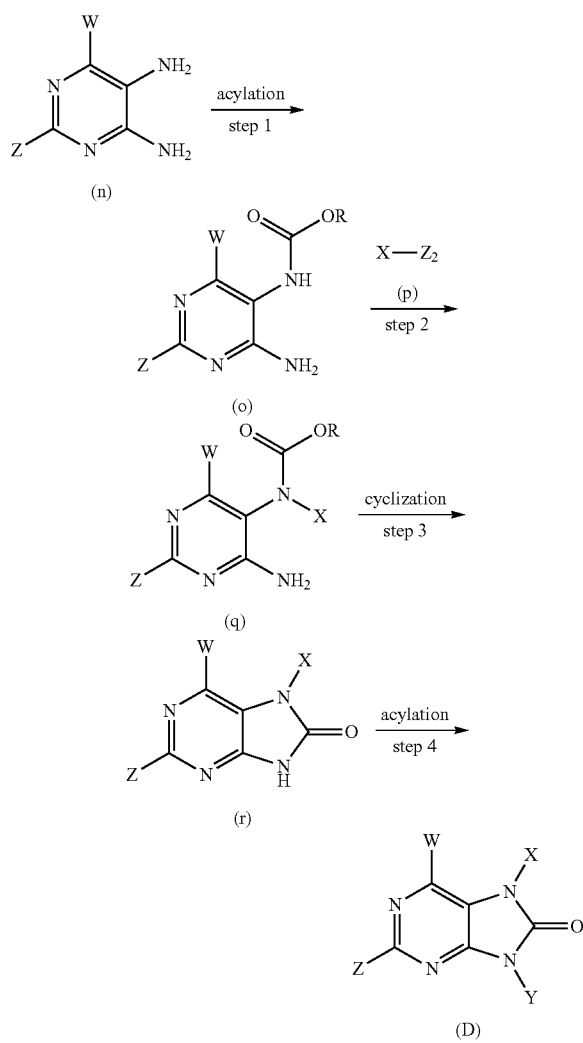

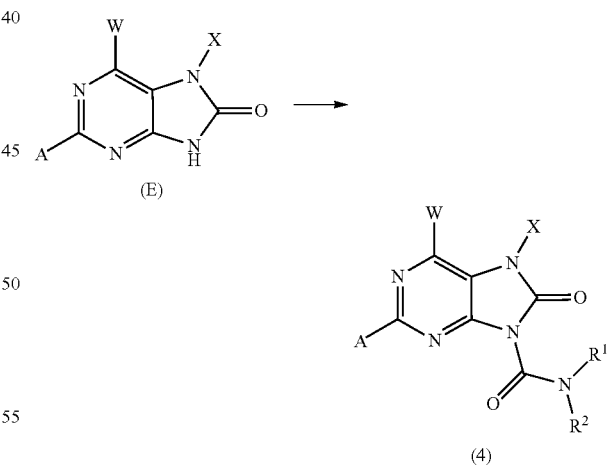

(4)

wherein R represents a $C_{1-6}$ alkyl group, and W, X and Y are the same as defined in the above-mentioned [1], and Z is the same as defined in the above-mentioned "Process 1 of Compound of Formula (A)" and $Z_2$ is the same as defined as Z.

The compound of the formula (n) can be prepared by reacting the above-mentioned compound of the formula (a) with an ammonia and then reducing a nitro group.

Step 1: Acylation Reaction

This reaction may be carried out by using the compound of the formula (n) and an alkyl chloroformate (such as methyl chloroformate and ethyl chloroformate) according to the similar method to those described in the above-mentioned Process A.

Step 2: Alkylation Reaction

The reaction between the compound of the formula (o) and the compound of the formula (p) can be carried out in a solvent-free or an appropriate solvent in the presence of a base under an atmospheric pressure condition or a pressured condition.

The solvent used should be selected depending on the kind of starting materials and the others and includes for example, benzene, toluene, xylene, diethylether, tetrahydrofuran, cyclopentylmethylether, dioxane, N,N-dimethylformamide and 1-methylpyrrolidin-2-one. These solvents may be used alone respectively or as a mixture of two or more of them.

Specific examples of the base include sodium hydride, sodium carbonate, potassium carbonate, sodium hydroxide, potassium hydroxide and the others. The reaction temperature may be varied depending on the kind of starting materials and the others and includes usually about −10° C. to about 100° C. and preferably about 0° C. to about 70° C.

Step 3: Cyclization Reaction

This cyclization reaction can be carried out by using the compound of the formula (q) in a solvent-free or an appropriate solvent in the presence of a base under an atmospheric pressure condition or a pressured condition.

The solvent used should be selected depending on the kind of starting materials and the others and includes for example, benzene, toluene, xylene, methanol, ethanol, 2-propanol, tetrahydrofuran, dioxane, N,N-dimethylformamide and 1-methylpyrrolidin-2-one. These solvents may be used alone respectively or as a mixture of two or more of them. Specific examples of the base include sodium methoxide, sodium ethoxide and the others. The reaction temperature may be varied depending on the kind of starting materials and the others and includes usually about 0° C. to about 150° C. and preferably about 20° C. to about 100° C.

Step 4: Acylation Reaction

This reaction may be carried out by using the compound of the formula (r) according to the similar method to those described in the above-mentioned Process A or Process B.

Process D

In the compound of the formula (1), the compound of the below-mentioned compound of the formula (4) wherein Y represents a group represented by the formula [Q] may be prepared by reacting the below-mentioned compound of the formula (E) and the compound of the formula (B), or alternatively may be prepared by reacting the below-mentioned compound of the formula (E), the compound of the formula (C) and phosgene or its equivalent compound (such as diphosgene, triphosgene and 4-nitrophenyl chloroformate).

wherein A, W and X are the same as defined in the above-mentioned [1].

This reaction may be carried out according to the similar method to those described in the above-mentioned "Process (A)" or "Process (B)".

The compound of the formula (E) can be prepared by using the compound of the formula (r) according to the similar method to the above-mentioned "Process 1 of Compound of Formula (A) (Step 4)".

EXAMPLES

Hereinafter, the present invention is explained in more detail with some Reference Examples and Examples, but the present invention should not be construed to be limited thereto. The compounds were identified by proton nuclear magnetic resonance spectrum ($^1$H-NMR), LC-MS and the others. Tetramethyl silane is used as an internal standard in the nuclear magnetic resonance spectrum analyses.

Hereinafter, the following abbreviations are sometimes used to simplify the description of the specification. Me: methyl, Et: ethyl, n-Pr: normal propyl, i-Pr: isopropyl, c-Pr: cyclopropyl, Bu: butyl, n-Bu: normal butyl, i-Bu: isobutyl, c-Bu: cyclobutyl, Ph: phenyl, Ac: acetyl, Boc: tert-butoxycarbonyl, Bn: benzyl, EDTA: ethylenediamine tetraacetate, BSA: bovine serum albumin, J: coupling constant, s: singlet, d: doublet, dd: double doublet, ddd: tetra doublet, td: triple doublet, t: triplet, dt: double triplet, tt: triple triplet, q: quartet, tq: triple quartet, quint: quintet, br: broad, m: multiplet.

Unless otherwise stated, the starting materials, the reagents and the solvents were commercially available.

Reference Example 1

Process of 2-chloro-9-methyl-7,9-dihydro-8H-purine-8-one

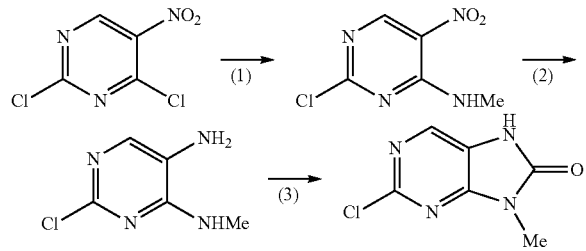

(1) To a solution of 2,4-dichloro-5-nitropyrimidine (20 g) in dichloromethane (200 ml) was added dropwise a mixture of 40% methylamine/methanol solution (7.5 ml) and triethylamine (15 mL) at 0° C. and the mixture was stirred for 1 hour. The solvent was evaporated under reduced pressure and the residue was dissolved in ethyl acetate, and was then filtered to remove the insoluble materials. The solvent was evaporated under reduced pressure and the residue was purified by silica gel column chromatography (eluent: hexane/ethyl acetate=100/0~0/100) to give 2-chloro-N-methyl-5-nitropyrimidin-4-amine 14 g.
$^1$H-NMR (CDCl$_3$) δ: 3.23 (3H, d, J=5.1 Hz), 8.40 (1H, s), 9.04 (1H, s).

(2) The mixture of the above-mentioned product (12.0 g), reduced iron (20.7 g), ammonium chloride (8.0 g), ethanol (100 ml) and water (100 ml) was heated under reflux for 1 hour. The reaction mixture was cooled to room temperature and was filtered through Celite, and ethanol was then evaporated under reduced pressure. To the obtained residue was added saturated brine (100 ml) and the mixture was extracted with chloroform (100 ml×2). The organic layer was dried over anhydrous sodium sulfate and was filtered, and the solvent was evaporated under reduced pressure to give 2-chloro-N$^4$-methylpyrimidin-4,5-diamine 7.3 g.
$^1$H-NMR (DMSO-d$_6$) δ: 2.83 (3H, d, J=4.6 Hz), 4.82 (2H, br s), 6.90-6.97 (1H, m), 7.35 (1H, s).

(3) The mixture of the above-mentioned product (2.1 g), carbonyldiimidazole (3.0 g) and tetrahydrofuran (20 ml) was heated under reflux for 12 hours. The solvent was evaporated under reduced pressure and the obtained crude solids were recrystallized from ethyl acetate to give the title compound 1.4 g.
$^1$H-NMR (DMSO-d$_6$) δ: 3.25 (3H, s), 8.10 (1H, s), 11.59 (1H, s).

Reference Example 2

Process of 2-chloro-7-methyl-7,9-dihydro-8H-purine-8-one

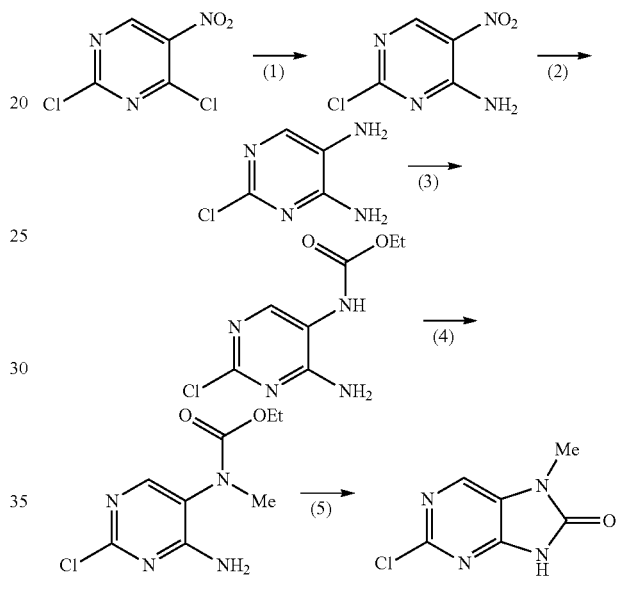

(1) To a solution of 2,4-dichloro-5-nitropyrimidine (50 g) in dichloromethane (400 ml) was added dropwise 2 mol/L ammonia/ethanol solution (387 mL) at 0° C. and the mixture was stirred at the same temperature for 20 minutes. The crystals precipitated were collected by filtration and was washed with ethyl acetate (100 ml) and water (150 ml), and was then dried to give 2-chloro-5-nitropyrimidin-4-amine 42 g.
$^1$H-NMR (DMSO-d$_6$) δ: 8.59 (1H, br s), 9.02 (1H, s), 9.19 (1H, br s).

(2) The mixture of the above-mentioned product (41 g), reduced iron (52 g), ammonium chloride (25 g), tetrahydrofuran (200 ml), ethanol (100 ml) and water (100 ml) was heated under reflux for 3 hours. The reaction mixture was cooled to room temperature and was filtered through Celite, and ethanol was then evaporated under reduced pressure. The crystals precipitated were collected by filtration and was dried to give 2-chloropyrimidin-4,5-diamine 28 g.
$^1$H-NMR (DMSO-d$_6$) δ: 4.89 (2H, br s), 6.89 (2H, br s), 7.40 (1H, s).

(3) To a solution of the above-mentioned product (22.0 g) in pyridine (100 ml) was added dropwise ethyl chloroformate (21.7 ml) at 0° C. and the mixture was stirred at room temperature for 3 hours. To the reaction mixture was added water (300 ml) and the mixture was extracted with ethyl acetate (500 ml×3). The organic layer was dried over anhydrous magnesium sulfate and was filtered, and the solvent was then evaporated under reduced pressure to give the crude solids. The obtained crude solids were recrystallized from a mixture solution of ethyl acetate and hexane to give ethyl (4-amino-2-chloropyrimidin-5-yl)carbamate 21.0 g.
$^1$H-NMR (CDCl$_3$) δ: 1.32 (3H, t, J=7.1 Hz), 4.24 (2H, q, J=7.1 Hz), 5.50 (2H, br s), 6.18 (1H, br s), 8.06 (1H, s).

(4) To a solution of the above-mentioned product (12.8 g) in N,N-dimethylformamide (80 ml) was added dropwise a suspension of 60% sodium hydride (2.6 g) in N,N-dimethylformamide (20 ml) at 0° C. Then, to the reaction mixture was added methyl iodide (7.4 ml) and the mixture was stirred at room temperature for 3 hours. To the reaction mixture was added water (200 ml) and the mixture was extracted with ethyl acetate (300 ml×3). The organic layer was dried over anhydrous magnesium sulfate and was filtered, and the solvent was then evaporated under reduced pressure to give crude solids. The obtained crude solids were recrystallized from a mixed solution of ethyl acetate and hexane to give ethyl (4-amino-2-chloropyrimidin-5-yl)methylcarbamate 7.2 g. And the filtrate was concentrated under reduced pressure, and the residue was purified by silica gel column chromatography (eluent: hexane/ethyl acetate=100/0~0/100) to give ethyl (4-amino-2-chloropyrimidin-5-yl)methylcarbamate 1.27 g.
$^1$H-NMR (CDCl$_3$) δ: 1.18-1.30 (3H, m), 3.20 (3H, s), 4.17 (2H, q, J=7.2 Hz), 5.49 (2H, br s), 8.01 (1H, s).

(5) To a solution of the above-mentioned product (8.40 g) in ethanol (80 ml) was added sodium ethoxide (4.96 g) and the mixture was heated under reflux for 1 hour. The ethanol was evaporated under reduced pressure, and the residue was adjusted to pH<1 with 1 mol/L hydrochloric acid (200 ml) and the mixture was extracted with ethyl acetate (200 ml×3). The organic layer was dried over anhydrous magnesium sulfate and was filtered, and the solvent was then evaporated under reduced pressure to give crude solids. The obtained crude solids were recrystallized from a mixed solution of ethyl acetate and hexane to give the title compound 6.63 g.
$^1$H-NMR (CDCl$_3$) δ: 3.46 (3H, s), 8.06 (1H, s).

Reference Example 3

Process of 9-methyl-2-[(E)-2-phenylethenyl]-7,9-dihydro-8H-purine-8-one

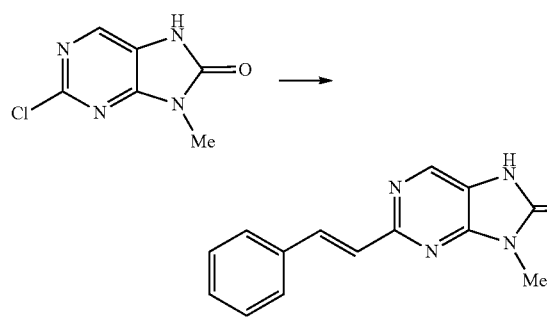

To a mixture of 2-chloro-9-methyl-7,9-dihydro-8H-purine-8-one <the compound of Reference Example 1> (200 mg), trans-2-phenylvinylboronic acid (192 mg), potassium carbonate (448 mg) and 1-methylpyrrolidin-2-one (3 ml) was added bis(tri-tert-butylphosphine)palladium (28 mg) under nitrogen atmosphere and the mixture was stirred at 150° C. under microwave irradiation for 1 hour. To the reaction mixture was added 1 mol/L hydrochloric acid (50 ml) and the crude solids precipitated were collected by filtration. The obtained crude solids were purified by silica gel column chromatography (eluent: chloroform/methanol=100/0~90/10) to give the title compound 179 mg.
$^1$H-NMR (DMSO-d$_6$) δ: 3.33 (3H, s), 7.19 (1H, d, J=16.0 Hz), 7.27-7.45 (3H, m), 7.65-7.72 (2H, m), 7.77 (1H, d, J=16.0 Hz), 8.22 (1H, s), 11.37 (1H, s).

Reference Examples 4 to 10

The compounds indicated in Table 1 were prepared according to the similar method to those of Reference Example 3.

TABLE 1

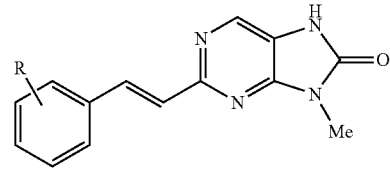

| Ref. Ex. No. | R | $^1$H-NMR (DMSO-d$_6$) δ |
|---|---|---|
| 4 | 4-Cl | 3.34 (3H, s), 7.23 (1H, d, J = 16.1 Hz), 7.43-7.49 (2H, m), 7.70-7.81 (3H, m), 8.23 (1H, s), 11.40 (1H, br s). |
| 5 | 4-OMe | 3.33 (3H, s), 3.79 (3H, s), 6.93-7.02 (2H, m), 7.06 (1H, d, J = 16.1 Hz), 7.60-7.69 (2H, m), 7.74 (1H, d, J = 16.1 Hz), 8.20 (1H, s), 11.33 (1H, br s). |
| 6 | 4-Me | 2.31 (3H, s), 3.32 (3H, s), 7.13 (1H, d, J = 16.1 Hz), 7.16-7.28 (2H, m), 7.53-7.66 (2H, m), 7.74 (1H, d, J = 16.1 Hz), 8.20 (1H, s), 11.35 (1H, br s). |
| 7 | 4-F | 3.32 (3H, s), 7.16-7.28 (3H, m), 7.70-7.83 (3H, m), 8.22 (1H, s), 11.39 (1H, s). |
| 8 | 3-F | 3.34 (3H, s), 7.12-7.20 (1H, m), 7.29 (1H, d, J = 16.1 Hz), 7.40-7.48 (1H, m), 7.50-7.56 (1H, m), 7.57-7.64 (1H, m), 7.77 (1H, d, J = 16.1 Hz), 8.24 (1H, s), 11.42 (1H, br s). |
| 9 | 3-CF$_3$ | 3.33 (3H, s), 7.36 (1H, d, J = 16.1 Hz), 7.58-7.70 (2H, m), 7.86 (1H, d, J = 16.1 Hz), 8.00-8.07 (2H, m), 8.24 (1H, s), 11.44 (1H, br s). |
| 10 | 3-OMe | 3.35 (3H, s), 3.80 (3H, s), 6.87-6.93 (1H, m), 7.20-7.34 (3H, m), 7.21 (1H, d, J = 16.1 Hz), 7.75 (1H, d, J = 16.1 Hz), 8.22 (1H, s), 11.38 (1H, br s). |

Reference Example 11

Process of 9-methyl-2-(2-phenylethyl)-7,9-dihydro-8H-purine-8-one

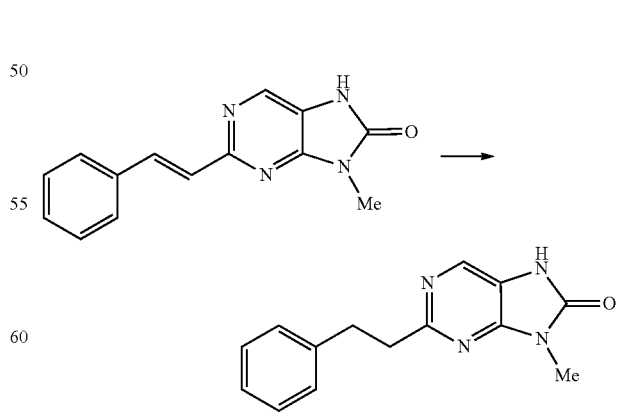

To a mixture of 9-methyl-2-[(E)-2-phenylethenyl]-7,9-dihydro-8H-purine-8-one <the compound of Reference Example 3> (80 mg), N,N-dimethylformamide (2 ml) and ethanol (3 ml) was added 10% palladium on carbon (2 mg) and the mixture was stirred at room temperature under hydrogen atmosphere for 1 hour. The reaction mixture was filtered through Celite and the filtrate was concentrated under reduced pressure. The obtained residue was purified by silica gel column chromatography (eluent: hexane/ethyl acetate=100/0~0/100) to give the title compound 47 mg.

$^1$H-NMR (CDCl$_3$) δ: 3.10-3.29 (4H, m), 3.48 (3H, s), 7.12-7.33 (5H, m), 8.20 (1H, s), 8.61 (1H, br s).

Reference Examples 12 to 14

The compounds indicated in Table 2 were prepared according to the similar method to those of Reference Example 11.

TABLE 2

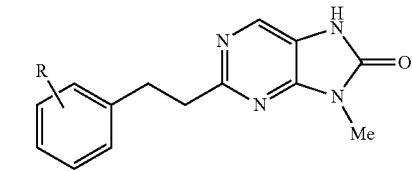

| Ref. Ex. No. | R | $^1$H-NMR |
|---|---|---|
| 12 | 4-OMe | (CDCl$_3$) δ: 3.05-3.25 (4H, m), 3.48 (3H, s), 3.78 (3H, s), 6.79-6.85 (2H, m), 7.14-7.20 (2H, m), 8.20 (1H, s), 8.67 (1H, br s). |
| 13 | 3-F | (DMSO-d$_6$) δ: 3.02-3.17 (4H, m), 3.26 (3H, s), 6.93-7.02 (1H, m), 7.03-7.13 (2H, m), 7.23-7.33 (1H, m), 8.12 (1H, s), 11.25 (1H, br s). |
| 14 | 3-CF$_3$ | (DMSO-d$_6$) δ: 3.12-3.21 (4H, m), 3.27 (3H, s), 7.45-7.62 (4H, m), 8.14 (1H, s), 11.26 (1H, s). |
| 15 | 3-OMe | (DMSO-d$_6$) δ: 2.96-3.14 (4H, m), 3.28 (3H, s), 3.71 (3H, s), 6.67-6.77 (1H, m), 7.08-7.39 (3H, m), 8.14 (1H, s), 11.30 (1H, br s). |

Reference Example 16

Process of 2-chloro-9-methyl-7-(pyrrolidin-1-ylcarbonyl)-7,9-dihydro-8H-purine-8-one

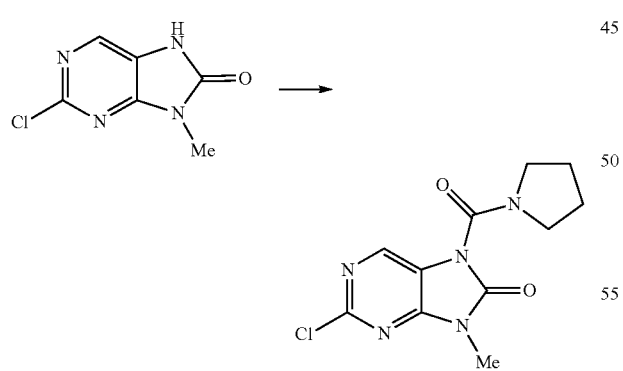

To a solution of 2-chloro-9-methyl-7,9-dihydro-8H-purine-8-one <the compound of Reference Example 1> (3.0 g) in N,N-dimethylformamide (50 ml) were added 1,4-diazabicyclo[2.2.2]octane (5.5 g) and 1-pyrrolidine carbonyl chloride (2.7 ml) and the mixture was stirred for 1 hour. The reaction mixture was poured into cold water and the crystals precipitated were collected by filtration to give the title compound 3.0 g.

$^1$H-NMR (CDCl$_3$) δ: 1.90-2.09 (4H, m), 3.47 (3H, s), 3.63-3.71 (4H, m), 8.43 (1H, s).

Reference Examples 17 to 18

The compounds indicated in Table 3 were prepared according to the similar method to those of Reference Example 16.

TABLE 3

| Ref. Ex. No. | Structure | $^1$H-NMR (CDCl$_3$) δ |
|---|---|---|
| 17 | 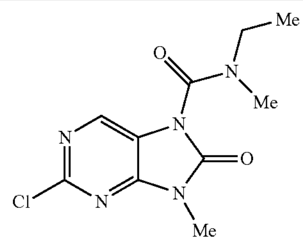 [SMILES: CCN(C)C(=O)n1c(=O)n(C)c2nc(Cl)ncc21] | 1.30 (3H, t, J = 7.0 Hz), 3.11 (3H, s), 3.41-3.61 (5H, m), 8.36 (1H, s). |
| 18 | 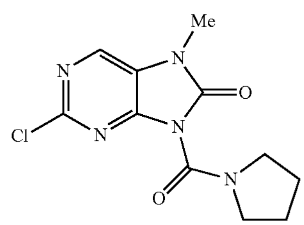 [SMILES: Cn1c(=O)n(C(=O)N2CCCC2)c2nc(Cl)ncc21] | 1.93-2.09 (4H, m), 3.46 (3H, s), 3.54 (2H, t, J = 6.6 Hz), 3.72 (2H, t, J = 7.0 Hz), 8.10 (1H, s). |

Reference Example 19

Process of 2-(3-chlorobenzyl)-9-methyl-7,9-dihydro-8H-purine-8-one

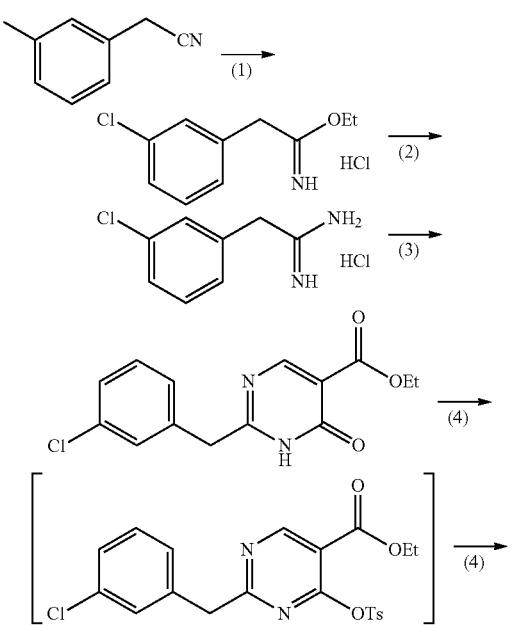

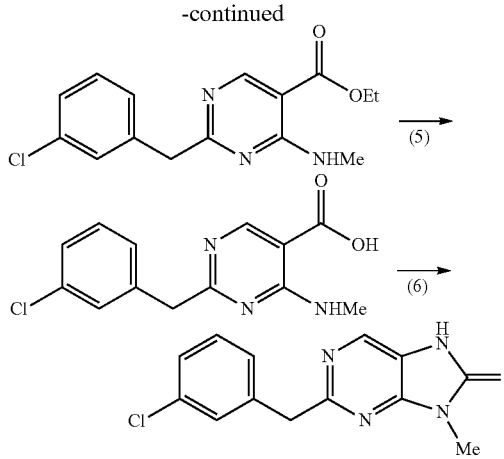

(1) To a solution of (3-chlorophenyl)acetonitrile (10 g) in ethanol (50 ml) was added dropwise 4 mol/L hydrogen chloride/dioxane solution (50 ml) at room temperature and the mixture was stirred for 12 hours. The solvent was evaporated under reduced pressure, and the obtained crystals were washed with diethyl ether (300 ml) and were dried to give ethyl 2-(3-chlorophenyl)ethaneimidate hydrochloric acid salt 11 g.

(2) To a mixture solution of the above-mentioned product (11 g) and 2-propanol (20 ml) was added 2 mol/L ammonia/2-propanol solution (40 ml) and the mixture was stirred for 12 hours. The solvent was evaporated under reduced pressure, and the obtained crystals were washed with ethyl acetate (100 ml) and were dried to give 2-(3-chlorophenyl)ethaneimidamide hydrochloric acid salt 5.0 g.
LC-MS, m/z; 169 (M+H)$^+$ESI (3) To a mixture of the above-mentioned product (4.7 g), sodium ethoxide (3.2 g) and ethanol (100 ml) was added diethyl ethoxymethylenemalonate (4.5 g) and the mixture was heated under reflux for 5 hours. The solvent was evaporated under reduced pressure and the residue was diluted with water and was then neutralized with 2 mol/L hydrochloric acid, and the mixture was extracted with chloroform (100 ml). The organic layer was dried over anhydrous sodium sulfate and was filtered, and the solvent was then evaporated under reduced pressure. The obtained residue was purified by silica gel column chromatography (eluent: chloroform/ethyl acetate=100/0~0/100) to give ethyl 2-(3-chlorobenzyl)-6-oxo-1,6-dihydro-pyrimidine-5-carboxylate 5.0 g.
$^1$H-NMR (CDCl$_3$) δ: 1.38 (3H, t, J=7.1 Hz), 4.06 (2H, s), 4.40 (2H, q, J=7.1 Hz), 7.25-7.32 (4H, m), 7.41 (1H, s), 8.77 (1H, br s).

(4) To a mixture of the above-mentioned product (5.0 g), triethylamine (5 ml) and dichloromethane (50 ml) was added p-toluenesulfonyl chloride (3.4 g) at room temperature and the mixture was stirred for 1 hour, and to the reaction mixture was then added 40% methylamine/methanol solution (5 ml) and the mixture was stirred for another 2 hours. The mixture was washed with water (30 ml) and the organic layer was then dried over anhydrous sodium sulfate and was filtered, and the solvent was evaporated under reduced pressure. The obtained residue was purified by silica gel column chromatography (eluent: hexane/ethyl acetate=100/0~0/100) to give ethyl 2-(3-chlorobenzyl)-4-(methylamino)pyrimidine-5-carboxylate 3.4 g.

$^1$H-NMR (CDCl$_3$) δ: 1.36 (3H, t, J=7.1 Hz), 3.06 (3H, d, J=5.0 Hz), 4.05 (2H, s), 4.32 (2H, q, J=7.1 Hz), 7.17-7.28 (3H, m), 7.40 (1H, s), 8.09 (1H, br s), 8.75 (1H, s).

(5) To a solution of the above-mentioned product (3.4 g) in ethanol (50 ml) was added 2 mol/L aqueous sodium hydroxide solution and the mixture was stirred at 40° C. for 30 minutes. The ethanol was evaporated under reduced pressure, and to the residue was added water and then the mixture was neutralized with 2 mol/L hydrochloric acid. The crystals precipitated were collected by filtration and was dried to give 2-(3-chlorobenzyl)-4-(methylamino)pyrimidine-5-carboxylate 3.0 g.
$^1$H-NMR (DMSO-d$_6$) δ: 2.95 (3H, d, J=4.8 Hz), 4.02 (2H, s), 7.25-7.36 (3H, m), 7.40 (1H, s), 8.34 (1H, br s), 8.62 (1H, s), 13.27 (1H, br s).

(6) The above-mentioned product (3.0 g), diphenylphosphoryl azide (3.5 g), triethylamine (2 ml) and 1-methylpyrrolidin-2-one (30 ml) were mixed, and the mixture was stirred at room temperature for 30 minutes and was then heated to 120° C. and was stirred for 3 hours. The reaction mixture was poured into water (100 ml) and the mixture was extracted with ethyl acetate (100 ml). The organic layer was dried over anhydrous sodium sulfate and was filtered, and the solvent was evaporated under reduced pressure. The obtained residue was purified by silica gel column chromatography (eluent: hexane/ethyl acetate=100/0~0/100) to give the title compound 2.0 g.
$^1$H-NMR (CDCl$_3$) δ: 3.47 (3H, s), 4.21 (2H, s), 7.16-7.28 (3H, m), 7.36 (1H, s), 8.20 (1H, s), 8.97 (1H, br s).

Reference Example 20

Process of 2-cyclohexyl-9-methyl-7,9-dihydro-8H-purine-8-one

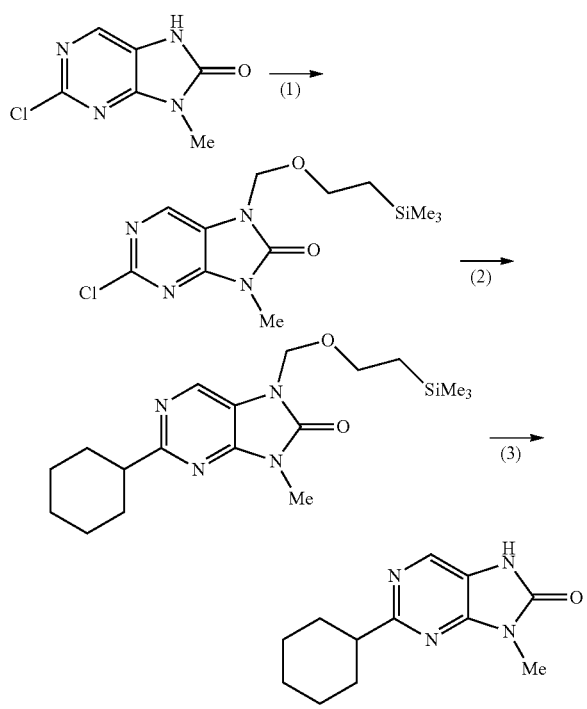

(1) To a mixture of 2-chloro-9-methyl-7,9-dihydro-8H-purine-8-one <the compound of Reference Example 1> (3.0 g), cesium carbonate (6.4 g) and N,N-dimethylformamide (50 ml) was added dropwise 2-(trimethylsilyl)ethoxymethylchloride (3.4 ml) at room temperature and the mixture was stirred for minutes. To the reaction mixture was added water (100 ml) and the mixture was extracted with ethyl acetate (100 ml×2). The organic layer was dried over anhydrous magnesium sulfate and was filtered, and the solvent was evaporated under reduced pressure. The obtained residue was purified by silica gel column chromatography (eluent: hexane/ethyl acetate=100/0~0/100) to give 2-chloro-9-methyl-7-{[2-(trimethylsilyl)ethoxy]methyl}-7,9-dihydro-8H-purine-8-one 3.1 g.

$^1$H-NMR (CDCl$_3$) δ: −0.01 (9H, s), 0.93 (2H, t, J=8.3 Hz), 3.49 (3H, s), 3.60 (2H, d, J=8.3 Hz), 5.31 (2H, s), 8.17 (1H, s).

(2) The above-mentioned product (1.0 g), bis(tri-tert-butylphosphine)palladium (49 mg) and 0.5 mol/L cyclohexyl zinc bromide/tetrahydrofuran solution (13.0 ml) were mixed under nitrogen atmosphere and the mixture was stirred at 100° C. under microwave irradiation for 1 hour. The reaction mixture was filtered through Celite and the filtrate was concentrated under reduced pressure. The obtained residue was purified by amino column chromatography (eluent: hexane/ethyl acetate=100/0~0/100) to give 2-cyclohexyl-9-methyl-7-{[2-(trimethylsilyl)ethoxy]methyl}-7,9-dihydro-8H-purine-8-one 899 mg.

$^1$H-NMR (CDCl$_3$) δ: −0.04 (9H, s), 0.87-0.99 (2H, m), 1.18-1.78 (6H, m), 1.80-2.06 (4H, m), 2.72-2.97 (1H, m), 3.45 (3H, s), 3.55-3.63 (2H, m), 5.28 (2H, s), 8.23 (1H, s).

(3) The above-mentioned product (899 mg) and 1 mol/L tetrabutyl ammonium fluoride/tetrahydrofuran solution (15 ml) were mixed and the mixture was heated under reflux for 24 hours. The reaction mixture was cooled to room temperature, and thereto was then added water (50 ml) and the mixture was extracted with ethyl acetate (50 ml×2). The solvent was evaporated under reduced pressure and the obtained residue was purified by silica gel column chromatography (eluent: hexane/ethyl acetate=100/0~0/100). The obtained crude crystals were recrystallized from a solution of ethyl acetate and hexane to give the title compound 304 mg.

$^1$H-NMR (CDCl$_3$) δ: 1.21-1.51 (4H, m), 1.56-1.80 (2H, m), 1.81-1.92 (2H, m), 1.95-2.07 (2H, m), 2.79-2.92 (1H, m), 3.50 (3H, s), 8.26 (1H, s), 9.94 (1H, br s).

Reference Examples 21 to 34

The compounds indicated in Table 4 were prepared according to the similar method to those of Reference Example 19 or 20.

TABLE 4

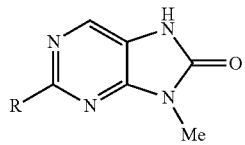

| Ref. Ex. No. | R | $^1$H-NMR or LC-MS |
|---|---|---|
| 21 | Ph | (CDCl$_3$) δ: 3.57 (3H, s), 7.45-7.53 (3H, m), 8.36 (1H, s), 8.40-8.45 (2H, m), 8.60 (1H, br s). |
| 22 | 3-Cl-C$_6$H$_4$ | (DMSO-d$_6$) δ: 3.36 (3H, s), 7.47-7.54 (2H, m), 8.25-8.34 (3H, m), 11.49 (1H, br s). |
| 23 | 4-Cl-C$_6$H$_4$ | (DMSO-d$_6$) δ: 3.33 (3H, s), 7.48-7.61 (2H, m), 8.27-8.43 (3H, m), 11.45 (1H, br s). |
| 24 | 3-MeO-C$_6$H$_4$ | (DMSO-d$_6$) δ: 3.36 (3H, s), 3.82 (3H, s), 6.98-7.19 (1H, m), 7.36 (1H, t, J = 8.0 Hz), 7.85-7.99 (2H, m), 8.31 (1H, s), 11.44 (1H, br s). |
| 25 | 4-Cl-C$_6$H$_4$-CH$_2$ | (CDCl$_3$) δ: 3.45 (3H, s), 4.19 (2H, s), 7.14-7.38 (4H, m), 8.17 (1H, s), 9.65 (1H, br s). |
| 26 | Ph-(CH$_2$)$_3$ | (CDCl$_3$) δ: 2.08-2.23 (2H, m), 2.72 (2H, t, J = 7.7 Hz), 2.98 (2H, t, J = 7.7 Hz), 3.43 (3H, s), 7.11-7.35 (5H, m), 8.20 (1H, s), 8.61 (1H, br s). |
| 27 | 3-pyridyl | (DMSO-d$_6$) δ: 3.27 (3H, s), 7.03-7.49 (4H, m), 8.16 (1H, s), 11.66 (1H, br s). |
| 28 | 4-pyridyl | (DMSO-d$_6$) δ: 3.38 (3H, s), 8.18-8.26 (2H, m), 8.38 (1H, s), 8.64-8.76 (2H, m), 11.61 (1H, br s). |
| 29 | c-Pr | (CDCl$_3$) δ: 0.97-1.15 (4H, m), 2.16-2.28 (1H, m), 3.31 (3H, s), 8.52 (1H, s), 9.94 (1H, br s). |
| 30 | n-Pr | LC-MS, m/z; 193 (M + H)$^+$ ESI |
| 31 | Me | LC-MS, m/z; 165 (M + H)$^+$ ESI |
| 32 | n-Bu | LC-MS, m/z; 185 (M + H)$^+$ ESI |
| 33 | CMe$_2$-CH$_2$-Me (t-pentyl) | LC-MS, m/z; 219 (M + H)$^+$ ESI |
| 34 | Bn | (DMSO-d$_6$) δ: 4.12 (3H, s), 5.34 (2H, s), 7.07-7.51 (5H, m), 7.96 (1H, s), 11.26 (1H, br s). |

Reference Example 35

Process of 2-[2-(3-fluorophenyl)ethyl]-7-methyl-7,9-dihydro-8H-purine-8-one

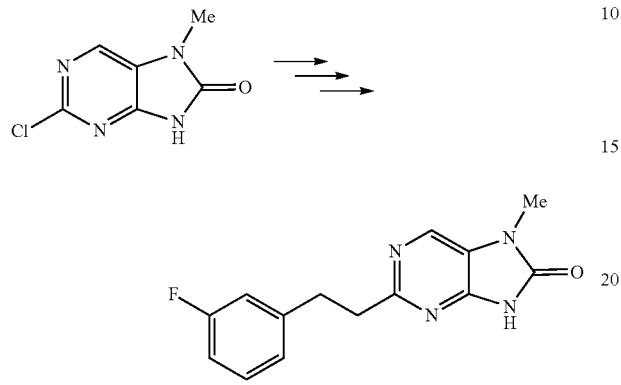

The title compound was prepared using the compound of Reference Example 2 according to the similar method to those of Reference Example 20.

$^1$H-NMR (CDCl$_3$) δ: 3.08-3.19 (2H, m), 3.20-3.32 (2H, m), 3.45 (3H, s), 6.79-7.07 (3H, m), 7.14-7.33 (1H, m), 8.15 (1H, s), 10.44 (1H, br s).

Example 1

Process of 9-methyl-2-[(E)-2-phenylethenyl]-7-(pyrrolidin-1-ylcarbonyl)-7,9-dihydro-8H-purine-8-one

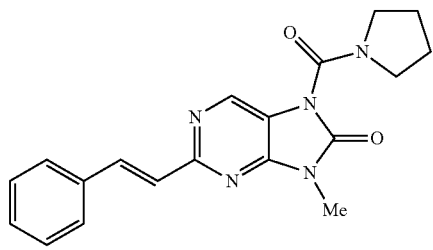 [SMILES: Cn1c(=O)n(C(=O)N2CCCC2)c2cnc(/C=C/c3ccccc3)nc21]

To a mixture of 9-methyl-2-[(E)-2-phenylethenyl]-7,9-dihydro-8H-purine-8-one <the compound of Reference Example 3> (100 mg), 1,4-diazabicyclo[2.2.2]octane (133 mg) and N,N-dimethylformamide (3 ml) was added dropwise 1-pyrrolidinecarbonyl chloride (106 mg) at room temperature and the mixture was stirred for 1 hour. To the reaction mixture was added water (50 ml) and the mixture was extracted with ethyl acetate (80 ml×2). The organic layer was dried over anhydrous magnesium sulfate and was filtered, and the solvent was evaporated under reduced pressure. The obtained residue was purified by silica gel column chromatography (eluent: hexane/ethyl acetate=100/0~0/100) to give the title compound 56 mg.

$^1$H-NMR (CDCl$_3$) δ: 1.90-2.10 (4H, m), 3.51 (3H, s), 3.65-3.74 (4H, m), 7.22 (1H, d, J=16.0 Hz), 7.30-7.44 (3H, m), 7.59-7.66 (2H, m), 7.93 (1H, d, J=16.0 Hz), 8.57 (1H, s).

Example 2

Process of N-ethyl-N,9-dimethyl-8-oxo-2-phenyl-8,9-dihydro-7H-purine-7-carboxamide

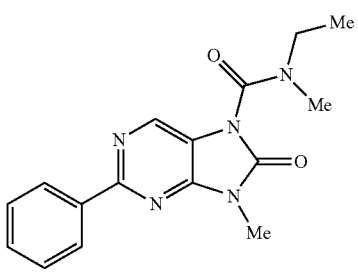 [SMILES: CCN(C)C(=O)n1c(=O)n(C)c2nc(-c3ccccc3)ncc21]

To a solution of N-ethylmethylamine (78 mg) and triphosgene (209 mg) in dichloromethane (10 ml) was added dropwise triethylamine (365 µl) at room temperature and the mixture was stirred for 10 minutes. To the reaction mixture was added a solution of 9-methyl-2-phenyl-7,9-dihydro-8H-purine-8-one <the compound of Reference Example 21> (200 mg) and 1,4-diazabicyclo[2.2.2]octane (220 mg) in dichloromethane (10 ml) and the mixture was stirred for 1 hour. The reaction mixture was washed with water and the organic layer was, dried over anhydrous magnesium sulfate, and the solvent was evaporated under reduced pressure. The obtained residue was purified by silica gel column chromatography (eluent: hexane/ethyl acetate=100/0~0/100) to give the title compound 156 mg.

$^1$H-NMR (CDCl$_3$) δ: 1.31 (3H, t, J=7.2 Hz), 3.14 (3H, s), 3.54 (3H, s), 3.57 (2H, q, J=7.2 Hz), 7.45-7.53 (3H, m), 8.39-8.47 (2H, m), 8.57 (1H, s).

Examples 3 to 165

The compounds indicated in Tables 5 to 31 were prepared according to the similar method to those of Example 1 or 2.

TABLE 5

| Ex. No. | R | $^1$H-NMR (CDCl$_3$) δ |
|---|---|---|
| 3 | 4-CF$_3$ | 1.93-2.10 (4H, m), 3.52 (3H, s), 3.67-3.73 (4H, m), 7.32-7.35 (1H, m), 7.62-7.68 (2H, m), 7.68-7.74 (2H, m), 7.93 (1H, d, J = 16.1 Hz), 8.59 (1H, s). |
| 4 | 4-OMe | 1.92-2.07 (4H, m), 3.50 (3H, s), 3.66-3.73 (4H, m), 3.85 (3H, s), 6.89-6.96 (2H, m), 7.09 (1H, d, J = 16.0 Hz), 7.52-7.61 (2H, m), 7.88 (1H, d, J = 16.0 Hz), 8.54 (1H, s). |

TABLE 5-continued

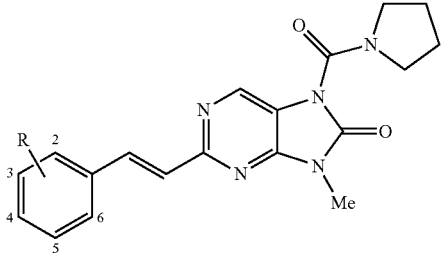

| Ex. No. | R | ¹H-NMR (CDCl₃) δ |
|---|---|---|
| 5 | 4-F | 1.93-2.11 (4H, m), 3.51 (3H, s), 3.66-3.76 (4H, m), 7.04-7.13 (2H, m), 7.14 (1H, d, J = 16.0 Hz), 7.55-7.64 (2H, m), 7.89 (1H, d, J = 16.0 Hz), 8.56 (1H, s). |
| 6 | 3-F | 1.91-2.11 (4H, m), 3.51 (3H, s), 3.64-3.77 (4H, m), 6.98-7.07 (1H, m), 7.21 (1H, d, J = 16.0 Hz), 7.28-7.42 (3H, m), 7.87 (1H, d, J = 16.0 Hz), 8.57 (1H, s). |
| 7 | 3-OMe | 1.88-2.12 (4H, m), 3.51 (3H, s), 3.66-3.75 (4H, m), 3.85 (3H, s), 6.89 (1H, dd, J = 7.9, 2.4 Hz), 7.15-7.35 (4H, m), 7.89 (1H, d, J = 16.0 Hz), 8.57 (1H, s). |
| 8 | 4-Cl | 1.88-2.13 (4H, m), 3.50 (3H, s), 3.64-3.81 (4H, m), 7.18 (1H, d, J = 16.1 Hz), 7.32-7.42 (2H, m), 7.51-7.61 (2H, m), 7.86 (1H, d, J = 16.1 Hz), 8.56 (1H, s). |
| 9 | 4-Me | 1.89-2.12 (4H, m), 2.38 (3H, s), 3.51 (3H, s), 3.65-3.77 (4H, m), 7.17 (1H, d, J = 16.1 Hz), 7.18-7.23 (2H, m), 7.49-7.55 (2H, m), 7.90 (1H, d, J = 16.1 Hz), 8.55 (1H, s). |
| 10 | 3-CF₃ | 1.93-2.09 (4H, m), 3.52 (3H, s), 3.66-3.74 (4H, m), 7.28 (1H, d, J = 16.0 Hz), 7.48-7.60 (2H, m), 7.76-7.81 (1H, m), 7.84-7.89 (1H, m), 7.94 (1H, d, J = 16.0 Hz), 8.58 (1H, s). |

TABLE 6

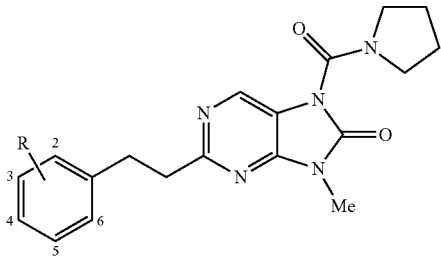

| Ex. No. | R | ¹H-NMR (CDCl₃) δ |
|---|---|---|
| 11 | H | 1.87-2.11 (4H, m), 3.09-3.30 (4H, m), 3.45 (3H, s), 3.64-3.74 (4H, m), 7.15-7.32 (5H, m), 8.50 (1H, s). |
| 12 | 4-OMe | 1.94-2.07 (4H, m), 3.04-3.26 (4H, m), 3.48 (3H, s), 3.62-3.72 (4H, m), 3.78 (3H, s), 6.79-6.86 (2H, m), 7.15-7.20 (2H, m), 8.20 (1H, s). |
| 13 | 3-F | 1.89-2.09 (4H, m), 3.11-3.29 (4H, m), 3.45 (3H, s), 3.65-3.73 (4H, m), 6.83-6.92 (1H, m), 6.94-7.00 (1H, m), 7.01-7.06 (1H, m), 7.18-7.26 (1H, m), 8.50 (1H, s). |
| 14 | 3-CF₃ | 1.90-2.08 (4H, m), 3.18-3.30 (4H, m), 3.44 (3H, s), 3.65-3.71 (4H, m), 7.36-7.47 (3H, m), 7.51-7.54 (1H, m), 8.50 (1H, s). |
| 15 | 3-OMe | 1.90-2.09 (4H, m), 3.09-3.30 (4H, m), 3.46 (3H, s), 3.65-3.76 (4H, m), 3.79 (3H, s), 6.71-6.78 (1H, m), 6.81-6.90 (2H, m), 7.17-7.24 (1H, m), 8.50 (1H, s). |

TABLE 7

| Ex. No. | R | ¹H-NMR (CDCl₃) δ |
|---|---|---|
| 16 | Ph | 2.98-3.12 (4H, m), 3.54 (3H, s), 3.65-3.80 (4H, m), 7.42-7.55 (3H, m), 8.39-8.48 (2H, m), 8.65 (1H, s). |
| 17 | 3-Cl-C₆H₄ | 1.92-2.10 (4H, m), 3.54 (3H, s), 3.67-3.75 (4H, m), 7.40-7.44 (2H, m), 8.31-8.34 (1H, m), 8.43-8.45 (1H, m), 8.64 (1H, s). |
| 18 | 4-Cl-C₆H₄ | 1.92-2.10 (4H, m), 3.53 (3H, s), 3.66-3.75 (4H, m), 7.42-7.47 (2H, m), 8.36-8.41 (2H, m), 8.63 (1H, s). |
| 19 | 3-Cl-C₆H₄-CH₂ | 1.89-2.09 (4H, m), 3.44 (3H, s), 3.62-3.71 (4H, m), 4.21 (2H, s), 7.15-7.29 (3H, m), 7.33-7.37 (1H, m), 8.50 (1H, s). |
| 20 | 4-Cl-C₆H₄-CH₂ | 1.88-2.07 (4H, m), 3.43 (3H, s), 3.61-3.71 (4H, m), 4.20 (2H, s), 7.23-7.32 (4H, m), 8.49 (1H, s). |
| 21 | Ph-(CH₂)₃ | 1.90-2.08 (4H, m), 2.10-2.22 (2H, m), 2.72 (2H, t, J = 7.7 Hz), 2.98 (2H, t, J = 7.7 Hz), 3.45 (3H, s), 3.64-3.73 (4H, m), 7.14-7.32 (5H, m), 8.50 (1H, s). |

TABLE 8

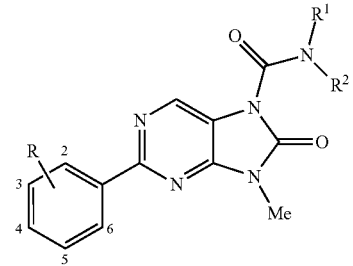

| Ex. No. | R | NR¹R² | ¹H-NMR (CDCl₃) δ |
|---|---|---|---|
| 22 | H | N(Me)Me | 3.18 (6H, s), 3.54 (3H, s), 7.45-7.52 (3H, m), 8.41-8.46 (2H, m), 8.59 (1H, s). |

TABLE 8-continued
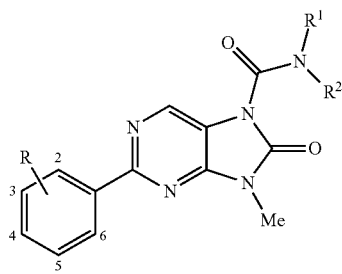
| Ex. No. | R | NR¹R² | ¹H-NMR (CDCl₃) δ |
|---|---|---|---|
| 23 | H | 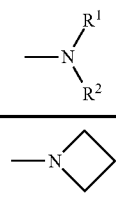 | 2.34-2.48 (2H, m), 3.52 (3H, s), 4.19-4.57 (4H, m), 7.44-7.53 (3H, m), 8.39-8.48 (2H, m), 8.86 (1H, s). |
| 24 | H | 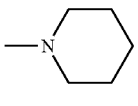 | 1.67-1.80 (6H, m), 3.54 (3H, s), 3.52-3.67 (4H, m), 7.45-7.53 (3H, m), 8.40-8.46 (2H, m), 8.60 (1H, s). |
| 25 | H | 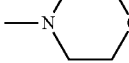 | 3.53 (3H, s), 3.62-3.74 (4H, m), 3.82-3.89 (4H, m), 7.45-7.53 (3H, m), 8.40-8.47 (2H, m), 8.63 (1H, s). |
| 26 | H | 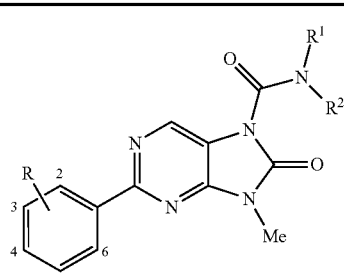 | 2.37 (3H, s), 2.55-2.60 (4H, m), 3.54 (3H, s), 3.55-3.82 (4H, m), 7.45-7.53 (3H, m), 8.40-8.47 (2H, m), 8.62 (1H, s). |
| 27 | H | 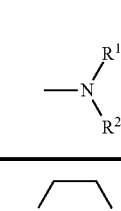 | 3.33 (3H, s), 3.56 (3H, s), 7.17-7.28 (3H, m), 7.29-7.37 (2H, m), 7.44-7.53 (3H, m), 8.38-8.46 (2H, m), 8.65 (1H, s). |
TABLE 9
| Ex. No. | R | NR¹R² | ¹H-NMR (CDCl₃) δ |
|---|---|---|---|
| 28 | H | 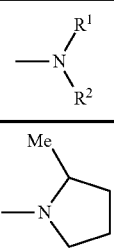 | 1.32-1.47 (3H, m), 1.79-1.94 (2H, m), 1.96-2.07 (2H, m), 2.21-2.30 (1H, m), 3.54 (3H, s), 3.82-3.94 (1H, m), 4.22-4.35 (1H, m), 7.44-7.53 (3H, m), 8.40-8.47 (2H, m), 8.65 (1H, s). |
| 29 | H |  | 1.79-2.11 (3H, m), 2.12-2.29 (1H, m), 3.09-3.91 (10H, m), 4.35-4.55 (1H, m), 7.43-7.54 (3H, m), 8.39-8.48 (2H, m), 8.61 (1H, s). |
| 30 | H | 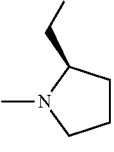 | 3.54 (3H, s), 4.52-4.81 (4H, m), 7.44-7.54 (3H, m), 8.40-8.48 (2H, m), 8.93 (1H, s). |
| 31 | H |  | 2.75 (2H, t, J = 8.0 Hz), 3.56 (3H, s), 4.15-4.26 (4H, m), 7.46-7.54 (3H, m), 8.40-8.48 (2H, m), 8.68 (1H, s). |
| 32 | H | 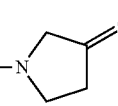 | 2.06-2.31 (1H, m), 2.32-2.51 (1H, m), 3.49-3.58 (4H, m), 3.69-4.03 (4H, m), 7.21-7.41 (5H, m), 7.45-7.54 (3H, m), 8.39-8.48 (2H, m), 8.68 (1H, s). |
| 33 | H | 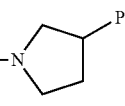 | 1.84-2.11 (4H, m), 2.74-2.91 (1H, m), 3.09-3.51 (3H, m), 3.55 (3H, s), 3.93-4.63 (1H, m), 7.20-7.38 (5H, m), 7.45-7.54 (3H, m), 8.41-8.48 (2H, m), 8.64 (1H, s). |

TABLE 9-continued

| Ex. No. | R | NR¹R² | ¹H-NMR (CDCl₃) δ |
|---|---|---|---|
| 34 | H | —N(Bn)(Me) | 3.09 (3H, s), 3.55 (3H, s), 4.75 (2H, s), 7.24-7.56 (8H, m), 8.41-8.49 (2H, m), 8.61 (1H, s). |

TABLE 10

| Ex. No. | R | NR¹R² | ¹H-NMR (CDCl₃) δ |
|---|---|---|---|
| 35 | H | —N(Me)CH₂CH₂CH₂Ph | 1.96-2.12 (2H, m), 2.56-2.83 (2H, m), 3.15 (3H, s), 3.43-3.67 (5H, m), 7.05-7.37 (5H, m), 7.46-7.55 (3H, m), 8.41-8.47 (2H, m), 8.55 (1H, s). |
| 36 | H | —N(Me)CH₂CH₂CH₂CH₂Ph | 1.61-1.82 (4H, m), 2.57-2.76 (2H, m), 3.11 (3H, s), 3.47-3.62 (5H, m), 7.05-7.34 (5H, m), 7.43-7.54 (3H, m), 8.38-8.47 (2H, m), 8.54 (1H, s). |
| 37 | H | —N(Me)CH₂C(O)OEt | 1.19-1.42 (3H, m), 3.23 (3H, s), 3.54 (3H, s), 4.14-4.35 (4H, m), 7.44-7.53 (3H, m), 8.39-8.47 (2H, m), 8.63 (1H, s). |
| 38 | H | —N(Me)CH₂C(O)OMe | 3.24 (3H, s), 3.54 (3H, s), 3.73-3.88 (3H, m), 4.21-4.30 (2H, m), 7.45-7.54 (3H, m), 8.40-8.49 (2H, m), 8.63 (1H, s). |
| 39 | H | —N(Me)CH₂CH₂OMe | 3.21 (3H, br s), 3.35 (3H, br s), 3.54 (3H, s), 3.60-3.74 (4H, m), 7.43-7.53 (3H, m), 8.39-8.46 (2H, m), 8.55 (1H, s). |
| 40 | H | —N(Et)₂ | 1.30 (6H, t, J = 7.2 Hz), 3.54 (3H, s), 3.56 (4H, q, J = 7.2 Hz), 7.45-7.54 (3H, m), 8.39-8.48 (2H, m), 8.52 (1H, s). |
| 41 | H | azepan-1-yl | 1.59-1.71 (4H, m), 1.72-1.82 (2H, m), 1.86-1.97 (2H, m), 3.54 (3H, s), 3.62-3.72 (4H, m), 7.44-7.52 (3H, m), 8.40-8.47 (2H, m), 8.53 (1H, s). |

TABLE 11

| Ex. No. | R | NR¹R² | ¹H-NMR (CDCl₃) δ |
|---|---|---|---|
| 42 | H | azocan-1-yl | 1.48-1.77 (8H, m), 1.86-1.98 (2H, m), 3.54 (3H, s), 3.56-3.69 (4H, m), 7.43-7.53 (3H, m), 8.40-8.46 (2H, m), 8.50 (1H, s). |
| 43 | H | —N(Me)cyclohexyl | 1.07-1.23 (1H, m), 1.32-1.81 (5H, m), 1.84-1.99 (4H, m), 3.02 (3H, s), 3.53 (3H, s), 3.90-4.31 (1H, m), 7.45-7.54 (3H, m), 8.40-8.47 (2H, m), 8.54 (1H, s). |
| 44 | H | 2-benzylpyrrolidin-1-yl | 1.72-2.12 (4H, m), 2.69-2.83 (2H, m), 3.44-3.66 (4H, m), 3.79-3.89 (1H, m), 4.40-4.60 (1H, m), 7.21-7.39 (3H, m), 7.44-7.54 (4H, m), 8.38-8.48 (3H, m), 8.68 (1H, s). |

TABLE 11-continued
| Ex. No. | R | | ¹H-NMR (CDCl₃) δ |
|---|---|---|---|
| 45 | H | 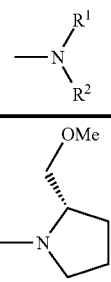 | 1.77-2.12 (3H, m), 2.12-2.29 (1H, m), 3.10-3.90 (10H, m), 4.37-4.54 (1H, m), 7.51-7.54 (3H, m), 8.37-8.48 (2H, m), 8.61 (1H, s). |
| 46 | 3-OMe | 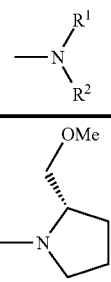 | 2.02-2.16 (1H, m), 2.16-2.30 (1H, m), 3.37 (3H, s), 3.53 (3H, s), 3.64-3.83 (4H, m), 3.92 (3H, s), 4.05-4.12 (1H, m), 6.98-7.07 (1H, m), 7.39 (1H, t, J = 7.9 Hz), 7.98-8.10 (2H, m), 9.33 (1H, s). |
| 47 | 3-OMe | 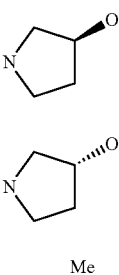 | 2.03-2.15 (1H, m), 2.19-2.28 (1H, m), 3.37 (3H, s), 3.54 (3H, s), 3.65-3.81 (4H, m), 3.93 (3H, s), 4.06-4.12 (1H, m), 6.99-7.05 (1H, m), 7.39 (1H, t, J = 7.9 Hz), 7.99-8.09 (2H, m), 9.34 (1H, s). |
| 48 | 3-OMe | 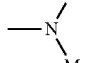 | 3.18 (6H, s), 3.54 (3H, s), 3.92 (3H, s), 7.00-7.05 (1H, m), 7.40 (1H, t, J = 8.0 Hz), 7.97-8.07 (2H, m), 8.59 (1H, s). |
| 49 | 3-OMe | 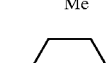 | 1.64-1.82 (6H, m), 3.53 (3H, s), 3.42-3.70 (4H, m), 3.92 (3H, s), 6.98-7.05 (1H, m), 7.40 (1H, t, J = 8.0 Hz), 7.96-8.06 (2H, m), 8.59 (1H, s). |
TABLE 12
| Ex. No. | R | | ¹H-NMR (CDCl₃) δ |
|---|---|---|---|
| 50 | H | 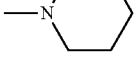 | 3.56 (3H, s), 3.73-3.92 (8H, m), 6.70 (1H, d, J = 8.9 Hz), 7.46-7.54 (3H, m), 7.70 (1H, dd, J = 8.9, 2.7 Hz), 8.41-8.48 (3H, m), 8.66 (1H, s). |
| 51 | H | 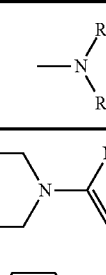 | 3.56 (3H, s), 3.66-3.84 (4H, m), 4.00-4.08 (4H, m), 6.57 (1H, t, J = 4.7 Hz), 7.46-7.54 (3H, m), 8.35 (2H, d, J = 4.7 Hz), 8.40-8.48 (2H, m), 8.65 (1H, s). |
| 52 | H | 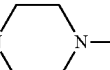 | 3.56 (3H, s), 3.64-3.85 (4H, m), 4.01-4.08 (4H, m), 6.57 (1H, t, J = 4.9 Hz), 7.46-7.55 (3H, m), 8.35-8.45 (5H, m), 8.65 (1H, s). |
| 53 | H | 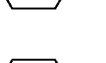 | 2.41 (3H, s), 3.55 (3H, s), 3.65-3.93 (8H, m), 6.48 (1H, d, J = 8.5 Hz), 6.56 (1H, d, J = 7.3 Hz), 7.38-7.55 (4H, m), 8.39-8.50 (2H, m), 8.64 (1H, s). |
| 54 | H | 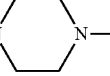 | 3.55 (3H, s), 3.69-3.85 (8H, m), 3.88 (3H, s), 6.18 (2H, dd, J = 17.5, 8.0 Hz), 7.39-7.56 (4H, m), 8.39-8.51 (2H, m), 8.65 (1H, s). |

TABLE 12-continued

![structure: —N(R¹)(R²)]

| Ex. No. | R | NR¹R² | ¹H-NMR (CDCl₃) δ |
|---|---|---|---|
| 55 | H | 4-(thiazol-2-yl)piperazin-1-yl | 3.55 (3H, s), 3.64-3.89 (8H, m), 6.66 (1H, d, J = 3.7 Hz), 7.24 (1H, d, J = 3.7 Hz), 7.45-7.54 (3H, m), 8.39-8.48 (2H, m), 8.65 (1H, s) |
| 56 | H | 4-(5-methylpyridin-2-yl)piperazin-1-yl | 2.22 (3H, s), 3.55 (3H, s), 3.60-3.89 (8H, m), 6.60-6.66 (1H, m), 7.32-7.40 (1H, m), 7.43-7.55 (3H, m), 8.01-8.07 (1H, m), 8.38-8.48 (2H, m), 8.64 (1H, s). |

TABLE 13

![structure: —N(R¹)(R²)]

| Ex. No. | R | NR¹R² | ¹H-NMR (CDCl₃) δ |
|---|---|---|---|
| 57 | 3-OMe | azetidin-1-yl | 2.33-2.48 (2H, m), 3.52 (3H, s), 3.92 (3H, s), 4.22-4.54 (4H, m), 6.98-7.06 (1H, m), 7.40 (1H, t, J = 8.1 Hz), 7.97-8.08 (2H, m), 8.85 (1H, s). |
| 58 | 3-OMe | morpholin-4-yl | 3.53 (3H, s), 3.61-3.75 (4H, m), 3.82-3.90 (4H, m), 3.92 (3H, s), 7.00-7.06 (1H, m), 7.40 (1H, t, J = 8.0 Hz), 7.97-8.08 (2H, m), 8.63 (1H, s). |
| 59 | 3-OMe | N(Me)CH₂CH₂OMe | 3.14-3.49 (5H, m), 3.53 (3H, s), 3.60-3.81 (2H, m), 3.92 (3H, s), 7.00-7.09 (1H, m), 7.40 (1H, t, J = 8.0 Hz), 7.96-8.09 (2H, m), 8.54 (1H, s). |
| 60 | 3-OMe | N(Me)(Et) | 1.31 (3H, t, J = 7.2 Hz), 3.14 (3H, s), 3.53 (3H, s), 3.57 (2H, q, J = 7.2 Hz), 3.92 (3H, s), 6.99-7.07 (1H, m), 7.40 (1H, t, J = 8.0 Hz), 7.96-8.09 (2H, m), 8.56 (1H, s). |
| 61 | 3-OMe | 4-phenylpiperidin-1-yl | 3.29-3.35 (4H, m), 3.55 (3H, s), 3.63-3.91 (5H, m), 3.92 (3H, s), 6.87-6.92 (2H, m), 7.01-7.06 (1H, m), 7.23-7.28 (3H, m), 7.40 (1H, t, J = 8.0 Hz), 7.99-8.07 (2H, m), 8.64 (1H, s). |
| 62 | 3-OMe | (3-fluoropyrrolidin-1-yl) | 1.99-2.50 (2H, m), 3.54 (3H, s), 3.66-4.15 (4H, m), 3.92 (3H, s), 5.17-5.51 (1H, m), 6.99-7.06 (1H, m), 7.40 (1H, t, J = 8.0 Hz), 7.97-8.07 (2H, m), 8.68 (1H, s). |

TABLE 14

![structure: —N(R¹)(R²)]

| Ex. No. | R | NR¹R² | ¹H-NMR (CDCl₃) δ |
|---|---|---|---|
| 63 | 3-OMe | (3-fluoropyrrolidin-1-yl) | 1.99-2.50 (2H, m), 3.55 (3H, s), 3.66-4.15 (4H, m), 3.93 (3H, s), 5.17-5.51 (1H, m), 6.99-7.06 (1H, m), 7.40 (1H, t, J = 8.0 Hz), 7.95-8.07 (2H, m), 8.68 (1H, s). |
| 64 | 3-OMe | N(Me)CH₂CH₂Ph | 3.29 (3H, s), 3.52 (3H, s), 3.92 (3H, s), 3.94 (2H, t, J = 5.1 Hz), 4.14-4.38 (2H, m), 6.60-7.08 (4H, m), 7.16-7.34 (2H, m), 7.40 (1H, t, J = 8.0 Hz), 7.96-8.08 (2H, m), 8.57 (1H, s). |
| 65 | 3-OMe | N(Me)CH₂CH₂OPh | 3.29 (3H, br s), 3.52 (3H, s), 3.89-3.99 (5H, m), 4.14-4.40 (2H, m), 6.67-7.09 (3H, m), 7.17-7.35 (3H, m), 7.40 (1H, t, J = 8.0 Hz), 7.97-8.10 (2H, m), 8.57 (1H, s). |
| 66 | 3-OMe | 4-benzylpiperidin-1-yl | 1.37-1.63 (4H, m), 1.71-1.91 (3H, m), 2.57-2.67 (2H, m), 2.92-3.17 (2H, m), 3.53 (3H, s), 3.92 (3H, s), 6.99-7.07 (1H, m), 7.13-7.35 (5H, m), 7.40 (1H, t, J = 8.0 Hz), 7.96-8.07 (2H, m), 8.59 (1H, s). |

TABLE 14-continued
| Ex. No. | R |  | ¹H-NMR (CDCl₃) δ |
|---|---|---|---|
| 67 | 3-OMe | 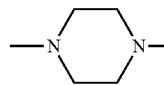 | 2.64-2.74 (6H, m), 2.79-2.88 (2H, m), 3.54 (3H, s), 3.57-3.83 (4H, m), 3.92 (3H, s), 6.99-7.06 (1H, m), 7.17-7.34 (5H, m), 7.40 (1H, t, J = 8.0 Hz), 7.97-8.07 (2H, m), 8.62 (1H, s). |
TABLE 15
| Ex. No. | R |  | ¹H-NMR (CDCl₃) δ |
|---|---|---|---|
| 68 | 3-OMe | 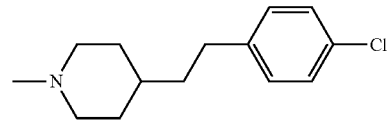 | 1.35-1.71 (5H, m), 1.81-1.94 (2H, m), 2.59-2.69 (2H, m), 2.96-3.22 (2H, m), 3.53 (3H, s), 3.79-4.59 (2H, m), 3.92 (3H, s), 6.99-7.06 (1H, m), 7.06-7.15 (2H, m), 7.22-7.31 (2H, m), 7.40 (1H, t, J = 8.0 Hz), 7.96-8.08 (2H, m), 8.59 (1H, s). |
| 69 | 3-OMe | 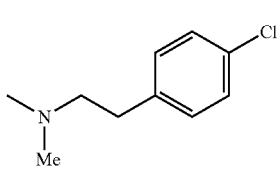 | 2.90-3.04 (2H, m), 3.14 (3H, br s), 3.52 (3H, s), 3.76 (2H, t, J = 7.2 Hz), 3.92 (3H, s), 6.98-7.34 (5H, m), 7.40 (1H, t, J = 8.0 Hz), 7.97-8.07 (2H, m), 8.49 (1H, br s). |
| 70 | 3-OMe |  | 1.29 (6H, t, J = 7.2 Hz), 3.48-3.62 (7H, m), 3.92 (3H, s), 6.99-7.06 (1H, m), 7.40 (1H, t, J = 8.0 Hz), 7.97-8.07 (2H, m), 8.51 (1H, s). |
| 71 | 3-OMe | 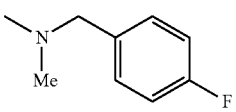 | 3.07 (3H, s), 3.62 (3H, s), 3.99 (3H, s), 4.69 (2H, s), 7.04-7.20 (3H, m), 7.23-7.55 (3H, m), 8.11-8.30 (2H, m), 8.75 (1H, s). |
| 72 | 3-OMe | 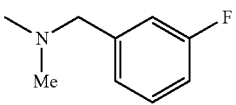 | 3.10 (3H, s), 3.62 (3H, s), 3.98 (3H, s), 4.72 (2H, s), 6.97-7.25 (4H, m), 7.32-7.52 (2H, m), 8.11-8.24 (2H, m), 8.74 (1H, s). |
| 73 | 3-OMe | 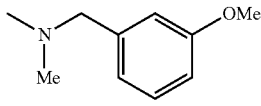 | 3.10 (3H, s), 3.55 (3H, s), 3.82 (3H, s), 3.92 (3H, s), 4.72 (2H, s), 6.79-7.10 (4H, m), 7.23-7.35 (1H, m), 7.40 (1H, t, J = 8.1 Hz), 7.97-8.08 (2H, m), 8.60 (1H, s). |
TABLE 16
| Ex. No. | R |  | ¹H-NMR (CDCl₃) δ |
|---|---|---|---|
| 74 | 3-OMe | 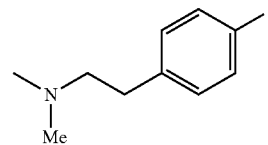 | 2.86-3.21 (5H, m), 3.53 (3H, s), 3.75 (2H, t, J = 7.2 Hz), 3.92 (3H, s), 6.79-7.35 (5H, m), 7.40 (1H, t, J = 8.0 Hz), 7.95-8.62 (3H, m). |

TABLE 16-continued
| Ex. No. | R | NR¹R² | ¹H-NMR (CDCl₃) δ |
|---|---|---|---|
| 75 | 3-OMe |  | 2.93-3.26 (5H, m), 3.53 (3H, s), 3.78 (2H, t, J = 7.2 Hz), 3.92 (3H, s), 6.73-7.34 (5H, m), 7.40 (1H, t, J = 7.9 Hz), 7.97-8.57 (3H, m). |
| 76 | 3-OMe | 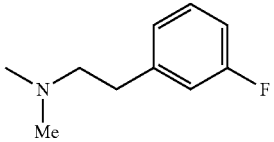 | 2.86-3.23 (5H, m), 3.53 (3H, s), 3.77 (2H, t, J = 7.2 Hz), 3.92 (3H, s), 6.88-7.36 (5H, m), 7.40 (1H, t, J = 8.0 Hz), 7.95-8.59 (3H, m). |
| 77 | 3-OMe | 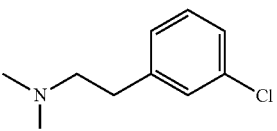 | 3.28 (3H, s), 3.52 (3H, s), 3.89-4.04 (5H, m), 4.12-4.38 (2H, m), 6.60-6.96 (2H, m), 7.00-7.09 (1H, m), 7.12-7.34 (2H, m), 7.40 (1H, t, J = 8.0 Hz), 7.97-8.10 (2H, m), 8.56 (1H, s). |
| 78 | 3-OMe | 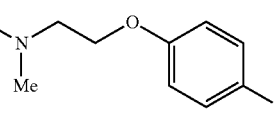 | 3.08 (3H, s), 3.55 (3H, s), 3.92 (3H, s), 4.71 (2H, s), 6.99-7.06 (1H, m), 7.22-7.44 (5H, m), 7.98-8.08 (2H, m), 8.61 (1H, s). |
| 79 | 3-OMe | 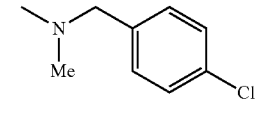 | 3.10 (3H, s), 3.55 (3H, s), 3.92 (3H, s), 4.72 (2H, s), 6.99-7.08 (1H, m), 7.19-7.46 (5H, m), 7.97-8.09 (2H, m), 8.62 (1H, s). |
TABLE 17
| Ex. No | R | NR¹R² | ¹H-NMR (CDCl₃) δ |
|---|---|---|---|
| 80 | 3-OMe | 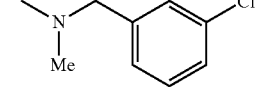 | 3.05 (3H, s), 3.54 (3H, s), 3.81 (3H, s), 3.92 (3H, s), 4.67 (2H, s), 6.84-6.95 (2H, m), 6.99-7.06 (1H, m), 7.19-7.44 (3H, m), 7.97-8.08 (2H, m), 8.60 (1H, s). |
| 81 | 3-OMe |  | 3.12 (3H, s), 3.55 (3H, s), 3.92 (3H, s), 4.81 (2H, s), 7.00-7.06 (1H, m), 7.41 (1H, t, J = 8.0 Hz), 7.45-7.61 (2H, m), 7.61-7.70 (2H, m), 7.98-8.09 (2H, m), 8.62 (1H, s). |
| 82 | 3-OMe | 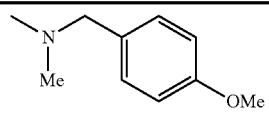 | 3.12 (3H, s), 3.55 (3H, s), 3.92 (3H, s), 4.81 (2H, s), 6.99-7.07 (1H, m), 7.40 (1H, t, J = 7.9 Hz), 7.47-7.72 (4H, m), 7.98-8.08 (2H, m), 8.61 (1H, s). |
| 83 | 3-OMe | 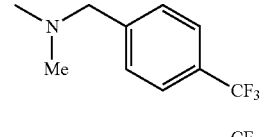 | 3.10 (3H, s), 3.55 (3H, s), 3.92 (3H, s), 4.75 (2H, s), 7.00-7.06 (1H, m), 7.20-7.29 (2H, m), 7.34-7.51 (3H, m), 7.98-8.08 (2H, m), 8.61 (1H, s). |
| 84 | 3-OMe | 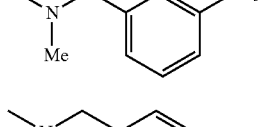 | 2.54-2.64 (4H, m), 3.52 (3H, s), 3.54 (2H, s), 3.57-3.75 (4H, m), 3.92 (3H, s), 6.97-7.07 (3H, m), 7.24-7.35 (2H, m), 7.40 (1H, t, J = 8.0 Hz), 7.96-8.07 (2H, m), 8.61 (1H, s). |

TABLE 17-continued

| Ex. No | R | R¹, R² (N-R¹R²) | ¹H-NMR (CDCl₃) δ |
|---|---|---|---|
| 85 | 3-OMe | 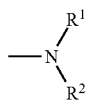 | 2.55-2.65 (4H, m), 3.52 (3H, s), 3.54-3.76 (6H, m), 3.92 (3H, s), 6.91-7.14 (4H, m), 7.23-7.34 (1H, m), 7.40 (1H, t, J = 8.0 Hz), 7.96-8.06 (2H, m), 8.61 (1H, s). |

TABLE 18

| Ex. No. | R | R¹, R² (N-R¹R²) | ¹H-NMR (CDCl₃) δ |
|---|---|---|---|
| 86 | 3-OMe | 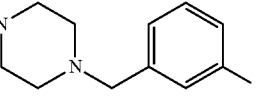 | 2.54-2.64 (4H, m), 3.52 (3H, s), 3.54 (2H, s), 3.57-3.77 (4H, m), 3.92 (3H, s), 6.98-7.07 (1H, m), 7.22-7.35 (4H, m), 7.40 (1H, t, J = 8.0 Hz), 7.97-8.07 (2H, m), 8.61 (1H, s). |
| 87 | 3-OMe | 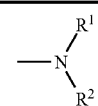 | 2.56-2.66 (4H, m), 3.52 (3H, s), 3.55 (2H, s), 3.58-3.78 (4H, m), 3.92 (3H, s), 6.99-7.06 (1H, m), 7.17-7.31 (3H, m), 7.34-7.45 (2H, m), 7.96-8.08 (2H, m), 8.61 (1H, s). |
| 88 | 3-OMe | 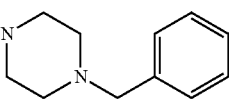 | 3.09 (3H, s), 3.55 (3H, s), 3.92 (3H, s), 4.75 (2H, s), 6.99-7.07 (1H, m), 7.20-7.51 (6H, m), 7.97-8.09 (2H, m), 8.60 (1H, s). |
| 89 | 3-OMe | 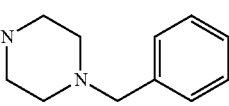 | 2.56-2.66 (4H, m), 3.52 (3H, s), 3.59-3.76 (6H, m), 3.92 (3H, s), 6.98-7.06 (1H, m), 7.40 (1H, t, J = 8.0 Hz), 7.44-7.52 (2H, m), 7.56-7.63 (2H, m), 7.96-8.07 (2H, m), 8.61 (1H, s). |
| 90 | 3-OMe | 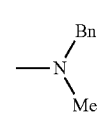 | 3.28 (3H, s), 3.52 (3H, s), 3.82-3.97 (5H, m), 4.17-4.35 (2H, m), 6.56-6.98 (3H, m), 6.98-7.06 (1H, m), 7.07-7.28 (1H, m), 7.40 (1H, t, J = 8.0 Hz), 7.95-8.08 (2H, m), 8.56 (1H, s). |
| 91 | 3-OMe | 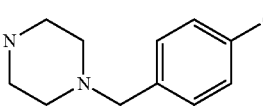 | 3.28 (3H, s), 3.52 (3H, s), 3.88-3.98 (5H, m), 4.17-4.31 (2H, m), 6.58-7.07 (5H, m), 7.40 (1H, t, J = 8.0 Hz), 7.96-8.09 (2H, m), 8.57 (1H, s). |

TABLE 19

| Ex. No. | R | R¹, R² (N-R¹R²) | ¹H-NMR (CDCl₃) δ |
|---|---|---|---|
| 92 | 3-OMe | 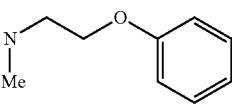 | 2.75-3.04 (2H, m), 3.15 (3H, s), 3.52 (3H, br s), 3.75 (2H, t, J = 6.8 Hz), 3.92 (3H, s), 6.53-7.24 (5H, m), 7.39 (1H, t, J = 7.8 Hz), 7.97-8.10 (2H, m), 8.49 (1H, br s). |

TABLE 19-continued

| Ex. No. | R | (structure with R¹, R²) | ¹H-NMR (CDCl₃) δ |
|---|---|---|---|
| 93 | 3-OMe | (4-methoxyphenethyl)(methyl)amine group | 2.79-3.06 (2H, m), 3.15 (3H, br s), 3.49-3.89 (5H, m), 3.52 (3H, s), 3.92 (3H, s), 6.51-7.24 (5H, m), 7.40 (1H, t, J = 8.0 Hz), 7.96-8.11 (2H, m), 8.47 (1H, br s). |
| 94 | 3-OMe | 1-methyl-4-[(E)-2-(4-chlorophenyl)vinyl]-1,2,3,6-tetrahydropyridine | 2.61-2.71 (2H, m), 3.55 (3H, s), 3.72-3.89 (2H, m), 3.92 (3H, s), 4.28-4.36 (2H, m), 5.79-5.91 (1H, m), 6.50 (1H, d, J = 16.0 Hz), 6.79 (1H, d, J = 16.0 Hz), 6.98-7.07 (1H, m), 7.24-7.45 (5H, m), 7.97-8.09 (2H, m), 8.63 (1H, s). |
| 95 | 3-OMe | 1-methyl-4-[(E)-2-(4-fluorophenyl)vinyl]-1,2,3,6-tetrahydropyridine | 2.57-2.74 (2H, m), 3.55 (3H, s), 3.69-3.90 (2H, m), 3.92 (3H, s), 4.25-4.39 (2H, m), 5.76-5.91 (1H, m), 6.51 (1H, d, J = 16.0 Hz), 6.73 (1H, d, J = 16.0 Hz), 6.97-7.08 (3H, m), 7.34-7.44 (3H, m), 7.97-8.08 (2H, m), 8.63 (1H, s). |
| 96 | 3-OMe | 1-methyl-4-[2-(4-fluorophenyl)ethyl]piperidine | 1.36-1.72 (5H, m), 1.81-1.96 (2H, m), 2.64 (2H, t, J = 7.6 Hz), 2.97-3.20 (2H, m), 3.53 (3H, s), 3.88-4.52 (2H, m), 3.92 (3H, s), 6.92-7.07 (3H, m), 7.08-7.18 (2H, m), 7.40 (1H, t, J = 8.0 Hz), 7.97-8.08 (2H m), 8.59 (1H, s). |

TABLE 20

| Ex. No | R | (structure with R¹, R²) | ¹H-NMR (CDCl₃) δ |
|---|---|---|---|
| 97 | 3-OMe | 4-cyclohexyl-1-methylpiperazine | 1.10-1.35 (5H, m), 1.60-1.69 (1H, m), 1.77-1.92 (4H, m), 2.29-2.41 (1H, m), 2.68-2.76 (4H, m), 3.53 (3H, s), 3.56-3.77 (4H, m), 3.92 (3H, s), 6.99-7.06 (1H, m), 7.40 (1H, t, J = 8.0 Hz), 7.96-8.07 (2H, m), 8.61 (1H, s). |
| 98 | 3-OMe | 4-cyclopentyl-1-methylpiperazine | 1.35-1.50 (2H, m), 1.51-1.79 (4H, m), 1.83-1.97 (2H, m), 2.52-2.72 (5H, m), 3.53 (3H, s), 3.58-3.81 (4H, m), 3.92 (3H, s), 6.99-7.07 (1H, m), 7.40 (1H, t, J = 7.9 Hz), 7.97-8.08 (2H, m), 8.62 (1H, s). |
| 99 | 3-OMe | 1-methyl-4-(2,2,2-trifluoroethyl)piperazine | 2.79-2.93 (4H, m), 3.06 (2H, q, J = 9.4 Hz), 3.53 (3H, s), 3.57-3.80 (4H, m), 3.92 (3H, s), 6.98-7.08 (1H, m), 7.40 (1H, t, J = 8.0 Hz), 7.95-8.09 (2H, m), 8.61 (1H, s). |
| 100 | 3-OMe | 1-(2-cyclohexylethyl)-4-methylpiperazine | 0.84-1.01 (2H, m), 1.10-1.33 (4H, m), 1.35-1.47 (2H, m), 1.55-1.77 (5H, m), 2.38-2.48 (2H, m), 2.54-2.65 (4H, m), 3.53 (3H, s), 3.57-3.79 (4H, m), 3.92 (3H, s), 6.98-7.06 (1H, m), 7.40 (1H, t, J = 7.9 Hz), 7.96-8.07 (2H, m), 8.61 (1H, s). |

TABLE 20-continued
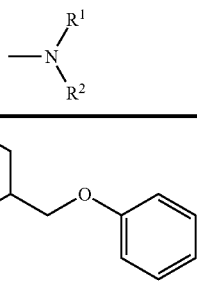
| Ex. No | R | | $^1$H-NMR (CDCl$_3$) δ |
|---|---|---|---|
| 101 | 3-OMe | 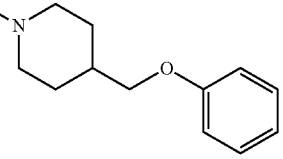 | 1.48-1.70 (2H, m), 1.94-2.25 (4H, m), 3.04-3.31 (2H, m), 3.53 (3H, s), 3.79-4.62 (6H, m), 6.84-7.07 (4H, m), 7.23-7.35 (2H, m), 7.40 (1H, t, J = 8.0 Hz), 7.96-8.09 (2H, m), 8.61 (1H, s). |
TABLE 21
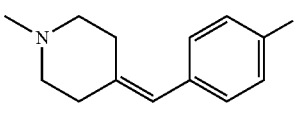
| Ex. No. | R | | $^1$H-NMR (CDCl$_3$) δ |
|---|---|---|---|
| 102 | 3-OMe | 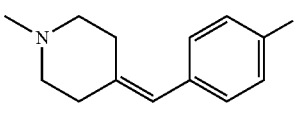 | 2.54-2.61 (2H, m), 2.63-2.72 (2H, m), 3.47-3.83 (7H, m), 3.92 (3H, s), 6.40 (1H, s), 7.00-7.06 (1H, m), 7.11-7.19 (2H, m), 7.25-7.36 (2H, m), 7.40 (1H, t, J = 7.9 Hz), 7.98-8.08 (2H, m), 8.62 (1H, s). |
| 103 | 3-OMe | 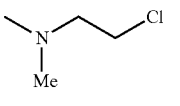 | 3.14-3.31 (2H, m), 3.54 (3H, s), 3.72-3.92 (5H, m), 3.92 (3H, s), 6.99-7.07 (1H, m), 7.40 (1H, t, J = 8.0 Hz), 7.98-8.08 (2H, m), 8.57 (1H, s). |
| 104 | 3-OMe | 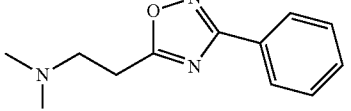 | 3.22 (3H, s), 3.41 (2H, t, J = 6.9 Hz), 3.52 (3H, s), 3.92 (3H, s), 4.06 (2H, t, J = 6.9 Hz), 6.98-7.06 (1H, m), 7.33-7.56 (4H, m), 7.87-8.14 (4H, m), 8.50 (1H, br s). |
| 105 | 3-OMe | 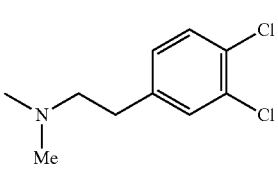 | 2.89-3.03 (2H, m), 3.15 (3H, br s), 3.53 (3H, s), 3.75 (2H, t, J = 7.2 Hz), 3.92 (3H, s), 6.95-7.49 (5H, m), 7.95-8.07 (2H, m), 8.10-8.66 (1H, m). |
| 106 | 3-OMe | 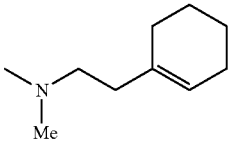 | 1.40-1.69 (4H, m), 1.87-2.09 (4H, m), 2.22-2.39 (2H, m), 3.14 (3H, m), 3.53 (3H, s), 3.60 (2H, t, J = 7.1 Hz), 3.92 (3H, s), 5.43-5.60 (1H, m), 6.98-7.06 (1H, m), 7.40 (1H, t, J = 8.0 Hz), 7.96-8.08 (2H, m), 8.53 (1H, s). |
TABLE 22
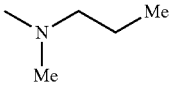
| Ex. No. | R | | $^1$H-NMR (CDCl$_3$) δ |
|---|---|---|---|
| 107 | 3-OMe | 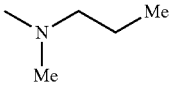 | 0.85-1.08 (3H, br m), 1.66-1.81 (2H, br m), 3.14 (3H, s), 3.46-3.56 (2H, br m), 3.54 (3H, s), 3.92 (3H, s), 7.00-7.05 (1H, m), 7.40 (1H, t, J = 7.9 Hz), 7.98-8.06 (2H, m), 8.55 (1H, s). |

TABLE 22-continued
| Ex. No. | R | 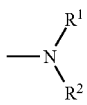 | ¹H-NMR (CDCl₃) δ |
|---|---|---|---|
| 108 | 3-OMe | 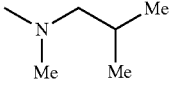 | 0.79-1.10 (6H, br m), 2.01-2.18 (1H, m), 3.15 (3H, s), 3.36-3.46 (2H, m), 3.54 (3H, s), 3.92 (3H, s), 7.00-7.07 (1H, m), 7.37-7.44 (H, m), 7.98-8.08 (2H, m), 8.55 (1H, s). |
| 109 | 3-OMe | 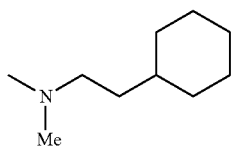 | 0.78-1.84 (13H, m), 3.13 (3H, s), 3.47-3.59 (5H, m), 3.92 (3H, s), 6.97-7.06 (1H, m), 7.40 (1H, t, J = 8.0 Hz), 7.96-8.07 (2H, m), 8.54 (1H, s). |
| 110 | 3-OMe | 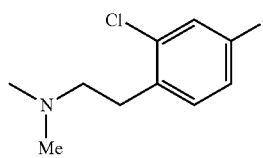 | 2.89-3.36 (5H, m), 3.52 (3H, s), 3.70-3.89 (2H, m), 3.92 (3H, s), 6.97-7.32 (4H, m), 7.40 (1H, t, J = 7.9 Hz), 7.96-8.61 (3H, m). |
| 111 | 3-OMe | 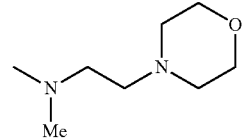 | 2.32-2.79 (6H, m), 3.19 (3H, s), 3.48-3.82 (6H, m), 3.54 (3H, s), 3.92 (3H, s), 6.97-7.09 (1H, m), 7.40 (1H, t, J = 8.0 Hz), 7.94-8.12 (2H, m), 8.57 (1H, s). |
TABLE 23
| Ex. No. | R | 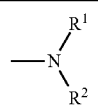 | ¹H-NMR (CDCl₃) δ |
|---|---|---|---|
| 112 | 3-OMe | 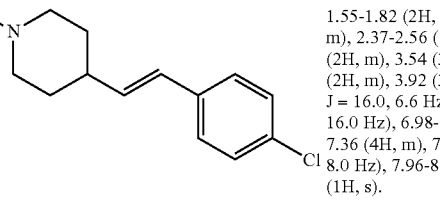 | 1.55-1.82 (2H, m), 1.86-2.04 (2H, m), 2.37-2.56 (1H, m), 3.06-3.35 (2H, m), 3.54 (3H, s), 3.84-4.48 (2H, m), 3.92 (3H, s), 6.16 (1H, dd, J = 16.0, 6.6 Hz), 6.40 (1H, d, J = 16.0 Hz), 6.98-7.09 (1H, m), 7.22-7.36 (4H, m), 7.40 (1H, t, J = 8.0 Hz), 7.96-8.10 (2H, m), 8.61 (1H, s). |
| 113 | 3-OMe | 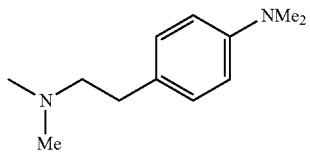 | 2.56-3.09 (8H, m), 3.20 (3H, br s), 3.51 (3H, s), 3.68-3.85 (2H, m), 3.92 (3H, s), 6.23-6.51 (1H, m), 6.60-7.24 (4H, m), 7.39 (1H, t, J = 7.9 Hz), 7.92-8.59 (3H, m). |
| 114 | 3-OMe | 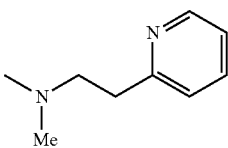 | 2.93-3.31 (5H, m), 3.52 (3H, s), 3.84-4.04 (2H, m), 3.92 (3H, s), 6.87-7.35 (3H, m), 7.40 (1H, t, J = 8.0 Hz), 7.48-7.71 (1H, m), 7.94-8.07 (2H, m), 8.07-8.68 (2H, m). |
| 115 | 3-OMe | 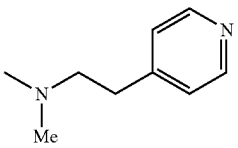 | 3.03 (2H, t, J = 7.2 Hz), 3.15 (3H, s), 3.53 (3H, s), 3.80 (2H, t, J = 7.2 Hz), 3.92 (3H, s), 6.98-7.07 (1H, m), 7.09-7.33 (2H, m), 7.40 (1H, t, J = 8.0 Hz), 7.96-8.09 (2H, m), 8.21-8.66 (3H, m). |

TABLE 23-continued

| Ex. No. | R | 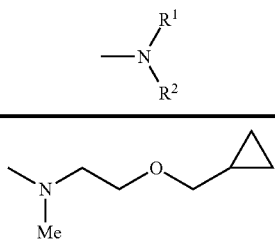 | ¹H-NMR (CDCl₃) δ |
|---|---|---|---|
| 116 | 3-OMe | 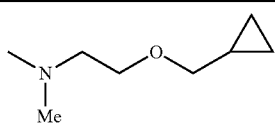 | 0.05-2.36 (2H, m), 0.40-0.68 (2H, m), 0.84-1.17 (1H, m), 3.16-3.42 (2H, m), 3.22 (3H, s), 3.53 (3H, s), 3.63-3.85 (4H, m), 3.92 (3H, s), 6.96-7.12 (1H, m), 7.39 (1H, t, J = 8.0 Hz), 7.93-8.15 (2H, m), 8.55 (1H, s). |

TABLE 24

| Ex. No. | R | 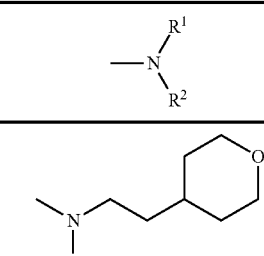 | ¹H-NMR (CDCl₃) δ |
|---|---|---|---|
| 117 | 3-OMe | 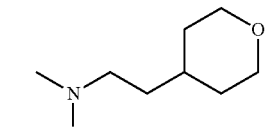 | 1.22-1.44 (2H, m), 1.44-1.74 (5H, m), 3.14 (3H, s), 3.27-3.45 (2H, m), 3.47-3.65 (2H, m), 3.54 (3H, s), 3.81-4.02 (2H, m), 3.92 (3H, s), 6.97-7.06 (1H, m), 7.40 (1H, t, J = 8.0 Hz), 7.95-8.08 (2H, m), 8.55 (1H, s). |
| 118 | 3-OMe | | 1.34-1.73 (7H, m), 1.80-1.98 (2H, m), 2.55-2.71 (2H, m), 2.96-3.22 (2H, m), 3.53 (3H, s), 3.80 (3H, s), 3.92 (3H, s), 6.80-6.92 (2H, m), 6.99-7.17 (3H, m), 7.40 (1H, t, J = 8.0 Hz), 7.97-8.10 (2H, m), 8.59 (1H, s). |
| 119 | 3-OMe | | (CDCl3) δ: 1.33-1.52 (2H, m), 1.54-1.94 (5H, m), 2.97-3.22 (2H, m), 3.35 (3H, s), 3.45 (2H, t, J = 6.3 Hz), 3.53 (3H, s), 3.92 (3H, s), 4.01-4.60 (2H, m), 6.98-7.07 (1H, m), 7.40 (1H, t, J = 7.9 Hz), 7.97-8.09 (2H, m), 8.59 (1H, s). |

TABLE 25

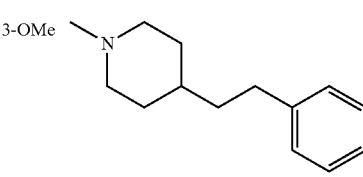

| Ex. No. | R' | R" | ¹H-NMR (CDCl₃) δ |
|---|---|---|---|
| 120 | H | H | 3.33-3.38 (4H, m), 3.56 (3H, s), 3.77-3.90 (4H, m), 6.90-7.00 (3H, m), 7.27-7.34 (2H, m), 7.47-7.53 (3H, m), 8.41-8.47 (2H, m), 8.65 (1H, s). |
| 121 | H | 3-OMe | 3.32-3.39 (4H, m), 3.55 (3H, s), 3.81 (3H, s), 3.75-3.90 (4H, m), 6.45-6.55 (2H, m), 6.55-6.62 (1H, m), 7.21 (1H, t, J = 8.0 Hz), 7.46-7.54 (3H, m), 8.41-8.47 (2H, m), 8.65 (1H, s). |

TABLE 25-continued

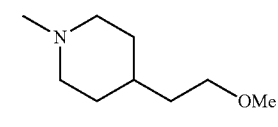

| Ex. No. | R' | R" | ¹H-NMR (CDCl₃) δ |
|---|---|---|---|
| 122 | H | 2-OMe | 3.20-3.28 (4H, m), 3.55 (3H, s), 3.90 (3H, s), 3.79-3.98 (4H, m), 6.89-7.01 (3H, m), 7.03-7.10 (1H, m), 7.46-7.54 (3H, m), 8.41-8.50 (2H, m), 8.66 (1H, s). |
| 123 | H | 4-F | 3.21-3.29 (4H, m), 3.55 (3H, s), 3.74-3.90 (4H, m), 6.88-7.04 (4H, m), 7.44-7.52 (3H, m), 8.39-8.47 (2H, m), 8.65 (1H, s). |

TABLE 25-continued

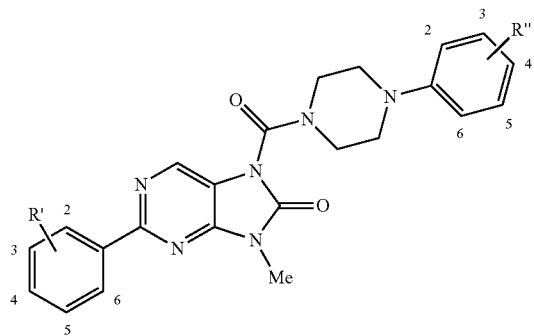

| Ex. No. | R' | R" | $^1$H-NMR (CDCl$_3$) δ |
|---|---|---|---|
| 124 | H | 3-F | 3.31-3.44 (4H, m), 3.55 (3H, s), 3.69-3.96 (4H, m), 6.56-6.68 (1H, m), 6.68-6.76 (1H, m), 7.18-7.29 (2H, m), 7.44-7.54 (3H, m), 8.40-8.48 (2H, m), 8.65 (1H, s). |
| 125 | H | 2-F | 3.20-3.31 (4H, m), 3.55 (3H, s), 3.72-3.96 (4H, m), 6.93-7.13 (4H, m), 7.43-7.54 (3H, m), 8.38-8.47 (2H, m), 8.66 (1H, s). |

TABLE 25-continued

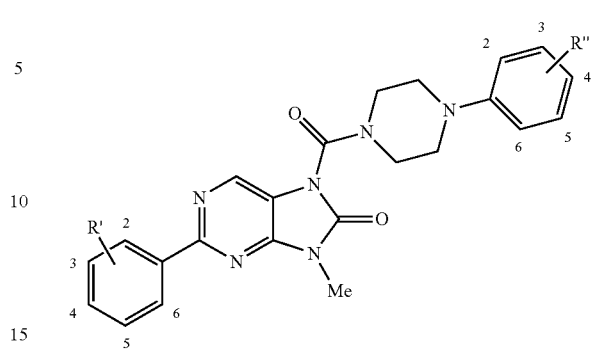

| Ex. No. | R' | R" | $^1$H-NMR (CDCl$_3$) δ |
|---|---|---|---|
| 126 | H | 4-Cl | 3.26-3.35 (4H, m), 3.55 (3H, s), 3.71-3.92 (4H, m), 6.85-6.93 (2H, m), 7.21-7.28 (2H, m), 7.44-7.54 (3H, m), 8.39-8.48 (2H, m), 8.65 (1H, s). |

TABLE 26

| Ex. No. | R' | R" | $^1$H-NMR (CDCl$_3$) δ |
|---|---|---|---|
| 127 | H | 2-Cl | 3.13-3.27 (4H, m), 3.55 (3H, s), 3.69-3.99 (4H, m), 6.98-7.11 (2H, m), 7.20-7.29 (1H, m), 7.40 (1H, dd, J = 7.9, 1.5 Hz), 7.43-7.53 (3H, m), 8.39-8.43 (2H, m), 8.65 (1H, s). |
| 128 | H | 4-Me | 2.29 (3H, s), 3.23-3.34 (4H, m), 3.55 (3H, s), 3.70-3.97 (4H, m), 6.84-6.93 (2H, m), 7.07-7.15 (2H, m), 7.44-7.54 (3H, m), 8.40-8.48 (2H, m), 8.65 (1H, s). |
| 129 | H | 3-Me | 2.34 (3H, s), 3.29-3.37 (4H, m), 3.55 (3H, s), 3.73-3.91 (4H, m), 6.72-6.82 (3H, m), 7.19 (1H, t, J = 7.6 Hz), 7.44-7.54 (3H, m), 8.39-8.47 (2H, m), 8.65 (1H, s). |
| 130 | H | 2-Me | 2.35 (3H, s), 2.99-3.14 (4H, m), 3.55 (3H, s), 3.69-3.99 (4H, m), 6.99-7.09 (2H, m), 7.14-7.24 (2H, m), 7.43-7.54 (3H, m), 8.39-8.47 (2H, m), 8.66 (1H, s). |
| 131 | H | 4-OEt | 1.40 (3H, t, J = 7.0 Hz), 3.18-3.28 (4H, m), 3.55 (3H, s), 3.71-3.95 (4H, m), 4.00 (2H, q, J = 7.0 Hz), 6.82-7.00 (4H, m), 7.43-7.56 (3H, m), 8.39-8.49 (2H, m), 8.65 (1H, s). |
| 132 | H | 4-CN | 3.49-3.62 (7H, m), 3.73-3.95 (4H, m), 6.87-6.96 (2H, m), 7.46-7.55 (3H, m), 7.88-7.95 (2H, m), 8.40-8.48 (2H, m), 8.66 (1H, s). |
| 133 | H | 4-Ac | 2.55 (3H, s), 3.49-3.64 (4H, m), 3.55 (3H, s), 3.72-3.97 (4H, m), 6.87-6.96 (2H, m), 7.44-7.55 (3H, m), 7.87-7.96 (2H, m), 8.40-8.49 (2H, m), 8.66 (1H, s). |
| 134 | H | 4-CF$_3$ | 3.42-3.51 (4H, m), 3.56 (3H, s), 3.75-3.91 (4H, m), 6.94-7.01 (2H, m), 7.45-7.56 (5H, m), 8.40-8.47 (2H, m), 8.66 (1H, s). |
| 135 | H | 4-OMe | 3.19-3.26 (4H, m), 3.55 (3H, s), 3.79 (3H, s), 3.75-3.92 (4H, m), 6.82-6.90 (2H, m), 6.92-6.98 (2H, m), 7.46-7.54 (3H, m), 8.40-8.47 (2H, m), 8.65 (1H, s). |
| 136 | 3-OMe | 4-F | 3.22-3.32 (4H, m), 3.55 (3H, s), 3.73-3.91 (4H, m), 3.92 (3H, s), 6.88-7.07 (5H, m), 7.40 (1H, t, J = 8.0 Hz), 7.98-8.08 (2H, m), 8.64 (1H, s). |

TABLE 27

| Ex. No. | R' | R" | $^1$H-NMR (CDCl$_3$) δ |
|---|---|---|---|
| 137 | 3-OMe | 3-F | 3.32-3.42 (4H, m), 3.55 (3H, s), 3.72-3.91 (4H, m), 3.92 (3H, s), 6.56-6.68 (2H, m), 6.68-6.76 (1H, m), 7.00-7.07 (1H, m), 7.18-7.28 (1H, m), |

TABLE 27-continued

| Ex. No. | R' | R" | $^1$H-NMR (CDCl$_3$) δ |
|---|---|---|---|
| | | | 7.41 (1H, t, J = 8.0 Hz), 7.98-8.07 (2H, m), 8.65 (1H, s). |
| 138 | 3-OMe | 4-Me | 2.29 (3H, s), 3.25-3.33 (4H, m), 3.55 (3H, s), 3.75-3.90 (4H, m), 3.92 (3H, s), 6.86-6.93 (2H, m), 7.00-7.06 (1H, m), 7.07-7.15 (2H, m), 7.40 (1H, t, J = 8.0 Hz), 7.98-8.08 (2H, m), 8.64 (1H, s). |
| 139 | 3-OMe | 3-Me | 2.34 (3H, s), 3.30-3.40 (4H, m), 3.55 (3H, s), 3.71-3.90 (4H, m), 3.92 (3H, s), 6.70-6.84 (3H, m), 7.00-7.07 (1H, m), 7.13-7.24 (1H, m), 7.40 (1H, t, J = 8.0 Hz), 7.98-8.09 (2H, m), 8.64 (1H, s). |
| 140 | 3-OMe | H | 3.32-3.40 (4H, m), 3.55 (3H, s), 3.74-3.90 (4H, m), 3.92 (3H, s), 6.88-7.07 (4H, m), 7.24-7.35 (2H, m), 7.40 (1H, t, J = 8.0 Hz), 7.98-8.08 (2H, m), 8.64 (1H, s). |
| 141 | 3-OMe | 4-OEt | 1.40 (3H, t, J = 7.0 Hz), 3.20-3.26 (4H, m), 3.55 (3H, s), 3.74-3.89 (4H, m), 3.92 (3H, s), 4.00 (2H, q, J = 7.0 Hz), 6.82-6.98 (4H, m), 7.00-7.07 (1H, m), 7.40 (1H, t, J = 7.9 Hz), 7.98-8.08 (2H, m), 8.64 (1H, s). |
| 142 | 3-OMe | 4-Cl | 3.28-3.34 (4H, m), 3.55 (3H, s), 3.76-3.88 (4H, m), 3.92 (3H, s), 6.86-6.92 (2H, m), 7.00-7.06 (1H, m), 7.20-7.30 (2H, m), 7.41 (1H, t, J = 8.0 Hz), 7.98-8.07 (2H, m), 8.64 (1H, s). |

TABLE 28

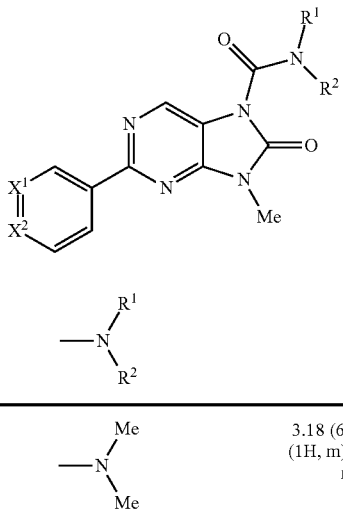

| Ex. No. | X$^1$ | X$^2$ | –N(R$^1$)(R$^2$) | $^1$H-NMR (CDCl$_3$) δ |
|---|---|---|---|---|
| 143 | N | CH | 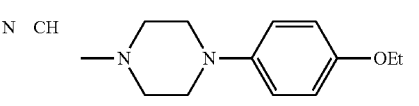 | 3.18 (6H, s), 3.55 (3H, s), 7.38-7.44 (1H, m), 8.61 (1H, s), 8.66-8.73 (2H, m), 9.62-9.66 (1H, m). |
| 144 | N | CH | 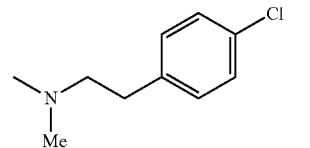 | 1.40 (3H, t, J = 7.0 Hz), 3.19-3.27 (4H, m), 3.56 (3H, s), 3.73-3.93 (4H, m), 4.00 (2H, q, J = 7.0 Hz), 6.82-6.90 (2H, m), 6.90-6.98 (2H, m), 7.38-7.45 (1H, m), 8.64-8.74 (3H, m), 9.62-9.67 (1H, m). |
| 145 | N | CH | 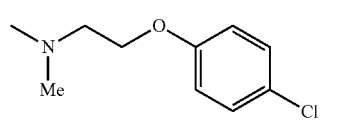 | 2.87-3.07 (2H, br m), 3.15 (3H, br s), 3.53 (3H, s), 3.77 (2H, t, J = 7.1 Hz), 6.93-7.37 (4H, m), 7.37-7.47 (1H, m), 8.51 (1H, br s), 8.64-8.78 (2H, m), 9.61-9.67 (1H, m). |
| 146 | N | CH | | 3.29 (3H, br s), 3.53 (3H, s), 3.93 (2H, t, J = 5.1 Hz), 4.15-4.36 (2H, m), 6.56-6.96 (2H, m), 7.07-7.36 (2H, m), 7.38-7.47 (1H, m), 8.58 (1H, s), 8.65-8.76 (2H, m), 9.61-9.70 (1H, m). |

TABLE 28-continued
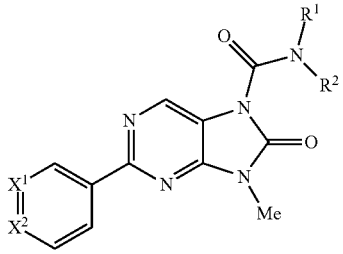
| Ex. No. | X¹ | X² | 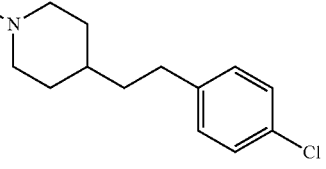 | ¹H-NMR (CDCl₃) δ |
|---|---|---|---|---|
| 147 | N | CH | 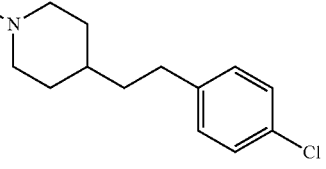 | 1.32-1.74 (5H, m), 1.76-2.00 (2H, m), 2.64 (2H, t, J = 7.7 Hz), 2.85-3.30 (2H, m), 3.54 (3H, s), 3.69-4.66 (2H, m), 7.08-7.13 (2H, m), 7.23-7.29 (2H, m), 7.38-7.44 (1H, m), 8.61 (1H, s), 8.65-8.75 (2H, m), 9.61-9.65 (1H, m). |
TABLE 29
| Ex. No. | X¹ | X² | 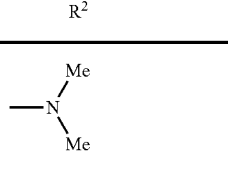 | ¹H-NMR (CDCl₃) δ |
|---|---|---|---|---|
| 148 | CH | N | 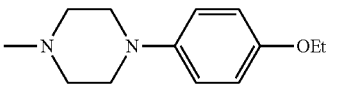 [SMILES: CCOc1ccc(N2CCN(C)CC2)cc1] | 3.18 (6H, s), 3.56 (3H, s), 8.25-8.31 (2H, m), 8.64 (1H, s), 8.73-8.79 (2H, m). |
| 149 | CH | N | 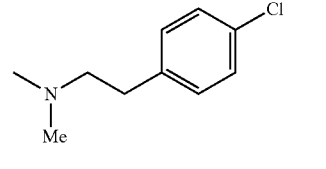 | 1.40 (3H, t, J = 7.0 Hz), 3.18-3.28 (4H, m), 3.57 (3H, s), 3.72-3.94 (4H, m), 4.00 (2H, q, J = 7.0 Hz), 6.82-6.98 (4H, m), 8.26-8.32 (2H, m), 8.69 (1H, s), 8.74-8.79 (2H, m). |
| 150 | CH | N | 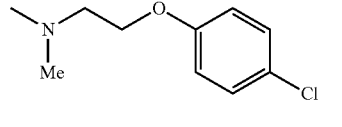 | 2.85-3.29 (5H, m), 3.54 (3H, s), 3.77 (2H, t, J = 7.1 Hz), 6.93-7.48 (4H, m), 8.26-8.32 (2H, m), 8.58 (1H, br s), 8.74-8.80 (2H, m). |
| 151 | CH | N | 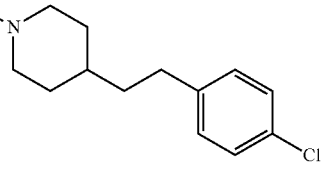 | 3.29 (3H, s), 3.54 (3H, s), 3.93 (2H, t, J = 5.0 Hz), 4.06-4.42 (2H, m), 6.54-6.98 (2H, m), 7.08-7.35 (2H, m), 8.25-8.34 (2H, m), 8.60 (1H, s), 8.72-8.82 (2H, m). |
| 152 | CH | N | | 1.34-1.71 (5H, m), 1.80-1.95 (2H, m), 2.64 (2H, t, J = 7.6 Hz), 2.94-3.23 (2H, m), 3.55 (3H, s), 3.83-4.54 (2H, br m), 7.07-7.15 (2H, m), 7.22-7.32 (2H, m), 8.26-8.30 (2H, m), 8.64 (1H, s), 8.73-8.79 (2H, m). |

TABLE 30

| Ex. No. | Structure | ¹H-NMR (CDCl₃) δ |
|---|---|---|
| 153 | 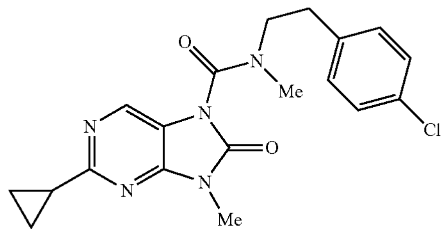 [SMILES: CN(CCc1ccc(Cl)cc1)C(=O)n1c(=O)n(C)c2nc(C3CC3)ncc21] | 0.95-1.26 (4H, m), 2.14-2.31 (1H, m), 2.82-3.27 (5H, m), 3.40 (3H, s), 3.72 (2H, t, J = 7.2 Hz), 6.93-7.49 (4H, m), 7.91-8.37 (1H, m). |
| 154 | 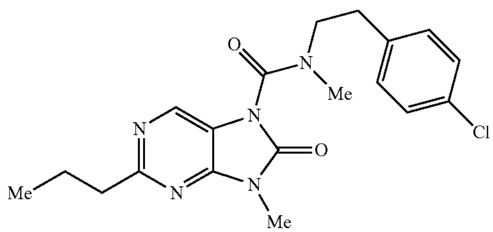 [SMILES: CCCc1ncc2c(n1)n(C)c(=O)n2C(=O)N(C)CCc1ccc(Cl)cc1] | 0.99 (3H, t, J = 7.3 Hz), 1.76-1.93 (2H, m), 2.84-3.06 (2H, m), 2.89 (2H, t, J = 7.7 Hz), 3.11 (3H, br s), 3.44 (3H, s), 3.74 (2H, t, J = 7.2 Hz), 6.93-7.43 (4H, m), 7.60-8.46 (1H, m). |
| 155 | 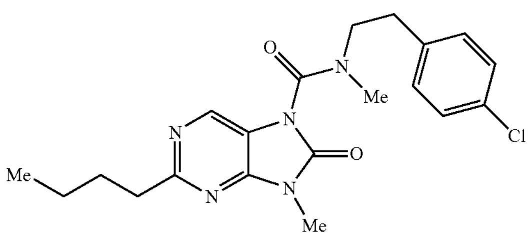 [SMILES: CCCCc1ncc2c(n1)n(C)c(=O)n2C(=O)N(C)CCc1ccc(Cl)cc1] | 0.95 (3H, t, J = 7.3 Hz), 1.33-1.48 (2H, m), 1.72-1.87 (2H, m), 2.85-3.03 (4H, m), 3.11 (3H, br s), 3.44 (3H, s), 3.73 (2H, t, J = 7.2 Hz), 6.85-7.49 (4H, m), 7.87-8.52 (1H, m). |
| 156 | 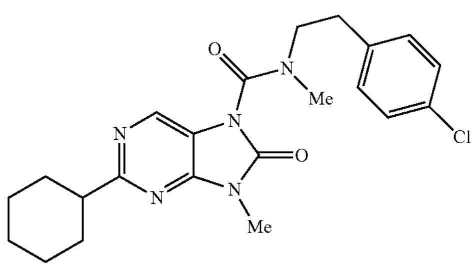 [SMILES: CN(CCc1ccc(Cl)cc1)C(=O)n1c(=O)n(C)c2nc(C3CCCCC3)ncc21] | 1.21-1.51 (2H, m), 1.55-1.79 (4H, m), 1.79-1.91 (2H, m), 1.92-2.08 (2H, m), 2.77-3.02 (3H, m), 3.11 (3H, br s), 3.44 (3H, s), 3.73 (2H, t, J = 7.2 Hz), 6.92-7.41 (4H, m), 7.84-8.55 (1H, m). |
| 157 | 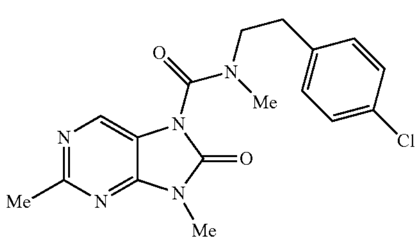 [SMILES: Cc1ncc2c(n1)n(C)c(=O)n2C(=O)N(C)CCc1ccc(Cl)cc1] | 2.70 (3H, s), 2.86-3.06 (2H, m), 3.12 (3H, br s), 3.44 (3H, s), 3.74 (2H, t, J = 6.8 Hz), 6.89-7.48 (4H, m), 7.96-8.47 (1H, m). |
| 158 | 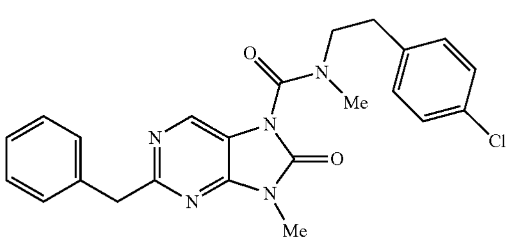 [SMILES: CN(CCc1ccc(Cl)cc1)C(=O)n1c(=O)n(C)c2nc(Cc3ccccc3)ncc21] | 2.86-3.25 (5H, m), 3.42 (3H, s), 3.72 (2H, t, J = 7.2 Hz), 4.24 (2H, s), 6.88-7.57 (9H, m), 7.96-8.49 (1H, m). |

TABLE 31

| Ex. No. | Structure | ¹H-NMR (CDCl₃) δ |
| --- | --- | --- |
| 159 | 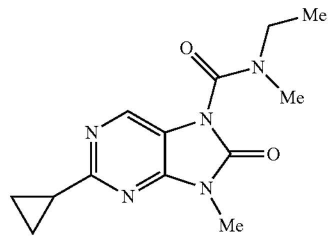 [SMILES: CCN(C)C(=O)n1c(=O)n(C)c2nc(C3CC3)ncc21] | 0.97-1.15 (4H, m), 1.28 (3H, t, J = 7.2 Hz), 2.16-2.28 (1H, m), 3.10 (3H, s), 3.41 (3H, s), 3.54 (2H, q, J = 7.2 Hz), 8.32 (1H, s). |
| 160 | 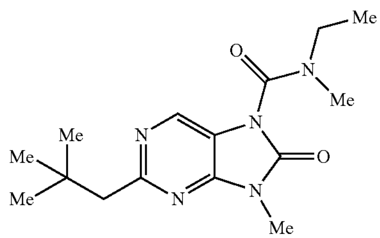 [SMILES: CCN(C)C(=O)n1c(=O)n(C)c2nc(CC(C)(C)C)ncc21] | 1.01 (9H, s), 1.30 (3H, t, J = 7.1 Hz), 2.83 (2H, m), 3.12 (3H, s), 3.45 (3H, s), 3.49-3.64 (2H, m), 8.43 (1H, s). |
| 161 | 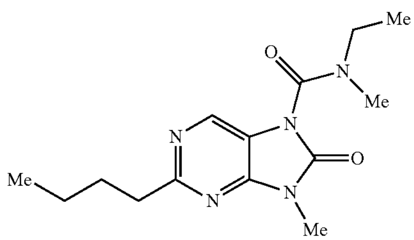 [SMILES: CCCCc1ncc2c(n1)n(C)c(=O)n2C(=O)N(C)CC] | 0.95 (3H, t, J = 7.3 Hz), 1.29 (3H, t, J = 7.2 Hz), 1.33-1.50 (2H, m), 1.70-1.87 (2H, m), 2.92 (2H, t, J = 7.8 Hz), 3.11 (3H, s), 3.45 (3H, s), 3.47-3.62 (2H, m), 8.41 (1H, s). |
| 162 | 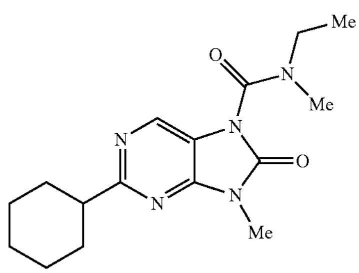 [SMILES: CCN(C)C(=O)n1c(=O)n(C)c2nc(C3CCCCC3)ncc21] | 1.22-1.50 (5H, m), 1.53-1.79 (4H, m), 1.79-1.91 (2H, m), 1.92-2.03 (2H, m), 2.78-2.92 (1H, m), 3.11 (3H, s), 3.45 (3H, s), 3.47-3.62 (2H, m), 8.41 (1H, s). |
| 163 | 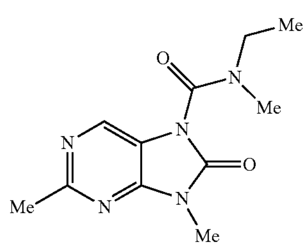 [SMILES: CCN(C)C(=O)n1c(=O)n(C)c2nc(C)ncc21] | 1.29 (3H, t, J = 7.1 Hz), 2.70 (3H, s), 3.11 (3H, s), 3.41-3.63 (5H, m), 8.39 (1H, s). |
| 164 | 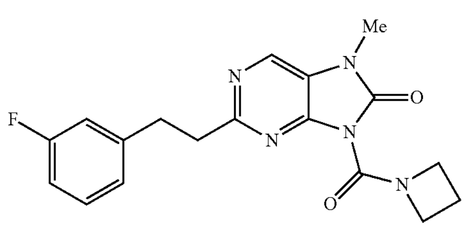 [SMILES: Cn1c(=O)n(C(=O)N2CCC2)c2nc(CCc3cccc(F)c3)ncc21] | 2.31-2.43 (2H, m), 3.10-3.21 (2H, m), 3.24-3.35 (2H, m), 3.43 (3H, s), 4.23 (2H, t, J = 7.8 Hz), 4.34 (2H, t, J = 7.8 Hz), 6.82-7.07 (3H, m), 7.18-7.31 (1H, m), 8.17 (1H, s). |

TABLE 31-continued

| Ex. No. | Structure | ¹H-NMR (CDCl₃) δ |
|---|---|---|
| 165 | 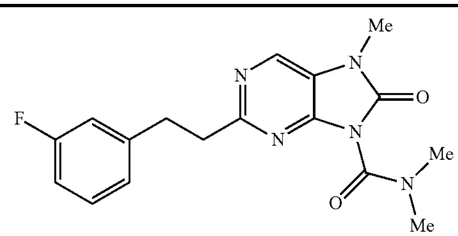 | 2.96-3.38 (4H, m), 3.04 (3H, s), 3.23 (3H, s), 3.44 (3H, s), 6.80-7.11 (3H, m), 7.13-7.36 (1H, m), 8.17 (1H, s). |

Example 166

Process of 2-(2-fluorophenyl)-9-methyl-7-(pyrrolidin-1-ylcarbonyl)-7,9-dihydro-8H-purine-8-one

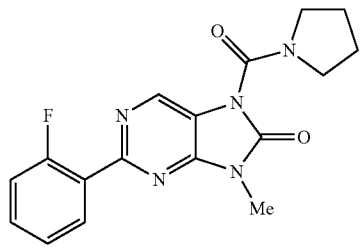 [SMILES: Cn1c(=O)n(C(=O)N2CCCC2)c2cnc(-c3ccccc3F)nc21]

To a mixture of 2-chloro-9-methyl-7-(pyrrolidin-1-ylcarbonyl)-7,9-dihydro-8H-purine-8-one <the compound of Reference Example 16> (100 mg), 2-fluorophenylboronic acid (74 mg), potassium carbonate (145 mg), toluene (3 ml) and ethanol (1 ml) was added bis(tri-tert-butylphosphine)palladium (9 mg) under nitrogen atmosphere and the mixture was stirred at 130° C. under microwave irradiation for 1 hour. The reaction mixture was filtered through Celite and the filtrate was concentrated under reduced pressure. The obtained residue was purified by silica gel column chromatography (eluent: chloroform/methanol=100/0~90/10) to give the title compound 58 mg.

¹H-NMR (CDCl₃) δ: 1.89-2.15 (4H, m), 3.52 (3H, s), 3.64-3.82 (4H, m), 7.14-7.31 (2H, m), 7.38-7.49 (1H, m), 7.97-8.06 (1H, m), 8.70 (1H, s).

Examples 167 to 252

The compounds indicated in Tables 32 to 43 were prepared according to the similar method to those of Example 166.

TABLE 32

| Ex. No. | R | ¹H-NMR (CDCl₃) δ |
|---|---|---|
| 167 | 3-F | 1.92-2.10 (4H, m), 3.54 (3H, s), 3.68-3.74 (4H, m), 7.12-7.19 (1H, m), 7.40-7.49 (1H, m), 8.11-8.18 (1H, m), 8.21-8.27 (1H, m), 8.64 (1H, s). |
| 168 | 4-F | 1.91-2.10 (4H, m), 3.53 (3H, s), 3.66-3.75 (4H, m), 7.11-7.19 (2H, m), 8.40-8.48 (2H, m), 8.62 (1H, s). |
| 169 | 2-Me | 1.88-2.13 (4H, m), 2.56 (3H, s), 3.50 (3H, s), 3.60-3.82 (4H, m), 7.23-7.39 (3H, m), 7.75-7.83 (1H, m), 8.68 (1H, s). |
| 170 | 3-Me | 1.91-2.18 (4H, m), 2.46 (3H, s), 3.54 (3H, s), 3.64-3.86 (4H, m), 7.24-7.46 (2H, m), 8.20-8.32 (2H, m), 8.64 (1H, s). |
| 171 | 4-Me | 1.93-2.10 (4H, m), 2.42 (3H, s), 3.53 (3H, s), 3.67-3.74 (4H, m), 7.27-7.31 (2H, m), 8.30-8.34 (2H, m), 8.62 (1H, s). |
| 172 | 2-OMe | 1.90-2.12 (4H, m), 3.51 (3H, s), 3.65-3.77 (4H, m), 3.86 (3H, s), 7.00-7.11 (2H, m), 7.37-7.46 (1H, m), 7.61-7.68 (1H, m), 8.69 (1H, s). |
| 173 | 3-OMe | 1.92-2.09 (4H, m), 3.54 (3H, s), 3.67-3.74 (4H, m), 3.92 (3H, s), 6.99-7.06 (1H, m), 7.40 (1H, t, J = 8.0 Hz), 7.98-8.08 (2H, m), 8.65 (1H, s). |
| 174 | 4-OMe | 2.00-2.03 (4H, m), 3.52 (3H, s), 3.69-3.71 (4H, m), 3.88 (3H, s), 6.98-7.01 (2H, m), 8.37-8.40 (2H, m), 8.60 (1H, s). |
| 175 | 3-OEt | 1.46 (3H, t, J = 7.0 Hz), 1.92-2.11 (4H, m), 3.53 (3H, s), 3.66-3.76 (4H, m), 4.16 (2H, q, J = 7.0 Hz), 7.01 (1H, dd, J = 8.2, 2.7 Hz), 7.39 (1H, t, J = 8.0 Hz), 7.97-8.05 (2H, m), 8.63 (1H, s). |
| 176 | 4-OEt | 1.45 (3H, t, J = 7.0 Hz), 1.93-2.08 (4H, m), 3.52 (3H, s), 3.67-3.73 (4H, m), 4.11 (2H, q, J = 7.0 Hz), 6.96-7.00 (2H, m), 8.35-8.39 (2H, m), 8.59 (1H, s). |

TABLE 33

| Ex. No. | R | ¹H-NMR (CDCl₃) δ |
|---|---|---|
| 177 | 4-OCF₃ | 1.92-2.09 (4H, m), 3.53 (3H, s), 3.67-3.74 (4H, m), 7.28-7.34 (2H, m), 8.44-8.52 (2H, m), 8.64 (1H, s). |
| 178 | 4-CF₃ | 1.93-2.11 (4H, m), 3.55 (3H, s), 3.67-3.75 (4H, m), 7.70-7.77 (2H, m), 8.53-8.59 (2H, m), 8.67 (1H, s). |
| 179 | 4-Ph | 1.93-2.10 (4H, m), 3.55 (3H, s), 3.66-3.76 (4H, m), 7.35-7.41 (1H, m), 7.44-7.51 (2H, m), 7.64-7.76 (4H, m), 8.48-8.54 (2H, m), 8.66 (1H, s). |
| 180 | 4-n-Pr | 0.96 (3H, t, J = 7.3 Hz), 1.69 (2H, dd, J = 15.0, 7.4 Hz), 1.93-2.09 (4H, m), 2.66 (2H, t, J = 7.6 Hz), 3.53 (3H, s), |

TABLE 33-continued

| Ex. No. | R | ¹H-NMR (CDCl₃) δ |
|---|---|---|
|  |  | 3.67-3.73 (4H, m), 7.27-7.31 (2H, m), 8.31-8.35 (2H, m), 8.62 (1H, s). |
| 181 | 4-CN | 1.93-2.10 (4H, m), 3.55 (3H, s), 3.68-3.74 (4H, m), 7.75-7.80 (2H, m), 8.54-8.60 (2H, m), 8.67 (1H, s). |
| 182 | 4-NMe₂ | 1.91-2.08 (4H, m), 3.05 (6H, s), 3.51 (3H, s), 3.64-3.74 (4H, m), 6.75-6.80 (2H, m), 8.29-8.34 (2H, m), 8.56 (1H, s). |
| 183 | 4-SMe | 1.93-2.09 (4H, m), 2.55 (3H, s), 3.53 (3H, s), 3.67-3.73 (4H, m), 7.31-7.35 (2H, m), 8.33-8.38 (2H, m), 8.61 (1H, s). |
| 184 | 4-Ac | 1.93-2.11 (4H, m), 2.67 (3H, s), 3.56 (3H, s), 3.67-3.75 (4H, m), 8.04-8.10 (2H, m), 8.51-8.56 (2H, m), 8.68 (1H, s). |
| 185 | 4-tert-Bu | 1.37 (9H, s), 1.92-2.08 (4H, m), 3.53 (3H, s), 3.67-3.74 (4H, m), 7.48-7.53 (2H, m), 8.32-8.37 (2H, m), 8.63 (1H, s). |
| 186 | 3-Ac | 1.89-2.12 (4H, m), 2.72 (3H, s), 3.56 (3H, s), 3.61-3,75 (4H, m), 7.59 (1H, t, J = 1.2 Hz), 8.02-8.10 (1H, m), 8.61-8.69 (1H, m), 8.67 (1H, s), 8.90-9.03 (1H, m). |
| 187 | 2-F 3-F | 1.90-2.10 (4H, m), 3.52 (3H, s), 3.66-3.75 (4H, m), 7.14-7.31 (2H, m), 7.77-7.83 (1H, m), 8.70 (1H, s). |
| 188 | 2-F 4-F | 1.91-2.10 (4H, m), 3.52 (3H, s), 3.65-3.76 (4H, m), 6.89-7.04 (2H, m), 8.02-8.12 (1H, m), 8.68 (1H, s). |

TABLE 34

| Ex. No. | R | ¹H-NMR (CDCl₃) δ |
|---|---|---|
| 189 | 2-F 5-F | 1.93-2.09 (4H, m), 3.52 (3H, s), 3.67-3.74 (4H, m), 7.07-7.19 (2H, m), 7.74-7.81 (1H, m), 8.70 (1H, s). |
| 190 | 3-F 4-F | 1.91-2.11 (4H, m), 3.53 (3H, s), 3.66-3.75 (4H, m), 7.20-7.30 (1H, m), 8.17-8.33 (2H, m), 8.62 (1H, s). |
| 191 | 3-F 4-OMe | 1.91-2.11 (4H, m), 3.52 (3H, s), 3.66-3.75 (4H, m), 3.97 (3H, s), 7.04 (1H, t, J = 8.7 Hz), 8.14-8.25 (2H, m), 8.60 (1H, s). |
| 192 | 3-F 4-Me | 1.91-2.11 (4H, m), 2.34 (3H, s), 3.53 (3H, s), 3.66-3.75 (4H, m), 7.24-7.31 (1H, m), 8.05-8.15 (2H, m), 8.62 (1H, s). |
| 193 | 3-OEt 5-F | 1.46 (3H, t, J = 7.0 Hz), 1.91-2.11 (4H, m), 3.53 (3H, s), 3.64-3.78 (4H, m), 4.13 (2H, q, J = 7.0 Hz), 6.71 (1H, dt, J = 10.3, 2.3 Hz), 7.69-7.84 (2H, m), 8.62 (1H, s). |
| 194 | 3-Me 4-F | 1.92-2.10 (4H, m), 2.35 (3H, s), 3.51 (3H, s), 3.66-3.75 (4H, m), 7.03-7.11 (1H, m), 7.17 (1H, td, J = 8.0, 1.3 Hz), 7.50-7.57 (1H, m), 8.69 (1H, s). |
| 195 | 2-OMe 5-F | 1.92-2.12 (4H, m), 3.51 (3H, s), 3.66-3.77 (4H, m), 3.84 (3H, s), 6.94-7.00 (1H, m), 7.07-7.15 (1H, m), 7.42 (1H, dd, J = 8.9, 3.2 Hz), 8.69 (1H, s). |
| 196 | 2-F 3-OMe | 1.92-2.10 (4H, m), 3.51 (3H, s), 3.66-3.75 (4H, m), 3.94 (3H, s), 7.03-7.11 (1H, m), 7.17 (1H, td, J = 8.0, 1.3 Hz), 7.50-7.57 (1H, m), 8.69 (1H, s). |
| 197 | 3-Me 5-Me | 1.94-2.09 (4H, m), 2.42 (6H, s), 3.55 (3H, s), 3.67-3.76 (4H, m), 7.09-7.14 (1H, m), 8.01-8.08 (2H, m), 8.63 (1H, s). |
| 198 | 3-F 4-OCF₃ | 1.93-2.11 (4H, m), 3.54 (3H, s), 3.68-3.74 (4H, m), 7.36-7.44 (1H, m), 8.23-8.35 (2H, m), 8.64 (1H, s). |
| 199 | 2-F 5-CF₃ | 1.93-2.12 (4H, m), 3.54 (3H, s), 3.67-3.76 (4H, m), 7.31 (1H, t, J = 9.4 Hz), 7.66-7.74 (1H, m), 8.37 (1H, dd, J = 6.8, 2.2 Hz), 8.72 (1H, s). |

TABLE 35

| Ex. No. | R | ¹H-NMR (CDCl₃) δ |
|---|---|---|
| 200 | 2-F 5-OMe | 1.93-2.09 (4H, m), 3.52 (3H, s), 3.67-3.76 (4H, m), 3.86 (3H, s), 6.92-7.00 (1H, m), 7.06-7.16 (1H, m), 7.54 (1H, dd, J = 6.1, 3.3 Hz), 8.70 (1H, s). |
| 201 | 3-F 5-Me | 1.91-2.13 (4H, m), 2.45 (3H, s), 3.54 (3H, s), 3.66-3.76 (4H, m), 6.94-7.03 (1H, m), 7.90-7.97 (1H, m), 8.02-8.07 (1H, m), 8.63 (1H, s). |
| 202 | 3-OBn | 1.91-2.10 (4H, m), 3.53 (3H, s), 3.63-3.75 (4H, m), 5.18 (2H, s), 7.05-7.12 (1H, m), 7.30-7.44 (4H, m), 7.46-7.52 (2H, m), 8.02-8.12 (2H, m), 8.64 (1H, s). |
| 203 | 3-NO₂ | 1.92-2.14 (4H, m), 3.57 (3H, s), 3.65-3.79 (4H, m), 7.66 (1H, t, J = 8.1 Hz), 8.28-8.35 (1H, m), 8.68 (1H, s), 8.77-8.82 (1H, m), 9.28-9.32 (1H, m). |
| 204 | 3-OCF₃ | 1.91-2.11 (4H, m), 3.54 (3H, s), 3.67-3.75 (4H, m), 7.28-7.35 (1H, m), 7.50 (1H, t, J = 8.0 Hz), 8.28-8.33 (1H, m), 8.36-8.42 (1H, m), 8.65 (1H, s). |

TABLE 36

[Structure: pyridinyl-substituted purine with pyrrolidine carbonyl, positions labeled 2,4,5,6 on pyridine; N-Me on imidazolone]

| Ex. No. | R | ¹H-NMR (CDCl₃) δ |
|---|---|---|
| 205 | H | 1.92-2.11 (4H, m), 3.55 (3H, s), 3.65-3.77 (4H, m), 7.38-7.44 (1H, m), 8.65-8.71 (3H, m), 9.63 (1H, t, J = 1.1 Hz). |
| 206 | 6-OMe | 1.93-2.10 (4H, m), 3.52 (3H, s), 3.66-3.75 (4H, m), 4.02 (3H, s), 6.81-6.85 (1H, m), 8.57 (1H, dd, J = 8.7, 2.5 Hz), 8.60 (1H, s), 9.21-9.24 (1H, m). |
| 207 | 6-F | 1.91-2.12 (4H, m), 3.54 (3H, s), 3.64-3.80 (4H, m), 7.00-7.06 (1H, m), 8.64 (1H, s), 8.74-8.76 (1H, m), 9.25-9.28 (1H, m). |
| 208 | 5-OMe | 1.94-2.09 (4H, m), 3.55 (3H, s), 3.68-3.74 (4H, m), 3.97 (3H, s), 8.19-8.22 (1H, m), 8.39-8.41 (1H, m), 8.65 (1H, s), 9.24-9.27 (1H, m). |
| 209 | 2-F | 1.93-2.09 (4H, m), 3.53 (3H, s), 3.67-3.75 (4H, m), 7.31-7.36 (1H, m), 8.29-8.33 (1H, m), 8.50-8.57 (1H, m), 8.71 (1H, s). |
| 210 | 6-OEt | 1.43 (3H, t, J = 7.1 Hz), 1.94-2.09 (4H, m), 3.51 (3H, s), 3.68-3.74 (4H, m), 4.44 (2H, q, J = 7.1 Hz), 6.79-6.82 (1H, m), 8.56 (1H, dd, J = 8.8, 2.4 Hz), 8.60 (1H, s), 9.18-9.22 (1H, m). |
| 211 | 5-F | 1.94-2.11 (4H, m), 3.55 (3H, s), 3.64-3.67 (4H, m), 8.38-8.44 (1H, m), 8.54-8.57 (1H, m), 8.66 (1H, s), 9.45-9.48 (1H, m). |

TABLE 36-continued

[Structure: pyridinyl-substituted purine isomer with N-Me on other nitrogen]

| Ex. No. | R | ¹H-NMR (CDCl₃) δ |
|---|---|---|
| 212 | 5-Me | 1.94-2.11 (4H, m), 2.44 (3H, s), 3.55 (3H, s), 3.67-3.75 (4H, m), 8.47-8.54 (2H, m), 8.66 (1H, s), 9.42-9.44 (1H, m). |

TABLE 37

[Structure: 4-pyridyl-substituted purine with pyrrolidine carbonyl, positions 2,3,5,6 on pyridine]

| Ex. No. | R | ¹H-NMR (CDCl₃) δ |
|---|---|---|
| 213 | H | 1.91-2.11 (4H, m), 3.55 (3H, s), 3.67-3.76 (4H, m), 8.26-8.31 (2H, m), 8.69 (1H, s), 8.73-8.78 (2H, m). |
| 214 | 2-Cl | 1.92-2.13 (4H, m), 3.56 (3H, s), 3.67-3.76 (4H, m), 8.20-8.25 (1H, m), 8.32-8.36 (1H, m), 8.49-8.54 (1H, m), 8.68 (1H, s). |
| 215 | 2-F | 1.94-2.12 (4H, m), 3.55 (3H, s), 3.67-3.75 (4H, m), 7.92-7.95 (1H, m), 8.17-8.20 (1H, m), 8.33-8.35 (1H, m), 8.69 (1H, s). |

TABLE 38

| Ex. No. | Structure | ¹H-NMR (CDCl₃) δ |
|---|---|---|
| 216 | [benzofuran-2-yl-substituted purine with pyrrolidine carbonyl and N-Me] | 1.90-2.10 (4H, m), 3.53 (3H, s), 3.65-3.74 (4H, m), 7.24-7.30 (1H, m), 7.33-7.40 (1H, m), 7.61-7.68 (3H, m), 8.66 (1H, s). |
| 217 | [propenyl-substituted purine with pyrrolidine carbonyl and N-Me] | 1.87-2.10 (7H, m), 3.45 (3H, s), 3.61-3.73 (4H, m), 6.49-6.60 (1H, m), 7.03-7.19 (1H, m), 8.49 (1H, s). |

TABLE 38-continued

| Ex. No. | Structure | ¹H-NMR (CDCl₃) δ |
|---|---|---|
| 218 | 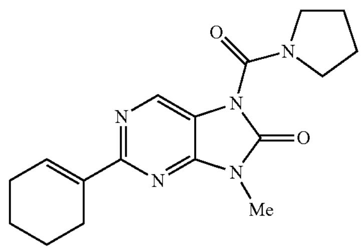 [SMILES: Cn1c(=O)n(C(=O)N2CCCC2)c2cnc(C3=CCCCC3)nc21] | 1.50-1.83 (4H, m), 1.89-2.11 (4H, m), 2.25-2.35 (2H, m), 2.54-2.65 (2H, m), 3.36 (3H, s), 3.51-3.76 (4H, m), 7.16-7.25 (1H, m), 8.51 (1H, s). |
| 219 | 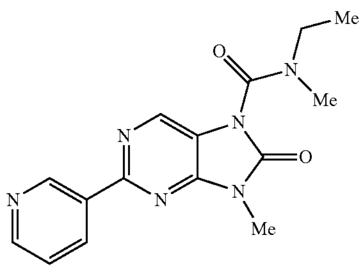 [SMILES: CCN(C)C(=O)n1c(=O)n(C)c2nc(-c3cccnc3)ncc21] | 1.32 (3H, t, J = 7.1 Hz), 3.15 (3H, s), 3.51-3.64 (5H, m), 7.36-7.47 (1H, m), 8.59 (1H, s), 8.64-8.74 (2H, m), 9.60-9.67 (1H, m). |
| 220 | 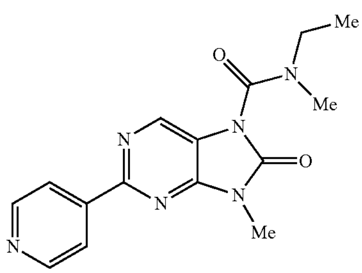 [SMILES: CCN(C)C(=O)n1c(=O)n(C)c2nc(-c3ccncc3)ncc21] | 1.32 (3H, t, J = 7.2 Hz), 3.15 (3H, s), 3.51-3.67 (5H, m), 8.26-8.32 (2H, m), 8.61 (1H, s), 8.73-8.80 (2H, m). |

TABLE 39

| Ex. No. | Structure | ¹H-NMR (CDCl₃) δ |
|---|---|---|
| 221 | 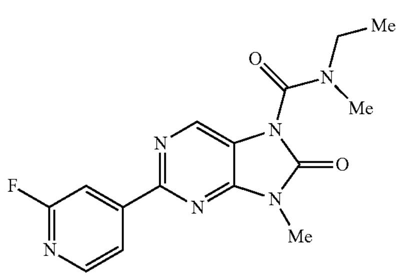 [SMILES: CCN(C)C(=O)n1c(=O)n(C)c2nc(-c3ccnc(F)c3)ncc21] | 1.32 (3H, t, J = 7.2 Hz), 3.15 (3H, s), 3.52-3.66 (5H, m), 7.91-7.97 (1H, m), 8.16-8.22 (1H, m), 8.31-8.39 (1H, m), 8.61 (1H, s). |
| 222 | 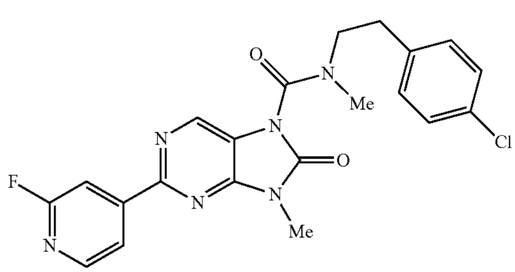 [SMILES: CN(CCc1ccc(Cl)cc1)C(=O)n1c(=O)n(C)c2nc(-c3ccnc(F)c3)ncc21] | 2.83-3.33 (5H, m), 3.54 (3H, s), 3.77 (2H, t, J = 7.2 Hz), 6.89-7.50 (4H, m), 7.90-7.96 (1H, m), 8.14-8.22 (1H, m), 8.29-8.62 (2H, m). |

TABLE 39-continued

| Ex. No. | Structure | ¹H-NMR (CDCl₃) δ |
|---|---|---|
| 223 | 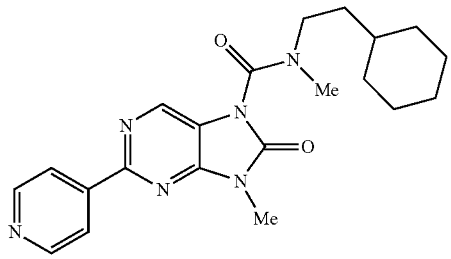 [SMILES: CN(CCC1CCCCC1)C(=O)n1c(=O)n(C)c2nc(-c3ccncc3)ncc21] | 0.76-1.93 (13H, m), 3.13 (3H, s), 3.44-3.67 (2H, m), 3.55 (3H, s), 8.25-8.33 (2H, m), 8.59 (1H, s), 8.71-8.80 (2H, m). |

TABLE 40

| Ex. No. | R | ¹H-NMR (CDCl₃) δ |
|---|---|---|
| 224 | H | 1.92-2.12 (4H, m), 3.49 (3H, s), 3.61 (2H, t, J = 6.7 Hz), 3.78 (2H, t, J = 6.8 Hz), 7.42-7.49 (3H, m), 8.31 (1H, s), 8.35-8.41 (2H, m). |
| 225 | 2-F | 1.91-2.11 (4H, m), 3.50 (3H, s), 3.63 (2H, t, J = 6.5 Hz), 3.75 (2H, t, J = 6.8 Hz), 7.13-7.29 (2H, m), 7.37-7.46 (1H, m), 7.96-8.04 (1H, m), 8.37 (1H, s). |
| 226 | 3-F | 1.92-2.15 (4H, m), 3.49 (3H, s), 3.60 (2H, t, J = 6.7 Hz), 3.78 (2H, t, J = 6.8 Hz), 7.09-7.19 (1H, m), 7.37-7.47 (1H, m), 8.04-8.12 (1H, m), 8.14-8.20 (1H, m), 8.31 (1H, s). |
| 227 | 4-F | 1.93-2.13 (4H, m), 3.48 (3H, s), 3.60 (2H, t, J = 6.6 Hz), 3.78 (2H, t, J = 6.8 Hz), 7.08-7.18 (2H, m), 8.29 (1H, s), 8.34-8.43 (2H, m). |
| 228 | 3-Me | 1.92-2.13 (4H, m), 2.44 (3H, s), 3.49 (3H, s), 3.61 (2H, t, J = 6.6 Hz), 3.78 (2H, t, J = 6.8 Hz), 7.24-7.29 (1H, m), 7.35 (1H, t, J = 7.4 Hz), 8.13-8.20 (2H, m), 8.30 (1H, s). |
| 229 | 4-Me | 1.92-2.12 (4H, m), 2.41 (3H, s), 3.48 (3H, s), 3.61 (2H, t, J = 6.7 Hz), 3.78 (2H, t, J = 6.9 Hz), 7.24-7.29 (2H, m), 8.23-8.28 (2H, m), 8.29 (1H, s). |
| 230 | 3-OMe | 1.92-2.13 (4H, m), 3.49 (3H, s), 3.61 (2H, t, J = 6.6 Hz), 3.78 (2H, t, J = 6.9 Hz), 3.90 (3H, s), 6.97-7.03 (1H, m), 7.37 (1H, t, J = 8.0 Hz), 7.91-8.01 (2H, m), 8.30 (1H, s). |
| 231 | 4-OMe | 1.91-2.12 (4H, m), 3.47 (3H, s), 3.60 (2H, t, J = 6.6 Hz), 3.78 (2H, t, J = 6.8 Hz), 3.87 (3H, s), 6.93-7.00 (2H, m), 8.26 (1H, s), 8.28-8.37 (2H, m). |

TABLE 41

| Ex. No. | R | ¹H-NMR (CDCl₃) δ |
|---|---|---|
| 232 | 3-OEt | 1.45 (3H, t, J = 7.1 Hz), 1.92-2.12 (4H, m), 3.48 (3H, s), 3.60 (2H, t, J = 6.6 Hz), 3.78 (2H, t, J = 6.8 Hz), 4.14 (2H, q, J = 7.1 Hz), 6.96-7.02 (1H, m), 7.36 (1H, t, J = 8.0 Hz), 7.90-7.99 (2H, m), 8.30 (1H, s). |
| 233 | 4-OEt | 1.45 (3H, t, J = 7.0 Hz), 1.92-2.12 (4H, m), 3.47 (3H, s), 3.60 (2H, t, J = 6.8 Hz), 3.78 (2H, t, J = 6.9 Hz), 4.10 (2H, q, J = 7.0 Hz), 6.92-6.99 (2H, m), 8.26 (1H, s), 8.28-8.33 (2H, m). |
| 234 | 3-CF₃ | 1.94-2.14 (4H, m), 3.50 (3H, s), 3.62 (2H, t, J = 6.5 Hz), 3.79 (2H, t, J = 6.9 Hz), 7.54-7.62 (1H, m), 7.67-7.72 (1H, m), 8.33 (1H, s), 8.55-8.60 (1H, m), 8.64-8.68 (1H, m). |
| 235 | 4-CF₃ | 1.92-2.15 (4H, m), 3.51 (3H, s), 3.61 (2H, t, J = 6.7 Hz), 3.79 (2H, t, J = 6.9 Hz), 7.68-7.74 (2H, m), 8.34 (1H, s), 8.47-8.53 (2H, m). |
| 236 | 3-OCF₃ | 1.94-2.15 (4H, m), 3.50 (3H, s), 3.61 (2H, t, J = 6.7 Hz), 3.79 (2H, t, J = 6.8 Hz), 7.25-7.35 (1H, m), 7.48 (1H, t, J = 8.0 Hz), 8.23-8.28 (1H, m), 8.32 (1H, s), 8.30-8.36 (1H, m). |
| 237 | 4-OCF₃ | 1.92-2.15 (4H, m), 3.49 (3H, s), 3.60 (2H, t, J = 6.6 Hz), 3.78 (2H, t, J = 6.8 Hz), 7.25-7.34 (2H, m), 8.31 (1H, s), 8.38-8.47 (2H, m). |
| 238 | 3-Ac | 1.95-2.15 (4H, m), 2.70 (3H, s), 3.51 (3H, s), 3.63 (2H, t, J = 6.6 Hz), 3.79 (2H, t, J = 6.8 Hz), 7.57 (1H, t, J = 7.8 Hz), 8.01-8.08 (1H, m), 8.34 (1H, s), 8.56-8.62 (1H, m), 8.93-8.98 (1H, m). |

TABLE 41-continued

| Ex. No. | R | $^1$H-NMR (CDCl$_3$) δ |
|---|---|---|
| 239 | 4-Ph | 1.95-2.13 (4H, m), 3.50 (3H, s), 3.63 (2H, t, J = 6.7 Hz), 3.80 (2H, t, J = 7.0 Hz), 7.34-7.41 (1H, m), 7.43-7.52 (2H, m), 7.63-7.77 (4H, m), 8.33 (1H, s), 8.42-8.47 (2H, m). |
| 240 | 2-OMe | 1.91-2.08 (4H, m), 3.49 (3H, s), 3.63 (2H, t, J = 6.4 Hz), 3.72 (2H, t, J = 6.6 Hz), 3.85 (3H, s), 6.99-7.09 (2H, m), 7.36-7.44 (1H, m), 7.66 (1H, dd, J = 7.7, 1.8 Hz), 8.36 (1H, s). |

TABLE 42

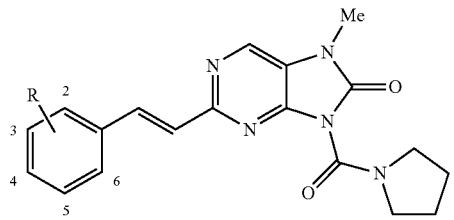

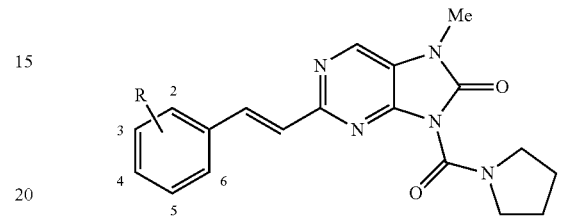

| Ex. No. | R | $^1$H-NMR (CDCl$_3$) δ |
|---|---|---|
| 241 | H | 1.93-2.12 (4H, m), 3.47 (3H, s), 3.60 (2H, t, J = 6.7 Hz), 3.78 (2H, t, J = 6.8 Hz), 7.22 (1H, d, J = 16.1 Hz), 7.28-7.43 (3H, m), 7.57-7.63 (2H, m), 7.86 (1H, d, J = 16.1 Hz), 8.23 (1H, s). |
| 242 | 4-OMe | 1.92-2.12 (4H, m), 3.46 (3H, s), 3.60 (2H, t, J = 6.6 Hz), 3.77 (2H, t, J = 6.8 Hz), 3.84 (3H, s), 6.87-6.95 (2H, m), 7.09 (1H, d, J = 16.0 Hz), 7.51-7.59 (2H, m), 7.81 (1H, d, J = 16.0 Hz), 8.21 (1H, s). |
| 243 | 4-CF$_3$ | 1.94-2.13 (4H, m), 3.48 (3H, s), 3.61 (2H, t, J = 6.5 Hz), 3.78 (2H, t, J = 7.0 Hz), 7.29 (1H, d, J = 16.1 Hz), 7.61-7.74 (4H, m), 7.87 (1H, d, J = 16.1 Hz), 8.25 (1H, s). |
| 244 | 3-CF$_3$ | 1.95-2.12 (4H, m), 3.48 (3H, s), 3.60 (2H, t, J = 6.7 Hz), 3.78 (2H, t, J = 6.8 Hz), 7.25-7.32 (1H, m), 7.47-7.60 (2H, m), 7.73-7.79 (1H, m), 7.83-7.90 (2H, m), 8.25 (1H, s). |
| 245 | 4-F | 1.92-2.12 (4H, m), 3.47 (3H, s), 3.60 (2H, t, J = 6.5 Hz), 3.77 (2H, t, J = 6.9 Hz), 7.03-7.17 (3H, m), 7.53-7.61 (2H, m), 7.82 (1H, d, J = 16.0 Hz), 8.23 (1H, s). |
| 246 | 3-F | 1.93-2.13 (4H, m), 3.47 (3H, s), 3.60 (2H, t, J = 6.6 Hz), 3.78 (2H, t, J = 6.9 Hz), 6.97-7.07 (1H, m), 7.21 (1H, d, J = 16.1 Hz), 7.25-7.42 (3H, m), 7.81 (1H, d, J = 16.1 Hz), 8.24 (1H, s). |
| 247 | 3-OMe | 1.93-2.13 (4H, m), 3.47 (3H, s), 3.60 (2H, t, J = 6.9 Hz), 3.78 (2H, t, J = 6.9 Hz), 3.85 (3H, s), 6.84-6.94 (1H, m), 7.11-7.35 (4H, m), 7.83 (1H, d, J = 16.1 Hz), 8.23 (1H, s). |

TABLE 43

| Ex. No. | Structure | $^1$H-NMR (CDCl$_3$) δ |
|---|---|---|
| 248 | 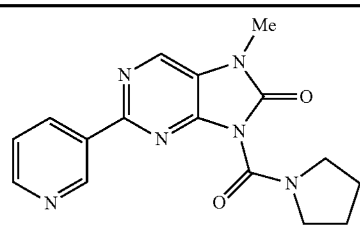 | 1.93-2.15 (4H, m), 3.50 (3H, s), 3.61 (2H, t, J = 6.6 Hz), 3.78 (2H, t, J = 6.8 Hz), 7.34-7.43 (1H, m), 8.33 (1H, s), 8.59-8.72 (2H, m), 9.54-9.60 (1H, m). |
| 249 | 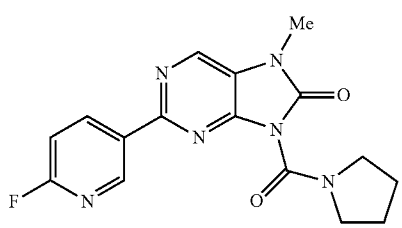 [SMILES: Cn1c(=O)n(C(=O)N2CCCC2)c2nc(-c3ccc(F)nc3)ncc21] | 1.93-2.16 (4H, m), 3.50 (3H, s), 3.60 (2H, t, J = 6.5 Hz), 3.78 (2H, t, J = 6.8 Hz), 7.01 (1H, dd, J = 8.5, 3.0 Hz), 8.31 (1H, s), 8.71-8.80 (1H, m), 9.18-9.22 (1H, m). |
| 250 | 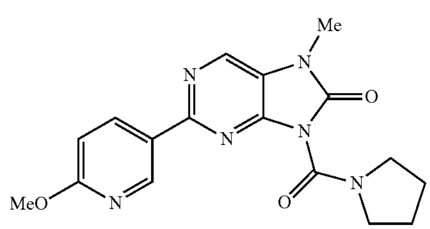 [SMILES: COc1ccc(-c2ncc3c(n2)n(C(=O)N2CCCC2)c(=O)n3C)cn1] | 1.92-2.14 (4H, m), 3.48 (3H, s), 3.60 (2H, t, J = 6.7 Hz), 3.77 (2H, t, J = 6.9 Hz), 4.01 (3H, s), 6.81 (1H, d, J = 8.6 Hz), 8.27 (1H, s), 8.52 (1H, dd, J = 8.8, 2.4 Hz), 9.12-9.17 (1H, m). |

TABLE 43-continued

| Ex. No. | Structure | $^1$H-NMR (CDCl$_3$) δ |
|---|---|---|
| 251 | (structure) | 1.93-2.14 (4H, m), 3.50 (3H, s), 3.61 (2H, t, J = 6.5 Hz), 3.78 (2H, t, J = 6.8 Hz), 3.95 (3H, s), 8.13-8.16 (1H, m), 8.32 (1H, s), 8.37-8.40 (1H, m), 9.17-9.20 (1H, m). |
| 252 | (structure) | 1.91-2.16 (4H, m), 3.52 (3H, s), 3.61 (2H, t, J = 6.7 Hz), 3.79 (2H, t, J = 6.8 Hz), 8.36 (1H, s), 8.21-8.26 (2H, m), 8.71-8.76 (2H, m). |

Example 253

Process of 2-benzyl-9-methyl-7-(pyrrolidin-1-ylcarbonyl)-7,9-dihydro-8H-purine-8-one

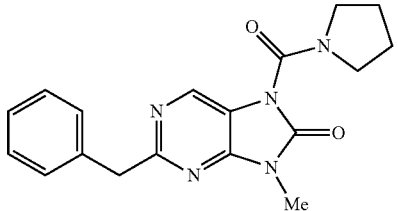 [SMILES: Cn1c(=O)n(C(=O)N2CCCC2)c2cnc(Cc3ccccc3)nc21]

To a mixture of 2-chloro-9-methyl-7-(pyrrolidin-1-ylcarbonyl)-7,9-dihydro-8H-purine-8-one <the compound of Reference Example 16> (200 mg), bis(tri-tert-butylphosphine)palladium (18 mg) and tetrahydrofuran (1.0 ml) was added dropwise 0.5 mol/L benzyl zinc bromide/tetrahydrofuran solution (2.14 ml) under nitrogen atmosphere and the mixture was stirred at 130° C. under microwave irradiation for 1 hour. The reaction mixture was filtered through Celite and the filtrate was concentrated under reduced pressure. The obtained residue was purified by silica gel column chromatography (eluent: chloroform/methanol=100/0~90/10). The obtained crude solids were recrystallized from a mixed solution of ethyl acetate and hexane to give the title compound 68 mg.

$^1$H-NMR (CDCl$_3$) δ: 1.89-2.07 (4H, m), 3.44 (3H, s), 3.61-3.70 (4H, m), 4.25 (2H, s), 7.17-7.40 (5H, m), 8.50 (1H, s).

Examples 254 to 300

The compounds indicated in Tables 44 to 49 were prepared according to the similar method to those of Example 253.

TABLE 44

(structure)

| Ex. No. | R | $^1$H-NMR |
|---|---|---|
| 254 | 2-F | (CDCl$_3$) δ: 1.86-2.11 (4H, m), 3.42 (3H, s), 3.60-3.73 (4H, m), 4.30 (2H, s), 7.00-7.11 (2H, m), 7.17-7.33 (2H, m), 8.50 (1H, s). |
| 255 | 3-F | (CDCl$_3$) δ: 1.90-2.07 (4H, m), 3.44 (3H, s), 3.62-3.70 (4H, m), 4.23 (2H, s), 6.87-6.93 (1H, m), 7.05-7.10 (1H, m), 7.11-7.16 (1H, m), 7.22-7.28 (1H, m), 8.50 (1H, s). |
| 256 | 4-F | (CDCl$_3$) δ: 1.87-2.11 (4H, m), 3.44 (3H, s), 3.61-3.73 (4H, m), 4.21 (2H, s), 6.93-7.02 (2H, m), 7.28-7.37 (2H, m), 8.49 (1H, s). |
| 257 | 2-Me | (CDCl$_3$) δ: 1.89-2.07 (4H, m), 2.40 (3H, s), 3.41 (3H, s), 3.62-3.70 (4H, m), 4.26 (2H, s), 7.11-7.29 (4H, m), 8.49 (1H, s). |
| 258 | 3-Me | (CDCl$_3$) δ: 1.82-2.12 (4H, m), 2.31 (3H, s), 3.44 (3H, s), 3.57-3.76 (4H, m), 4.21 (2H, s), 6.97-7.07 (1H, m), 7.11-7.23 (2H, m), 7.25-7.28 (1H, m), 8.50 (1H, s). |
| 259 | 4-Me | (CDCl$_3$) δ: 1.88-2.08 (4H, m), 2.30 (3H, s), 3.43 (3H, s), 3.60-3.70 (4H, m), 4.20 (2H, s), 7.07-7.13 (2H, m), 7.23-7.28 (2H, m), 8.49 (1H, s). |
| 260 | 2-OMe | (CDCl$_3$) δ: 1.89-2.07 (4H, m), 3.41 (3H, s), 3.62-3.69 (4H, m), 3.77 (3H, s), 4.26 (2H, s), 7.11-7.18 (3H, m), 7.20-7.25 (1H, m), 8.48 (1H, s). |
| 261 | 3-OMe | (CDCl$_3$) δ: 1.87-2.09 (4H, m), 3.44 (3H, s), 3.61-3.71 (4H, m), 3.79 (3H, s), 4.22 (2H, s), 6.73-6.79 (1H, m), 6.90-6.98 (2H, m), 7.21 (1H, t, J = 7.9 Hz), 8.50 (1H, s). |

TABLE 45

| Ex. No. | R | ¹H-NMR |
|---|---|---|
| 262 | 4-OMe | (CDCl₃) δ: 1.87-2.09 (4H, m), 3.43 (3H, s), 3.60-3.70 (4H, m), 3.77 (3H, s), 4.18 (2H, s), 6.80-6.85 (2H, m), 7.27-7.31 (2H, m), 8.49 (1H, s). |
| 263 | 4-OEt | (CDCl₃) δ: 1.38 (3H, t, J = 7.0 Hz), 1.88-2.06 (4H, m), 3.43 (3H, s), 3.60-3.70 (4H, m), 3.99 (2H, q, J = 7.0 Hz), 4.17 (2H, s), 6.79-6.84 (2H, m), 7.25-7.29 (2H, m), 8.49 (1H, s). |
| 264 | 4-CN | (CDCl₃) δ: 1.88-2.08 (4H, m), 3.43 (3H, s), 3.60-3.72 (4H, m), 4.29 (2H, s), 7.44-7.51 (2H, m), 7.55-7.62 (2H, m), 8.50 (1H, s). |
| 265 | 4-Ph | (CDCl₃) δ: 1.87-2.08 (4H, m), 3.44 (3H, s), 3.60-3.71 (4H, m), 4.25 (2H, s), 7.17-7.40 (9H, m), 8.50 (1H, s). |
| 266 | 2-F 4-F | (DMSO-d₆) δ: 1.74-1.95 (4H, m), 3.27 (3H, s), 3.45-3.60 (4H, m), 4.19 (2H, s), 6.98-7.06 (1H, m), 7.13-7.23 (1H, m), 7.34-7.44 (1H, m), 8.30 (1H, s). |
| 267 | 2-F 5-F | (CDCl₃) δ: 1.89-2.07 (4H, m), 3.43 (3H, s), 3.61-3.71 (4H, m), 4.27 (2H, s), 6.83-6.94 (1H, m), 6.95-7.05 (2H, m), 8.51 (1H, s). |
| 268 | 2-F 6-F | (CDCl₃) δ: 1.89-2.07 (4H, m), 3.39 (3H, s), 3.62-3.70 (4H, m), 4.34 (2H, s), 6.85-6.95 (2H, m), 7.17-7.28 (1H, m), 8.47 (1H, s). |
| 269 | 3-F 4-F | (DMSO-d₆) δ: 1.73-1.96 (4H, m), 3.28 (3H, s), 3.44-3.60 (4H, m), 4.16 (2H, s), 7.09-7.18 (1H, m), 7.27-7.40 (2H, m), 8.34 (1H, s). |
| 270 | 3-F 5-F | (CDCl₃) δ: 1.91-2.08 (4H, m), 3.44 (3H, s), 3.63-3.71 (4H, m), 4.24 (2H, s), 6.66-6.71 (1H, m), 6.83-6.93 (2H, m), 8.55 (1H, s). |
| 271 | 3-OMe 5-OMe | (DMSO-d₆) δ: 1.75-1.94 (4H, m), 3.29 (3H, s), 3.44-3.59 (4H, m), 3.68 (6H, s), 4.07 (2H, s), 6.30-6.34 (1H, m), 6.43-6.47 (2H, m), 8.34 (1H, s). |
| 272 | 3-Ph | (CDCl₃) δ: 1.89-2.00 (4H, m), 3.37 (3H, s), 3.60-3.74 (4H, m), 4.25 (2H, s), 7.21-7.48 (9H, m), 8.47 (1H, s). |

TABLE 46

| Ex. No. | Structure | ¹H-NMR (CDCl₃) δ |
|---|---|---|
| 273 | 2-(1-phenylethyl)-9-methyl-7-(pyrrolidine-1-carbonyl)-purin-8(9H)-one | 1.74 (3H, d, J = 7.2 Hz), 1.88-2.08 (4H, m), 3.44 (3H, s), 3.59-3.70 (4H, m), 4.40 (1H, q, J = 7.2 Hz), 7.14-7.32 (3H, m), 7.35-7.44 (2H, m), 8.49 (1H, s). |
| 274 | 2-butyl-9-methyl-7-(pyrrolidine-1-carbonyl)-purin-8(9H)-one | 0.95 (3H, t, J = 7.3 Hz), 1.33-1.48 (2H, m), 1.73-1.86 (2H, m), 1.89-2.08 (4H, m), 2.90-3.00 (2H, m), 3.46 (3H, s), 3.62-3.72 (4H, m), 8.53 (1H, s). |
| 275 | 2-isopropyl-9-methyl-7-(pyrrolidine-1-carbonyl)-purin-8(9H)-one | 1.34 (6H, d, J = 7.0 Hz), 1.88-2.10 (4H, m), 3.13-3.24 (1H, m), 3.46 (3H, s), 3.64-3.72 (4H, m), 8.49 (1H, s). |

TABLE 46-continued

| Ex. No. | Structure | ¹H-NMR (CDCl₃) δ |
|---|---|---|
| 276 | 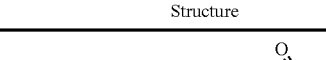 | 1.23 (3H, t, J = 7.2 Hz), 1.87-2.07 (4H, m), 2.85 (2H, t, J = 7.2 Hz), 3.25 (2H, t, J = 7.2 Hz), 3.41 (3H, s), 3.59-3.70 (4H, m), 4.12 (2H, q, J = 7.2 Hz), 8.45 (1H, s). |

TABLE 47

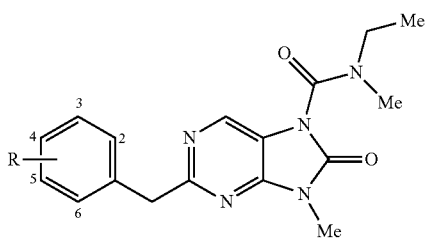

| Ex. No. | R | ¹H-NMR (CDCl₃) δ |
|---|---|---|
| 277 | 3-OMe | 1.28 (3H, t, J = 7.1 Hz), 3.10 (3H, s), 3.44 (3H, s), 3.47-3.59 (2H, m), 3.79 (3H, s), 4.22 (2H, s), 6.72-6.79 (1H, m), 6.91-6.99 (2H, m), 7.21 (1H, t, J = 7.8 Hz), 8.42 (1H, s). |
| 278 | H | 1.27 (3H, t, J = 7.1 Hz), 3.09 (3H, s), 3.44 (3H, s), 3.47-3.58 (2H, m), 4.24 (2H, s), 7.17-7.40 (5H, m), 8.42 (1H, s). |
| 279 | 4-F | 1.28 (3H, t, J = 7.1 Hz), 3.10 (3H, s), 3.35-3.62 (5H, m), 4.21 (2H, s), 6.91-7.04 (2H, m), 7.23-7.40 (2H, m), 8.41 (1H, s). |
| 280 | 4-OMe | 1.27 (3H, t, J = 7.1 Hz), 3.09 (3H, s), 3.41-3.59 (5H, m), 3.77 (3H, s), 4.18 (2H, s), 6.80-6.87 (2H, m), 7.24-7.33 (2H, m), 8.41 (1H, s) |
| 281 | 4-Me | 1.27 (3H, t, J = 7.2 Hz), 2.30 (3H, s), 3.09 (3H, s), 3.38-3.62 (5H, m), 4.20 (2H, s), 7.06-7.15 (2H, m), 7.21-7.31 (2H, m), 8.41 (1H, s) |
| 282 | 3-Me | 1.27 (3H, t, J = 7.2 Hz), 2.31(3H, s), 3.09 (3H, s), 3.43 (3H, s), 3.45-3.62 (2H, m), 4.20 (2H, s), 6.96-7.06 (1H, m), 7.10-7.22 (3H, m), 8.41 (1H, s). |
| 283 | 4-CF₃ | 1.28 (3H, t, J = 7.2 Hz), 3.10 (3H, s), 3.43 (3H, s), 3.46-3.63 (2H, m), 4.29 (2H, s), 7.44-7.59 (4H, m), 8.42 (1H, s). |
| 284 | 3-F | 1.28 (3H, t, J = 7.2 Hz), 3.10 (3H, s), 3.44 (3H, s), 3.46-3.61 (2H, m), 4.23 (2H, s), 6.85-6.95 (1H, m), 7.03-7.17 (2H, m), 7.19-7.30 (1H, m), 8.42 (1H, s). |

TABLE 48

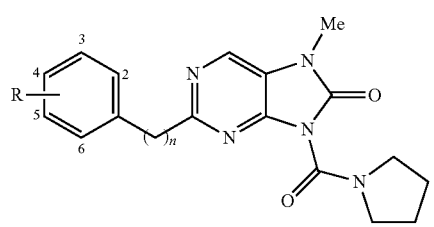

| Ex. No. | n | R | ¹H-NMR (CDCl₃) δ |
|---|---|---|---|
| 285 | 1 | H | 1.78-2.09 (4H, m), 3.34-3.52 (5H, m), 3.72 (2H, t, J = 6.9 Hz), 4.26 (2H, s), 7.16-7.44 (5H, m), 8.16 (1H, s). |
| 286 | 1 | 3-F | 1.85-2.09 (4H, m), 3.43 (3H, s), 3.46 (2H, t, J = 6.8 Hz), 3.73 (2H, t, J = 6.9 Hz), 4.24 (2H, s), 6.86-6.94 (1H, m), 7.02-7.14 (2H, m), 7.19-7.29 (1H, m), 8.17 (1H, s). |
| 287 | 1 | 4-OMe | 1.85-2.07 (4H, m), 3.41 (3H, s), 3.46 (2H, t, J = 6.8 Hz), 3.73(2H, t, J = 7.0 Hz), 3.77 (3H, s), 4.19 (2H, s), 6.78-6.86 (2H, m), 7.21-7.30 (2H, m), 8.16 (1H, s). |
| 288 | 1 | 3-OMe | 1.85-2.07 (4H, m), 3.42 (3H, s), 3.46 (2H, t, J = 6.6 Hz), 3.72 (2H, t, J = 7.0 Hz), 3.78 (3H, s), 4.23 (2H, s), 6.71-6.79 (1H, m), 6.87-6.95 (2H, m), 7.20 (1H, t, J = 7.8 Hz), 8.16 (1H, s). |
| 289 | 1 | 4-Me | 1.84-2.06 (4H, m), 2.30 (3H, s), 3.41 (3H, s), 3.45 (2H, t, J = 6.9 Hz), 3.73 (2H, t, J = 6.9 Hz), 4.21 (2H, s), 7.07-7.13 (2H, m), 7.21-7.29 (2H, m), 8.15 (1H, s). |
| 290 | 2 | H | 1.89-2.09 (4H, m), 3.09-3.30 (4H, m), 3.44 (3H, s), 3.49 (2H, t, J = 6.4 Hz), 3.74 (2H, t, J = 6.9 Hz), 7.14-7.30 (5H, m), 8.17 (1H, s). |
| 291 | 1 | 2-OMe | 1.80-2.02 (4H, m), 3.38-3.45 (5H, m), 3.68 (2H, t, J = 7.0 Hz), 3.76 (3H, s), 4.29 (2H, s), 6.83-6.93 (2H, m), 7.14-7.28 (2H, m), 8.15 (1H, s). |

TABLE 49

| Ex. No. | n | R | ¹H-NMR (CDCl₃) δ |
|---|---|---|---|
| 292 | 1 | 2-Me | 1.79-2.03 (4H, m), 2.33 (3H, s), 3.38 (2H, t, J = 6.9 Hz), 3.41 (3H, s), 3.69 (2H, t, J = 7.0 Hz), 4.27 (2H, s), 7.09-7.24 (4H, m), 8.15 (1H, s). |
| 293 | 1 | 3-F 4-F | 1.87-2.10 (4H, m), 3.43 (3H, s), 3.49 (2H, t, J = 7.0 Hz), 3.73 (2H, t, J = 7.0 Hz), 4.20 (2H, s), 7.02-7.11 (2H, m), 7.12-7.21 (1H, m), 8.16 (1H, s). |
| 294 | 1 | 3-Me | 1.85-2.07 (4H, m), 2.31 (3H, s), 3.42 (3H, s), 3.46 (2H, t, J = 6.8 Hz), 3.73 (2H, t, J = 7.1 Hz), 4.21 (2H, s), 6.99-7.04 (1H, m), 7.11-7.19 (3H, m), 8.16 (1H, s). |

TABLE 49-continued

| Ex. No. | n | R | ¹H-NMR (CDCl₃) δ |
|---|---|---|---|
| 295 | 1 | 4-F | 1.85-2.09 (4H, m), 3.42 (3H, s), 3.46 (2H, t, J = 6.7 Hz), 3.73 (2H, t, J = 7.0 Hz), 4.22 (2H, s), 6.91-7.01 (2H, m), 7.25-7.34 (2H, m), 8.16 (1H, s). |
| 296 | 1 | 2-F 4-F | 1.82-2.03 (4H, m), 3.42 (3H, s), 3.45 (2H, t, J = 6.8 Hz), 3.68 (2H, t, J = 6.9 Hz), 4.35 (2H, s), 6.83-6.95 (2H, m), 7.16-7.29 (1H, m), 8.13 (1H, s). |
| 297 | 1 | 2-F 5-F | 1.87-2.06 (4H, m), 3.43 (3H, s), 3.47 (2H, t, J = 6.8 Hz), 3.71 (2H, t, J = 7.0 Hz), 4.28 (2H, s), 6.85-7.08 (3H, m), 8.17 (1H, s). |
| 298 | 1 | 2-F 6-F | 1.85-2.06 (4H, m), 3.42 (3H, s), 3.47 (2H, t, J = 6.7 Hz), 3.71 (2H, t, J = 6.9 Hz), 4.27 (2H, s), 6.74-6.86 (2H, m), 7.20-7.30 (1H, m), 8.15 (1H, s). |
| 299 | 1 | 3-F 5-F | 1.88-2.07 (4H, m), 3.44 (3H, s), 3.48 (2H, t, J = 6.9 Hz), 3.74 (2H, t, J = 6.6 Hz), 4.22 (2H, s), 6.60-6.70 (1H, m), 6.80-6.93 (2H, m), 8.17 (1H, s). |
| 300 | 1 | 2-F | 1.82-2.03 (4H, m), 3.42 (3H, s), 3.44 (2H, t, J = 6.8 Hz), 3.70 (2H, t, J = 6.9 Hz), 4.31 (2H, s), 6.98-7.11 (2H, m), 7.17-7.31 (2H, m), 8.16 (1H, s). |

Example 301

Process of 2-phenyl-7-(pyrrolidin-1-ylcarbonyl)-7,9-dihydro-8H-purine-8-one

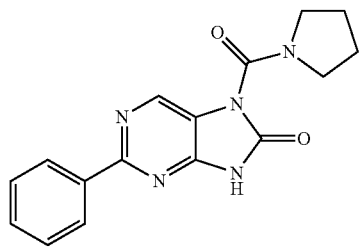 [SMILES: O=C(N1CCCC1)n1c(=O)[nH]c2nc(-c3ccccc3)ncc21]

To a mixture of 2-phenyl-7,9-dihydro-8H-purine-8-one <prepared according to the similar method to those of Reference Example 19> (4.0 g), 1,4-diazabicyclo[2.2.2]octane (2.2 g) and N,N-dimethylformamide (50 ml) was added dropwise 1-pyrrolidinecarbonyl chloride (2.6 g) at room temperature and the mixture was stirred for 10 hours. To the reaction mixture was added water (100 ml), and the crystals precipitated were collected by filtration and was dried to give the title compound 4.8 g.

¹H-NMR (CDCl₃) δ: 1.95-2.10 (4H, m), 3.68-3.77 (4H, m), 7.45-7.53 (3H, m), 8.30-8.40 (2H, m), 8.71 (1H, s), 8.95 (1H, br s).

Example 302

Process of 9-(2-hydroxyethyl)-2-phenyl-7-(pyrrolidin-1-ylcarbonyl)-7,9-dihydro-8H-purine-8-one

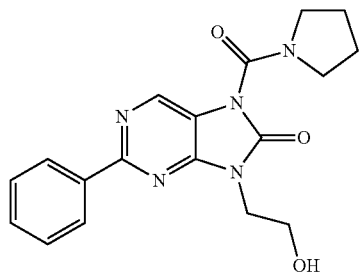 [SMILES: O=C(N1CCCC1)n1c(=O)n(CCO)c2nc(-c3ccccc3)ncc21]

(1) To a solution of 2-phenyl-7-(pyrrolidin-1-ylcarbonyl)-7,9-dihydro-8H-purine-8-one <the compound of Example 301> (200 mg) in N,N-dimethylformamide (5 ml) was added 60% sodium hydride (30 mg) at room temperature and the mixture was stirred for 10 minutes, and thereto was then added benzyl 2-bromoethylether (200 mg) and the mixture was stirred for 10 hours. To the reaction mixture was added water (20 ml), and the mixture was stirred and was then extracted with ethyl acetate. The organic layer was dried over anhydrous sodium sulfate and was filtered, and the solvent was evaporated under reduced pressure. The obtained residue was purified by silica gel column chromatography (eluent: hexane/ethyl acetate=100/0~0/100) to give 9-[2-(benzyloxy)ethyl]-2-phenyl-7-(pyrrolidin-1-ylcarbonyl)-7,9-dihydro-8H-purine-8-one 200 mg.

¹H-NMR (CDCl₃) δ: 1.86-2.09 (4H, br m), 3.59-3.74 (4H, br m), 3.93 (2H, t, J=5.6 Hz), 4.27 (2H, t, J=5.6 Hz), 4.56 (2H, s), 7.19-7.23 (5H, m), 7.44-7.50 (3H, m), 8.36-8.42 (2H, m), 8.65 (1H, br s).

(2) To a solution of the above-mentioned product (200 mg) in methanol (5 ml) was added 10% palladium on carbon (20 mg) and the mixture was stirred for 2 hours at room temperature under hydrogen atmosphere. After removing the catalyst from the reaction mixture, the solvent was evaporated under reduced pressure, and the residue was purified by silica gel column chromatography (eluent: hexane/ethyl acetate=100/0~0/100) to give the title compound 20 mg.

¹H-NMR (CDCl₃) δ: 1.94-2.12 (4H, m), 3.56 (1H, t, J=6.1 Hz), 3.71 (4H, t, J=6.7 Hz), 4.04-4.10 (2H, m), 4.25 (2H, t, J=4.9 Hz), 7.46-7.53 (3H, m), 8.33-8.40 (2H, m), 8.69 (1H, s).

Examples 303 to 310

The compounds indicated in Table 50 were prepared according to the similar method to those of Example 1 or Example 302 (1).

TABLE 50

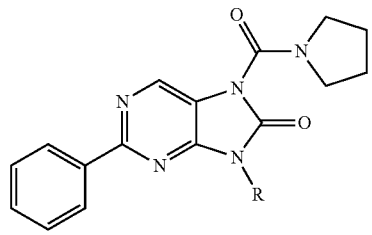

| Ex. No. | R | $^1$H-NMR (CDCl$_3$) δ |
|---|---|---|
| 303 | Et | 1.45 (3H, t, J = 7.2 Hz), 1.93-2.10 (4H, m), 3.71 (4H, t, J = 6.7 Hz), 4.09 (2H, q, J = 7.2 Hz), 7.45-7.51 (3H, m), 8.40-8.46 (2H, m), 8.65 (1H, s) |
| 304 | n-Pr | 1.02 (3H, t, J = 7.4 Hz), 1.83-2.10 (6H, m), 3.71 (4H, t, J = 6.9 Hz), 4.00 (2H, t, J = 7.2 Hz), 7.47-7.51 (3H, m), 8.42 (2H, dd, J = 7.3, 2.6 Hz), 8.65 (1H, s). |
| 305 | i-Pr | 1.67 (6H, d, J = 7.0 Hz), 1.90-2.13 (4H, br m), 3.71 (4H, t, J = 6.8 Hz), 4.91-4.36 (1H, m), 7.45-7.52 (3H, m), 8.39-8.45 (2H, m), 8.63 (1H, s). |
| 306 | n-Bu | 1.00 (3H, t, J = 7.3 Hz), 1.43 (2H, td, J = 14.9, 7.5 Hz), 1.91-1.79 (2H, m), 1.92-2.10 (4H, br m), 3.71 (4H, t, J = 6.8 Hz), 4.04 (2H, t, J = 7.1 Hz), 7.45-7.53 (3H, m), 8.39-8.46 (2H, m), 8.65 (1H, s). |
| 307 | i-Bu | 1.02 (6H, d, J = 6.6 Hz), 1.90-2.13 (4H, br m), 2.29-2.44 (1H, m), 3.70 (4H, t, J = 6.9 Hz), 3.85 (2H, d, J = 7.2 Hz), 7.44-7.54 (3H, m), 8.38-8.46 (2H, m), 8.66 (1H, s). |
| 308 | Bn | 1.90-2.08 (4H, m), 3.75-3.64 (4H, m), 5.17 (2H, s), 7.29-7.38 (3H, m), 7.46-7.59 (5H, m), 8.45 (2H, dd, J = 7.4, 2.3 Hz), 8.64 (1H, s). |
| 309 | ⏤⏤NMe$_2$ | 1.93-2.09 (4H, m), 2.31-2.34 (6H, br m), 2.79 (2H, t, J = Hz), 3.66-3.75 (4H, m), 4.15 (2H, t, J = 6.4 Hz), 7.45-7.51 (3H, m), 8.45-8.40 (2H, m), 8.65 (1H, s). |
| 310 | ⏤⏤N(pyrrolidine) | 1.69-1.80 (4H, m), 1.90-2.10 (4H, br m), 2.59-2.69 (4H, m), 2.93 (2H, t, J = 6.6 Hz), 3.65-3.75 (4H, m), 4.17 (2H, t, J = 6.6 Hz), 7.42-7.55 (3H, m), 8.38-8.47 (2H, m), 8.65 (1H, s). |

Example 311

Process of 2-(3-hydroxyphenyl)-9-methyl-7-(pyrrolidin-1-ylcarbonyl)-7,9-dihydro-8H-purine-8-one

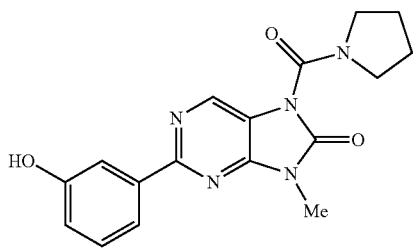 [SMILES: Cn1c(=O)n(C(=O)N2CCCC2)c2cnc(-c3cccc(O)c3)nc21]

To a solution of 2-(3-benzyloxyphenyl)-9-methyl-7-(pyrrolidin-1-ylcarbonyl)-7,9-dihydro-8H-purine-8-one <the compound of Example 202> (30 mg) in methanol (10 ml) was added 10% palladium on carbon (3 mg) and the mixture was stirred for 4 hours at room temperature under hydrogen atmosphere. After removing the catalyst from the reaction mixture, the solvent was evaporated under reduced pressure, and the residue was dried to give the title compound 24 mg.

$^1$H-NMR (CD$_3$OD) δ: 1.91-2.08 (4H, br m), 3.51 (3H, s), 3.60-3.74 (4H, br m), 6.85-6.92 (1H, m), 7.28 (1H, t, J=7.8 Hz), 7.81-7.89 (2H, m), 8.50 (1H, s).

Example 312

Process of 7-methyl-9-(pyrrolidin-1-ylcarbonyl)-2-{2-[4-(trifluoromethyl)phenyl]ethyl}-7,9-dihydro-8H-purine-8-one To a solution of 7-methyl-9-(pyrrolidin-1-ylcarbonyl)-2-{(E)-2-[4-(trifluoromethyl)phenyl]ethenyl}-7,9-dihydro-8H-purine-8-one <the compound of Example 243> (50 mg) in methanol (10 ml) was added 10% palladium on carbon (5 mg) and the mixture was stirred for 2 hours at room temperature under hydrogen atmosphere. After removing the catalyst from the reaction mixture, the solvent was evaporated under reduced pressure, and the residue was dried to give the title compound 38 mg.

¹H-NMR (CDCl₃) δ: 1.88-2.12 (4H, m), 3.14-3.33 (4H, m), 3.44 (3H, s), 3.50 (2H, t, J=6.3 Hz), 3.74 (2H, t, J=6.8 Hz), 7.30-7.39 (2H, m), 7.47-7.55 (2H, m), 8.16 (1H, s).

Examples 313 to 315

The compounds indicated in Table 51 were prepared according to the similar method to those of Example 312.

TABLE 51

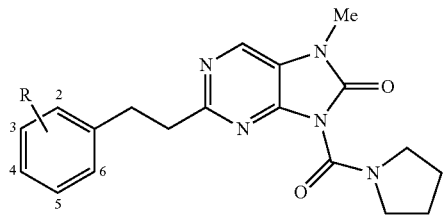

| Ex. No. | R | ¹H-NMR (CDCl₃) δ |
|---|---|---|
| 313 | 3-CF₃ | 1.89-2.09 (4H, m), 3.15-3.31 (4H, m), 3.44 (3H, s), 3.50 (2H, t, J = 6.6 Hz), 3.74 (2H, t, J = 6.8 Hz), 7.33-7.50 (4H, m), 8.17 (1H, s). |
| 314 | 4-F | 1.88-2.11 (4H, m), 3.05-3.27 (4H, m), 3.44 (3H, s), 3.49 (2H, t, J = 6.6 Hz), 3.74 (2H, t, J = 6.8 Hz), 6.89-6.98 (2H, m), 7.12-7.21 (2H, m), 8.16 (1H, s). |
| 315 | 3-F | 1.89-2.09 (4H, m), 3.10-3.28 (4H, m), 3.43-3.53 (5H, m), 3.74 (2H, t, J = 7.0 Hz), 6.82-6.89 (1H, m), 6.90-6.96 (1H, m), 6.97-7.02 (1H, m), 7.17-7.24 (1H, m), 8.17 (1H, s). |

Example 316

Process of 2-cyclohexy-9-methyl-7-(pyrrolidin-1-ylcarbonyl)-7,9-dihydro-8H-purine-8-one

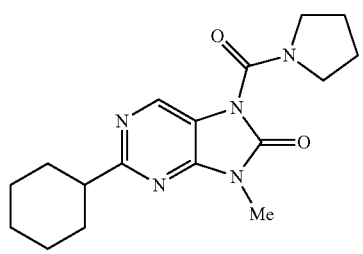 [SMILES: Cn1c(=O)n(C(=O)N2CCCC2)c2cnc(C3CCCCC3)nc21]

The title compound was prepared by using 2-(cyclohexen-1-yl)-9-methyl-7-(pyrrolidin-1-ylcarbonyl)-7,9-dihydro-8H-purine-8-one <the compound of Example 218> as a starting material according to the similar reaction and treatment to those of Example 312.

¹H-NMR (CDCl₃) δ: 1.20-1.51 (4H, m), 1.52-2.11 (10H, m), 2-7.9-2.91 (1H, m), 3.45 (3H, s), 3.63-3.72 (4H, m), 8.49 (1H, s).

Example 317

Process of 2-(3-aminophenyl)-9-methyl-7-(pyrrolidin-1-ylcarbonyl)-7,9-dihydro-8H-purine-8-one

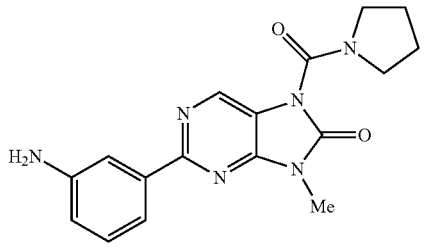 [SMILES: Cn1c(=O)n(C(=O)N2CCCC2)c2cnc(-c3cccc(N)c3)nc21]

To a solution of 2-(3-nitrophenyl)-9-methyl-7-(pyrrolidin-1-ylcarbonyl)-7,9-dihydro-8H-purine-8-one <the compound of Example 203> (41 mg) in methanol (10 ml) was added 10% palladium on carbon (10 mg) and the mixture was stirred for 2 hours at room temperature under hydrogen atmosphere. After removing the catalyst from the reaction mixture, the solvent was evaporated under reduced pressure, and the residue was dried to give the title compound 35 mg.

¹H-NMR (CD₃OD) δ: 1.80-2.00 (4H, m), 3.43 (3H, s), 3.50-3.67 (4H, m), 7.38-7.44 (1H, m), 7.58 (1H, t, J=7.9 Hz), 8.38-8.41 (1H, m), 8.44-8.49 (1H, m), 8.48 (1H, s).

Examples 318 to 370

The compounds indicated in Tables 52 to 56 were prepared according the similar method to those of Example 166.

TABLE 52

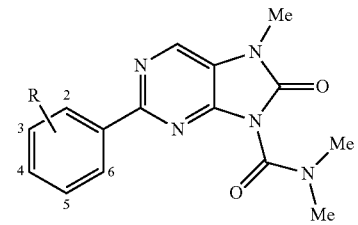

| Ex. No. | R | ¹H-NMR (CDCl₃) δ |
|---|---|---|
| 318 | 4-OCF₃ | 3.12 (3H s), 3.27 (3H, s), 3.49 (3H, s), 7.29 (2H, d, J = 8.4 Hz), 8.31 (1H, s), 8.42 (2H, d, J = 8.8 Hz). |
| 319 | 3-OCF₃ | 3.12 (3H, s), 3.28 (3H, s), 3.50 (3H, s), 7.29 (1H, d, J = 8.0 Hz), 7.48 (1H, t, J = 8.0 Hz), 8.24 (1H, s), 8.32 (1H, s), 8.33 (1H, d, J = 7.6 Hz). |
| 320 | 4-OEt | 1.43 (3H, t, J = 7.2 Hz), 3.10 (3H, s), 3.25 (3H, s), 3.45 (3H, s), 4.09 (3H, q, J = 7.2 Hz), 6.95 (2H, d, J = 8.8 Hz), 8.25 (2H, d, J = 8.4 Hz), 8.35 (1H, s). |
| 321 | 3-OEt | 1.45 (3H, t, J = 7.2 Hz), 3.12 (3H, s), 3.27 (3H, s), 3.49 (3H, s), 4.14 (3H, q, J = 7.2 Hz), 6.97-7.00 (1H, m), 7.36 (1H, t, J = 8.0 Hz), 7.91-7.58 (2H, m), 8.31 (1H, s). |
| 322 | 3-OMe | 3.12 (3H, s), 3.27 (3H, s), 3.50 (3H, s), 3.91 (3H, s), 6.97-7.02 (1H, m), 7.30-40 (1H, m), 7.90-8.00 (2H, m), 8.33 (1H, s). |
| 323 | 3-F | 3.12 (3H, s), 3.28 (3H, s), 3.50 (3H, s), 7.10-7.17 (1H, m), 7.30-7.40 (1H, m), 8.05-8.12 (1H, m), 8.15-8.20 (1H, m), 8.31 (1H, s). |
| 324 | 3-Me | 2.44 (3H, s), 3.12 (3H, s), 3.28 (3H, s), 3.49 (3H, s), 7.22-7.30 (1H, m), 7.31-7.38 (1H, m), 8.12-8.20 (2H, m), 8.31 (1H, s). |
| 325 | 3-CF₃ | 3.13 (3H, s), 3.29 (3H, s), 3.51 (3H, s), 7.53-7.61 (1H, m), 7.67-7.71 (1H, m), 8.34 (1H, s), 8.54-8.60 (1H, m), 8.66 (1H, s). |

TABLE 52-continued

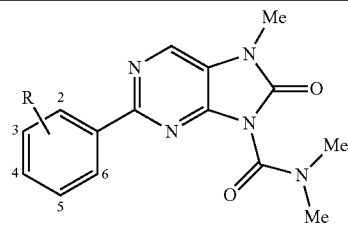

| Ex. No. | R | ¹H-NMR (CDCl₃) δ |
|---|---|---|
| 326 | 4-CF₃ | 3.13 (3H, s), 3.29 (3H, s), 3.51 (3H, s), 7.71 (2H, d, J = 8.3 Hz), 8.35 (1H, s), 8.50 (2H, d, J = 7.9 Hz). |
| 327 | 3-OBn | 3.10 (3H, s), 3.27 (3H, s), 3.49 (3H, s), 5.17 (2H, s), 7.08 (1H, dd, J = 8.0, 2.0 Hz), 7.30-7.44 (4H, m), 7.48 (2H, d, J = 7.2 Hz), 7.98 (1H, d, J = 7.6 Hz), 8.02 (1H, s), 8.32 (1H, s). |
| 328 | 3-Cl | 3.12 (3H, s), 3.28 (3H, s), 3.50 (3H, s), 7.35-7.44 (2H, m), 8.25-8.29 (1H, m), 8.31 (1H, s), 8.36-8.39 (1H, m). |
| 329 | 4-Cl | 3.12 (3H, s), 3.28 (3H, s), 3.49 (3H, s), 7.39-7.46 (2H, m), 8.28-8.35 (3H, m). |
| 330 | 4-CF₂H | 3.13 (3H, s), 3.28 (3H, s), 3.50 (3H, s), 6.71 (1H, t, J = 56.4 Hz), 7.60 (2H, d, J = 8.6 Hz), 8.34 (1H, s), 8.47 (2H, d, J = 8.6 Hz). |
| 331 | 3-OCF₂H | 3.12 (3H, s), 3.28 (3H, s), 3.50 (3H, s), 6.60 (1H, t, J =74.0 Hz), 7.17-7.23 (1H, m), 7.45 (1H, t, J = 8.0 Hz), 8.13-8.17 (1H, m), 8.22-8.27 (1H, m), 8.32 (1H, s). |
| 332 | 3-CF₂H | 3.13 (3H, s), 3.29 (3H, s), 3.50 (3H, s), 6.74 (1H, t, J = 56.4 Hz), 7.52-7.64 (2H, m), 8.33 (1H, s), 8.47-8.55 (2H, m). |

TABLE 53

| Ex. No. | R | ¹H-NMR (CDCl₃) δ |
|---|---|---|
| 333 | 4-OCH₂CF₂H | 3.12 (3H, s), 3.27 (3H, s), 3.48 (3H, s), 4.25 (2H, td, J = 13.0, 4.1 Hz), 6.12 (1H, tt, J = 55.0, 4.1 Hz), 6.94-7.02 (2H, m), 8.27 (1H, s), 8.31-8.39 (2H, m). |
| 334 | 4-OCH₂CF₃ | 3.12 (3H, s), 3.27 (3H, s), 3.48 (3H, s), 4.42 (2H, q, J = 8.1 Hz), 6.97-7.04 (2H, m), 8.28 (1H, s), 8.32-8.39 (2H, m). |
| 335 | 3-OCH₂CF₂H | 3.12 (3H, s), 3.28 (3H, s), 3.49 (3H, s), 4.30 (2H, td, J = 13.1, 4.1 Hz), 6.13 (1H, tt, J = 55.1, 4.1 Hz), 6.99-7.05 (1H, m), 7.40 (1H, t, J = 8.0 Hz), 7.94-7.97 (1H, m), 8.03-8.08 (1H, m), 8.31 (1H, s). |
| 336 | 3-OCH₂CF₃ | 3.12 (3H, s), 3.28 (3H, s), 3.50 (3H, s), 4.46 (2H, q, J = 8.2 Hz), 7.02-7.08 (1H, m), 7.41 (1H, t, J = 8.0 Hz), 7.96-7.99 (1H, m), 8.06-8.11 (1H, m), 8.31 (1H, s). |
| 337 | 4-OCF₂H | 3.12 (3H, s), 3.28 (3H, s), 3.49 (3H, s), 6.58 (1H, t, J = 73.7 Hz), 7.15-7.23 (2H, m), 8.30 (1H, s), 8.35-8.44 (2H, m). |
| 338 | 2-F 4-CF₃ | 3.12 (3H, s), 3.25 (3H, s), 3.52 (3H, s), 7.41-7.53 (2H, m), 8.12-8.19 (1H, m), 8.40 (1H, s). |
| 339 | 2-Cl 4-CF₃ | 3.12 (3H, s), 3.22 (3H, s), 3.53 (3H, s), 7.61 (1H, d, J = 8.1 Hz), 7.76 (1H, s), 7.85 (1H, d, J = 8.1 Hz), 8.40 (1H, s). |

TABLE 54

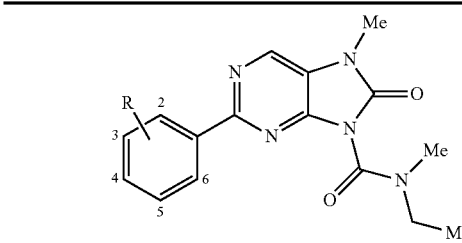

| Ex. No. | R | ¹H-NMR (CDCl₃) δ |
|---|---|---|
| 340 | 3-Me | 1.20-1.43 (3H, m), 2.44 (3H, s), 3.05-3.28 (3H, m), 3.37-3.79 (5H, m), 7.22-7.29 (1H, m), 7.31-7.39 (1H, m), 8.13-8.21 (2H, m), 8.30 (1H, s). |

TABLE 54-continued

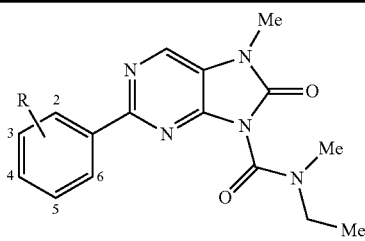

| Ex. No. | R | ¹H-NMR (CDCl₃) δ |
|---|---|---|
| 341 | 3-OCF₃ | 1.22-1.43 (3H, m), 3.04-3.28 (3H, m), 3.35-3.86 (5H, 7.25-7.32 (1H, m), 7.44-7.52 (1H, m), 8.22-8.36 (3H, m). |
| 342 | 3-Cl | 1.21-1.43 (3H, m), 3.05-3.29 (3H, m), 3.35-3.81 (5H, m), 7.35-7.44 (2H, m), 8.23-8.29 (1H, m), 8.31 (1H, s), 8.36-8.39 (1H, m). |
| 343 | 3-OCF₂H | 1.21-1.43 (3H, m), 3.05-3.29 (3H, m), 3.36-3.85 (5H, m), 6.60 (1H, t, J = 74.0 Hz), 7.17-7.23 (1H, m), 7.41-7.49 (1H, m), 8.12-8.16 (1H, m), 8.21-8.27 (1H, m), 8.31 (1H, s). |
| 344 | 3-CF₂H | 1.20-1.43 (3H, m), 3.06-3.29 (3H, m), 3.36-3.82 (5H, m), 6.73 (1H, t, J = 56.4 Hz), 7.50-7.64 (2H, m), 8.32 (1H, s), 8.46-8.56 (2H, m). |
| 345 | 4-OCF₂H | 1.21-1.42 (3H, m), 3.05-3.28 (3H, m), 3.36-3.79 (5H, m), 6.58 (1H, t, J = 73.7 Hz), 7.14-7.23 (2H, m), 8.29 (1H, s), 8.35-8.43 (2H, m). |

TABLE 55

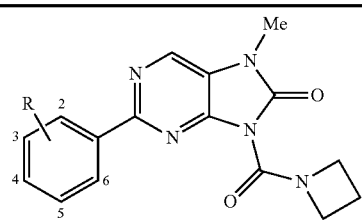

| Ex. No. | R | ¹H-NMR (CDCl₃) δ |
|---|---|---|
| 346 | 3-OEt | 1.46 (3H, t, J = 7.0 Hz), 2.34-2.47 (2H, m), 3.48 (3H, s), 4.15 (2H, q, J = 7.0 Hz), 4.30-4.42 (4H, m), 7.00 (1H, ddd, J = 8.2, 2.6, 1.0 Hz), 7.38 (1H, t, J = 7.9 Hz), 7.94-8.02 (2H, m), 8.30 (1H, s). |

TABLE 55-continued

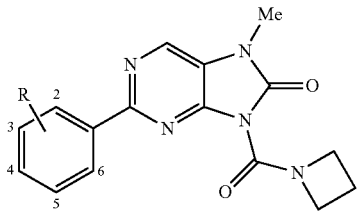

| Ex. No. | R | $^1$H-NMR (CDCl$_3$) δ |
|---|---|---|
| 347 | 4-OEt | 1.45 (3H, t, J = 7.0 Hz), 2.33-2.47 (2H, m), 3.46 (3H, s), 4.11 (2H, q, J = 7.0 Hz), 4.29-4.41 (4H, m), 6.92-7.01 (2H, m), 8.26 (1H, s), 8.29-8.38 (2H, m). |
| 348 | 3-O—n-Bu | 1.00 (3H, t, J = 7.4 Hz), 146-1.61 (2H, m), 1.75-1.87 (2H, m), 2.34-2.47 (2H, m), 3.48 (3H, s), 4.08 (2H, t, J = 6.5 Hz), 4.29-4.42 (4H, m), 7.00 (1H, ddd, J = 8.2, 2.7, 1.0 Hz), 7.37 (1H, t, J = 8.0 Hz), 7.93-8.01 (2H, m), 8.30 (1H, s). |
| 349 | 4-O—n-Bu | 0.99 (3H, t, J = 7.4 Hz), 1.45-1.59 (2H, m), 1.74-1.86 (2H, m), 2.34-2.47 (2H, m), 3.46 (3H, s), 4.04 (2H, t, J = 6.5 Hz), 4.30-4.41 (4H, m), 6.93-7.01 (2H, m), 8.26 (1H, s), 8.29-8.37 (2H, m). |
| 350 | 3-OCF$_3$ | 2.37-2.47 (2H, m), 3.49 (3H, s), 4.32-4.42 (4H, m), 7.27-7.33 (1H, m), 7.47-7.53 (1H, m), 8.28 (1H, s), 8.32 (1H, s), 8.34-8.39 (1H, m). |
| 351 | 4-OCF$_3$ | 2.37-2.47 (2H, m), 3.48 (3H, s), 4.29-4.42 (4H, m), 7.30 (2H, d, J = 8.4 Hz), 8.31 (1H, s), 8.44 (2H, d, J = 8.8 Hz). |

TABLE 55-continued

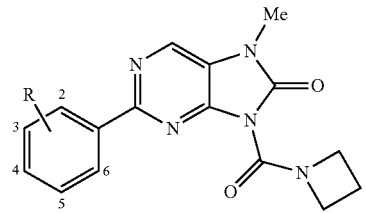

| Ex. No. | R | $^1$H-NMR (CDCl$_3$) δ |
|---|---|---|
| 352 | H | 2.35-2.45 (2H, m), 3.47 (3H, s), 4.34 (2H, t, J = 7.8 Hz), 4.38 (2H, t, J = 7.8 Hz), 7.45-7.49 (3H, m), 8.30 (1H, s), 8.38-8.41 (2H, m). |
| 353 | 3-F | 2.39-2.45 (2H, m), 3.48 (3H, s), 4.33 (2H, t, J = 8.0 Hz), 4.39 (2H, t, J = 8.0 Hz), 7.07-7.18 (1H, m), 7.44 (1H, dd, J = 8.0, 2.4 Hz), 8.09 (1H, dd, J = 8.0, 2.4 Hz), 8.20 (1H, d, J = 8.0 Hz), 8.31 (1H, s). |
| 354 | 4-F | 2.38-2.46 (2H, m), 3.48 (3H, s), 4.32-4.40 (4H, m), 7.15 (2H, t, J = 8.8 Hz), 8.33 (1H, s), 8.37-8.41 (2H, m). |
| 355 | 3-OMe | 2.32-2.49 (2H, m), 3.48 (3H, s), 3.91 (3H, s), 4.29-4.42 (4H, m), 7.00-7.02 (1H, m), 7.39 (1H, t, J = 7.8 Hz), 7.95-8.02 (2H, m), 8.30 (1H, s). |
| 356 | 4-OMe | 2.30-2.49 (2H, m), 3.46 (3H, s), 3.88 (3H, s), 4.26-4.41 (4H, m), 6.97-7.00 (2H, m), 8.25 (1H, s), 8.34-8.37 (2H, m). |
| 357 | 3-CF$_3$ | 2.34-2.48 (2H, m), 3.49 (3H, s), 4.28-4.45 (4H, m), 7.54-7.62 (1H, m), 7.70 (1H, d, J = 7.8 Hz), 8.61 (1H, d, J = 8.4 Hz), 8.68 (1H, s). |

TABLE 56

| Ex. No. | R | $^1$H-NMR (CDCl$_3$) δ |
|---|---|---|
| 358 | 4-CF$_3$ | 2.33-2.52 (2H, m), 3.49 (3H, s), 4.25-4.48 (4H, m), 7.64-7.79 (2H, m), 8.33 (1H, s), 8.44-8.62 (2H, m). |
| 359 | 3-Me | 2.31-2.52 (2H, m), 2.45 (3H, s), 3.47 (3H, s), 4.28-4.46 (4H, m), 7.20-7.32 (1H, m), 7.37 (1H, t, J = 7.6 Hz), 8.12-8.25 (2H, m), 8.33 (1H, s). |
| 360 | 4-Me | 2.35-2.50 (2H, m), 2.42 (3H, s), 3.48 (3H, s), 4.30-4.42 (4H, m), 7.25-7.33 (2H, m), 8.17-8.26 (2H, m), 8.42 (1H, s). |
| 361 | 3-OBn | 2.32-2.47 (2H, m), 3.48 (3H, s), 4.27-4.46 (4H, m), 5.18 (2H, s), 7.06-7.11 (1H, m), 7.30-7.45 (3H, m), 7.49 (2H, d, J = 7.6 Hz), 7.99-8.10 (2H, m), 8.31 (1H, s). |
| 362 | 3-Cl | 2.35-2.49 (2H, m), 3.48 (3H, s), 4.28-4.44 (4H, m), 7.36-7.45 (2H, m), 8.26-8.34 (2H, m), 8.38-8.42 (1H, m). |
| 363 | 4-Cl | 2.35-2.48 (2H, m), 3.48 (3H, s), 4.28-4.44 (4H, m), 7.40-7.47 (2H, m), 8.29 (1H, s), 8.32-8.38 (2H, m). |
| 364 | 3-CF$_2$H | 2.36-2.48 (2H, m), 3.49 (3H, s), 4.30-4.43 (4H, m), 6.75 (1H, t, J = 56.4 Hz), 7.53-7.65 (2H, m), 8.32 (1H, s), 8.50-8.57 (2H, m). |
| 365 | 4-CF$_2$H | 2.35-2.48 (2H, m), 3.49 (3H, s), 4.30-4.43 (4H, m), 6.71 (1H, t, J = 56.4 Hz), 7.61 (2H, d, J = 8.4 Hz), 8.33 (1H, s), 8.50 (2H, d, J = 8.4 Hz). |
| 366 | 3-OCF$_2$H | 2.35-2.48 (2H, m), 3.48 (3H, s), 4.30-4.43 (4H, m), 6.62 (1H, t, J = 73.9 Hz), 7.18-7.24 (1H, m), 7.47 (1H, t, J = 8.1 Hz), 8.16-8.20 (1H, m), 8.25-8.30 (1H, m), 8.31 (1H, s). |
| 367 | 4-OCF$_2$H | 2.34-2.48 (2H, m), 3.48 (3H, s), 4.29-4.42 (4H, m), 6.59 (1H, t, J = 73.7 Hz), 7.16-7.23 (2H, m), 8.29 (1H, s), 8.39-8.45 (2H, m). |
| 368 | 4-OCH$_2$CF$_2$H | 2.34-2.48 (2H, m), 3.47 (3H, s), 4.19-4.42 (6H, m), 6.13 (1H, tt, J = 55.1, 4.1 Hz), 6.97-7.03 (2H, m), 8.27 (1H, s), 8.34-8.41 (2H, m). |
| 369 | 3-OCH$_2$CF$_2$H | 2.34-2.48 (2H, m), 3.48 (3H, s), 4.23-4.43 (6H, m), 6.14 (1H, tt, J = 55.1, 4.2 Hz), 7.00-7.06 (1H, m), 7.38-7.44 (1H, m), 7.96-8.00 (1H, m), 8.05-8.11 (1H, m), 8.30 (1H, s). |
| 370 | 3-OCH$_2$CF$_3$ | 2.34-2.48 (2H, m), 3.48 (3H, s), 4.27-4.54 (6H, m), 7.03-7.09 (1H, m), 7.42 (1H, t, J = 8.0 Hz), 7.97-8.02 (1H, m), 8.09-8.14 (1H, m), 8.30 (1H, s). |

Examples 371 to 379

The compounds indicated in Table 57 were prepared according to the similar method to those of Reference Example 16 and Example 253.

TABLE 57

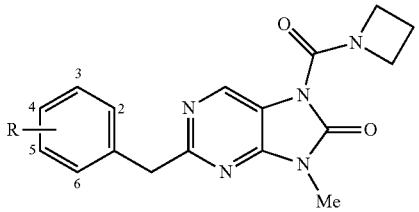

| Ex. No. | R | $^1$H-NMR (CDCl$_3$) δ |
|---|---|---|
| 371 | 3-Me | 2.31 (3H, s), 2.34-2.43 (2H, m), 3.43 (3H, s), 4.20 (2H, s), 4.22-4.46 (4H, m), 6.99-7.04 (1H, m), 7.13-7.21 (3H, m), 8.71 (1H, s). |
| 372 | 3-F | 2.31-2.47 (2H, m), 3.43 (3H, s), 4.19-4.50 (4H, m), 4.23 (2H, s), 6.86-6.95 (1H, m), 7.04-7.16 (2H, m), 7.20-7.31 (1H, m), 8.71 (1H, s). |
| 373 | 4-F | 2.33-2.44 (2H, m), 3.42 (3H, s), 4.13-4.50 (4H, m), 4.20 (2H, s), 6.94-7.01 (2H, m), 7.29-7.35 (2H, m), 8.70 (1H, s). |
| 374 | 2-F | 2.33-2.44 (2H, m), 3.41 (3H, s), 4.19-4.49 (4H, m), 4.30 (2H, s), 7.01-7.10 (2H, m), 7.18-7.32 (2H, m), 8.71 (1H, s). |
| 375 | 3-OMe | 2.47-2.29 (2H, m), 3.42 (3H, s), 3.78 (3H, s), 4.11-4.51 (4H, m), 4.21 (2H, s), 6.72-6.79 (1H, m), 6.90-6.98 (2H, m), 7.17-7.24 (1H, m), 8.71 (1H, s). |
| 376 | 4-OMe | 2.33-2.43 (2H, m), 3.42 (3H, s), 3.78 (3H, s), 4.18 (2H, s), 4.21-4.47 (4H, m), 6.81-6.86 (2H, m), 7.27-7.31 (2H, m), 8.70 (1H, s). |
| 377 | 2-Cl | 2.31-2.47 (2H, m), 3.40 (3H, s), 4.17-4.58 (4H, m), 4.41 (2H, s), 7.15-7.32 (3H, m), 7.33-7.43 (1H, m), 8.72 (1H, s). |
| 378 | 4-Cl | 2.45-2.32 (2H, m), 3.42 (3H, s), 4.20 (2H, s), 4.21-4.48 (4H, m), 7.20-7.32 (4H, m), 8.70 (1H, s). |
| 379 | 3-CF$_3$ | 2.43-2.34 (2H, m), 3.42 (3H, s), 4.29-4.40 (4H, m), 4.29 (2H, s), 7.40 (1H, t, J = 7.7 Hz), 7.48 (1H, d, J = 8.0 Hz), 7.55 (1H, d, J = 7.3 Hz), 7.65 (1H, s), 8.71 (1H, s). |

Example 380

Process of 2-(3-methoxypropyl)-9-methyl-7-({3-[4-(trifluoromethyl)phenyl]azetidin-1-yl}carbonyl)-7,9-dihydro-8H-purine-8-one

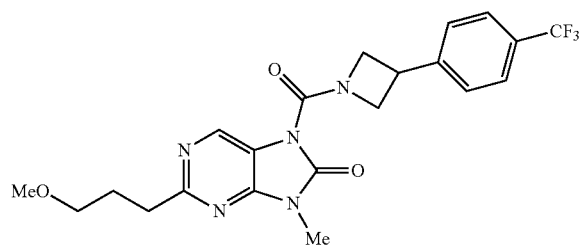 [SMILES: COCCCc1ncc2c(n1)n(C)c(=O)n2C(=O)N1CC(c2ccc(C(F)(F)F)cc2)C1]

(1) Under nitrogen atmosphere, a mixture of 2-chloro-9-methyl-7-{[2-(trimethylsilyl)ethoxy]methyl}-7,9-dihydro-8H-purine-8-one <the compound of Reference Example 20(1)> (2 g), 3-methoxyprop-1-yn (890 mg), potassium carbonate (2.6 g), bis(acetonitrile)dichloropalladium (82 mg), 2-dicyclohexylphosphino-2',4',6'-triisopropyl-1,1'-biphenyl (300 mg) and acetonitrile (20 ml) was stirred for 30 minutes at 120° C. under microwave irradiation. The reaction mixture was filtered through Celite and the filtrate was concentrated under reduced pressure. The obtained residue was purified by silica gel column chromatography (eluent: hexane/ethyl acetate=100/0~0/100) to give 2-(3-methoxyprop-1-yn-1-yl)-9-methyl-7-{[2-(trimethylsilyl)ethoxy]methyl}-7,9-dihydro-8H-purine-8-one as a mixture.

(2) To a solution of the above-mentioned product (total amount) in methanol (30 ml) was added 10% palladium on carbon (200 mg) and the resulting mixture was stirred for 2 hours under hydrogen atmosphere. The reaction mixture was filtered through Celite and the filtrate was concentrated under reduced pressure to give 2-(3-methoxypropyl)-9-methyl-7-{[2-(trimethylsilyl)ethoxy]methyl}-7,9-dihydro-8H-purine-8-one as a crude product. This crude product was used to the next reaction without purification.

(3) 1 mol/L Tetrabutylammonium fluoride/tetrahydrofuran solution (30 ml) was mixed with a total amount of the above-mentioned crude product and the mixture was heated under reflux for 12 hours. After concentrating the solution under reduced pressure, the residue was purified by silica gel column chromatography (eluent: chloroform/methanol=100/0~80/20). The obtained crude solids were recrystallized from a solution of ethyl acetate/hexane to give 2-(3-methoxypropyl)-9-methyl-7,9-dihydro-8H-purine-8-one 480 mg.

$^1$H-NMR (CDCl$_3$) δ: 2.04-2.18 (2H, m), 2.96-3.03 (2H, m), 3.35 (3H, s), 3.44-3.51 (5H, m), 8.24 (1H, s), 9.72 (1H, s).

(4) To a solution of triphosgene (220 mg) in dichloromethane (7 ml) was added dropwise a solution of 3-[4-(trifluoromethyl)phenyl]azetidine trifluoroacetate salt (298 mg) and diisopropylethylamine (0.7 ml) in dichloromethane (3 ml) and the mixture was stirred at room temperature for 10 minutes. The reaction mixture was added dropwise to the solution of the product of above-mentioned (3) (50 mg) and 1,4-diazabicyclo[2.2.2]octane (81 mg) in dichloromethane (2 ml) and the mixture was stirred at room temperature for 3 hours. The reaction mixture was purified by silica gel column chromatography (eluent: hexane/ethyl acetate=100/0~0/100). The obtained product and 5 to 10% hydrogen chloride/methanol solution were mixed and the mixture was stirred at room temperature for 10 minutes, and the solvent was then evaporated under reduced pressure. The obtained crude solids were recrystallized from diethylether to give the title compound 43 mg.

$^1$H-NMR (CDCl$_3$) δ: 2.13-2.27 (2H, m), 3.27 (3H, s), 3.33-3.44 (2H, m), 3.46-3.65 (6H, m), 4.00-5.01 (4H, m), 7.44-7.61 (2H, m), 7.61-7.71 (2H, m), 8.82 (1H, br s).

Examples 381 to 387

The compounds indicated in Table 58 were prepared according to the similar method to those of Example 380.

TABLE 58

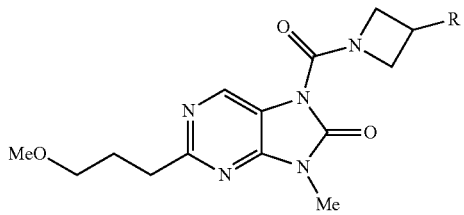

| Ex. No. | R | Salt | 1H-NMR (CDCl₃) δ |
|---|---|---|---|
| 381 | 4-F-C₆H₄-CH₂- (para-F benzyl) | HCl | 2.13-2.35 (2H, m), 3.29 (3H, s), 3.36-3.73 (7H, m), 3.93-4.28 (5H, m), 7.02-7.18 (2H, m), 727-7.46 (2H, m), 8.77 (1H, br s). |
| 382 | 3-F-C₆H₄-CH₂- (meta-F benzyl) | HCl | 2.11-2.27 (2H, m), 3.19-3.38 (5H, m), 3.42-3.61 (5H, m), 3.89-4.08 (1H, m), 4.18-4.93 (4H, m), 6.90-7.19 (3H, m), 7.32-7.44 (1H, m), 8.82 (1H, br s). |
| 383 | —Ph | HCl | 2.09-2.38 (2H, m), 3.28 (3H, s), 3.38-3.73 (7H, m), 3.96-4.19 (1H, m), 4.25-4.90 (4H, m), 7.28-7.42 (5H, m), 8.81 (1H, br s). |
| 384 | —OPh | HCl | 2.13-2.33 (2H, m), 3.27 (3H, s), 3.33-3.71 (7H, m), 4.24-4.82 (4H, m), 4.96-5.22 (1H, m), 6.70-6.85 (2H, m), 6.97-7.07 (1H, m), 7.27-7.35 (2H, m), 8.83 (1H, br s). |
| 385 | 4-OEt-C₆H₄-CH₂- | free | 1.42 (3H, t, J = 7.0 Hz), 2.05-2.17 (2H, m), 3.00 (2H, t, J = 7.7 Hz), 3.35 (3H, s), 3.42-3.50 (5H, m), 3.83-3.93 (1H, m), 4.03 (2H, q, J = 7.0 Hz), 4.15-4.82 (4H, m), 6.90 (2H, d, J = 8.6 Hz), 7.23-7.30 (2H, m), 8.74 (1H, s). |
| 386 | 3-CF₃-C₆H₄-CH₂- | HCl | 2.09-2.33 (2H, m), 3.18-3.42 (5H, m), 3.44-3.65 (5H, m), 3.96-4.98 (5H, m), 7.49-7.69 (4H, m), 8.86 (1H, br s). |
| 387 | 3-OEt-C₆H₄-CH₂- | HCl | 1.33-1.58 (3H, m), 2.07-2.39 (2H, m), 3.27 (3H, s), 3.33-3.76 (7H, m), 3.89-5.00 (7H, m), 6.64-7.15 (3H, m), 7.27-7.36 (1H, m), 8.91 (1H, br s). |

Example 388

Process of 2-(2-methoxyethyl)-9-methyl-7-({3-[4-(trifluoromethyl)phenyl]azetidin-1-yl}carbonyl)-7,9-dihydro-8H-purine-8-one hydrochloric acid salt

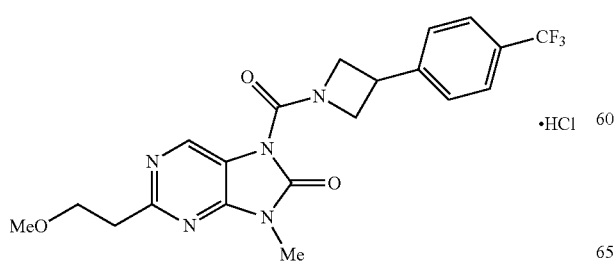

(1) Under nitrogen atmosphere, the mixture of 2-chloro-9-methyl-7-{[2-(trimethylsilyl)ethoxy]methyl}-7,9-dihydro-8H-purine-8-one <the compound of Reference Example 20(1)> (3 g), trimethylsilyl acethylene (1.8 g), bis(acetonitrile)dichloropalladium (124 mg), 2-dicyclohexylphosphino-2',4',6'-triisopropyl-1,1'-biphenyl (450 mg), triethylamine (10 ml) and acetonitrile (10 ml) was stirred at 120° C. under microwave irradiation for 30 minutes. The reaction mixture was filtered through Celite and the filtrate was concentrated under reduced pressure. The obtained residue was purified by silica gel column chromatography (eluent: hexane/ethyl acetate-100/0~0/100) to give 9-methyl-7-{[2-(trimethylsilyl)ethoxy]methyl}-2-[(trimethylsilyl)ethynyl]-7,9-dihydro-8H-purine-8-one 3 g.

$^1$H-NMR (CDCl₃) δ: −0.02 (9H, s), 0.30 (9H, s), 0.87-0.96 (2H, m), 3.50 (3H, s), 3.55-3.64 (2H, m), 5.32 (2H, s), 8.29 (1H, d, J=2.0 Hz).

(2) To a solution of the above-mentioned product (3 g) in methanol (30 ml) was added Cesium hydroxide monohydrate (2 g) and the mixture was heated under reflux for 1 hour. To the reaction mixture was added saturated aqueous sodium hydrogen carbonate solution (30 ml) and the mixture was extracted with ethyl acetate (15 ml×3). The organic layer was dried over anhydrous magnesium sulfate and was filtered, and the solvent was evaporated under reduced pressure. The obtained crude solids were recrystallized from a solution of ethyl acetate/hexane to give 2-[(Z)-2-methoxyethenyl]-9-methyl-7-{[2-(trimethylsilyl)ethoxy]methyl}-7,9-dihydro-8H-purine-8-one 1.7 g.

$^1$H-NMR (CDCl$_3$) δ: 0.00 (9H, s), 0.89-0.98 (2H, m), 3.50 (3H, s), 3.56-3.64 (2H, m), 3.95 (3H, s), 5.33 (2H, s), 5.54 (1H, d, J=7.3 Hz), 6.44 (1H, d, J=7.3 Hz), 8.38 (1H, s).

(3) To a solution of the above-mentioned product (total amount) in methanol (30 ml) was added 10% palladium on carbon (200 mg) and the mixture was stirred under hydrogen atmosphere for 2 hours. The reaction mixture was filtered through Celite and the filtrate was concentrated under reduced pressure to give 2-(2-methoxyethyl)-9-methyl-7-{[2-(trimethylsilyl)ethoxy]methyl}-7,9-dihydro-8H-purine-8-one as crude product. This crude product was used to the next reaction without purification.

(4) The total amount of the above-mentioned crude product and 1 mol/L tetrabutylammonium fluoride/tetrahydrofuran solution (30 ml) were mixed and the mixture was heated under reflux for 12 hours. After the reaction mixture was concentrated under reduced pressure, the residue was purified by silica gel column chromatography (eluent: chloroform/methanol=100/0~80/20). The obtained crude solids were recrystallized from a solution of ethyl acetate/hexane to give 2-(2-methoxyethyl)-9-methyl-7,9-dihydro-8H-purine-8-one 600 mg.

(5) To a solution of triphosgene (220 mg) in dichloromethane (7 ml) was added dropwise a solution of 3-[4-(trifluoromethyl)phenyl]azetidine trifluoroacetate salt (298 mg) and diisopropylethylamine (0.7 ml) in dichloromethane (3 ml) and the mixture was stirred at room temperature for 10 minutes. The reaction mixture was added dropwise to a solution of the product of above-mentioned (4) (50 mg) and 1,4-diazabicyclo[2.2.2]octane (81 mg) in dichloromethane (2 ml) and the mixture was stirred at room temperature for 3 hours. The reaction mixture was purified by silica gel column chromatography (eluent: hexane/ethyl acetate=100/0~0/100). The obtained product and 5-10% hydrogen chloride/methanol solution were mixed and the mixture was stirred at room temperature for 10 minutes, and the solvent was then evaporated under reduced pressure. The obtained crude solids were recrystallized from diethylether to give the title compound 28 mg.

$^1$H-NMR (CDCl$_3$) δ: 3.34 (3H, s), 3.45-3.65 (5H, m), 3.92-4.14 (3H, m), 4.19-4.39 (1H, m), 4.47-5.02 (3H, m), 7.45-7.75 (4H, m), 8.85 (1H, br s).

Examples 389 to 393

The compounds indicated in Table 59 were prepared according to the similar method to those of Example 388.

TABLE 59

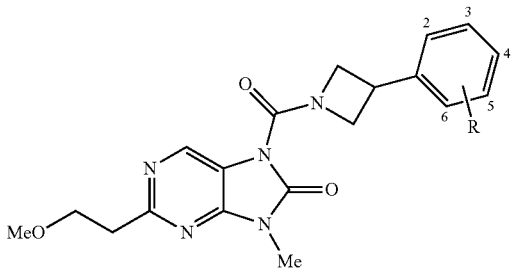

| Ex. No. | R | Salt | $^1$H-NMR (CDCl$_3$) δ |
|---|---|---|---|
| 389 | H | free | 3.21 (2H, t, J = 6.5 Hz), 3.36 (3H, s), 3.45 (3H, s), 3.85-4.02, (3H, m), 4.19-4.82 (4H, m), 7.26-7.41 (5H, m), 8.77 (1H, s). |
| 390 | 4-F | free | 3.21 (2H, t, J = 6.6 Hz), 3.36 (3H, s), 3.45 (3H, s), 3.85-3.98 (3H, m), 4.19-4.82 (4H, m), 7.07 (2H, t, J = 8.6 Hz), 7.33 (2H, dd, J = 8.6, 53 Hz), 8.76 (1H, s). |
| 391 | 3-F | free | 3.21 (2H, t, J = 6.6 Hz), 3.36 (3H, s), 3.45 (3H, s), 3.86-4.01 (3H, m), 4.15-4.84 (4H, m), 6.94-7.17 (3H m), 7.30-7.39 (1H, m), 8.77 (1H, d, J = 0.7 Hz). |
| 392 | 4-OEt | free | 1.42 (3H, t, J =7.0 Hz), 3.20 (2H, t, J = 6.6 Hz), 3.36 (3H, s), 3.45 (3H, s), 3.82-3.95 (3H, m), 4.03 (2H, q, J = 7.0 Hz), 4.18-4.78 (4H, m), 6.90 (2H, d, J = 8.6 Hz), 7.24-7.29 (2H, m), 8.76 (1H, s). |
| 393 | 3-CF$_3$ | HCl | 3.36 (3H, s), 3.42-3.65 (5H, m), 3.86-4.15 (3H, m), 4.21-4.98 (4H, m), 7.41-7.72 (4H, m), 8.86 (1H, br s). |

Example 394

Process of N,N,7-trimethyl-8-oxo-2-{3-[4-(trifluoromethyl)phenoxy]propyl}-7,8-dihydro-9H-purine-9-carboxamide hydrochloric acid salt

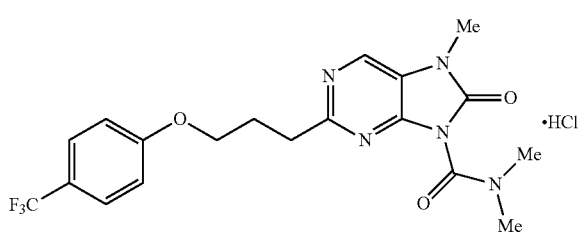 [SMILES: CN(C)C(=O)n1c(=O)n(C)c2cnc(CCCOc3ccc(C(F)(F)F)cc3)nc21 ; Cl]

(1) Under nitrogen atmosphere, a mixture of 2-chloro-N,N,7-trimethyl-8-oxo-7,8-dihydro-9H-purine-9-carboxamide <prepared according to the similar method to those of Reference Example 16> (1 g), prop-2-yn-1-ol (440 mg), bis(acetonitrile)dichloropalladium (50 mg), 2-dicyclohexylphosphino-2',4',6'-triisopropyl-1,1'-biphenyl (190 mg) triethylamine (10 ml) and acetonitrile (10 ml) was stirred at 120° C. under microwave irradiation for 30 minutes. The reaction mixture was filtered through Celite and the filtrate was concentrated under reduced pressure. The obtained residue was purified by amino silica gel column chromatography (eluent: ethyl acetate only) to give 2-(3-hydroxyprop-1-yn-1-yl)-N,N,7-trimethyl-8-oxo-7,8-dihydro-9H-purine-9-carboxamide 500 mg.

¹H-NMR (CDCl₃) δ: 2.19 (1H, t, J=6.3 Hz), 3.04 (3H, s), 3.19 (3H, s), 3.45 (3H, s), 4.48 (2H, d, J=6.2 Hz), 8.19 (1H, s).

(2) To a solution of the above-mentioned product (100 mg), triphenylphosphine (142 mg) and 4-(trifluoromethyl)phenol (70 mg) in toluene (2 ml) was added dropwise diisopropyl azodicarboxylate (90 μl) and the mixture was stirred at room temperature for 3 hours. The reaction mixture was purified by silica gel column chromatography (eluent: hexane/ethyl acetate=100/0~0/100) to give N,N,7-trimethyl-8-oxo-2-{3-[4-(trifluoromethyl)phenoxy]prop-1-yn-1-yl}-7,8-dihydro-9H-purine-9-carboxamide as a mixture. This mixture was used to the next reaction without further purification.

(3) To a solution of the above-mentioned product (total amount) in methanol (2 ml) was added 10% palladium on carbon (10 mg) and the mixture was stirred under hydrogen atmosphere for 2 hours. The reaction mixture was filtered through Celite and the filtrate was concentrated under reduced pressure. The obtained residue was purified by silica gel column chromatography (eluent: hexane/ethyl acetate-100/0~0/100). The obtained product and 5-10% hydrogen chloride/methanol solution were mixed and the mixture was stirred at room temperature for 10 minutes, and the solvent was then evaporated under reduced pressure. The obtained crude solids were recrystallized from diethylether to give the title compound 10 mg.

¹H-NMR (CDCl₃) δ: 2.11-2.29 (2H, m), 2.94 (3H, s), 2.98-3.11 (5H, m), 3.37 (3H, s), 4.12 (2H, t, J=6.1 Hz), 7.07 (2H, d, J=8.4 Hz), 7.62 (2H, d, J=8.4 Hz), 8.58 (1H, s).

Examples 395 to 401

The compounds indicated in Table 60 were prepared according to the similar method to those of Example 394.

TABLE 60

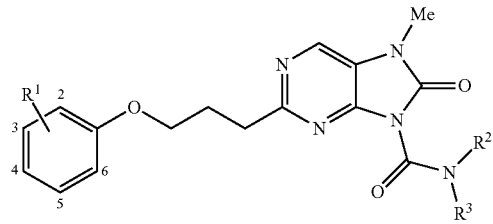

| Ex. No. | R¹ | NR²R³ | Salt | ¹H-NMR (CDCl₃) δ |
|---|---|---|---|---|
| 395 | 3-F | —NMe₂ | free | 2.25-2.35 (2H, m), 3.06 (3H, s), 3.12 (2H, t, J = 7.5 Hz), 3.22 (3H, s), 3.45 (3H, s), 4.03 (2H, t, J = 6.5 Hz), 6.55-6.70 (3H, m), 7.14-725 (1H, m), 8.17 (1H, s). |
| 396 | 4-Me | —NMe₂ | free | 2.24-2.32 (5H, m), 3.05 (3H, s), 3.12 (2H, t, J = 7.5 Hz), 3.21 (3H, s), 3.44 (3H, s), 4.01 (2H, t, J = 6.4 Hz), 6.77 (2H, d, J = 8.4 Hz), 7.06 (2H, d, J = 8.6 Hz), 8.17 (1H, s). |
| 397 | 3-Me | —NMe₂ | HCl | 2.28 (3H, s), 2.39-2.48 (2H, m), 2.97 (3H, s), 3.22 (3H, s), 3.39-3.68 (5H, m), 4.00-4.14 (2H, m), 6.49-6.60 (2H, m), 6.71 (1H, d, J = 7.7 Hz), 7.09 (1H, t, J = 7.7 Hz), 8.66 (1H, br s). |
| 398 | 4-F | —NMe₂ | free | 2.24-2.33 (2H, m), 3.06 (3H, s), 3.12 (2H, t, J = 7.5 Hz), 3.22 (3H, s), 3.45 (3H, s), 4.01 (2H, d, J = 6.4 Hz), 6.77-6.85 (2H, m), 6.90-6.99 2H, m), 8.17 (1H, s). |
| 399 | 3-CF₃ | —NMe₂ | HCl | 2.14-2.26 (2H, m), 2.92-2.95 (3H, m), 3.01-3.11 (5H, m), 3.38 (3H, s), 4.12 (2H, t, J = 6.2 Hz), 7.16-7.27 (3H, m), 7.50 (1H, t, J = 8.1 Hz), 8.61 (1H, s). |
| 400 | H | —N⬦ | free | 2.26-2.41 (4H, m), 3.16 (2H, t, J = 7.6 Hz), 3.43 (3H, s), 4.06 (2H, t, J = 6.3 Hz), 4.22-4.37 (4H, m), 6.85-6.96 (3H, m), 7.23-7.30 (2H, m), 8.17 (1H, s). |
| 401 | 4-F | —N⬦ | free | 2.26-2.41 (4H, m), 3.15 (2H, t, J = 7.5 Hz), 3.43 (3H, s), 4.01 (2H, t, J = 6.4 Hz), 4.26-4.36 (4H, m), 6.77-6.86 (2H, m), 6.90-7.01 (2H, m), 8.17 (1H, s). |

Example 402

Process of 7-(azetidin-1-ylcarbonyl)-2-[(4-fluorophenoxy)methyl]-9-methyl-7,9-dihydro-8H-purine-8-one

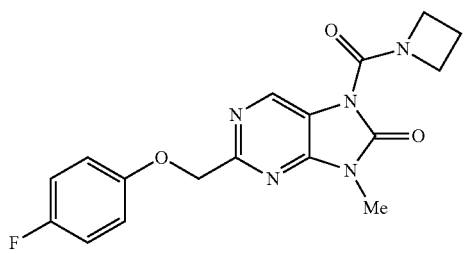 [SMILES: Cn1c(=O)n(C(=O)N2CCC2)c2cnc(COc3ccc(F)cc3)nc21]

(1) To a solution of triphosgene (3.5 g) in dichloromethane (70 ml) was added dropwise a solution of diisopropylethylamine (5.3 ml) and azetidine (1.6 ml) in dichloromethane (30 ml) over 10 minutes and the mixture was stirred at room temperature for 10 minutes. To the reaction mixture was added a suspension of 9-methyl-2-[(E)-2-phenylethenyl]-7,9-dihydro-8H-purine-8-one <the compound of Reference Example 3> (3.0 g) and 1,4-diazabicyclo[2.2.2]octane (2.7 g) in dichloromethane (30 ml) by small portions and the mixture was stirred for 1 hour. The reaction mixture was washed with water and the organic layer was dried over anhydrous magnesium sulfate, and the solvent was then evaporated under reduced pressure. The obtained residue was purified by silica gel column chromatography (eluent: hexane/ethyl acetate=100/0~0/100) to give 7-(azetidin-1-ylcarbonyl)-9-methyl-2-[(E)-2-phenylethenyl]-7,9-dihydro-8H-purine-8-one 2.7 g.

$^1$H-NMR (CDCl$_3$) δ: 2.30-2.50 (2H, m), 3.50 (3H, s), 4.17-4.61 (4H, m), 7.15-7.52 (3H, m), 7.22 (1H, d, J=16.0 Hz), 7.54-7.76 (2H, m), 7.93 (1H, d, J=16.0 Hz), 8.78 (1H, s).

(2) The above-mentioned product (1.3 g) was dissolved in a solution of methanol (80 ml) and dichloromethane (10 ml) and the resulting mixture was subjected to ozonolysis for 3 hours. After a completion of the reaction, the solution was cooled to 0° C. and thereto was added dropwise a suspension of sodium borohydride (440 mg) in ethanol (10 ml), and the resulting mixture was stirred at the same temperature for 1 hour. To the reaction mixture was added water (100 ml) and the resulting mixture was extracted with chloroform (100 ml×2). The organic layer was dried over anhydrous magnesium sulfate and the solvent was evaporated under reduced pressure. The obtained residue was purified by silica gel column chromatography (eluent: hexane/ethyl acetate=100/0~0/100) to give 7-(azetidin-1-ylcarbonyl)-2-(hydroxymethyl)-9-methyl-7,9-dihydro-8H-purine-8-one 682 mg.

$^1$H-NMR (CDCl$_3$) δ: 2.25-2.50 (2H, m), 3.46 (3H, s), 4.11-4.58 (4H, m), 4.80 (2H, s), 8.76 (1H, s).

(3) To a solution of the above-mentioned product (100 mg), triphenylphosphine (121 mg) and 4-fluorophenol (52 mg) in toluene (5 ml) was added dropwise diisopropyl azodicarboxylate (0.091 ml) and the mixture was stirred at room temperature for 1 hour. The toluene was evaporated, and to the residue was added diisopropylether and the crystals precipitated were then collected by filtration to give the title compound 107 mg.

$^1$H-NMR (CDCl$_3$) δ: 2.28-2.54 (2H, m), 3.46 (3H, s), 4.17-4.56 (4H, m), 5.22 (2H, s), 6.87-7.08 (4H, m), 8.80 (1H, s).

Examples 403 to 437

The compounds indicated in Tables 61 to 64 were prepared according to the similar method to those of Example 402.

TABLE 61

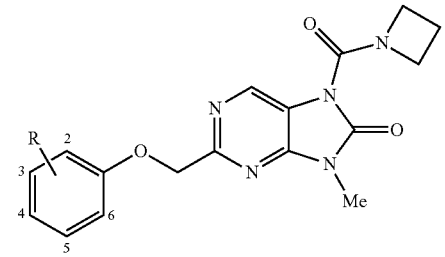

| Ex. No. | R | $^1$H-NMR (CDCl$_3$) δ |
|---|---|---|
| 403 | H | 2.30-2.49 (2H, m), 3.46 (3H, s), 4.18-4.53 (4H, m), 5.26 (2H, s), 6.91-7.05 (3H, m), 7.22-7.33 (2H, m), 8.80 (1H, s). |
| 404 | 3-OMe | 2.32-2.48 (2H, m), 3.46 (3H, s), 3.78 (3H, s), 4.19-4.52 (4H, m), 5.24 (2H, s), 6.48-6.66 (3H, m), 7.08-7.22 (1H, m), 8.80 (1H, s). |
| 405 | 3-F | 2.28-2.49 (2H, m), 3.46 (3H, s), 4.07-4.54 (4H, m), 5.24 (2H, s), 6.54-6.85 (2H, m), 7.09-7.31 (2H, m), 8.80 (1H, s). |
| 406 | 4-Cl | 2.31-2.50 (2H, m), 3.45 (3H, s), 4.17-4.56 (4H, m), 5.23 (2H, s), 6.89-7.01 (2H, m), 7.16-7.33 (2H, m), 8.79 (1H, s). |
| 407 | 3-Cl | 2.28-2.51 (2H, m), 3.46 (3H, s), 4.13-4.57 (4H, m), 5.24 (2H, s), 6.84-6.99 (2H, m), 7.00-7.08 (1H, m), 7.12-7.24 (1H, m), 8.80 (1H, s). |
| 408 | 2-F | 2.23-2.55 (2H, m), 3.45 (3H, s), 4.02-4.66 (4H, m), 5.32 (2H, s), 6.81-7.18 (4H, m), 8.79 (1H, s). |
| 409 | 2-Cl | 2.32-2.49 (2H, m), 3.44 (3H, s), 4.18-4.55 (4H, m), 5.34 (2H, s), 6.84-7.05 (2H, m), 7.09-7.20 (1H, m), 7.33-7.43 (1H, m), 8.79 (1H, s). |
| 410 | 3-CF$_3$ | 2.27-2.53 (2H, m), 3.45 (3H, s), 4.12-4.59 (4H, m), 5.29 (2H, s), 7.09-7.48 (4H, m), 8.81 (1H, s). |
| 411 | 3-Me | 2.19-2.51 (2H, m), 2.31 (3H, s), 3.46 (3H, s), 4.10-4.60 (4H, m), 5.24 (2H, s), 6.68-6.92 (3H, m), 7.09-7.20 (1H, m), 8.80 (1H, s). |
| 412 | 3-OCF$_3$ | 2.30-2.50 (2H, m), 3.45 (3H, s), 4.16-4.56 (4H, m), 5.26 (2H, s), 6.78-6.86 (1H, m), 6.88-6.99 (2H, m), 7.20-7.33 (1H, m), 8.80 (1H, s). |

TABLE 62

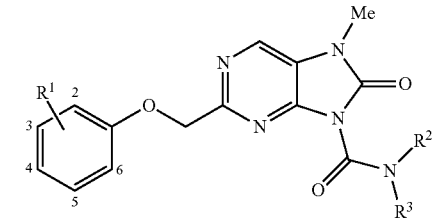

| Ex. No. | R$^1$ | NR$^2$R$^3$ | Salt | $^1$H-NMR |
|---|---|---|---|---|
| 413 | 3-Et | —NMe$_2$ | HCl | (DMSO-d$_6$) δ: 1.13 (3H, t, J = 7.6 Hz), 2.53 (2H, q, J = 7.6 Hz), 2.91 (3H, s), 3.06 (3H, s), 3.37 (3H, s), 5.15 (2H, s), 6.73-6.80 (2H, m), 6.82-2.86 (1H, m), 7.14 (1H, t, J = 7.9 Hz), 8.57 (1H, s). |
| 414 | 3-Cl | —NMe$_2$ | free | (CDCl$_3$) δ : 3.03 (3H, s), 3.22 (3H, s), 3.47 (3H, s), 5.25 (2H, s), 6.85-6.96 (2H, m), 7.00-7.03 (1H, m), 7.18 (1H, t, J = 8.2 Hz), 8.27 (1H, s). |

TABLE 62-continued

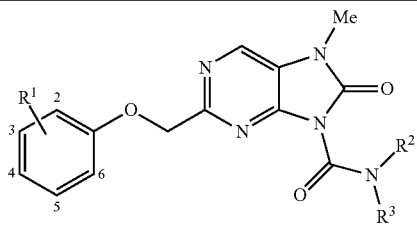

| Ex. No. | R¹ | NR²R³ | Salt | ¹H-NMR |
|---|---|---|---|---|
| 415 | H | azetidinyl | free | (CDCl₃) δ: 2.27-2.40 (2H, m), 3.45 (3H, s), 4.21 (2H, t, J = 7.8 Hz), 4.32 (2H, t, J = 7.8 Hz), 5.30 (2H, s), 6.91-7.04 (3H, m), 7.24-7.30 (2H, m), 8.27 (1H, s). |
| 416 | 2-Me | azetidinyl | HCl | (DMSO-d₆) δ: 2.17-2.24 (5H, m), 3.35 (3H, s), 4.03 (2H, t, J = 7.8 Hz), 4.11 (2H, t, J = 7.8 Hz), 5.22 (2H, s), 6.78-6.85 (1H, m), 6.91-6.98 (1H, m), 7.04-7.17 (2H, m), 8.55 (1H, s). |
| 417 | 3-Me | azetidinyl | HCl | (DMSO-d₆) δ: 2.14-2.29 (5H, m), 3.35 (3H, s), 4.01-4.18 (4H, m), 5.17 (2H, s), 6.70-6.79 (2H, m), 6.80-6.86 (1H, m), 7.13 (1H, t, J = 7.8 Hz), 8.55 (1H, s). |

TABLE 62-continued

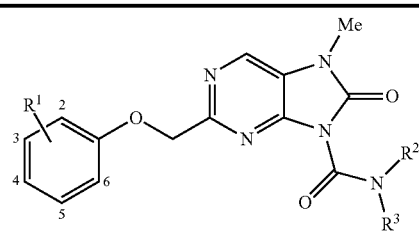

| Ex. No. | R¹ | NR²R³ | Salt | ¹H-NMR |
|---|---|---|---|---|
| 418 | 3-Et | azetidinyl | HCl | (DMSO-d₆) δ: 1.13 (3H, t, J = 7.6 Hz), 2.15-2.28 (2H, m), 2.54 (2H, q, J = 7.6 Hz), 3.36 (3H, s), 4.04-4.14 (4H, m), 5.18 (2H, s), 6.73-6.81 (2H, m), 6.83-6.87 (1H, m), 7.15 (1H, t, J =7.9 Hz), 8.55 (1H, s). |
| 419 | 3-Cl | azetidinyl | HCl | (DMSO-d₆) δ: 2.15-2.29 (2H, m), 3.35 (3H,s), 4.01-4.16 (4H, m), 5.24 (2H, s), 6.94-7.01 (2H, m), 7.09-7.12 (1H, m), 7.28 (1H, t, J = 8.2 Hz), 8.55 (1H, s). |
| 420 | 3-F | azetidinyl | HCl | (DMSO-d₆) δ: 2.15-2.29 (2H, m), 3.35 (3H, s), 4.02-4.16 (4H, m), 5.23 (2H, s), 6.71-6.80 (1H, m), 6.81-6.93 (2H, m), 7.24-7.34 (1H, m), 8.55 (1H, s). |

TABLE 63

| Ex. No | R¹ | NR²R³ | Salt | ¹H-NMR |
|---|---|---|---|---|
| 421 | 2-Cl | —NMe₂ | HCl | (DMSO-d₆) δ: 2.89 (3H, s), 3.05 (3H, s), 3.36 (3H, s), 529 (2H, s), 629-6.97 (1H, m), 7.12-7.26 (2H, m), 7.42 (1H, dd, J = 7.9 1.7 Hz), 8.56 (1H, s). |
| 422 | 3-CF₃ | —NMe₂ | HCl | (DMSO-d₆) δ: 2.89 (3H, s), 3.05 (3H, s), 3.37 (3H, s), 5.29 (2H, s), 7.24-7.36 (3H, m), 7.50 (1H, t, J = 7.9 Hz), 8.56 (1H, s). |
| 423 | 3-OCF₃ | —NMe₂ | HCl | (DMSO-d₆) δ: 2.90 (3H, s), 3.05 (3H, s), 3.37 (3H, s), 5.24 (2H, s), 6.88-6.95 (1H, m), 6.99-7.06 (2H, m), 7.38 (1H, t, J = 8.3 Hz), 8.57 (1H, s). |
| 424 | 4-Me | azetidinyl | HCl | (DMSO-d₆) δ: 2.15-2.28 (5H, m), 3.35 (3H, s), 4.01-4.16 (4H, m), 5.15 (2H, a), 6.83-6.90 (2H, m), 7.02-7.09 (2H, m), 8.54 (1H, s). |
| 425 | 2-F | azetidinyl | free | (CDCl₃) δ: 2.28-2.42 (2H, m), 3.45 (3H, s), 4.20-4.37 (4H, m), 5.24 (2H, s), 6.86-6.95 (1H, m), 6.97-7.14 (3H, m), 8.26 (1H, s). |
| 426 | 4-F | azetidinyl | HCl | (DMSO-d₆) δ: 2.15-2.29 (2H, m), 3.35 (3H, s), 4.01-4.17 (4H, m), 5.18 (2H, s), 6.95-7.14 (4H, m), 8.55 (1H, s). |
| 427 | 2-Cl | azetidinyl | HCl | (DMSO-d₆) δ: 2.14-2.28 (2H, m), 3.35 (3H, s), 4.00-4.17 (4H, m), 5.32 (2H, s), 6.89-6.98 (1H, m), 7.12-7.28 (2H, m), 740-7.46 (1H, m), 855 (1H, s). |
| 428 | 4-Cl | azetidinyl | free | (CDCl₃) δ: 2.29-2.42 (2H, m), 3.45 (3H, s), 4.24 (2H, t, J = 7.8 Hz), 4.33 (2H, t, J = 7.8 Hz), 5.27 (2H, s), 6.90-6.97 (2H, m), 7.18-725 (2H, m), 826 (1H, s). |
| 429 | 2-CF₃ | —NMe₂ | HCl | (DMSO-d₆) δ: 2.85 (3H, s), 3.03 (3H, s), 3.36 (3H, s), 5.35 (2H, s), 7.07 (1H, t, J = 7.6 Hz), 7.26 (1H, d, J = 8.4 Hz), 7.51-7.65 (2H, m), 8.56 (1H, s). |
| 430 | 2-OCF₃ | —NMe₂ | HCl | (DMSO-d₆) δ: 2.86 (3H, s), 3.03 (3H, s), 3.36 (3H, s), 5.30 (2H, s), 6.96-7.03 (1H, |

TABLE 63-continued

| Ex. No | R¹ | NR²R³ | Salt | ¹H-NMR |
|---|---|---|---|---|
| 431 | 3-OCF₂H | —NMe₂ | HCl | m), 7.20-7.29 (2H, m), 7.30-7.38 (1H, m), 8.56 (1H, s). (DMSO-d₆) δ: 2.91 (3H, s), 3.06 (3H, s), 3.37 (3H, s), 5.20 (2H, s), 6.70-6.76 (1H, m), 6.80-6.89 (2H, m), 7.22 (1H, t, J = 74.3 Hz), 7.29 (1H, t, J = 8.3 Hz), 8.56 (1H, s). |

TABLE 64

| Ex. No. | R¹ | NR²R³ | Salt | ¹H-NMR |
|---|---|---|---|---|
| 432 | 2-CF₃ | —N⟨azetidinyl⟩ | HCl | (DMSO-d₆) δ: 2.11-2.24 (2H, m), 3.35 (3H, s), 4.00 (2H, t, J = 7.7 Hz), 4.09 (2H, t, J = 7.7 Hz), 5.37 (2H, s), 7.03-7.12 (1H, m), 7.24-7.30 (1H, m), 7.52-7.66 (2H, m), 8.55 (1H, s). |
| 433 | 3-CF₃ | —N⟨azetidinyl⟩ | HCl | (DMSO-d₆) δ: 2.14-2.27 (2H, m). 3.35 (3H, s), 4.01-4.15 (4H, m), 5.32 (2H, s), 7.25-7.36 (3H, m), 7.50 (1H, t, J = 7.9 Hz), 8.55 (1H, s). |
| 434 | 4-CF₃ | —N⟨azetidinyl⟩ | HCl | (DMSO-d₆) δ: 2.13-2.27 (2H, m), 3.35 (3H, s), 3.98-4.15 (4H, m), 5.32 (2H, s), 7.17 (2H, d, J = 8.6 Hz), 7.63 (2H, d, J = 8.6 Hz), 8.54 (1H, s). |
| 435 | 2-OCF₃ | —N⟨azetidinyl⟩ | HCl | (DMSO-d₆) δ: 2.12-2.25 (2H, m), 3.35 (3H, s), 4.02 (2H, t, J = 7.8 Hz), 4.09 (2H, t, J = 7.8 Hz), 5.33 (2H, s), 6.97-7.04 (1H, m), 7.21-7.39 (3H, m), 8.55 (1H, s). |
| 436 | 3-OCF₃ | —N⟨azetidinyl⟩ | HCl | (DMSO-d₆) δ: 2.14-2.28 (2H, m), 3.35 (3H, s), 4.00-4.15 (4H, m), 5.26 (2H, s), 6.88-6.95 (1H, m), 6.99-7.07 (2H, m), 7.39 (1H, t, J = 8.3 Hz), 8.55 (1H, s). |
| 437 | 3-OCF₂H | —N⟨azetidinyl⟩ | HCl | (DMSO-d₆) δ: 2.15-2.29 (2H, m), 3.35 (3H, s), 4.03-4.17 (4H, m), 5.23 (2H, s), 6.70-6.77 (1H, m), 6.81-6.90 (2H, m), 7.23 (1H, t, J = 74.2 Hz), 7.30 (1H, t, J = 8.3 Hz), 8.55 (1H, s). |

Example 438

Process of 2-(methoxymethyl)-9-methyl-7-[(3-phenylazetidin-1-yl)carbonyl]-7,9-dihydro-8H-purine-8-one

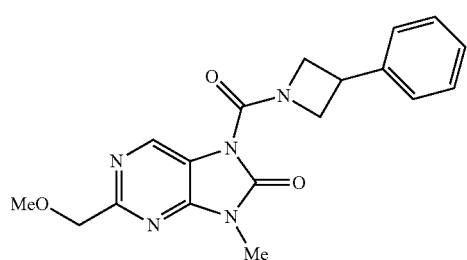 [SMILES: COCc1ncc2c(n1)n(C)c(=O)n2C(=O)N1CC(c2ccccc2)C1]

(1) To a mixture of 2-chloro-9-methyl-7-{[2-(trimethylsilyl)ethoxy]methyl}-7,9-dihydro-8H-purine-8-one <the compound of Reference Example 20(1)> (30.0 g), trans-2-phenylvinylboronic acid (21.2 g), potassium carbonate (26.3 g) and toluene (400 ml) was added tetrakistriphenylphosphine palladium (5.5 g) under nitrogen atmosphere and the mixture was heated under reflux for 17 hours. The reaction mixture was filtered through Celite and the filtrate was concentrated under reduced pressure. The obtained residue was purified by silica gel column chromatography (eluent: hexane/ethyl acetate=100/0~0/100) to give 9-methyl-2-[(E)-2-phenylethenyl]-7-{[2-(trimethylsilyl)ethoxy]methyl}-7,9-dihydro-8H-purine-8-one 32.1 g.

¹H-NMR (CDCl₃) δ: −0.01 (9H, s), 0.86-1.04 (2H, m), 3.43-3.70 (2H, m), 3.54 (3H, s), 5.33 (2H, s), 7.13-7.72 (5H, m), 7.23 (1H, d, J=16.1 Hz), 7.91 (1H, d, J=16.1 Hz), 8.33 (1H, s).

(2) The above-mentioned product (32.1 g) was dissolved in methanol (500 ml) and the resulting mixture was subjected to ozonolysis for 4 hours. After a completion of the reaction, the reaction mixture was cooled to 0° C. and thereto was added dropwise a suspension of sodium borohydride (12.7 g) in ethanol and the resulting mixture was stirred at the same temperature for 2 hours. To the reaction mixture was added water (300 ml) and the mixture was extracted with chloroform (400 ml×2). The organic layer was dried over anhydrous magnesium sulfate and the solvent was evaporated under reduced pressure. The obtained residue was purified by silica gel column chromatography (eluent: hexane/ethyl acetate=100/0~0/100) to give 2-(hydroxymethyl)-9-methyl-7-{[2-(trimethylsilyl)ethoxy]methyl}-7,9-dihydro-8H-purine-8-one 16.8 g.

¹H-NMR (CDCl₃) δ: −0.02 (9H, s), 0.86-1.02 (2H, m), 3.35-3.77 (3H, m), 3.49 (3H, s), 4.79 (2H, s), 5.33 (2H, s), 8.29 (1H, s).

(3) To a suspension of 60% sodium hydride in tetrahydrofuran (30 ml) was added dropwise a solution of the above-mentioned product (5.0 g) in tetrahydrofuran (20 ml) under nitrogen atmosphere and the mixture was stirred for 5 minutes. To the reaction mixture was added methyl iodide (1.5 ml) and the mixture was stirred for 2 hours. To the reaction mixture was added water (50 ml) and the mixture was extracted with ethyl acetate (80 ml×3). The organic layer was dried over anhydrous magnesium sulfate and the solvent was evaporated under reduced pressure. The obtained residue was purified by silica gel column chromatography (eluent: hexane/ethyl acetate=100/0~0/100) to give 2-(methoxymethyl)-9-methyl-7-{[2-(trimethylsilyl)ethoxy]methyl}-7,9-dihydro-8H-purine-8-one 5.06 g.

¹H-NMR (CDCl₃) δ: −0.02 (9H, s), 0.86-1.00 (2H, m), 3.45-3.69 (2H, m), 3.50 (3H, s), 3.55 (3H, s), 4.66 (2H, s), 5.33 (2H, s), 8.33 (1H, s).

(4) The above-mentioned product (5.06 g) and 1 mol/L tetrabutylammonium fluoride/tetrahydrofuran solution (156 ml) were mixed and the mixture was heated under reflux for 14 hours. After the reaction mixture was cooled to room temperature, to the reaction mixture were added 1,4-diazabicyclo[2.2.2]octane (5.3 g) and di-tert-butyl carbonate (6.8 g) and the mixture was stirred for 30 minutes. To the reaction mixture was added water (200 ml) and the mixture was extracted with ethyl acetate (150 ml×3). The organic layer was dried over anhydrous magnesium sulfate and the solvent was evaporated under reduced pressure. The obtained residue was purified by silica gel column chromatography (eluent: hexane/ethyl acetate=100/0~0/100) to give tert-butyl 2-(methoxymethyl)-9-methyl-8-oxo-8,9-dihydro-7H-purine-7-carboxylate 4.0 g.

¹H-NMR (CDCl₃) δ: 1.67 (9H, s), 3.47 (3H, s), 3.55 (3H, s), 4.66 (2H, s), 8.78 (1H, s).

(5) The above-mentioned product (4.0 g) and 5-10% hydrogen chloride/methanol solution (30 ml) were mixed and the mixture was stirred for 24 hours. The reaction mixture was evaporated and the obtained crude solids were washed with ethyl acetate to give 2-(methoxymethyl)-9-methyl-7,9-dihydro-8H-purine-8-one hydrochloric acid salt 2.4 g.

¹H-NMR (DMSO-d₆) δ: 3.30 (3H, s), 3.36 (3H, s), 4.53 (2H, s), 8.25 (1H, s).

(6) To a solution of triphosgene (119 mg) in dichloromethane (4 ml) was added dropwise a solution of diisopropylethylamine (0.265 ml) and 3-phenylazetidine trifluoroacetate salt (148 mg) in dichloromethane (3 ml) and the mixture was stirred at room temperature for 5 minutes. To the reaction mixture was added a solution of the product of above-mentioned (5) (92 mg) and 1,4-diazabicyclo[2.2.2]octane (90 mg) in dichloromethane (3 ml) and the mixture was stirred for 2 hours. The reaction mixture was washed with water and the organic layer was dried over anhydrous magnesium sulfate and the solvent was evaporated under reduced pressure. The obtained residue was purified by silica gel column chromatography (eluent: hexane/ethyl acetate=100/0~0/100) to give the title compound 59 mg.

¹H-NMR (CDCl₃) δ: 3.48 (3H, s), 3.54 (3H, s), 3.86-4.05 (1H, m), 4.20-4.88 (4H, m), 4.67 (2H, s), 7.17-7.50 (5H, m), 8.83 (1H, s).

Examples 439 to 492

The compounds indicated in Tables 65 to 69 were prepared according to the similar method to those of Example 438.

TABLE 65

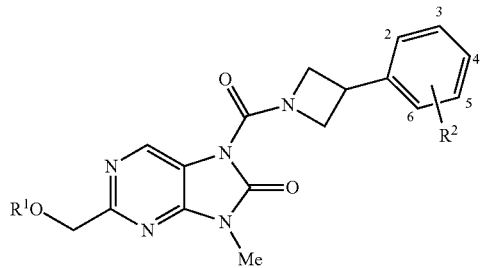

| Ex. No. | R¹ | R² | 塩 | ¹H-NMR |
|---|---|---|---|---|
| 439 | Me | 4-F | free | (CDCl₃) δ: 3.48 (3H, s), 3.55 (3H, s), 3.84-4.01 (1H, m), 4.12-4.86 (4H, m), 4.67 (2H, s), 7.00-7.13 (2H, m), 7.28-7.39 (2H, m), 8.83 (1H, s). |
| 440 | Me | 3-F | free | (CDCl₃) δ: 3.48 (3H, s), 3.54 (3H, s), 4.08-4.26 (1H, m), 4.29-4.94 (4H, m), 4.67 (2H, s), 7.00-7.45 (4H, m), 8.83 (1H, s). |
| 441 | Me | 2-F | free | (CDCl₃) δ: 3.48 (3H, s), 3.54 (3H, s), 4.05-4.95 (5H, m), 4.67 (2H, s), 6.97-7.50 (4H, m), 8.83 (1H, s). |
| 442 | Me | 2-Me | free | (CDCl₃) δ: 2.25 (3H, s), 3.48 (3H, s), 3.54 (3H, s), 4.05-4.92 (5H, m), 4.67 (2H, s), 7.06-7.50 (4H, m), 8.82 (1H, s). |
| 443 | Me | 3-CF₃ | free | (CDCl₃) δ: 3.48 (3H, s), 3.55 (3H, s), 3.93-4.10 (1H, m), 4.18-4.93 (4H, m), 4.67 (2H, s), 7.44-7.68 (4H, m), 8.85 (1H, s). |
| 444 | Me | 3-Me | free | (CDCl₃) δ: 2.37 (3H, s), 3.48 (3H, s), 3.54 (3H, s), 3.83-4.01, (1H, m), 4.19-4.86 (4H, m), 4.67 (2H, s), 7.04-7.34 (4H, m), 8.83 (1H, s). |
| 445 | Me | 4-OEt | free | (CDCl₃) δ: 1.42 (3H, t, J = 7.0 Hz), 3.47 (3H, s), 3.54 (3H, s), 3.80-3.98 (1H, m), 4.03 (2H, q, J = 7.0 Hz), 4.14-4.86 (4H, m), 4.67 (2H, s), 6.84-6.96 (2H, m), 7.17-7.34 (2H, m), 8.83 (1H, s). |
| 446 | Me | 4-Cl | free | (CDCl₃) δ: 3.48 (3H, s), 3.55 (3H, s), 3.86-3.98 (1H, m), 4.16-4.83 (4H, m), 4.67 (2H, s), 7.18-7.44 (4H, m), 8.83 (1H, s). |
| 447 | Me | 3-Cl | free | (CDCl₃) δ: 3.48 (3H, s), 3.55 (3H, s), 3.84-4.01 (1H, m), 4.17-4.88 (4H, m), 4.67 (2H, s), 7.16-7.44 (4H, m), 8.84 (1H, s). |
| 448 | Me | 4-CF₃ | free | (CDCl₃) δ: 3.48 (3H, s), 3.55 (3H, s), 3.91-4.10 (1H, m), 4.15-4.91 (4H, m), 4.67 (2H, s), 7.42-7.56 (2H, m), 7.58-7.74 (2H, m), 8.84 (1H, s). |
| 449 | Me | 3-OCF₃ | free | (CDCl₃) δ: 3.48 (3H, s), 3.55 (3H. s), 3.86-4.07 (1H, m), 4.12-4.92 (4H, m), 4.67 (2H, s), 7.06-7.51 (4H, m), 8.84 (1H, s). |
| 450 | Me | 4-OMe | free | (CDCl₃) δ: 3.47 (3H, s), 3.54 (3H, s), 3.70-4.00 (1H, m), 3.81 (3H, s), 4.10-4.86 (4H, m), 4.67 (2H, s), 6.81-7.01 (2H, m), 7.17-7.38 (2H, m), 8.83 (1H, s). |

TABLE 66

| Ex. No. | R¹ | R² | Salt | ¹H-NMR |
|---|---|---|---|---|
| 451 | Me | 3-OEt | free | (CDCl₃) δ: 1.42 (3H, t, J = 7.0 Hz), 3.47 (3H, s), 3.54 (3H, s), 3.83-4.13 (1H, m), 4.05 (2H, q, J = 7.0 Hz), 4.21-4.88 (4H, m), 4.67 (2H, s), 6.75-6.98 (3H, m), 7.20-7.37 (1H, m), 8.83 (1H, s). |

TABLE 66-continued

| Ex. No. | R¹ | R² | Salt | ¹H-NMR |
|---|---|---|---|---|
| 452 | Me | 4-Me | free | (CDCl₃) δ: 2.35 (3H, s), 3.47 (3H, s), 3.54 (3H, s), 3.82-4.00 (1H, m), 4.18-4.88 (4H, m), 4.67 (2H, s), 7.09-7.39 (4H, m), 8.83 (1H, s). |
| 453 | Me | 2-Cl | free | (CDCl₃) δ: 3.48 (3H, s), 3.54 (3H, s), 4.23-4.95 (5H, m), 4.67 (2H, s), 7.16-7.50 (4H, m), 8.82 (1H, s). |
| 454 | Me | 2-F 4-F | free | (CDCl₃) δ: 3.48 (3H, s), 3.54 (3H, s), 4.02-4.92 (5H, m), 4.67 (2H, s), 6.73-7.03 (2H, m), 7.20-7.48 (1H, m), 8.83 (1H, s). |
| 455 | Me | 3-Me 4-F | free | (CDCl₃) δ: 2.29 (3H, d, J = 2.0 Hz), 3.48 (3H, s), 3.55 (3H, s), 3.79-3.98 (1H, m), 4.09-4.87 (4H, m), 4.67 (2H, s), 6.93-7.33 (3H, m), 8.83 (1H, s). |
| 456 | Me | 4-OBn | free | (CDCl₃) δ: 3.47 (3H, s), 3.54 (3H, s), 3.78-4.02 (1H, m), 4.12-4.85 (4H, m), 4.67 (2H, s), 5.07 (2H, s), 6.95-7.03 (2H, m), 7.22-7.49 (7H, m), 8.83 (1H, s). |
| 457 | Me | 2-OMe | free | (CDCl₃) δ: 3.48 (3H, s), 3.54 (3H, s), 3.82 (3H, s), 4.03-4.20 (1H, m), 4.35-4.88 (4H, m), 4.67 (2H, s), 6.81-7.05 (2H, m), 7.17-7.37 (2H, m), 8.82 (1H, s). |
| 458 | Me | 4-OCF₃ | HCl | (DMSO-d₆) δ: 3.30 (3H, s), 3.36 (3H, s), 3.90-5.02 (5H, m), 4.53 (2H, s), 6.04-6.93 (4H, m), 8.59 (1H, s). |
| 459 | Me | 3-OMe | free | (CDCl₃) δ: 3.47 (3H, s), 3.54 (3H, s), 3.73-4.08 (1H, m), 3.83 (3H, s), 4.20-4.89 (4H, m), 4.67 (2H, s), 6.74-7.02 (3H, m), 7.20-7.39 (1H, m), 8.83 (1H, s). |
| 460 | Et | H | free | (CDCl₃) δ: 1.32 (3H, t, J = 7.0 Hz), 3.47 (3H, s), 3.70 (2H, q, J = 7.0 Hz), 3.87-4.05 (1H, m), 4.16-4.94 (4H, m), 4.71 (2H, s), 7.23-7.47 (5H, m), 8.83 (1H, s). |
| 461 | Et | 4-F | free | (CDCl₃) δ: 1.32 (3H, t, J = 7.0 Hz), 3.47 (3H, s), 3.70 (2H, q, J = 7.0 Hz), 3.84-4.01 (1H, m), 4.13-4.84 (4H, m), 4.71 (2H, s), 7.01-7.15 (2H, m), 7.21-7.42 (2H, m), 8.83 (1H, s). |
| 462 | Et | 3-F | free | (CDCl₃) δ: 1.32 (3H, t, J = 7.0 Hz), 3.47 (3H, s), 3.70 (2H, q, J = 7.0 Hz), 3.84-4.04 (1H, m), 4.13-4.91 (4H, m), 4.71 (2H, s), 6.90-7.48 (4H, m), 8.84 (1H, s). |
| 463 | Et | 4-OEt | free | (CDCl₃) δ: 1.31 (3H, t, J = 7.0 Hz), 1.42 (3H, t, J = 7.0 Hz), 3.47 (3H, s), 3.70 (2H, q, J = 7.0 Hz), 3.82-3.98 (1H, m), 4.03 (2H, q, J = 7.0 Hz), 4.17-4.83 (4H, m), 4.71 (2H, s), 6.84-6.98 (2H, m), 7.20-7.35 (2H, m), 8.83 (1H, s). |

TABLE 67

| Ex. No. | R¹ | R² | Salt | ¹H-NMR |
|---|---|---|---|---|
| 464 | Et | 3-CF₃ | free | (CDCl₃) δ: 1.32 (3H, t, J = 7.0 Hz), 3.48 (3H, s), 3.70 (2H, q, J = 7.0 Hz), 3.95-4.11 (1H, m), 4.17-4.95 (4H, m), 4.71 (2H, s), 7.46-7.71 (4H, m), 8.84 (1H, s). |
| 465 | Et | 2-F | free | (CDCl₃) δ: 1.31 (3H, t, J = 7.0 Hz), 3.47 (3H, s), 3.70 (2H, q, J = 7.0 Hz), 4.04-4.94 (5H, m), 4.71 (2H, s), 6.96-7.49 (4H, m), 8.83 (1H, s). |
| 466 | c-PrCH₂ | 3-F | free | (CDCl₃) δ: 0.16-0.40 (2H, m), 0.46-0.72 (2H, m), 1.04-1.33 (1H, m), 3.37-3.63 (5H, m), 3.68-4.91 (5H, m), 4.75 (2H, s), 6.83-7.46 (4H, m), 8.83 (1H, s). |
| 467 | n-Pr | H | free | (CDCl₃) δ: 0.96 (3H, t, J = 7.5 Hz), 1.44-1.85 (2H, m), 3.47 (3H, s), 3.58 (2H, t, J = 6.9 Hz), 3.85-4.05 (1H, m), 4.20-4.92 (4H, m), 4.70 (2H, s), 7.16-7.55 (5H, m), 8.83 (1H, s). |
| 468 | n-Pr | 3-F | HCl | (DMSO-d₆) δ: 0.87 (3H, t, J = 7.4 Hz), 1.45-1.62 (2H, m), 3.30 (3H, s), 3.46 (2H, t, J = 6.7 Hz), 3.87-5.00 (5H, m), 4.55 (2H, s), 6.99-7.49 (4H, m), 8.60 (1H, s). |
| 469 | n-Pr | 4-OEt | free | (CDCl₃) δ: 0.96 (3H, t, J = 7.4 Hz), 1.42 (3H, t, J = 7.0 Hz), 1.63-1.82 (2H, m), 3.47 (3H, s), 3.58 (2H, t, J = 6.9 Hz), 3.76-4.88 (5H, m), 4.03 (2H, q, J = 7.0 Hz), 4.70 (2H, s), 6.84-6.97 (2H, m), 7.20-7.35 (2H, m), 8.82 (1H, s). |
| 470 | n-Pr | 4-F | free | (CDCl₃) δ: 0.96 (3H, t, J = 7.4 Hz), 1.60-1.81 (2H, m), 3.47 (3H, s), 3.58 (2H, t, J = 6.9 Hz), 3.84-4.02 (1H, m), 4.17-4.84 (4H, m), 4.70 (2H, s), 7.01-7.14 (2H, m), 7.20-7.39 (2H, m), 8.83 (1H, s). |

TABLE 67-continued
| Ex. No. | R¹ | R² | Salt | ¹H-NMR |
|---|---|---|---|---|
| 471 | n-Pr | 3-CF₃ | free | (CDCl₃) δ: 0.96 (3H, t, J = 7.5 Hz), 1.60-1.82 (2H, m), 3.48 (3H, s), 3.58 (2H, t, J = 6.2 Hz), 3.92-4.12 (1H, m), 4.17-4.96 (4H, m), 4.71 (2H, s), 7.40-7.72 (4H, m), 8.84 (1H, s). |
| 472 | MeO(CH₂)₂ | 4-F | HCl | (DMSO-d₆) δ: 3.24 (3H, s), 3.30 (3H, s), 3.41-3.55 (2H, m), 3.59-3.73 (2H, m), 3.86-5.08 (5H, m), 4.59 (2H, s), 7.12-7.27 (2H, m), 7.35-7.51 (2H, m), 8.59 (1H, s). |
| 473 | MeO(CH₂)₂ | 3-F | HCl | (DMSO-d₆) δ: 3.24 (3H, s), 3.31 (3H, s), 3.40-3.56 (2H, m), 3.58-3.77 (2H, m), 3.86-4.81 (5H, m), 4.60 (2H, s), 7.00-7.52 (4H, m), 8.60 (1H, s). |
TABLE 68
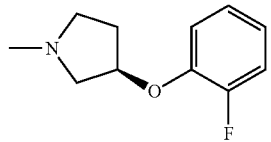
| Ex. No. | NR¹R² | ¹H-NMR (CDCl₃) δ |
|---|---|---|
| 474 | 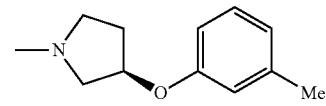 | 2.09-2.50 (2H, m), 3.48 (3H, s), 3.54 (3H, s), 3.65-4.28 (4H, m), 4.67 (2H, s), 4.86-5.16 (1H, m), 6.83-7.21 (4H, m), 8.51-8.74 (1H, m). |
| 475 | 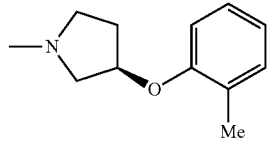 | 2.08-2.52 (5H, m), 3.31-4.34 (4H, m), 3.48 (3H, s), 3.53 (3H, s), 4.66 (2H, s), 4.85-5.13 (1H, m), 6.52-6.92 (3H, m), 7.01-7.40 (1H, m), 8.62 (1H, s). |
| 476 | 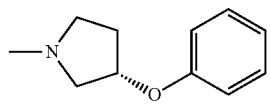 | 2.01-2.50 (5H, m), 3.48 (3H, s), 3.53 (3H, s), 3.60-4.26 (4H, m), 4.66 (2H, s), 4.91-5.14 (1H, m), 6.68-6.99 (2H, m), 7.03-7.36 (2H, m), 8.51-8.69 (1H, m). |
| 477 | 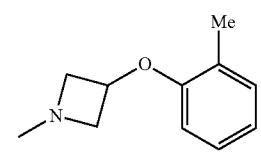 | 2.12-2.48 (2H, m), 3.48 (3H, s), 3.53 (3H, s), 3.63-4.31 (4H, m), 4.11 (2H, s), 4.91-5.16 (1H, m), 6.75-7.09 (3H, m), 7.18-7.43 (2H, m), 8.52-8.71 (1H, m). |
| 478 | 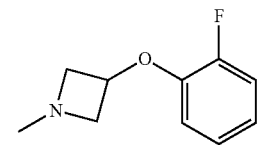 | 2.25 (3H, s), 3.47 (3H, s), 3.54 (3H, s), 4.29-4.93 (4H, m), 4.67 (2H, s). 4.98-5.10 (1H, m), 6.41-6.50 (1H, m), 6.87-6.96 (1H, m), 7.07-7.22 (2H, m), 8.84 (1H, s). |
| 479 | 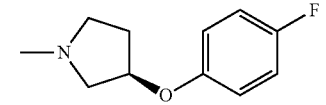 | 3.47 (3H, s), 3.54 (3H, s), 4.30-4.96 (4H, m), 4.67 (2H, s), 5.00-5.16 (1H, m), 6.67-6.81 (1H, m), 6.89-7.21 (3H, m), 8.83 (1H, s). |
| 480 |  | 2.11-2.44 (2H, m), 3.48 (3H, s), 3.54 (3H, s), 3.60-4.28 (4H, m), 4.66 (2H, s), 4.83-5.03 (1H, m), 6.73-7.09 (4H, m), 8.51-8.70 (1H, m). |

TABLE 68-continued
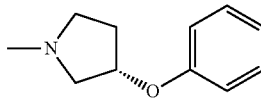
| Ex. No. | NR¹R² | ¹H-NMR (CDCl₃) δ |
|---|---|---|
| 481 | 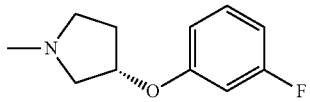 | 2.06-2.49 (2H, m), 3.12-4.35 (4H, m), 3.48 (3H, s), 3.54 (3H, s), 4.66 (2H, s), 4.80-5.09 (1H, m), 6.66-7.15 (4H, m), 8.62 (1H, s). |
| 482 | 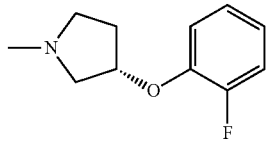 | 2.12-2.51 (2H, m), 3.19-4.38 (4H, m), 3.48 (3H, s), 3.53 (3H, s), 4.66 (2H, s), 4.85-5.16 (1H, m), 6.46-6.81 (3H, m), 7.11-7.39 (1H, m), 8.62 (1H, s). |
| 483 | 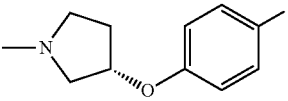 | 2.14-2.49 (2H, m), 3.48 (3H, s), 3.54 (3H, s), 3.65-4.24 (4H, m), 4.67 (2H, s), 4.91-5.14 (1H, m), 6.88-7.19 (4H, m), 8.55-8.71 (1H, m). |
TABLE 69
| Ex. No. | NR¹R² | ¹H-NMR (CDCl₃) δ |
|---|---|---|
| 484 | 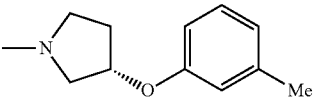 | 2.01-2.48 (2H, m), 2.27 (3H, s), 3.47 (3H, s), 3.53 (3H, s), 3.58-4.29 (4H, m), 4.66 (2H, s), 4.84-5.08 (1H, m), 6.64-6.87 (2H, m), 6.93-7.19 (2H, m), 8.48-8.70 (1H, m). |
| 485 | 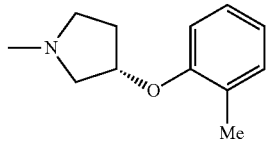 | 2.09-2.46 (5H, m), 3.48 (3H, s), 3.53 (3H, s), 3.59-4.30 (4H, m), 4.66 (2H, s), 4.85-5.12 (1H, m), 6.54-6.89 (3H, m), 7.01-7.33 (1H, m), 8.51-8.70 (1H, m). |
| 486 | 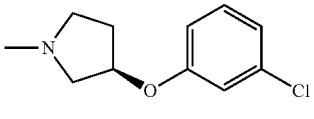 | 2.04-2.50 (5H, m), 3.48 (3H, s), 3.53 (3H, s), 3.59-4.26 (4H, m), 4.66 (2H, s), 4.90-5.15 (1H, m), 6.57-6.99 (2H, m), 7.01-7.33 (2H, m), 8.59 (1H, s). |
| 487 | 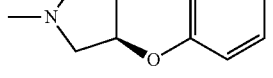 | 2.12-2.48 (2H, m), 3.48 (3H, s), 3.53 (3H, s), 3.61-4.34 (4H, m), 4.66 (2H, s), 4.86-5.13 (1H, m), 6.64-7.05 (3H, m), 7.09-7.33 (1H, m), 8.50-8.72 (1H, m). |
| 488 | 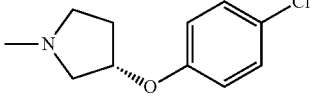 | 2.13-2.46 (2H, m), 3.48 (3H, s), 3.53 (3H, s), 3.60-4.31 (4H, m), 4.66 (2H, s), 4.89-5.11 (1H, m), 6.76-7.10 (3H, m), 7.17-7.39 (2H, m), 8.51-8.69 (1H, m). |
| 489 | | 2.13-2.47 (2H, m), 3.34-4.32 (4H, m), 3.48 (3H, s), 3.53 (3H, s), 4.66 (2H, s), 4.87-5.07 (1H, m), 6.71-6.91 (2H, m), 7.14-7.37 (2H, m), 8.52-8.69 (1H, m). |

TABLE 69-continued

| Ex. No. | NR¹R² | ¹H-NMR (CDCl₃) δ |
|---|---|---|
| 490 | ![structure] | 2.16-2.44 (2H, m), 3.49 (3H, s), 3.53 (3H, s), 3.59-4.31 (4H, m), 4.67 (2H, s), 4.88-5.08 (1H, m), 6.67-7.05 (3H, m), 7.13-7.32 (1H, m), 8.52-8.71 (1H, m). |
| 491 | ![structure] | 2.12-2.52 (2H, m), 3.34-4.25 (4H, m), 3.49 (3H, s), 3.54 (3H, s), 4.11 (2H, s), 4.90-5.17 (1H, m), 6.81-7.06 (2H, m), 7.11-7.50 (2H, m), 8.50-8.70 (1H, m). |
| 492 | ![structure] | 3.05-3.28 (1H, m), 3.47 (3H, s), 3.54 (3H, s), 4.02-4.76 (4H, m), 4.11 (2H, d, J = 6.2 Hz), 4.67 (2H, s), 6.75-7.09 (4H, m), 8.82 (1H, s). |

Example 493

Process of 2-{2-[4-(difluoromethoxy)phenyl]ethyl}-N,N,7-trimethyl-8-oxo-7,8-dihydro-9H-purine-9-carboxamide

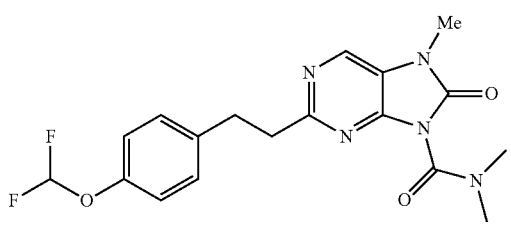 [SMILES: CN(C)C(=O)n1c(=O)n(C)c2cnc(CCc3ccc(OC(F)F)cc3)nc21]

(1) The 2-chloro-N,N,7-trimethyl-8-oxo-7,8-dihydro-9H-purine-9-carboxamide <prepared according to the similar method to those of Reference Example 16> (200 mg), trimethylsilylacetylene (154 mg), bis(acetonitrile)dichloropalladium (10 mg), 2-dicyclohexylphosphino-2',4',6'-triisopropyl-1,1'-biphenyl (37 mg), triethylamine (1 ml) and acetonitrile (2 ml) were mixed and the mixture was stirred at 120° C. under microwave irradiation for 30 minutes. The reaction mixture was filtered through Celite and the fitrate was evaporated under reduced pressure. The obtained residue was purified by amino silica gel column chromatography (eluent: hexane/ethyl acetate=100/0~0/100) to give N,N,7-trimethyl-2-[(trimethylsilyl)ethynyl]-7,8-dihydro-9H-purine-9-carboxamide as a mixture with 2-ethynyl-N,N,7-trimethyl-8-oxo-7,8-dihydro-9H-purine-9-carboxamide.

(2) To the solution of the above-mentioned product (total amount) in tetrahydrofuran (3 ml) was added an aqueous 1 mol/L cesium hydroxide solution (0.55 ml) and the mixture was stirred for 30 minutes. The reaction mixture was purified by amino silica gel column chromatography (eluent: hexane/ethyl acetate=100/0~0/100). The obtained crude solids were recrystallized from a solution of ethyl acetate and diisopropylether to give 2-ethynyl-N,N,7-trimethyl-8-oxo-7,8-dihydro-9H-purine-9-carboxamide 140 mg.

¹H-NMR (CDCl₃) δ: 3.06-3.08 (4H, m), 3.22 (3H, s), 3.48 (3H, s), 8.23 (1H, s).

(3) The above-mentioned product (50 mg), 1-bromo-4-(difluoromethoxy)benzene (94 mg), bis(acetonitrile)dichloropalladium (2.7 mg), 2-dicyclohexylphosphino-2',4',6'-triisopropyl-1,1'-biphenyl (10 mg), triethylamine (1 ml) and acetonitrile (2 ml) were mixed and the mixture was stirred at 130° C. under microwave irradiation for 30 minutes. The reaction mixture was purified by amino silica gel column chromatography (eluent: hexane/ethyl acetate=100/0~0/100) to give 2-{[4-(difluoromethoxy)phenyl]ethynyl}-N,N,7-trimethyl-8-oxo-7,8-dihydro-9H-purine-9-carboxamide as a crude product. This crude product was used to the next reaction without further purification.

(4) To a solution of the above-mentioned crude product (total amount) in ethanol (3 ml) were added ammonium formate (70 mg) and 10% palladium on carbon (10 mg) and the mixture was heated under reflux for 2 hours. The reaction mixture was filtered through Celite and the filtrate was concentrated under reduced pressure. The obtained residue was purified by silica gel column chromatography (eluent: ethyl acetate only) to give the title compound 34 mg.

¹H-NMR (CDCl₃) δ: 3.04 (3H, s), 3.07-3.16 (2H, m), 3.18-3.27 (5H, m), 3.44 (3H, s), 6.47 (1H, t, J=74.2 Hz), 6.99-7.02 (2H, m), 7.20-7.22 (2H, m), 8.17 (1H, s).

Examples 494 to 613

The compounds indicated in Tables 70 to 81 were prepared according to the similar method to those of Example 493.

TABLE 70

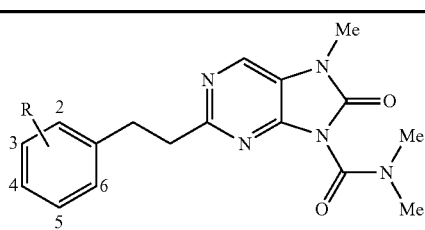

| Ex. No. | R | Salt | ¹H-NMR |
|---|---|---|---|
| 494 | 4-Me | free | (CDCl₃) δ: 2.30 (3H, s), 3.03-3.11 (5H, m), 3.20-3.26 (5H, m), 3.44 (3H, s), 7.03-7.17 (4H, m), 8.17 (1H, s). |

TABLE 70-continued

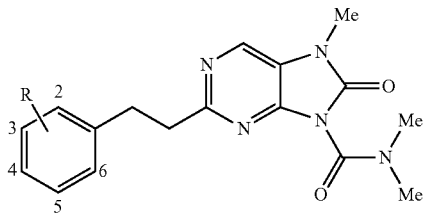

| Ex. No. | R | Salt | ¹H-NMR |
|---|---|---|---|
| 495 | 3-OCF$_3$ | free | (CDCl$_3$) δ: 3.03 (3H, s), 3.13-3.18 (2H, m), 3.24-328 (5H, m), 3.44 (3H, s), 7.02-7.05 (2H, m), 7.15-7.18 (1H, m), 7.26-7.29 (1H, m), 8.17 (1H, s). |
| 496 | 3-F 4-F | free | (CDCl$_3$) δ: 3.05-3.12 (5H, m), 3.20-3.25 (5H, m), 3.45 (3H, s), 6.88-6.96 (1H, m), 6.98-7.07 (2H, m), 8.16 (1H, s). |
| 497 | 3-F 5-F | free | (CDCl$_3$) δ: 3.05 (3H, s), 3.09-3.17 (2H, m), 3.20-3.28 (5H, m), 3.45 (3H, s), 6.57-6.65 (1H, m), 6.72-6.78 (2H, m), 8.17 (1H, s). |
| 498 | 3-Me | free | (CDCl$_3$) δ: 2.32 (3H, s), 3.02-3.12 (5H, m), 3.20-3.28 (5H, m), 3.44 (3H, s), 6.97-7.10 (3H, m), 7.16 (1H, t, J = 7.5 Hz), 8.18 (1H, s). |
| 499 | 2-F | free | (CDCl$_3$) δ: 3.03 (3H, s), 3.12-3.20 (2H, m), 3.21-3.29 (5H, m), 3.44 (3H, s), 6.95-7.05 (2H, m), 7.11-7.24 (2H, m), 8.17 (1H, s). |
| 500 | 4-n-Pr | free | (CDCl$_3$) δ: 0.93 (3H, t, J = 7.3 Hz), 1.54-1.69 (2H, m), 2.54 (2H, t, J = 7.7 Hz), 3.03 (3H, s), 3.05-3.13 (2H, m), 3.20-3.28 (5H, m), 3.44 (3H, s), 7.04-7.19 (4H, m), 8.18 (1H, s). |
| 501 | 4-O-n-Pr | free | (CDCl$_3$) δ: 1.02 (3H, t, J = 7.4 Hz), 1.79 (2H, tq, J = 6.6, 7.4 Hz), 3.02-3.10 (5H, m), 3.17-3.26 (5H, m), 3.44 (3H, s), 3.88 (2H, t, J = 6.6 Hz), 6.77-6.83 (2H, m), 7.10-7.16 (2H, m), 8.17 (1H, s). |
| 502 | 4-i-Pr | free | (CDCl$_3$) δ: 1.22-1.24 (6H, m), 2.78-2.95 (1H, m), 3.03 (3H, s), 3.05-3.13 (2H, m), 3.20-3.28 (5H, m), 3.45 (3H, s), 7.10-7.20 (4H, m), 8.18 (1H, s). |
| 503 | 4-Et | free | (CDCl$_3$) δ: 1.22 (3H, t, J = 7.6 Hz), 2.61 (2H, q, J = 7.6 Hz), 3.03 (3H, s), 3.05-3.13 (2H, m), 3.20-3.28 (5H, m), 3.44 (3H, s), 7.07-7.19 (4H, m), 8.18 (1H, s). |
| 504 | 3-F 4-F 5-F | free | (CDCl$_3$) δ: 3.05-3.13 (5H, m), 3.18-3.26 (5H, m), 3.45 (3H, s), 6.78-6.89 (2H, m), 8.16 (1H, s). |

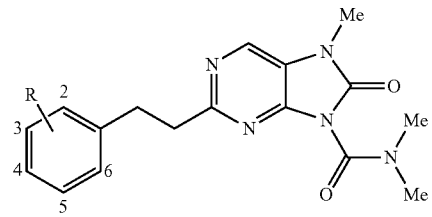

TABLE 71

| Ex. No. | R | Salt | ¹H-NMR |
|---|---|---|---|
| 505 | 2-Me 4-Me 5-Me | free | (CDCl$_3$) δ: 2.19 (6H, s), 2.29 (3H, s), 2.99-3.07 (5H, m), 3.13-3.25 (5H, m), 3.45 (3H, s), 6.88-7.01 (2H, m), 8.19 (1H, s). |
| 506 | 2-F 4-F | free | (CDCl$_3$) δ: 3.05 (3H, s), 3.08-3.16 (2H, m), 3.18-3.26 (5H, m), 3.44 (3H, s), 6.70-6.79 (2H, m), 7.10-7.20 (1H, m), 8.16 (1H, s). |
| 507 | 2-Me 5-Me | free | (CDCl$_3$) δ: 2.28 (3H, s), 2.31 (3H, s), 3.01-3.11 (5H, m), 3.15-3.25 (5H, m), 3.45 (3H, s), 6.89-6.94 (1H, m), 7.00-7.06 (2H, m), 8.19 (1H, s). |
| 508 | 4-n-Bu | free | (CDCl$_3$) δ: 0.92 (3H, t, J = 7.2 Hz), 1.27-1.41 (2H, m), 1.50-1.62 (2H, m), 2.56 (2H, t, J = 7.6 Hz), 3.01-3.13 (5H, m), 3.18-3.29 (5H, m), 3.44 (3H, s), 7.04-7.18 (4H, m), 8.18 (1H, s). |
| 509 | 3-Me 4-F | free | (CDCl$_3$) δ: 2.23 (3H, d, J = 1.8 Hz), 3.01-3.09 (5H, m), 3.17-3.25 (5H, m), 3.45 (3H, s), 6.83-6.91 (1H, m), 6.95-7.01 (1H, m), 7.03-7.08 (1H, m), 8.17 (1H, s). |
| 510 | 3-Me 4-Me | free | (CDCl$_3$) δ: 2.22 (3H, s), 2.23 (3H, s), 3.01-3.09 (5H, m), 3.18-3.26 (5H, m), 3.44 (3H, s), 6.94-7.96 (3H, m), 8.18 (1H, s). |
| 511 | 2-Me 4-Me 6-Me | free | (CDCl$_3$) δ: 2.26 (3H, s), 2.34 (6H, s), 3.04-3.09 (7H, m), 3.23 (3H, s), 3.46 (3H, s), 6.85 (2H, s), 8.20 (1H, s). |
| 512 | 3-F 4-Me | free | (CDCl$_3$) δ: 2.21 (3H, d, J = 1.7 Hz), 3.03-3.12 (5H, m), 3.19-3.26 (5H, m), 3.44 (3H, s), 6.84-6.92 (2H, m), 7.05 (1H, t, J = 8.2 Hz), 8.17 (1H, s). |
| 513 | 4-OCF$_3$ | free | (CDCl$_3$) δ: 3.03 (3H, s), 3.10-3.18 (2H, m), 3.20-3.29 (5H, m), 3.45 (3H, s), 7.07-7.13 (2H, m), 7.21-7.28 (2H, m), 8.17 (1H, s). |
| 514 | 3-Me 5-Me | free | (CDCl$_3$) δ: 2.28 (6H, s), 2.99-3.08 (5H, m), 3.18-3.26 (5H, m), 3.44 (3H, s), 6.81-6.91 (3H, m), 8.18 (1H, s). |
| 515 | 2-Et | free | (CDCl$_3$) δ: 1.24 (3H, t, J = 7.5 Hz), 2.72 (2H, q, J = 7.5 Hz), 3.03 (3H, s), 3.09-3.17 (2H, m), 3.18-3.26 (5H, m), 3.45 (3H, s), 7.06-7.21 (4H, m), 8.19 (1H, s). |
| 516 | 3-Et | free | (CDCl$_3$) δ: 1.22 (3H, t, J = 7.6 Hz), 2.61 (2H, q, J = 7.6 Hz), 3.04 (3H, s), 3.06-3.13 (2H, m), 3.20-3.29 (5H, m), 3.45 (3H, s), 6.99-7.11 (3H, m), 7.15-7.22 (1H, m), 8.18 (1H, s). |
| 517 | 3-cPr | free | (CDCl$_3$) δ: 0.63-0.69 (2H, m), 0.89-0.97 (2H, m), 1.80-1.90 (1H, m), 3.02-3.12 (5H, m), 3.19-3.28 (5H, m), 3.45 (3H, s), 6.86-6.91 (1H, m), 6.94-6.97 (1H, m), 6.99-7.04 (1H, m), 7.11-7.18 (1H, m), 8.18 (1H, s). |

TABLE 72

| Ex. No. | R | Salt | $^1$H-NMR |
|---|---|---|---|
| 518 | 3-n-Pr | free | (CDCl$_3$) δ: 0.92 (3H, t, J = 7.3 Hz), 1.54-1.68 (2H, m), 2.54 (2H, t, J = 7.6 Hz), 3.01-3.13 (5H, m), 3.20-3.29 (5H, m), 3.44 (3H, s), 6.97-7.08 (3H, m), 7.14-7.21 (1H, m), 8.18 (1H, s). |
| 519 | 3-OCH$_2$-c-Pr | free | (CDCl$_3$) δ: 0.31-0.37 (2H, m), 0.60-0.68 (2H, m), 1.21-1.31 (1H, m), 3.02-3.13 (5H, m), 3.20-3.28 (5H, m), 3.44 (3H, s), 3.77 (2H, d, J = 7.0 Hz), 6.69-6.75 (1H, m), 6.78-6.84 (2H, m), 7.12-7.20 (1H, m), 8.17 (1H, s). |
| 520 | 3-Cl | free | (CDCl$_3$) δ: 3.04 (3H, s), 3.07-3.16 (2H, m), 3.20-3.28 (5H, m), 3.44 (3H, s), 7.08-7.25 (4H, m), 8.17 (1H, s). |
| 521 | 4-c-Pr | free | (CDCl$_3$) δ: 0.61-0.68 (2H, m), 0.88-0.96 (2H, m), 1.79-1.90 (1H, m), 3.01-3.11 (5H, m), 3.18-3.26 (5H, m), 3.44 (3H, s), 6.93-7.00 (2H, m), 7.08-7.15 (2H, m), 8.17 (1H, s). |
| 522 | 4-Cl | free | (CDCl$_3$) δ: 3.04 (3H, s), 3.06-3.14 (2H, m), 3.19-3.28 (5H, m), 3.44 (3H, s), 7.12-7.25 (4H, m), 8.16 (1H, s). |
| 523 | 3-OCH$_2$-c-Bu | free | (CDCl$_3$) δ: 1.80-2.02 (4H, m), 2.07-2.19 (2H, m), 2.69-2.81 (1H, m), 3.02-3.13 (5H, m), 3.21-3.29 (5H, m), 3.45 (3H, s), 3.90 (2H, d, J = 6.6 Hz), 6.69-6.75 (1H, m), 6.78-6.84 (2H, m), 7.16 (1H, t, J = 8.1 Hz), 8.18 (1H, s). |
| 524 | 3-F 4-c-Pr | free | (CDCl$_3$) δ: 0.63-0.70 (2H, m), 0.89-0.97 (2H, m), 1.96-2.08 (1H, m), 3.02-3.11 (5H, m), 3.18-3.26 (5H, m), 3.44 (3H, s), 6.74-6.81 (1H, m), 6.84-6.92 (2H, m), 8.17 (1H, s). |
| 525 | 3-c-pentyloxy | free | (CDCl$_3$) δ: 1.55-1.66 (2H, m), 1.72-1.94 (6H, m), 3.01-3.12 (5H, m), 3.20-3.28 (5H, m), 3.44 (3H, s), 4.69-4.77 (1H, m), 6.66-6.72 (1H, m), 6.74-6.82 (2H, m), 7.11-7.18 (1H, m), 8.18 (1H, s). |
| 526 | 3-OCH$_2$CFH$_2$ | free | (CDCl$_3$) δ: 3.02-3.15 (5H, m), 3.21-3.29 (5H, m), 3.44 (3H, s), 4.12-4.17 (1H, m), 4.21-4.26 (1H, m), 4.64-4.69 (1H, m), 4.80-4.85 (1H, m), 6.71-6.77 (1H, m), 6.81-6.88 (2H, m), 7.14-7.22 (1H, m), 8.17 (1H, s). |
| 527 | 3-c-Pr 4-F | free | (CDCl$_3$) δ: 0.64-0.71 (2H, m), 0.91-0.99 (2H, m), 1.98-2.10 (1H, m), 2.99-3.07 (5H, m), 3.15-3.25 (5H, m), 3.45 (3H, s), 6.71-6.76 (1H, m), 6.84-6.91 (1H, m), 6.92-6.99 (1H, m), 8.17 (1H, s). |
| 528 | 3-F 5-F | HCl | (DMSO-d$_6$) δ: 2.94 (3H, s), 3.04-3.13 (5H, m), 3.16-3.26 (2H, m), 3.36 (3H, s), 6.95-7.05 (3H, m), 8.57 (1H, s). |

TABLE 73

| Ex. No. | R | Salt | $^1$H-NMR |
|---|---|---|---|
| 529 | 3-O-c-Bu | free | (CDCl$_3$) δ: 1.62-1.73 (1H, m), 1.78-1.91 (1H, m), 2.07-2.21 (2H, m), 2.37-2.49 (2H, m), 3.02-3.12 (5H, m), 3.20-3.28 (5H, m), 3.44 (3H, s), 4.55-4.67 (1H, m), 6.60-6.66 (1H, m), 6.69-6.73 (1H, m), 6.78-6.83 (1H, m), 7.11-7.18 (1H, m), 8.18 (1H, s). |
| 530 | 3-OCH$_2$CF$_2$H | free | (CDCl$_3$) δ: 3.05 (3H, s), 3.08-3.15 (2H, m), 3.21-3.29 (5H, m), 3.44 (3H, s), 4.16 (2H, td, J = 13.2, 4.1 Hz), 6.07 (1H, tt, J = 55.2, 4.1 Hz), 6.70-6.76 (1H, m), 6.79-6.84 (1H, m), 6.86-6.92 (1H, m), 7.15-7.23 (1H, m), 8.17 (1H, s). |
| 531 | 4-O-c-Bu | HCl | (DMSO-d$_6$) δ: 1.54-1.81 (2H, m), 1.90-2.06 (2H, m), 2.32-2.44 (2H, m), 2.92-3.00 (5H, m), 3.08-3.19 (5H, m), 3.37 (3H, s), 4.54-4.66 (1H, m), 6.67-6.73 (2H, m), 7.06-7.14 (2H, m), 8.62 (1H, s). |
| 532 | 4-c-pentyloxy | HCl | (DMSO-d$_6$) δ: 1.48-1.72 (6H, m), 1.78-1.94 (2H, m), 2.90-3.01 (5H, m), 3.06-3.20 (5H, m), 3.37 (3H, s), 4.68-4.78 (1H, m), 6.72-6.79 (2H, m), 7.06-7.13 (2H, m), 8.64 (1H, s). |
| 533 | 4-F | HCl | (DMSO-d$_6$) δ: 2.93 (3H, s), 3.00-3.11 (5H, m), 3.14-3.23 (2H, m), 3.37 (3H, s), 7.01-7.10 (2H, m), 7.20-7.29 (2H, m), 8.64 (1H, s). |
| 534 | 3-OEt | HCl | (DMSO-d$_6$) δ: 1.28 (3H, t, J = 7.0 Hz), 2.94 (3H, s), 2.97-3.06 (2H, m), 3.10 (3H, s), 3.15-3.26 (2H, m), 3.38 (3H, s), 3.97 (2H, q, J = 7.0 Hz), 6.66-6.83 (3H, m), 7.09-7.17 (1H, m), 8.67 (1H, s). |
| 535 | 3-O-n-Pr | HCl | (DMSO-d$_6$) δ: 0.94 (3H, t, J = 7.3 Hz), 1.60-1.76 (2H, m), 2.94 (3H, s), 2.97-3.06 (2H, m), 3.09 (3H, s), 3.13-3.26 (2H, m), 3.38 (3H, s), 3.82-3.90 (2H, m), 6.66-6.83 (3H, m), 7.13 (1H, t, J = 7.7 Hz), 8.67 (1H, br s). |
| 536 | 3-O-i-Pr | HCl | (DMSO-d$_6$) δ: 1.20-1.22 (6H, m), 2.94 (3H, s), 2.96-3.05 (2H, m), 3.09 (3H, s), 3.12-3.24 (2H, m), 3.37 (3H, s), |

TABLE 73-continued

| Ex. No. | R | Salt | ¹H-NMR |
|---|---|---|---|
| 537 | 3-CF₂H | free | 4.49-4.60 (1H, m), 6.65-6.80 (3H, m), 7.12 (1H, t, J = 7.8 Hz), 8.64 (1H, br s). (CDCl₃) δ: 3.03 (3H, s), 3.14-3.31 (7H, m), 3.44 (3H, s), 6.60 (1H, t, J = 56.6 Hz), 7.28-7.39 (4H, m), 8.17 (1H, s). |
| 538 | 4-OCH₂CF₂H | HCl | (DMSO-d₆) δ: 2.90-3.04 (5H, m), 3.06-3.20 (5H, m), 3.36 (3H, s), 4.24 (2H, td, J = 14.8, 3.6 Hz), 6.35 (1H, tt, J = 54.7, 3.6 Hz), 6.83-6.93 (2H, m), 7.09-7.24 (2H, m), 8.60 (1H, br s). |
| 539 | 3-CF₃ | free | (CDCl₃) δ: 3.03 (3H, s), 3.16-3.31 (7H, m), 3.44 (3H, s), 7.33-7.50 (4H, m), 8.17 (1H, s). |

TABLE 74

| Ex. No. | R | Salt | ¹H-NMR |
|---|---|---|---|
| 540 | 4-CF₃ | free | (CDCl₃) δ: 3.02 (3H, s), 3.15-3.31 (7H, m), 3.44 (3H, s), 7.30-7.37 (2H, m), 7.48-7.55 (2H, m), 8.17 (1H, s). |
| 541 | H | free | (CDCl₃) δ: 3.03 (3H, s), 3.09-3.17 (2H, m), 3.21-3.29 (5H, m), 3.44 (3H, s), 7.13-7.30 (5H, m), 8.17 (1H, s). |
| 542 | 2-CF₃ | free | (CDCl₃) δ: 3.04 (3H, s), 3.21-3.37 (7H, m), 3.45 (3H, s), 7.28-7.48 (3H, m), 7.60-7.65 (1H, m), 8.18 (1H, s). |
| 543 | 3-OMe | free | (CDCl₃) δ: 3.04 (3H, s), 3.07-3.14 (2H, m), 3.21-3.29 (5H, m), 3.44 (3H, s), 3.78 (3H, s), 6.69-6.75 (1H, m), 6.78-6.86 (2H, m), 7.18 (1H, t, J = 7.8 Hz), 8.18 (1H, s). |
| 544 | 4-OMe | free | (CDCl₃) δ: 3.02-3.10 (5H, m), 3.18-3.26 (5H, m), 3.44 (3H, s), 3.77 (3H, s), 6.77-6.83 (2H, m), 7.11-7.18 (2H, m), 8.17 (1H, s). |
| 545 | 2-Cl | free | (CDCl₃) δ: 3.03 (3H, s), 3.20-3.29 (7H, m), 3.44 (3H, s), 7.09-7.18 (2H, m), 7.20-7.26 (1H, m), 7.31-7.36 (1H, m), 8.18 (1H, s). |
| 546 | 2-CF₂H | free | (CDCl₃) δ: 3.03 (3H, s), 3.20-3.30 (7H, m), 3.44 (3H, s), 6.96 (1H, t, J = 55.4 Hz), 7.24-7.42 (3H, m), 7.50-7.56 (1H, m), 8.16 (1H, s). |
| 547 | 2-OCF₂H | free | (CDCl₃) δ: 3.03 (3H, s), 3.14-3.29 (7H, m), 3.44 (3H, s), 6.53 (1H, t, J = 74.3 Hz), 7.03-7.13 (2H, m), 7.15-7.27 (2H, m), 8.15 (1H, s). |
| 548 | 3-OCF₂H | free | (CDCl₃) δ: 3.04 (3H, s), 3.10-3.18 (2H, m), 3.21-3.29 (5H, m), 3.44 (3H, s), 6.49 (1H, t, J = 74.2 Hz), 6.89-6.99 (2H, m), 7.05-7.10 (1H, m), 7.21-7.28 (1H, m), 8.17 (1H, s). |
| 549 | 2-OCF₃ | free | (CDCl₃) δ: 3.03 (3H, s), 3.15-3.29 (7H, m), 3.44 (3H, s), 7.14-7.24 (3H, m), 7.25-7.32 (1H, m), 8.16 (1H, s). |
| 550 | 2-F 3-F | free | (CDCl₃) δ: 3.04 (3H, s), 3.14-3.30 (7H, m), 3.44 (3H, s), 6.90-7.03 (3H, m), 8.16 (1H, s). |
| 551 | 2-F 6-F | free | (CDCl₃) δ: 3.04 (3H, s) 3.13-3.25 (7H, m), 3.44 (3H, s), 6.76-6.86 (2H, m), 7.07-7.18 (1H, m), 8.16 (1H, s). |
| 552 | 3-OCH₂CF₃ | HCl | (DMSO-d₆) δ: 2.94 (3H, s), 2.99-3.11 (5H, m), 3.13-3.24 (2H, m), 3.36 (3H, s), 4.71 (2H, q, J = 8.9 Hz), 6.81-6.92 (2H, m), 6.93-6.99 (1H, m), 7.20 (1H, t, J = 7.9 Hz), 8 Salt, s). |
| 553 | 4-OCH₂CF₃ | free | (CDCl₃) δ: 3.00-3.13 (5H, m), 3.16-3.28 (5H, m), 3.44 (3H, s), 4.31 (2H, q, J = 7.7 Hz), 6.84 (2H, d, J = 7.7 Hz), 7.17 (2H, d, J = 7.7 Hz), 8.16 (1H, s). |

TABLE 75

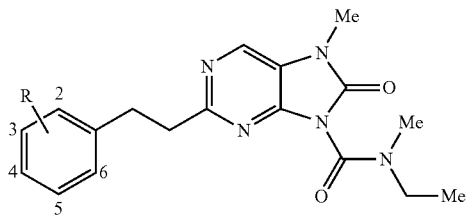

| Ex. No. | R | ¹H-NMR (CDCl₃) δ |
|---|---|---|
| 554 | 2-F | 1.16-1.38 (3H, m), 2.96-3.29 (7H, m), 3.30-3.71 (5H, m), 6.94-7.05 (2H, m), 7.11-7.25 (2H, m), 8.16 (1H, s). |
| 555 | 4-F | 1.17-1.37 (3H, m), 2.94-3.27 (7H, m), 3.28-3.72 (5H, m), 6.87-6.98 (2H, m), 7.12-721 (2H, m), 8.16 (1H, s). |
| 556 | 3-Me | 1.17-1.38 (3H, m), 2.32 (3H, s), 2.97-3.28 (7H, m), 3.30-3.74 (5H, m), 6.96-7.09 (3H, m), 7.15 (1H, t, J = 7.4 Hz), 8.17 (1H, s). |
| 557 | 3-OMe | 1.17-1.37 (3H, m), 2.97-3.29 (7H, m), 3.29-3.71 (5H, m), 3.78 (3H, s), 6.69-6.75 (1H, m), 6.78-6.85 (2H, m), 7.18 (1H, t, J = 7.9 Hz), 8.17 (1H, s). |
| 558 | 3-OCF₃ | 1.15-1.37 (3H, m), 2.96-3.29 (7H, m), 3.30-3.75 (5H, m), 6.98-7.08 (2H, m), 7.13-7.19 (1H, m), 7.23-7.31 (1H, m), 8.16 (1H, s). |

TABLE 76

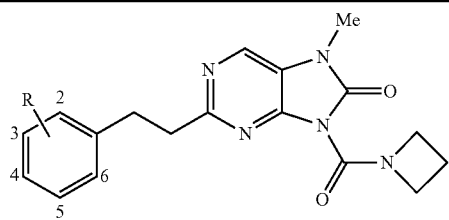

| Ex. No. | R | Salt | ¹H-NMR |
|---|---|---|---|
| 559 | 4-Me | free | (CDCl₃) δ: 2.28-2.42 (5H, m), 3.06-3.14 (2H, m), 3.22-3.30 (2H, m), 3.43 (3H, s), 4.21 (2H, t, J = 7.8 Hz), 4.34 (2H, t, J = 7.8 Hz), 7.03-7.16 (4H, m), 8.17 (1H, s). |

TABLE 76-continued

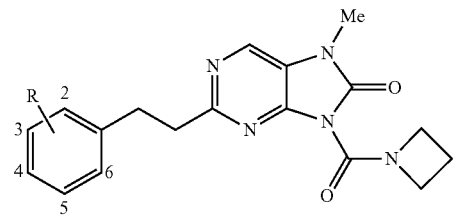

| Ex. No. | R | Salt | ¹H-NMR |
|---|---|---|---|
| 560 | 3-Me | free | (CDCl₃) δ: 2.30-2.42 (5H, m), 3.06-3.14 (2H, m), 3.23-3.31 (2H, m), 3.43 (3H, s), 423 (2H, t, J = 7.7 Hz), 4.34 (2H, t, J = 7.8 Hz), 6.96-720 (4H, m), 8.18 (1H, s). |
| 561 | 4-Et | free | (CDCl₃) δ: 1.21 (3H, t, J = 7.6 Hz), 2.31-2.41 (2H, m), 2.60 (2H, q, J = 7.6 Hz), 3.06-3.16 (2H, m), 3.22-3.31 (2H, m), 3.43 (3H, s), 4.21 (2H, t, J = 7.7 Hz), 4.34 (2H, t, J = 7.7 Hz), 7.07-7.19 (4H, m), 8.18 (1H, s). |
| 562 | 4-n-Pr | free | (CDCl₃) δ: 0.93 (3H, t, J = 7.3 Hz), 1.54-1.68 (2H, m), 2.31-2.41 (2H, m), 2.53 (2H, t, J = 7.7 Hz), 3.06-3.15 (2H, m), 3.22-3.31 (2H, m), 3.45 (3H, s), 4.22 (2H, t, J = 7.8 Hz), 4.34 (2H, t, J = 7.8 Hz), 7.05-7.18 (4H, m), 8.17 (1H, s). |
| 563 | 4-i-Pr | free | (CDCl₃) δ: 1.23 (6H, d, J = 7.0 Hz), 2.31-2.41 (2H, m), 2.79-2.94 (1H, m), 3.07-3.15 (2H, m), 3.23-3.31 (2H, m), 3.43 (3H, s), 4.22 (2H, t, J = 7.8 Hz), 4.34 (2H. t, J = 7.8 Hz), 7.11-7.20 (4H, m), 8.18 (1H, s). |
| 564 | 4-O-n-Pr | free | (CDCl₃) δ: 1.02 (3H, t, J = 7.4 Hz), 1.71-1.85 (2H, m), 2.29-2.42 (2H, m), 3.03-3.12 (2H, m), 3.20-3.28 (2H, m), 3.43 (3H, s), 3.88 (2H, t, J = 6.5 Hz), 6.76-6.83 (2H, m), 7.10-7.17 (2H, m), 8.17 (1 H, s). |
| 565 | 3-Me 4-Me | free | (CDCl₃) δ: 2.21 (3H, s), 2.23 (3H, s), 2.30-2.42 (2H, m), 3.02-3.11 (2H, m), 3.21-3.29 (2H, m), 3.43 (3H, s), 4.22 (2H, t, J = 7.8 Hz), 4.34 (2H, t, J = 7.8 Hz), 6.94-7.07 (3H, m), 8.18 (1H, s). |
| 566 | 2-Me 4-Me 6-Me | free | (CDCl₃) δ: 2.25 (3H, s), 2.30-2.42 (8H, m), 3.05-3.12 (4H, m), 3.44 (3H, s), 4.25 (2H, t, J = 7.8 Hz), 4.34 (2H, t, J = 7.8 Hz), 6.85 (2H, s), 8.19 (1 H, s). |

TABLE 77

| Ex. No. | R | Salt | ¹H-NMR |
|---|---|---|---|
| 567 | 3-F 4-F | free | (CDCl₃) δ: 2.31-2.44 (2H, m), 3.07-3.15 (2H, m), 3.21-3.29 (2H, m), 3.43 (3H, s), 4.25 (2H, t, J = 7.7 Hz), 4.34 (2H, t, J = 7.7 Hz), 6.90-6.97 (1H, m), 6.97-7.09 (2H, m), 8.16 (1H, s). |
| 568 | 3-Me 4-F | free | (CDCl₃) δ: 2.23 (3H, d, J = 1.8 Hz), 2.31-2.43 (2H, m), 3.03-3.11 (2H, m), 3.20-3.28 (2H, m), 3.43 (3H, s), 4.24 (2H, t, J = 7.7 Hz), 4.34 (2H, t, J = 7.7 Hz), 6.83-6.91 (1H, m), 6.95-7.02 (1H, m), 7.04-7.10 (1H, m), 8.17 (1H, s). |
| 569 | 3-Et | free | (CDCl₃) δ: 1.22 (3H, t, J = 7.6 Hz), 2.30-2.43 (2H, m), 2.62 (2H, q, J = 7.6 Hz), 3.07-3.16 (2H, m), 3.24-3.32 (2H, m), 3.43 (3H, s), 4.23 (2H, t, J = 7.7 Hz), 4.34 (2H, t, J = 7.7 Hz), 6.99-7.13 (3H, m), 7.15-7.24 (1H, m), 8.18 (1H, s). |
| 570 | 4-OEt | free | (CDCl₃) δ: 1.39 (3H, t, J = 7.0 Hz), 2.30-2.42 (2H, m), 3.04-3.12 (2H, m), 3.20-3.28 (2H, m), 3.43 (3H, s), 3.99 (2H, q, J = 7.0 Hz), 4.22 (2H, t, J = 7.8 Hz), 4.34 (2H, t, J = 7.8 Hz), 6.77-6.83 (2H, m), 7.10-7.16 (2H, m), 8.17 (1H, s). |
| 571 | 3-n-Pr | free | (CDCl₃) δ: 0.92 (3H, t, J = 7.3 Hz), 1.53-1.68 (2H, m), 2.30-2.42 (2H, m), 2.54 (2H, t, J = 7.6 Hz), 3.07-3.15 (2H, m), 3.24-3.31 (2H, m), 3.43 (3H, s), 4.23 (2H, t, J = 7.8 Hz), 4.34 (2H, t, J = 7.8 Hz), 6.97-7.09 (3H, m), 7.15-7.21 (1H, m), 8.18 (1H, s). |

TABLE 77-continued

| Ex. No. | R | Salt | $^1$H-NMR |
|---|---|---|---|
| 572 | 3-c-Pr | free | (CDCl$_3$) δ: 0.60-0.70 (2H, m), 0.85-1.06 (2H, m), 1.78-1.91 (1H, m), 2.27-2.43 (2H, m), 3.04-3.13 (2H, m), 3.21-3.30 (2H, m), 3.43 (3H, s), 4.22 (2H, t, J = 7.8 Hz), 4.34 (2H, t, J = 7.8 Hz), 6.84-7.05 (3H, m), 7.10-7.19 (1H, m), 8.18 (1H, s). |
| 573 | 4-c-Pr | free | (CDCl$_3$) δ: 0.61-0.68 (2H, m), 0.88-0.95 (2H, m), 1.78-1.89 (1H, m), 2.29-2.42 (2H, m), 3.05-3.13 (2H, m), 3.20-3.29 (2H, m), 3.43 (3H, s), 4.19 (2H, t, J = 7.8 Hz), 4.33 (2H, t, J = 7.8 Hz), 6.93-7.00 (2H, m), 7.08-7.16 (2H, m), 8.17 (1H, s). |
| 574 | 3-Cl | free | (CDCl$_3$) δ: 2.31-2.43 (2H, m), 3.09-3.17 (2H, m), 3.23-3.31 (2H, m), 3.43 (3H, s), 4.22 (2H, t, J = 7.8 Hz), 4.34 (2H, t, J = 7.8 Hz), 7.08-7.26 (4H, m), 8.17 (1H, s). |
| 575 | 4-Cl | free | (CDCl$_3$) δ: 2.30-2.43 (2H, m), 3.08-3.16 (2H, m), 3.22-3.29 (2H, m), 3.43 (3H, s), 4.21 (2H, t, J = 7.8 Hz), 4.34 (2H, t, J = 7.8 Hz), 7.13-7.25 (4H, m), 8.16 (1H, s). |

TABLE 78

| Ex. No. | R | Salt | $^1$H-NMR |
|---|---|---|---|
| 576 | 4-CF$_2$H | free | (CDCl$_3$) δ: 2.30-2.42 (2H, m), 3.15-3.23 (2H, m), 3.25-3.33 (2H, m), 3.43 (3H, s), 4.20 (2H, t, J = 7.8 Hz), 4.33 (2H, t, J = 7.8 Hz), 6.60 (1H, t, J = 56.6 Hz), 7.29-7.43 (4H, m), 8.17 (1H, s). |
| 577 | 3-F<br>4-c-Pr | free | (CDCl$_3$) δ: 0.63-0.70 (2H, m), 0.89-0.97 (2H, m), 1.96-2.07 (1H, m), 2.30-2.43 (2H, m), 3.06-3.13 (2H, m), 3.21-3.28 (2H, m), 3.43 (3H, s), 4.21 (2H, t, J = 7.8 Hz), 4.34 (2H, t, J = 7.8 Hz), 6.74-6.81 (1H, m), 6.85-6.92 (2H, m), 8.17 (1H, s). |
| 578 | 3-c-Pr<br>4-F | free | (CDCl$_3$) δ: 0.64-0.71 (2H, m), 0.91-0.99 (2H, m), 1.98-2.10 (1H, m), 2.30-2.44 (2H, m), 3.01-3.09 (2H, m), 3.17-3.26 (2H, m), 3.43 (3H, s), 4.23 (2H, t, J = 7.8 Hz), 4.34 (2H, t, J = 7.8 Hz), 6.71-6.77 (1H, m), 6.83-6.92 (1H, m), 6.93-6.99 (1H, m), 8.17 (1H, s). |
| 579 | 3-OCH$_2$—c-Pr | free | (CDCl$_3$) δ: 0.29-0.38 (2H, m), 0.59-0.69 (2H, m), 1.18-1.33 (1H, m), 2.29-2.43 (2H, m), 3.05-3.16 (2H, m), 3.22-3.32 (2H, m), 3.43 (3H, s), 3.78 (2H, d, J = 7.0 Hz), 4.22 (2H, t, J = 7.8 Hz), 4.34 (2H, t, J = 7.8 Hz), 6.69-6.75 (1H, m), 6.78-6.85 (2H, m), 7.11-7.20 (1H, m), 8.17 (1H, s). |
| 580 | 3-F<br>5-F | free | (CDCl$_3$) δ: 2.31-2.44 (2H, m), 3.10-3.19 (2H, m), 3.23-3.31 (2H, m), 3.43 (3H, s), 4.24 (2H, t, J = 7.8 Hz), 4.34 (2H, t, J = 7.8 Hz), 6.56-6.66 (1H, m), 6.72-6.81 (2H, m), 8.17 (1H, s). |
| 581 | 3-O—c-Bu | HCl | (DMSO-d$_6$) δ: 1.53-1.81 (2H, m), 1.89-2.06 (2H, m), 2.19-2.43 (4H, m), 2.98-3.06 (2H, m), 3.13-3.22 (2H, m), 3.35 (3H, s), 4.06 (2H, t, J = 7.8 Hz), 4.14 (2H, t, J = 7.8 Hz), 4.54-4.67 (1H, m), 6.58-6.64 (1H, m), 6.66-6.70 (1H, m), 6.74-6.79 (1H, m), 7.12 (1H, t, J = 7.8 Hz), 8.58 (1H, s). |
| 582 | 3-OCH$_2$CF$_2$H | HCl | (DMSO-d$_6$) δ: 2.18-2.34 (2H, m), 3.01-3.10 (2H, m), 3.16-3.26 (2H, m), 3.35 (3H, s), 4.07 (2H, t, J = 7.7 Hz), 4.15 (2H, t, J = 7.7 Hz), 4.26 (2H, td, J = 14.8, 3.6 Hz), 6.35 (1H, tt, J = 54.6, 3.6 Hz), 6.76-6.94 (3H, m), 7.18 (1H, t, J = 7.9 Hz), 8.60 (1H, s). |
| 583 | 2-F | free | (CDCl$_3$) δ: 2.30-2.42 (2H, m), 3.14-3.22 (2H, m), 3.25-3.32 (2H, m), 3.43 (3H, s), 4.22 (2H, t, J = 7.8 Hz), 4.34 (2H, t, J = 7.8 Hz), 6.95-7.06 (2H, m), 7.11-7.25 (2H, m), 8.17 (1H, s). |
| 584 | 2-F<br>4-F | free | (CDCl$_3$) δ: 2.32-2.44 (2H, m), 3.10-3.18 (2H, m), 3.21-3.29 (2H, m), 3.43 (3H, s), 4.25 (2H, t, J = 7.8 Hz), 4.34 (2H, t, J = 7.8 Hz), 6.70-6.80 (2H, m), 7.12-7.22 (1H, m), 8.16 (1H, s). |

TABLE 79

| Ex. No. | R | Salt | ¹H-NMR |
|---|---|---|---|
| 585 | 2-F, 5-F | free | (CDCl$_3$) δ: 2.31-2.43 (2H, m), 3.12-3.21 (2H, m), 3.23-3.31 (2H, m), 3.43 (3H, s), 4.25 (2H, t, J = 7.8 Hz), 4.34 (2H, t, J = 7.8 Hz), 6.78-6.88 (1H, m), 6.89-7.00 (2H, m), 8.17 (1H, s). |
| 586 | 3-F, 4-Me | free | (CDCl$_3$) δ: 2.21 (3H, d, J = 1.7 Hz), 2.30-2.43 (2H, m), 3.07-3.14 (2H, m), 3.22-3.29 (2H, m), 3.43 (3H, s), 4.22 (2H, t, J = 7.8 Hz), 4.34 (2H, t, J = 7.8 Hz), 6.85-6.92 (2H, m), 7.05 (1H, t, J = 8.0 Hz), 8.17 (1H, s). |
| 587 | 4-F | HCl | (DMSO-d$_6$) δ: 2.19-2.33 (2H, m), 3.02-3.10 (2H, m), 3.13-3.22 (2H, m), 3.35 (3H, s), 4.07 (2H, t, J = 7.8 Hz), 4.15 (2H, t, J = 7.8 Hz), 7.01-7.11 (2H, m), 7.21-7.30 (2H, m), 8.57 (1H, s). |
| 588 | 4-OCH$_2$CFH$_2$ | HCl | (DMSO-d$_6$) δ: 2.18-2.33 (2H, m), 2.96-3.06 (2H, m), 3.12-3.21 (2H, m), 3.35 (3H, s), 4.01-4.23 (6H, m), 4.70 (2H, dt, J = 47.8, 3.9 Hz), 6.80-6.87 (2H, m), 7.10-7.18 (2H, m), 8.60 (1H, s). |
| 589 | 4-O—c-Bu | HCl | (DMSO-d$_6$) δ: 1.53-1.81 (2H, m), 1.89-2.07 (2H, m), 2.18-2.44 (4H, m), 2.92-3.03 (2H, m), 3.07-3.19 (2H, m), 3.35 (3H, s), 4.06 (2H, t, J = 7.8 Hz), 4.15 (2H, t, J = 7.8 Hz), 4.53-4.66 (1H, m), 6.66-6.74 (2H, m), 7.06-7.14 (2H, m), 8.59 (1H, s). |
| 590 | 4-c-pentyloxy | HCl | (DMSO-d$_6$) δ: 1.47-1.73 (6H, m), 1.77-1.95 (2H, m), 2.18-2.32 (2H, m), 2.93-3.04 (2H, m), 3.05-3.19 (2H, m), 3.35 (3H, s), 4.06 (2H, t, J = 7.8 Hz), 4.15 (2H, t, J = 7.8 Hz), 4.67-4.78 (1H, m), 6.71-6.80 (2H, m), 7.05-7.14 (2H, m), 8.58 (1H, br s). |
| 591 | 2-Me | free | (CDCl$_3$) δ: 2.28-2.41 (5H, m), 3.09-3.17 (2H, m), 3.21-3.28 (2H, m), 3.43 (3H, s), 4.21 (2H, t, J = 7.8 Hz), 4.33 (2H, t, J = 7.8 Hz), 7.06-7.20 (4H, m), 8.18 (1H, s). |
| 592 | 3-OCH$_2$CFH$_2$ | HCl | (DMSO-d$_6$) δ: 2.19-2.33 (2H, m), 3.00-3.09 (2H, m), 3.13-3.23 (2H, m), 3.35 (3H, s), 4.01-4.27 (6H, m), 4.70 (2H, dt, J = 47.9, 3.9 Hz), 6.71-6.89 (3H, m), 7.16 (1H, t, J = 7.9 Hz), 8.57 (1H, s). |
| 593 | 4-OCH$_2$CF$_2$H | HCl | (DMSO-d$_6$) δ: 2.16-2.34 (2H, m), 2.95-3.06 (2H, m), 3.07-3.26 (2H, m), 3.34 (3H, s), 4.00-4.30 (6H, m), 6.34 (1H, tt, J = 54.6, 3.6 Hz), 6.84-6.94 (2H, m), 7.10-7.22 (2H, m), 8.56 (1H, br s). |
| 594 | 3-CF$_2$H | free | (CDCl$_3$) δ: 2.29-2.43 (2H, m), 3.16-3.24 (2H, m), 3.25-3.34 (2H, m), 3.43 (3H, s), 4.22 (2H, t, J = 7.8 Hz), 4.34 (2H, t, J = 7.8 Hz), 6.61 (1H, t, J = 56.6 Hz), 7.28-7.41 (4H, m), 8.17 (1H, s). |

TABLE 80

| Ex. No. | R | Salt | ¹H-NMR |
|---|---|---|---|
| 595 | 4-OCF$_2$H | free | (CDCl$_3$) δ: 2.30-2.43 (2H, m), 3.10-3.18 (2H, m), 3.22-3.30 (2H, m), 3.43 (3H, s), 4.23 (2H, t, J = 7.8 Hz), 4.34 (2H, t, J = 7.8 Hz), 6.47 (1H, t, J = 74.3 Hz), 6.98-7.04 (2H, m), 7.19-7.25 (2H, m), 8.17 (1H, s). |
| 596 | 3-CF$_3$ | free | (CDCl$_3$) δ: 2.29-2.45 (2H, m), 3.18-3.25 (2H, m), 3.26-3.34 (2H, m), 3.43 (3H, s), 4.23 (2H, t, J = 7.8 Hz), 4.34 (2H, t, J = 7.8 Hz), 7.33-7.51 (4H, m), 8.17 (1H, s). |
| 597 | 4-CF$_3$ | free | (CDCl$_3$) δ: 2.29-2.43 (2H, m), 3.17-3.25 (2H, m), 3.26-3.34 (2H, m), 3.43 (3H, s), 4.21 (2H, t, J = 7.8 Hz), 4.33 (2H, t, J = 7.8 Hz), 7.31-7.38 (2H, m), 7.47-7.55 (2H, m), 8, 17 (1H, s). |
| 598 | H | free | (CDCl$_3$) δ: 2.29-2.43 (2H, m), 3.11-3.20 (2H, m), 3.23-3.32 (2H, m), 3.43 (3H, s), 4.21 (2H, t, J = 7.8 Hz), 4.33 (2H, t, J = 7.8 Hz), 7.13-7.31 (5 free), 8.17 (1H, s). |
| 599 | 2-CF$_3$ | free | (CDCl$_3$) δ: 2.30-2.44 (2H, m), 3.24-3.40 (4H, m), 3.43 (3H, s), 4.25 (2H, t, J = 7.8 Hz), 4.33 (2H, t, J = 7.8 Hz), 7.28-7.33 (1H, m), 7.35-7.49 (2H, m), 7.60-7.67 (1H, m), 8.18 (1H, s). |
| 600 | 3-OMe | free | (CDCl$_3$) δ: 2.29-2.43 (2H, m), 3.08-3.17 (2H, m), 3.24-3.32 (2H, m), 3.43 (3H, s), 3.78 (3H, s), 4.22 (2H, t, J = 7.8 Hz), 4.34 (2H, t, J = 7.8 Hz), 6.69-6.76 (1H, m), 6.78-6.87 (2H, m), 7.18 (1H, t, J = 7.8 Hz), 8.18 (1H, s). |

TABLE 80-continued

| Ex. No. | R | Salt | $^1$H-NMR |
|---|---|---|---|
| 601 | 4-OMe | free | (CDCl$_3$) δ: 2.30-2.42 (2H, m), 3.04-3.13 (2H, m), 3.20-3.28 (2H, m), 3.43 (3H, s), 3.77 (3H, s), 4.22 (2H, t, J = 7.8 Hz), 4.34 (2H, t, J = 7.8 Hz), 6.77-6.84 (2H, m), 7.11-7.19 (2H, m), 8.17 (1H, s). |
| 602 | 2-Cl | free | (CDCl$_3$) δ: 2.30-2.42 (2H, m), 3.24-3.34 (4H, m), 3.43 (3H, s), 4.23 (2H, t, J = 7.8 Hz), 4.33 (2H, t, J = 7.8 Hz), 7.09-7.19 (2H, m), 7.22-7.27 (1H, m), 7.32-7.36 (1H, m), 8.17 (1H, s). |
| 603 | 2-CF$_2$H | free | (CDCl$_3$) δ: 2.29-2.43 (2H, m), 3.25-3.34 (4H, m), 3.42 (3H, s), 4.22 (2H, t, J = 7.8 Hz), 4.34 (2H, t, J = 7.8 Hz), 7.00 (1H, t, J = 55.4 Hz), 7.24-7.42 (3H, m), 7.50-7.57 (1H, m), 8.16 (1H, s). |
| 604 | 3-OEt | free | (CDCl$_3$) δ: 1.40 (3H, t, J = 7.0 Hz), 2.30-2.43 (2H, m), 3.07-3.15 (2H, m), 3.23-3.31 (2H, m), 3.43 (3H, s), 4.01 (2H, q, J = 7.0 Hz), 4.22 (2H, t, J = 7.8 Hz), 4.34 (2H, t, J = 7.8 Hz), 6.68-6.74 (1H, m), 6.79-6.84 (2H, m), 7.13-7.20 (1H, m), 8.17 (1H, s). |

TABLE 81

| Ex. No. | R | Salt | $^1$H-NMR |
|---|---|---|---|
| 605 | 2-OCF$_2$H | free | (CDCl$_3$) δ: 2.30-2.43 (2H, m), 3.16-3.32 (4H, m), 3.42 (3H, s), 4.23 (2H, t, J = 7.8 Hz), 4.33 (2H, t, J = 7.8 Hz), 6.55 (1H, t, J = 74.3 Hz), 7.03-7.28 (4H, m), 8.15 (1H, s). |
| 606 | 3-OCF$_2$H | free | (CDCl$_3$) δ: 2.29-2.45 (2H, m), 3.12-3.20 (2H, m), 3.24-3.32 (2H, m), 3.43 (3H, s), 4.23 (2H, t, J = 7.8 Hz), 4.34 (2H, t, J = 7.8 Hz), 6.49 (1H, t, J = 74.2 Hz), 6.89-7.00 (2H, m), 7.07-7.12 (1H, m), 7.22-7.29 (1H, m), 8.17 (1H, s). |
| 607 | 2-OCF$_3$ | free | (CDCl$_3$) δ: 2.29-2.42 (2H, m), 3.13-3.32 (4H, m), 3.43 (3H, s), 4.23 (2H, t, J = 7.8 Hz), 4.33 (2H, t, J = 7.8 Hz), 7.15-7.23 (3H, m), 7.24-7.33 (1H, m), 8.16 (1H, s). |
| 608 | 3-OCF$_3$ | free | (CDCl$_3$) δ: 2.30-2.43 (2H, m), 3.13-3.22 (2H, m), 3.24-3.33 (2H, m), 3.43 (3H, s), 4.23 (2H, t, J = 7.8 Hz), 4.34 (2H, t, J = 7.8 Hz), 6.99-7.09 (2H, m), 7.15-7.21 (1H, m), 7.24-7.32 (1H, m), 8.17 (1H, s). |
| 609 | 4-OCF$_3$ | free | (CDCl$_3$) δ: 2.30-2.43 (2H, m), 3.11-3.20 (2H, m), 3.22-3.32 (2H, m), 3.43 (3H, s), 4.23 (2H, t, J = 7.8 Hz), 4.34 (2H, t, J = 7.8 Hz), 7.07-7.14 (2H, m), 7.21-7.29 (2H, m), 8.17 (1H, s). |
| 610 | 2-F 3-F | free | (CDCl$_3$) δ: 2.30-2.44 (2H, m), 3.17-3.33 (4H, m), 3.43 (3H, s), 4.24 (2H, t, J = 7.8 Hz), 4.34 (2H, t, J = 7.8 Hz), 6.90-7.05 (3H, m), 8.16 (1H, s). |
| 611 | 2-F 6-F | free | (CDCl$_3$) δ: 2.30-2.42 (2H, m), 3.14-3.28 (4H, m), 3.43 (3H, s), 4.24 (2H, t, J = 7.8 Hz), 4.33 (2H, t, J = 7.8 Hz), 6.77-6.88 (2H, m), 7.07-7.19 (1H, m), 8.16 (1H, s). |
| 612 | 3-OCH$_2$CF$_3$ | HCl | (DMSO-d$_6$) δ: 2.19-2.33 (2H, m), 3.01-3.10 (2H, m), 3.14-3.23 (2H, m), 3.34 (3H, s), 4.02-4.19 (4H, m), 4.71 (2H, q, J = 8.9 Hz), 6.80-6.92 (2H, m), 6.94-6.99 (1H, m), 7.20 (1H, t, J = 7.9 Hz), 8.55 (1H, s). |
| 613 | 4-OCH$_2$CF$_3$ | HCl | (DMSO-d$_6$) δ: 2.18-2.32 (2H, m), 2.98-3.07 (2H, m), 3.09-3.20 (2H, m), 3.35 (3H, s), 4.05 (2H, t, J = 7.8 Hz), 4.14 (2H, t, J = 7.8 Hz), 4.67 (2H, q, J = 8.9 Hz), 6.88-6.95 (2H, m), 7.13-7.22 (2H, m), 8.58 (1H, s). |

Examples 614 to 620

The compounds indicated in Table 82 were prepared using the corresponding acetylene compound instead of trimethylsilylacethylene of Example 493 (1) according to the similar method to those of Examples 493 (1) and (4).

TABLE 82

| Ex. No. | Structure | $^1$H-NMR (CDCl$_3$) δ |
|---|---|---|
| 614 | 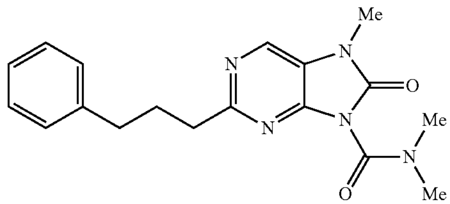 [SMILES: CN(C)C(=O)n1c(=O)n(C)c2cnc(CCCc3ccccc3)nc21] | 2.06-2.19 (2H, m), 2.69 (2H, t, J = 7.8 Hz), 2.97 (2H, t, J = 7.8 Hz), 3.07 (3H, s), 3.22 (3H, s), 3.44 (3H, s), 7.13-7.30 (5H, m), 8.16 (1H, s). |
| 615 | 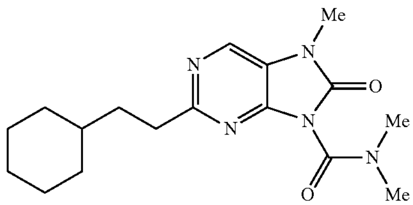 [SMILES: CN(C)C(=O)n1c(=O)n(C)c2cnc(CCC3CCCCC3)nc21] | 0.85-1.01 (2H, m), 1.09-1.36 (5H, m), 1.55-1.82 (6H, m), 2.89-2.97 (2H, m), 3.08 (3H, s), 3.23 (3H, s), 3.44 (3H, s), 8.16 (1H, s). |
| 616 | 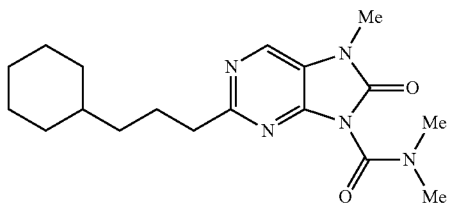 [SMILES: CN(C)C(=O)n1c(=O)n(C)c2cnc(CCCC3CCCCC3)nc21] | 0.77-0.94 (2H, m), 1.07-1.31 (6H, m), 1.61-1.86 (7H, m), 2.85-2.93 (2H, m), 3.08 (3H, s), 3.23 (3H, s), 3.44 (3H, s), 8.16 (1H, s). |
| 617 | 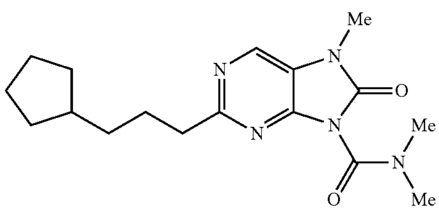 [SMILES: CN(C)C(=O)n1c(=O)n(C)c2cnc(CCCC3CCCC3)nc21] | 0.99-1.14 (2H, m), 1.31-1.42 (2H, m), 1.43-1.62 (4H, m), 1.69-1.86 (5H, m), 2.91 (2H, t, J = 7.8 Hz), 3.08 (3H, s), 3.23 (3H, s), 3.44 (3H, s), 8.17 (1H, s). |
| 618 | 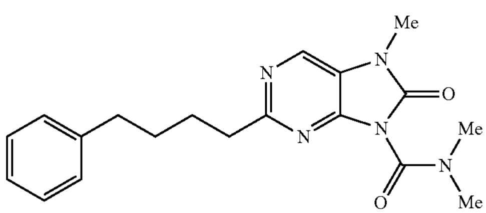 [SMILES: CN(C)C(=O)n1c(=O)n(C)c2cnc(CCCCc3ccccc3)nc21] | 1.59-1.75 (2H, m), 1.78-1.91 (2H, m), 2.65 (2H, t, J = 7.6 Hz), 2.95 (2H, t, J = 7.6 Hz), 3.05 (3H, s), 3.22 (3H, s), 3.43 (3H, s), 7.12-7.20 (3H, m), 7.21-7.30 (2H, m), 8.15 (1H, s). |
| 619 | 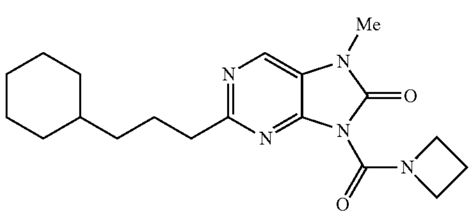 [SMILES: Cn1c(=O)n(C(=O)N2CCC2)c2nc(CCCC3CCCCC3)ncc21] | 0.79-0.94 (2H, m), 1.07-1.31 (6H, m), 1.62-1.89 (7H, m), 2.31-2.44 (2H, m), 2.88-2.96 (2H, m), 3.43 (3H, s), 4.26-4.38 (4H, m), 8.16 (1H, s). |
| 620 | 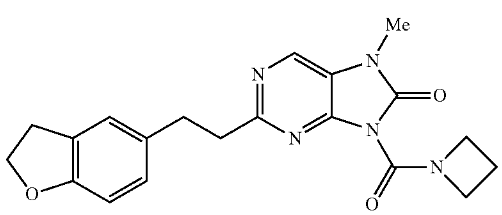 [SMILES: Cn1c(=O)n(C(=O)N2CCC2)c2nc(CCc3ccc4c(c3)CCO4)ncc21] | 2.30-2.44 (2H, m), 3.02-3.10 (2H, m), 3.13-3.27 (4H, m), 3.43 (3H, s), 4.24 (2H, t, J = 7-8 Hz), 4.34 (2H, t, J = 7.8 Hz), 4.53 (2H, t, J = 8.7 Hz), 6.67 (1H, d, J = 8.3 Hz), 6.93-6.98 (1H, m), 7.08-7.11 (1H, m), 8.17 (1H, s). |

Examples 621 to 637

The compounds indicated in Tables 83 to 85 were prepared according to the similar method to those of Example 2.

TABLE 83

| Ex. No. | R¹ | R² | ¹H-NMR (CDCl₃) δ |
|---|---|---|---|
| 621 | c-Pr | 4-F | 0.98-1.19 (4H, m), 2.15-2.32 (1H, m), 3.41 (3H, s), 3.81-3.99 (1H, m), 4.13-4.86 (4H, m), 6.98-7.16 (2H, m), 7.19-7.40 (2H, m), 8.66 (1H, s). |
| 622 | c-Pr | 3-F | 0.90-1.21 (4H, m), 2.12-2.40 (1H, m), 3.42 (3H, s), 3.77-4.01 (1H, m), 4.21-4.49 (2H, m), 4.52-4.83 (2H, m), 6.90-7.47 (4H, m), 8.09 (1H, s). |
| 623 | c-Pr | H | 0.93-1.22 (4H, m), 2.11-2.36 (1H, m), 3.42 (3H, s), 3.80-3.99 (1H, m), 4.22-4.48 (2H, m), 4.50-4.82 (2H, m), 7.15-7.50 (5H, m), 8.08 (1H, s). |

TABLE 83-continued

| Ex. No. | R¹ | R² | ¹H-NMR (CDCl₃) δ |
|---|---|---|---|
| 624 | n-Pr | 4-F | 0.99 (3H, t, J = 7.3 Hz), 1.72-1.96 (2H, m), 2.90 (2H, t, J = 7.6 Hz), 3.45 (3H, s), 3.80-4.03 (1H, m), 4.08-4.94 (4H, m), 6.93-7.46 (4H, m), 8.75 (1H, s). |
| 625 | n-Pr | 3-F | 0.99 (3H, t, J = 7.3 Hz), 1.76-1.94 (2H, m), 2.84-2.97 (2H, m), 3.45 (3H, s), 3.83-4.03 (1H, m), 4.07-4.88 (4H, m), 6.88-7.43 (4H, m), 8.75 (1H, s). |
| 626 | n-Pr | H | 0.99 (3H, t, J = 7.3 Hz), 1.72-1.97 (2H, m), 2.79-3.01 (2H, m), 3.45 (3H, s), 3.84-4.07 (1H, m), 4.14-4.91 (4H, m), 7.11-7.56 (5H, m), 8.75 (1H, s). |
| 627 | Et | H | 1.36 (3H, t, J = 7.6 Hz), 2.96 (2H, q, J = 7.6 Hz), 3.45 (3H, s), 3.85-4.06 (1H, m), 4.18-4.93 (4H, m), 7.07-7.60 (5H, m), 8.75 (1H, s). |
| 628 | Et | 4-F | 1.36 (3H, t, J = 7.6 Hz), 2.96 (2H, q, J = 7.6 Hz), 3.45 (3H, s), 3.82-4.01 (1H, m), 4.08-4.89 (4H, m), 7.00-7.16 (2H, m), 7.20-7.41 (2H, m), 8.75 (1H, s). |

TABLE 84

| Ex. No. | Structure | Salt | ¹H-NMR |
|---|---|---|---|
| 629 | 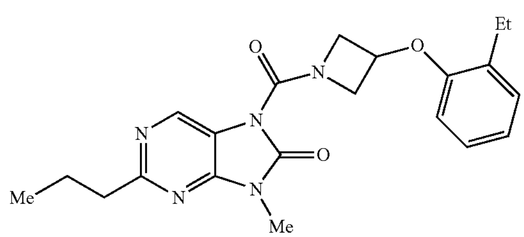 [SMILES: CCCc1ncc2c(n1)n(C)c(=O)n2C(=O)N1CC(Oc2ccccc2CC)C1] | free | (CDCl₃) δ: 1.00 (3H, t, J = 7.6 Hz), 1.20 (3H, t, J = 7.6 Hz), 1.82-1.91 (2H, m), 2.67 (2H, q, J = 7.6 Hz), 2.98 (2H, t, J = 7.6 Hz), 3.49 (3H, s), 4.30-4.52 (2H, br m), 4.60-4.85 (2H, br m), 5.00-5.10 (1H, m), 6.46 (1H, d, J = 8.0 Hz), 6.95 (1H, t, J = 7.6 Hz), 7.13 (1H, dt, J = 8.0. 1.6 Hz), 7.19 (1H, dd, J = 7.6, 1.6 Hz), 8.84 (1H, s). |
| 630 | 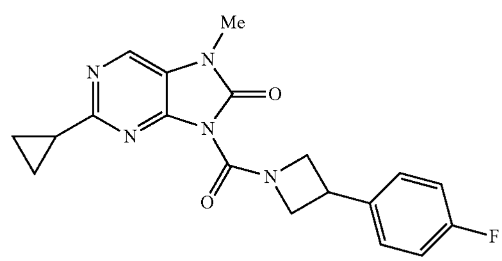 [SMILES: Cn1c(=O)n(C(=O)N2CC(c3ccc(F)cc3)C2)c2nc(C3CC3)ncc21] | HCl | (DMSO-d₆) δ: 0.85-1.19 (4H, m), 2.16-2.37 (1H, m), 3.35 (3H, s), 3.46-4.70 (5H, m), 7.10-7.33 (2H, m), 7.35-7.57 (2H, m), 8.50 (1H, s). |
| 631 | 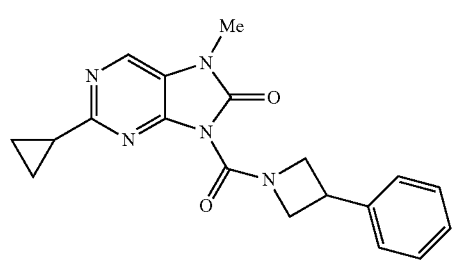 [SMILES: Cn1c(=O)n(C(=O)N2CC(c3ccccc3)C2)c2nc(C3CC3)ncc21] | free | (CDCl₃) δ: 0.92-1.21 (4H, m), 2.19-2.36 (1H, m), 3.42 (3H, s), 3.80-4.00 (1H, m), 4.26-4.49 (2H, m), 4.53-4.82 (2H, m), 7.20-7.51 (5H, m), 8.08 (1H, s). |

TABLE 84-continued

| Ex. No. | Structure | Salt | ¹H-NMR |
|---|---|---|---|
| 632 | 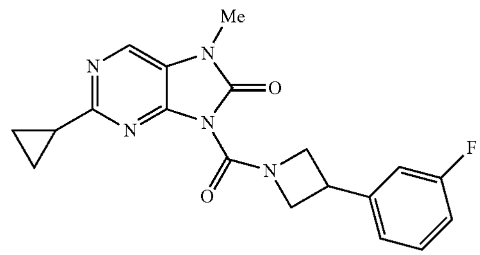 [SMILES: Cn1c(=O)n(C(=O)N2CC(c3cccc(F)c3)C2)c2nc(C3CC3)ncc21] | free | (CDCl₃) δ: 0.87-1.23 (4H, m), 2.17-2.39 (1H, m), 3.42 (3H, s), 3.79-3.99 (1H, m), 4.19-4.49 (2H, m), 4.52-4.85 (2H, m), 6.90-7.51 (4H, m). 8.09 (1H, s). |
| 633 | 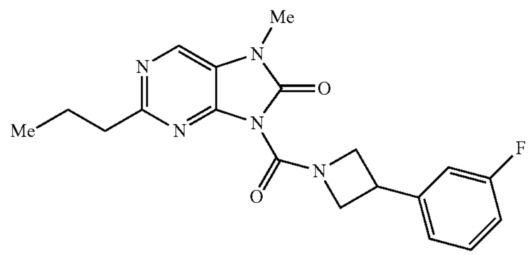 [SMILES: CCCc1ncc2c(n1)n(C(=O)N1CC(c3cccc(F)c3)C1)c(=O)n2C] | free | (CDCl₃) δ: 0.98 (3H, t, J = 7.3 Hz), 1.73-1.94 (2H, m), 2.87-3.05 (2H, m), 3.44 (3H, s), 3.79-3.99 (1H, m), 4.19-4.87 (4H, m), 6.92-7.50 (4H, m), 8.18 (1H, s). |

TABLE 85

| Ex. No. | Structure | Salt | ¹H-NMR |
|---|---|---|---|
| 634 | 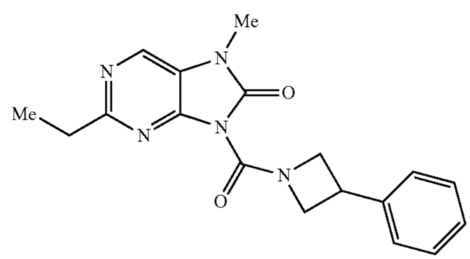 [SMILES: CCc1ncc2c(n1)n(C(=O)N1CC(c3ccccc3)C1)c(=O)n2C] | HCl | (DMSO-d₆) δ: 1.26 (3H, t, J = 7.5 Hz), 2.88 (2H, q, J = 7.5 Hz), 3.36 (3H, s), 3.83-4.34 (3H, m), 4.43-4.70 (2H, m), 7.21-7.52 (5H, m), 8.52 (1H, s). |
| 635 | 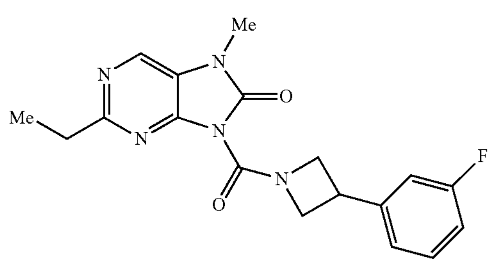 [SMILES: CCc1ncc2c(n1)n(C(=O)N1CC(c3cccc(F)c3)C1)c(=O)n2C] | HCl | (DMSO-d₆) δ: 1.25 (3H, t, J = 7.6 Hz), 2.89 (2H, q, J = 7.6 Hz), 3.36 (3H, s), 3.84-4.33 (3H, m), 4.44-4.73 (2H, m), 7.01-7.54 (4H, m), 8.54 (1H, s). |
| 636 | 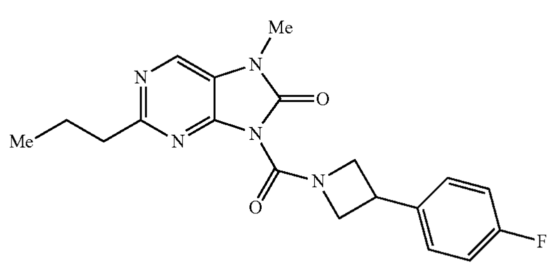 [SMILES: CCCc1ncc2c(n1)n(C(=O)N1CC(c3ccc(F)cc3)C1)c(=O)n2C] | HCl | (DMSO-d₆) δ: 0.89 (3H, t, J = 7.3 Hz), 1.57-1.84 (2H, m), 2.84 (2H, t, J = 7.4 Hz), 3.36 (3H, s), 3.83-429 (3H, m), 4.47-4.67 (2H, m), 7.10-7.28 (2H, m), 7.36-7.54 (2H, m), 8.54 (1H, s). |

| Ex. No. | Structure | Salt | ¹H-NMR |
|---|---|---|---|
| 637 | 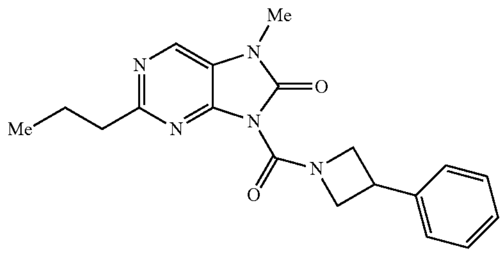 [SMILES: CCCc1ncc2c(n1)n(C(=O)N1CC(c3ccccc3)C1)c(=O)n2C] | HCl | (DMSO-d$_6$) δ: 0.90 (3H, t, J = 7.3 Hz), 1.63-1.87 (2H, m), 2.84 (2H, t, J = 7.5 Hz), 3.36 (3H, s), 3.85-4.02 (1H, m), 4.04-4.82 (4H, m), 7.23-7.50 (5H, m), 8.52 (1H, s). |

Example 638

Process of N,N,7-trimethyl-8-oxo-2-{2-[4-(trifluoromethyl)phenoxy]ethyl}-7,8-dihydro-9H-purine-9-carboxamide hydrochloric acid salt

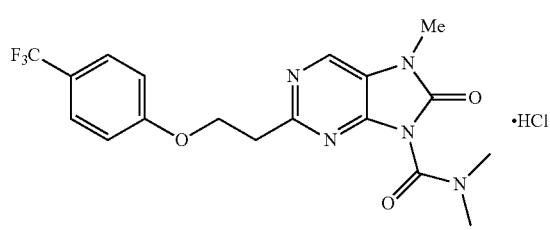 [SMILES: CN(C)C(=O)n1c(=O)n(C)c2cnc(CCOc3ccc(C(F)(F)F)cc3)nc21 ; Cl]

(1) To a suspension of 55% sodium hydride (3.1 g) in tetrahydrofuran (100 ml) was added dropwise benzylethyl malonate (16 g) under ice-cooling and the mixture was stirred at room temperature for 15 minutes. To the reaction mixture was added dropwise a solution of 2-chloro-5-nitropyrimidin-4-amine <the compound of Reference Example 2(1)> (5 g) in tetrahydrofuran (50 ml) and the mixture was stirred for 1 hour. The reaction mixture was poured into a saturated aqueous ammonium chloride solution (200 ml) and the mixture was extracted with ethyl acetate (80 ml×3). The organic layer was dried over anhydrous magnesium sulfate and was filtered, and the filtrate was concentrated under reduced pressure. The obtained residue was purified by silica gel column chromatography (eluent: hexane/ethyl acetate=100/0~0/100) to give benzylethyl (4-amino-5-nitropyrimidin-2-yl)propanedioate 12 g.

¹H-NMR (CDCl$_3$) δ: 1.25 (3H, t, J=7.2 Hz), 4.26 (2H, q, J=7.2 Hz), 4.98 (1H, s), 5.26 (2H, d, J=4.6 Hz), 6.01-6.13 (1H, br m), 7.32-7.38 (5H, br m), 7.85 (1H, br s), 9.19 (1H, s).

(2) To a solution of the above-mentioned product (12 g) in methanol (200 ml) were added 10% palladium on carbon (2.4 g) and ammonium formate (9 g) and the mixture was heated under reflux for 1 hour. The reaction mixture was filtered through Celite and the filtrate was concentrated under reduced pressure. The obtained residue was purified by amino silica gel column chromatography (eluent: chloroform/methanol=100/0~80/20) to give ethyl (4,5-diaminopyridin-2-yl)acetate 3.6 g.

¹H-NMR (CDCl$_3$) δ: 1.26 (3H, t, J=7.2 Hz), 1.75-2.07 (1H, br m), 3.10-3.30 (1H, br m), 3.74 (2H, s), 4.19 (2H, q, J=7.2 Hz), 4.99-5.07 (2H, br m), 7.79 (1H, s).

(3) To a solution of the above-mentioned product (3.6 g) in pyridine (50 ml) was added dropwise ethyl chloroformate (2 ml) under ice-cooling and the mixture was stirred at room temperature for 2 hours. To the reaction mixture was added water (300 ml) and the mixture was extracted with ethyl acetate (80 ml×3). The organic layer was dried over anhydrous magnesium sulfate and was filtered, and the filtrate was concentrated under reduced pressure. The obtained residue was recrystallized from diethylether to give ethyl {4-amino-5-[(ethoxycarbonyl)amino]pyrimidin-2-yl}acetate 3.3 g.

¹H-NMR (CDCl$_3$) δ: 1.21-1.31 (6H, m), 3.76 (2H, s), 4.14-4.24 (4H, m), 5.30 (2H, br s), 6.47 (1H, br s), 8.15 (1H, s).

(4) To a suspension of lithium aluminium hydride (1.2 g) in tetrahydrofuran (50 ml) was added dropwise a solution of the above-mentioned product (3.3 g) in tetrahydrofuran (15 ml) under ice-cooling and the mixture was stirred for 1 hour. To the reaction mixture were added water (1.2 ml), a 15% aqueous sodium hydroxide solution (1.2 ml) and water (3.6 ml) sequentially and the mixture was stirred for 30 minutes. The mixture was filtered through Celite and the filtrate was concentrated under reduced pressure. The obtained residue was recrystallized from a solution of ethyl acetate and hexane to give ethyl [4-amino-2-(2-hydroxyethyl)pyrimidin-5-yl]carbamate 1.5 g.

¹H-NMR (CDCl$_3$) δ: 1.29 (3H, t, J=7.1 Hz), 2.96 (2H, t, J=5.4 Hz), 3.97 (2H, t, J=5.4 Hz), 4.21 (2H, q, J=7.1 Hz), 5.25 (2H, br s), 6.03-6.38 (1H, br m), 8.09 (1H, s).

(5) A mixture of the above-mentioned product (1.3 g), imidazole (550 mg), tert-butyl dimethylsilylchloride (1.2 g) and acetonitrile (12 ml) was stirred at room temperature for 1 hour. To the reaction mixture was added water (30 ml) and the mixture was extracted with ethyl acetate (20 ml×3). The organic layer was dried over anhydrous magnesium sulfate and was filtered, and the filtrate was concentrated under reduced pressure. The obtained residue was recrystallized from diethylether to give ethyl [4-amino-2-(2-{[tert-butyl(dimethyl)silyl]oxy}ethyl)pyrimidin-5-yl]carbamate 1.4 g.

¹H-NMR (CDCl$_3$) δ: 0.00 (6H, s), 0.84 (9H, s), 1.29 (3H, t, J=7.2 Hz), 2.95 (2H, t, J=7.1 Hz), 4.03 (2H, t, J=7.1 Hz), 4.21 (2H, q, J=7.2 Hz), 5.19 (2H, br s), 6.20 (1H, br s), 8.10 (1H, s).

(6) A mixture of the above-mentioned product (1.4 g), cesium carbonate (1.7 g), methyl iodide (0.4 ml) and N,N-dimethylformamide (10 ml) was stirred at room temperature for 8 hours. To the reaction mixture was added water (50 ml) and the mixture was extracted with ethyl acetate (10 ml×3). The organic layer was dried over anhydrous magnesium sulfate and was filtered, and the filtrate was concentrated under reduced pressure to give ethyl [4-amino-2-(2-{[tert-butyl (dimethyl)silyl]oxy}ethyl)pyrimidin-5-yl]methylcarbamate as a crude product. This crude product was used to the next reaction without purification.

(7) The total amount of the above-mentioned crude product and 20% sodium ethoxide/ethanol solution (5 ml) were mixed and the mixture was heated under reflux for 1 hour. Under ice-cooling, the reaction mixture was neutralized with 1 mol/L hydrochloric acid and the crystals precipitated were collected by filtration. The obtained crystals were washed with water and were dried to give 2-(2-{[tert-butyl(dimethyl)silyl]oxy}ethyl)-7-methyl-7,9-dihydro-8H-purine-8-one 740 mg.

$^1$H-NMR (CDCl$_3$) δ: −0.01 (6H, s), 0.82 (9H, s), 3.15 (2H, t, J=6.8 Hz), 3.44 (3H, s), 4.10 (2H, t, J=6.8 Hz), 8.14 (1H, s).

(8) To a solution of the above-mentioned product (740 mg) and 1,4-diazabicyclo[2.2.2]octane (540 mg) in dichloromethane (5 ml) was added dropwise dimethylcarbamoyl chloride (400 mg) and the mixture was stirred at room temperature for 12 hours. The reaction mixture was purified by silica gel column chromatography (eluent: hexane/ethyl acetate=100/0~0/100) to give 2-(2-{[tert-butyl(dimethyl)silyl]oxy}ethyl)-N,N,7-trimethyl-8-oxo-7,8-dihydro-9H-purine-9-carboxamide 570 mg.

$^1$H-NMR (CDCl$_3$) δ: −0.01 (6H, s), 0.82 (9H, s), 3.07 (3H, s), 3.15 (2H, t, J=6.9 Hz), 3.22 (3H, s), 3.44 (3H, s), 4.08 (2H, t, J=6.9 Hz), 8.17 (1H, s).

(9) The above-mentioned product (570 mg) and 5-10% hydrogen chloride/methanol solution were mixed and the mixture was stirred for 10 minutes. The solvent was evaporated under reduced pressure and the residue was purified by amino silica gel column chromatography (eluent: chloroform/methanol=100/0~80/20) to give 2-(2-hydroxyethyl)-N,N,7-trimethyl-8-oxo-7,8-dihydro-9H-purine-9-carboxamide 400 mg.

$^1$H-NMR (CDCl$_3$) δ: 3.08 (3H, s), 3.18 (2H, t, J=5.6 Hz), 3.22 (3H, s), 3.45 (3H, s), 3.79 (1H, t, J=6.1 Hz), 4.04 (2H, q, J=5.6 Hz), 8.17 (1H, s).

(10) To a solution of the above-mentioned product (50 mg), triphenylphosphine (75 mg) and 4-(trifluoromethyl)phenol (93 mg) in toluene (2 ml) was added dropwise diisopropyl azodicarboxylate (57 µl) and the mixture was stirred at room temperature for 3 hours. The reaction mixture was purified by silica gel column chromatography (eluent: hexane/ethyl acetate=100/0~0/100). The obtained product and 5-10% hydrogen chloride/methanol solution were mixed and the mixture was stirred for 10 minutes. The solvent was evaporated under reduced pressure and the obtained crude solids were recrystallized from diethylether to give the title compound 22 mg.

$^1$H-NMR (CDCl$_3$) δ: 3.03 (3H, br s), 3.21 (3H, s), 3.55-3.83 (5H, m), 4.54-4.65 (2H, m), 6.95 (2H, d, J=7.9 Hz), 7.51 (2H, d, J=7.9 Hz), 8.63-9.00 (1H, br m).

Examples 639 to 642

The compounds indicated in Table 86 were prepared according to the similar method to those of Example 638.

TABLE 86

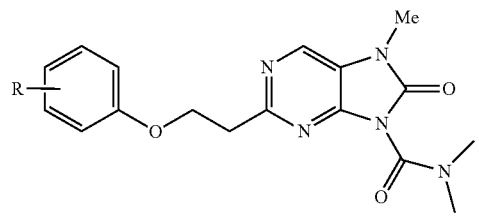

| Ex. No. | R | Salt | $^1$H-NMR (CDCl$_3$) δ |
|---|---|---|---|
| 639 | 3-F | HCl | 2.94-3.38 (6H, m), 3.49-3.90 (5H, m), 4.45-4.71 (2H, m), 6.46-6.82 (3H, m), 7.11-7.28 (1H, m), 8.44-9.27 (1H, br m). |
| 640 | 4-Cl | free | 3.04 (3H, s), 3.21 (3H, s), 3.40 (2H, t, J = 6.5 Hz), 3.45 (3H, s), 4.43 (2H, t, J = 6.5 Hz), 6.83 (2H, d, J = 9.2 Hz), 7.20 (2H, d, J = 9.2 Hz), 8.19 (1H, s). |
| 641 | 3-Cl | HCl | 3.03 (3H, br s), 322 (3H, s), 3.51-3.76 (5H, m), 4.52 (2H, br s), 6.74-6.95 (3H, m), 7.17 (1H, t, J = 7.3 Hz), 8.52-8.91 (1H, br m). |
| 642 | 3-CF$_3$ | HCl | 3.03 (3H, br s), 3.21 (3H, s), 3.56-3.78 (5H, m), 4.53-4.63 (2H, m), 7.04-7.10 (2H, m), 7.18-7.22 (1H, m), 7.33-7.41 (1H, m), 8.63-9.06 (1H, br m). |

Examples 643 to 651

The compounds indicated in Table 87 were prepared according to the similar method to those of Reference Example 2 and Example 493.

TABLE 87

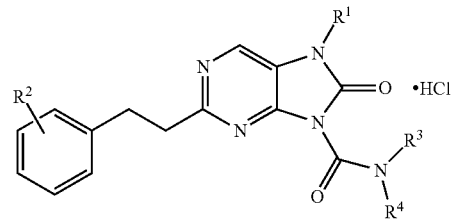

| Ex. No. | R$^1$ | R$^2$ | NR$^3$R$^4$ | $^1$H-NMR (DMSO-d$_6$) δ |
|---|---|---|---|---|
| 643 | Et | 2-F | —NMe$_2$ | 1.26 (3H, t, J = 7.2 Hz), 2.92 (3H, s), 3.00-3.25 (7H, m), 3.80-3.97 (2H, m), 7.03-7.17 (2H, m), 7.18-7.36 (2H, m), 8.70 (1H, s). |
| 644 | Et | 3-F | —NMe$_2$ | 1.25 (3H, t, J = 7.2 Hz), 2.93 (3H, s), 3.00-3.30 (7H, m), 3.81-3.96 (2H, m), 6.91-7.16 (3H, m), 7.20-7.34 (1H, m), 8.65 (1H, s). |
| 645 | Et | 4-F | —NMe$_2$ | 1.26 (3H, t, J = 7.2 Hz), 2.93 (3H, s), 3.00-3.25 (7H, m), 3.82-3.96 (2H, m), 7.01-7.12 (2H, m), 7.21-7.32 (2H, m), 8.71 (1H, s). |
| 646 | n-Pr | 2-F | —NMe$_2$ | 0.87 (3H, t, J = 7.3 Hz), 1.62-1.77 (2H, m), 2.92 (3H, s), 3.00-323 (7H, m), 3.75-3.88 (2H, m), 7.04-7.15 (2H, m), 7.17-7.35 (2H, m), 8.63 (1H, s). |
| 647 | n-Pr | 3-F | —NMe$_2$ | 0.87 (3H, t, J = 7.4 Hz), 1.62-1.77 (2H, m), 2.93 (3H, s), 3.01-3.27 (7H, m), 3.76-3.87 (2H, m), 6.93-7.14 (3H, m), 7.22-7.33 (1H, m), 8.71 (1H, s). |
| 648 | n-Pr | 4-F | —NMe$_2$ | 0.88 (3H, t, J = 7.4 Hz), 1.62-1.78 (2H, m), 2.93 (3H, s), 2.98-3.24 (7H, m), 3.75-3.89 (2H, m), 7.01-7.11 (2H, m), 7.20-7.32 (2H, m), 8.71 (1H, s). |

TABLE 87-continued

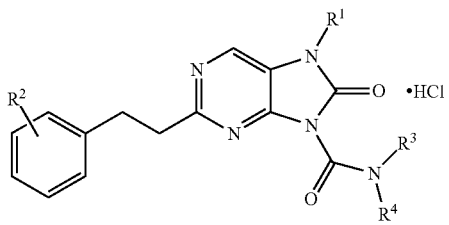

| Ex. No. | R¹ | R² | NR³R⁴ | ¹H-NMR (DMSO-d₆) δ |
|---|---|---|---|---|
| 649 | Et | 2-F | —N◇ | 1.24 (3H, t, J = 7.2 Hz), 2.18-2.33 (2H, m), 3.03-3.24 (4H, m), 3.88 (2H, q, J = 11 Hz), 4.03-4.19 (4H, m), 7.05-7.17 (2H, m), 7.18-7.36 (2H, m), 8.64 (1H, s). |
| 650 | Et | 3-F | —N◇ | 1.24 (3H, t, J = 11 Hz), 2.18-2.33 (2H, m), 3.04-3.26 (4H, m), 3.89 (2H, q, J = 7.2 Hz), 4.03-4.19 (4H, m), 6.93-7.03 (1H, m), 7.04-7.16 (2H, m), 752-7.34 (1H, m), 8.66 (1H, s). |
| 651 | Et | 4-F | —N◇ | 1.24 (3H, t, J = 7.2 Hz), 2.18-2.33 (2H, m), 3.00-3.27 (4H, m), 3.81-3.95 (2H, m), 4.02-4.20 (4H, m), 7.01-7.12 (2H, m), 7.22-7.32 (2H, m), 8.69 (1H, s) |

Examples 652 to 654

The compounds indicated in Table 88 were prepared according to the similar method to those of Reference Example 16 and Example 253.

TABLE 88

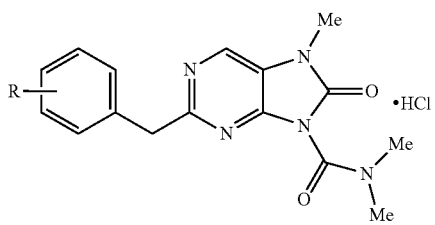

| Ex. No. | R | ¹H-NMR (DMSO-d₆) δ |
|---|---|---|
| 652 | 2-Cl | 2.90 (3H, s), 3.05 (3H, s), 3.36 (3H, s), 4.32 (2H, s), 7.26-7.35 (3H, m), 7.41-7.46 (1H, m), 8.48 (1H, s). |
| 653 | 4-Cl | 3.02 (3H, s), 3.17 (3H, s), 3.45 (3H, s), 4.27 (2H, s), 7.36-7.49 (4H, m), 8.62 (1H, s). |
| 654 | 3-CF₃ | 2.91 (3H, s), 3.07 (3H, s), 3.35 (3H, s), 4.29 (2H, s), 7.49-7.63 (3H, m), 7.69 (1H, s), 8.51 (1H, s). |

Examples 655 to 665

The compounds indicated in Table 89 were prepared according to the similar method to those of Reference Example 1 and Example 438.

TABLE 89

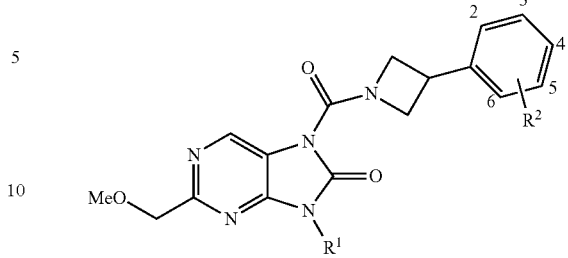

| Ex. No. | R¹ | R² | Salt | ¹H-NMR |
|---|---|---|---|---|
| 655 | Et | H | HCl | (DMSO-d₆) δ: 1.26 (3H, t, J = 7.2 Hz), 3.36 (3H, s), 3.74-4.86 (5H, m), 3.87 (2H, q, J = 7.2 Hz), 4.53 (2H, s), 7.19-7.50 (5H, m), 8.61 (1H, s). |
| 656 | Et | 4-F | HCl | (DMSO-d₆) δ: 1.26 (3H, t, J = 7.2 Hz), 3.36 (3H, s), 3.79-4.79 (5H, m), 3.86 (2H, q, J = 7.2 Hz), 4.52 (2H, s), 7.13-7.27 (2H, m), 7.38-7.50 (2H, m), 8.61 (1H, s). |
| 657 | Et | 3-F | HCl | (DMSO-d₆) δ: 1.27 (3H, t, J = 12 Hz), 3.36 (3H, s), 3.76-4.80 (5H, m), 3.87 (2H, q, J = 7.2 Hz), 4.52 (2H, s), 7.02-7.49 (4H, m), 8.61 (1H, s). |
| 658 | n-Pr | H | HCl | (DMSO-d₆) δ: 0.87 (3H, t, J = 7.4 Hz), 1.61-1.83 (2H, m), 3.35 (3H, s), 3.68-4.82 (7H, m), 4.52 (2H, s), 7.20-7.47 (5H, m), 8.62 (1H, s). |
| 659 | n-Pr | 4-F | free | (CDCl₃) δ: 0.97 (3H, t, J = 7.5 Hz), 1.69-1.98 (2H, m), 3.54 (3H, s), 3.76-4.92 (7H, m), 4.66 (2H, s), 6.94-7.50 (4H, m), 8.84 (1H, s). |
| 660 | n-Pr | 3-F | HCl | (DMSO-d₆) δ: 0.87 (3H, t, J = 7.4 Hz), 1.59-1.86 (2H, m), 3.35 (3H, s), 3.68-4.83 (7H, m), 4.52 (2H, s), 7.00-7.52 (4H, m), 8.62 (1H, s). |
| 661 | n-Pr | 2-F | HCl | (DMSO-d₆) δ: 0.88 (3H, t, J = 7.4 Hz), 1.63-1.86 (2H, m), 3.23-4.69 (7H, m), 3.35 (3H, s), 4.51 (2H, s), 7.08-7.67 (4H, m), 8.60 (1H, s). |
| 662 | n-Pr | 3-CF₃ | HCl | (DMSO-d₆) δ: 0.88 (3H, t, J = 7.4 Hz), 1.63-1.84 (2H, m), 3.35 (3H, s), 3.46-3.89 (2H, m), 3.98-4.86 (5H, m), 4.51 (2H, s), 7.55-7.82 (4H, m), 8.62 (1H, s). |
| 663 | c-Pr | H | HCl | (DMSO-d₆) δ: 0.92-1.17 (4H, m), 2.85-3.02 (1H, m), 3.37 (3H, s), 3.83-4.83 (5H, m), 4.52 (2H, s), 7.17-7.50 (5H, m), 8.58 (1H, s). |
| 664 | c-Pr | 4-F | free | (CDCl₃) δ: 1.06-1.38 (4H, m), 2.92-3.08 (1H, m), 3.55 (3H, s), 3.83-4.04 (1H, m), 4.11-4.88 (4H, m), 4.68 (2H, s), 6.96-7.16 (2H, m), 7.19-7.44 (2H, m), 8.83 (1H, s). |
| 665 | c-Pr | 3-F | free | (CDCl₃) δ: 1.03-1.38 (4H, m), 2.92-3.10 (1H, m), 3.55 (3H, s), 3.85-4.03 (1H, m), 4.13-4.91 (4H, m), 4.68 (2H, s), 6.87-7.47 (4H, m), 8.83 (1H, s). |

Test Example

Determination of FAAH Inhibitory Activity in Rat

The preparation of rat brain membranes preparations and the determination of FAAH inhibitory activity were carried out according to the Jonsson et al. method [Br. J. Pharmacol., 133, 1263 (2001)].

(1) Preparation of Rat Brain Membranes Preparations (FAAH Enzyme Solution)

The cerebrum was extracted from rats and was freeze-stored at −80° C. To the frozen cerebrum was added 4° C. enzyme homogenization buffer (20 mM HEPES-buffer pH 7.0, 1 mM MgCl₂) and the mixture was homogenized using a homogenizer in ice and the homogenates were centrifuged (36,000×g for 20 minutes). After repeating operations of homogenization and centrifugation, the tissue pellets were re-suspended with 4° C. enzyme homogenization buffer. The re-suspensions were incubated at 37° C. for 15 minutes and were centrifuged (36,000×g for 20 minutes), and the resulting tissue membranes were then re-suspended with enzyme solution preparation buffer (50 mM Tris-HCl buffer pH 7.4, 1 mM EDTA, 3 mM $MgCl_2$). The protein concentration in the resulting membrane preparations were determined according to a colorimetry method (BCA Protein Assay: Pierce Inc.) and the preparations were freeze-stored at −80° C. until used for assay.

(2) Screening of Substances for Inhibiting FAAH Activity

To the above membrane preparations (final concentration 100 μg/mL) were added a solution of test substances in DMSO (final concentration in DMSO 1%) and an assay buffer (for final preparation; 22 mM Tris-HCl (pH 7.6), 1.4 mM EDTA, 1.5% BSA, 0.6 mM $MgCl_2$) and the resulting mixtures were preincubated at 37° C. for 10 minutes. Thereto was added a substrate solution (for final preparation; 2 nM [$^3$H]-Anandamide (American Radiolabeled Chemicals Inc.)+2 μM Anandamide (Sigma-Aldrich Co.)) (final assay volume of 200 μL) and the resulting mixtures were incubated at 37° C. for 10 minutes. Here in control experiment, DMSO was added instead of the solution of test substance in DMSO. Also in blank experiment, DMSO was added instead of the solution of test substance in DMSO and an enzyme solution preparation buffer was also added instead of the membrane preparations. After the incubation, thereto was added a 400 μL ice-cooled solution of chloroform and methanol (1:1 ratio by volume) and the resulting mixtures were stirred. An ethanolamine (ethanolamine-1-[$^3$H]) as a decomposed product was separated into an upper layer (water/methanol layer) by centrifugation (1,000×g for 10 minutes). The upper layer 200 μL was transferred into 96 well Deepwell Luma Plate-96 (PerkinElmer Inc.) and the radioactivity was measured by microplate scintillation counter (TopCount NXT™: Hewlett-Packard Development Co.). The substances showing a lower measured value compared to those of control were selected as the compound having a FAAH inhibitory activity.

(3) Determination of $IC_{50}$ Value

The test substances were prepared such that the final concentration of the compounds is within the range of 0.1 nM to 1 μM and were then examined on the effect on FAAH activity according to the above-mentioned protocol. The FAAH activity of the control was defined as 100%, and the FAAH activity of the blank was defined as 0%, and the inhibition rate when each concentration of the test substance was added was calculated to give $IC_{50}$ value. These results are shown in Tables 90 to 99.

TABLE 90

| | FAAH Inhibition | |
|---|---|---|
| Ex. No. | $IC_{50}$ (nM) | Inhibition Rate at 100 nM (%) |
| 1 | 6 | 100 |
| 2 | 10 | 99 |
| 3 | 86 | 59 |
| 4 | 10 | 99 |
| 5 | 15 | 98 |
| 6 | 9 | 100 |
| 7 | 70 | 72 |
| 8 | 57 | 87 |
| 9 | 47 | 92 |
| 10 | >100 | 23 |
| 11 | 66 | 79 |
| 12 | 46 | 93 |

TABLE 90-continued

| | FAAH Inhibition | |
|---|---|---|
| Ex. No. | $IC_{50}$ (nM) | Inhibition Rate at 100 nM (%) |
| 13 | 42 | 91 |
| 14 | >100 | 40 |
| 15 | 63 | 75 |
| 16 | 7 | 100 |
| 17 | 8 | 101 |
| 18 | 7 | 99 |
| 19 | 9 | 99 |
| 20 | 40 | 95 |
| 21 | 84 | 57 |
| 22 | 12 | 102 |
| 23 | 5 | 102 |
| 24 | 29 | 97 |
| 25 | 65 | 73 |
| 26 | >100 | 38 |
| 27 | 63 | 76 |
| 28 | 94 | 54 |
| 29 | 75 | 67 |
| 30 | 100 | 49 |
| 31 | 48 | 84 |
| 32 | 71 | 70 |
| 33 | 47 | 91 |
| 34 | 23 | 101 |
| 35 | 8 | 100 |
| 36 | 7 | 98 |
| 37 | 46 | 91 |
| 38 | 76 | 73 |
| 39 | 43 | 98 |
| 40 | >100 | 20 |
| 41 | >100 | 33 |
| 42 | >100 | 25 |
| 43 | >100 | 20 |
| 44 | >100 | 30 (1000 nM) |
| 45 | >100 | 20 (1000 nM) |
| 46 | >100 | 33 |
| 47 | >100 | 16 |
| 48 | 4 | 100 |
| 49 | 6 | 99 |
| 50 | 9 | 98 |
| 51 | 25 | 97 |
| 52 | 27 | 96 |
| 53 | 19 | 97 |
| 54 | 24 | 99 |
| 55 | 25 | 94 |
| 56 | 7 | 100 |
| 57 | 5 | 101 |
| 58 | 62 | 76 |
| 59 | 26 | 99 |
| 60 | 6 | 99 |
| 61 | 49 | 89 |
| 62 | 26 | 90 |
| 63 | 17 | 100 |
| 64 | 4 | 99 |
| 65 | 3 | 98 |
| 66 | 46 | 93 |
| 67 | 7 | 97 |
| 68 | 6 | 98 |
| 69 | 2 | 101 |
| 70 | >100 | 41 |

TABLE 91

| | FAAH Inhibition | |
|---|---|---|
| Ex. No. | $IC_{50}$ (nM) | Inhibition Rate at 100 nM (%) |
| 71 | 9 | 103 |
| 72 | 23 | 99 |
| 73 | 45 | 89 |
| 74 | <1 | 104 |
| 75 | <1 | 103 |
| 76 | 3 | 102 |

TABLE 91-continued

| Ex. No. | FAAH Inhibition IC$_{50}$ (nM) | Inhibition Rate at 100 nM (%) |
|---|---|---|
| 77 | 3 | 116 |
| 78 | 10 | 108 |
| 79 | 51 | 87 |
| 80 | 44 | 92 |
| 81 | 11 | 94 |
| 82 | 36 | 90 |
| 83 | 25 | 93 |
| 84 | 13 | 98 |
| 85 | 31 | 93 |
| 86 | 22 | 96 |
| 87 | 10 | 99 |
| 88 | 43 | 93 |
| 89 | 44 | 92 |
| 90 | 2 | 105 |
| 91 | 1 | 103 |
| 92 | 4 | 103 |
| 93 | 5 | 100 |
| 94 | 7 | 101 |
| 95 | 3 | 101 |
| 96 | 6 | 100 |
| 97 | 37 | 99 |
| 98 | 40 | 93 |
| 99 | 7 | 100 |
| 100 | 9 | 100 |
| 101 | 7 | 102 |
| 102 | 5 | 101 |
| 103 | 7 | 100 |
| 104 | 3 | 101 |
| 105 | 1 | 108 |
| 106 | 1 | 110 |
| 107 | 7 | 101 |
| 108 | 22 | 94 |
| 109 | 2 | 103 |
| 110 | 3 | 103 |
| 111 | 60 | 46 |
| 112 | 4 | 103 |
| 113 | 3 | 103 |
| 114 | 2 | 103 |
| 115 | 5 | 103 |
| 116 | 2 | 110 |
| 117 | 4 | 107 |
| 118 | 5 | 103 |
| 119 | 7 | 100 |
| 120 | 11 | 101 |
| 121 | 42 | 98 |
| 122 | 35 | 97 |
| 123 | 4 | 101 |
| 124 | 6 | 101 |
| 125 | 30 | 96 |
| 126 | 7 | 99 |
| 127 | 50 | 94 |
| 128 | 7 | 99 |
| 129 | 7 | 98 |
| 130 | 42 | 94 |
| 131 | 4 | 99 |
| 132 | 6 | 99 |
| 133 | 6 | 100 |
| 134 | 7 | 96 |
| 135 | 5 | 99 |
| 136 | 3 | 99 |
| 137 | 5 | 98 |
| 138 | 6 | 99 |
| 139 | 6 | 99 |
| 140 | 7 | 99 |

TABLE 92

| Ex. No. | FAAH Inhibition IC$_{50}$ (nM) | Inhibition Rate at 100 nM (%) |
|---|---|---|
| 141 | 4 | 100 |
| 142 | 5 | 99 |
| 143 | 15 | 100 |
| 144 | <1 | 100 |
| 145 | <1 | 100 |
| 146 | <1 | 99 |
| 147 | <1 | 96 |
| 148 | 30 | 97 |
| 149 | <1 | 102 |
| 150 | <1 | 106 |
| 151 | 0.5 | 102 |
| 152 | 0.6 | 102 |
| 153 | 27 | 99 |
| 154 | 2 | 101 |
| 155 | 4 | 102 |
| 156 | 10 | 96 |
| 157 | <10 | 103 |
| 158 | <1 | 102 |
| 159 | 81 | 61 |
| 160 | 14 | 98 |
| 161 | 19 | 93 |
| 162 | 38 | 72 |
| 163 | >100 | 27 |
| 164 | 5 | 98 |
| 165 | 4 | 103 |
| 166 | 24 | 99 |
| 167 | 6 | 101 |
| 168 | 6 | 100 |
| 169 | 41 | 78 |
| 170 | 7 | 98 |
| 171 | 19 | 102 |
| 172 | 69 | 67 |
| 173 | 7 | 101 |
| 174 | 6 | 102 |
| 175 | 7 | 101 |
| 176 | 10 | 100 |
| 177 | 58 | 78 |
| 178 | 42 | 96 |
| 179 | 44 | 97 |
| 180 | 38 | 99 |
| 181 | 4 | 101 |
| 182 | 28 | 100 |
| 183 | 3 | 101 |
| 184 | 4 | 102 |
| 185 | 89 | 58 |
| 186 | 7 | 102 |
| 187 | 7 | 100 |
| 188 | 9 | 99 |
| 189 | 7 | 100 |
| 190 | 6 | 100 |
| 191 | 7 | 105 |
| 192 | 39 | 103 |
| 193 | 42 | 102 |
| 194 | 18 | 103 |
| 195 | 66 | 83 |
| 196 | 23 | 101 |
| 197 | 70 | 69 |
| 198 | 46 | 92 |
| 199 | 72 | 68 |
| 200 | 30 | 97 |
| 201 | 26 | 99 |
| 202 | 95 | 53 |
| 203 | 24 | 98 |
| 204 | 56 | 81 |
| 205 | 5 | 98 |
| 206 | 4 | 98 |
| 207 | 6 | 99 |
| 208 | 10 | 106 |
| 209 | 24 | 103 |
| 210 | 8 | 103 |

TABLE 93

| Ex. No. | FAAH Inhibition IC$_{50}$ (nM) | Inhibition Rate at 100 nM (%) |
|---|---|---|
| 211 | 8 | 101 |
| 212 | 54 | 88 |
| 213 | 5 | 100 |
| 214 | 18 | 99 |
| 215 | 10 | 98 |
| 216 | 7 | 99 |
| 217 | 27 | 99 |
| 218 | 25 | 95 |
| 219 | 9 | 96 |
| 220 | 7 | 105 |
| 221 | 4 | 100 |
| 222 | <1 | 99 |
| 223 | <1 | 105 |
| 224 | 53 | 91 |
| 225 | 89 | 57 |
| 226 | 27 | 99 |
| 227 | 34 | 97 |
| 228 | 31 | 99 |
| 229 | 53 | 90 |
| 230 | 44 | 94 |
| 231 | 51 | 91 |
| 232 | 20 | 101 |
| 233 | 40 | 97 |
| 234 | 9 | 100 |
| 235 | 39 | 98 |
| 236 | 6 | 100 |
| 237 | 32 | 98 |
| 238 | 58 | 84 |
| 239 | 52 | 89 |
| 240 | >100 | 43 |
| 241 | 43 | 94 |
| 242 | >100 | 40 |
| 243 | 5 | 89 |
| 244 | 11 | 86 |
| 245 | 58 | 80 |
| 246 | 23 | 98 |
| 247 | 39 | 97 |
| 248 | >100 | 33 |
| 249 | 91 | 55 |
| 250 | 63 | 78 |
| 251 | >100 | 28 |
| 252 | >100 | 40 |
| 253 | 5 | 100 |
| 254 | 33 | 98 |
| 255 | 14 | 100 |
| 256 | 7 | 99 |
| 257 | 51 | 88 |
| 258 | 40 | 98 |
| 259 | 41 | 95 |
| 260 | 58 | 84 |
| 261 | 16 | 100 |
| 262 | 24 | 99 |
| 263 | 68 | 75 |
| 264 | 54 | 91 |
| 265 | 9 | 98 |
| 266 | 41 | 92 |
| 267 | 23 | 99 |
| 268 | 48 | 93 |
| 269 | 42 | 96 |
| 270 | 32 | 96 |
| 271 | >100 | 39 |
| 272 | >100 | 35 |
| 273 | 47 | 89 |
| 274 | 10 | 98 |
| 275 | 64 | 73 |
| 276 | 75 | 63 |
| 277 | 7 | 96 |
| 278 | 8 | 99 |
| 279 | 3 | 98 |
| 280 | 11 | 105 |

TABLE 94

| Ex. No. | FAAH Inhibition IC$_{50}$ (nM) | Inhibition Rate at 100 nM (%) |
|---|---|---|
| 281 | 14 | 98 |
| 282 | 10 | 97 |
| 283 | 74 | 59 |
| 284 | 3 | 100 |
| 285 | 77 | 66 |
| 286 | 59 | 86 |
| 287 | 29 | 96 |
| 288 | 47 | 86 |
| 289 | 15 | 96 |
| 290 | 47 | 93 |
| 291 | 75 | 58 |
| 292 | 9 | 91 |
| 293 | 24 | 97 |
| 294 | 37 | 93 |
| 295 | 43 | 91 |
| 296 | 45 | 92 |
| 297 | 47 | 89 |
| 298 | 48 | 98 |
| 299 | 37 | 100 |
| 300 | 40 | 88 |
| 301 | 23 | 90 |
| 302 | 46 | 94 |
| 303 | 7 | 101 |
| 304 | 9 | 100 |
| 305 | 12 | 99 |
| 306 | 15 | 99 |
| 307 | 41 | 96 |
| 308 | 74 | 66 |
| 309 | >100 | 45 (1000 nM) |
| 310 | >100 | 5.0 |
| 311 | 53 | 88 |
| 312 | 8 | 99 |
| 313 | 11 | 103 |
| 314 | 37 | 100 |
| 315 | 19 | 95 |
| 316 | 55 | 80 |
| 317 | <10 | 103 |

TABLE 95

| Ex. No. | FAAH Inhibition IC$_{50}$ (nM) | Inhibition Rate at 100 nM (%) |
|---|---|---|
| 318 | 27 | 90 |
| 319 | 18 | 95 |
| 320 | 113 | 45 |
| 321 | 100 | 54 |
| 322 | 100 | 45 |
| 323 | 77 | 57 |
| 324 | 82 | 55 |
| 325 | 11 | 101 |
| 326 | 52 | 83 |
| 327 | 109 | 23 |
| 328 | 5 | 118 |
| 329 | 12 | 95 |
| 330 | 95 | 62 |
| 331 | 33 | 77 |
| 332 | 38 | 78 |
| 333 | 56 | 73 |
| 334 | 25 | 88 |
| 335 | 33 | 74 |
| 336 | 20 | 85 |
| 337 | 46 | 82 |
| 338 | 21 | 83 |
| 339 | 7 | 80 |
| 340 | 50 | 71 |
| 341 | <1 | 102 |
| 342 | 52 | 76 |
| 343 | 14 | 95 |
| 344 | 13 | 93 |

TABLE 95-continued

FAAH Inhibition

| Ex. No. | IC$_{50}$ (nM) | Inhibition Rate at 100 nM (%) |
|---|---|---|
| 345 | 9 | 101 |
| 346 | 21 | 99 |
| 347 | 61 | 72 |
| 348 | 28 | 90 |
| 349 | 10 | 103 |
| 350 | 10 | 94 |
| 351 | 10 | 104 |
| 352 | 164 | 42 |
| 353 | 92 | 72 |
| 354 | 52 | 79 |
| 355 | 86 | 76 |
| 356 | 95 | 72 |
| 357 | 11 | 107 |
| 358 | 39 | 76 |
| 359 | 25 | 85 |
| 360 | 86 | 75 |
| 361 | 44 | 78 |
| 362 | 19 | 91 |
| 363 | 14 | 88 |
| 364 | 10 | 109 |
| 365 | 10 | 109 |
| 366 | 9 | 106 |
| 367 | 5 | 113 |
| 368 | 17 | 99 |
| 369 | 22 | 86 |
| 370 | 30 | 79 |
| 371 | 149 | 43 |
| 372 | 32 | 80 |
| 373 | 17 | 90 |
| 374 | 12 | 85 |
| 375 | 24 | 94 |
| 376 | 24 | 89 |
| 377 | 39 | 82 |
| 378 | 31 | 80 |
| 379 | 13 | 96 |
| 380 | 8 | 100 |
| 381 | 8 | 84 |
| 382 | 5 | 80 |
| 383 | 14 | 65 |
| 384 | >100 | 8 |
| 385 | 5 | 99 |
| 386 | 7 | 93 |
| 387 | 22 | 92 |

TABLE 96

FAAH Inhibition

| Ex. No. | IC$_{50}$ (nM) | Inhibition Rate at 100 nM (%) |
|---|---|---|
| 388 | 5 | 100 |
| 389 | 9 | 105 |
| 390 | 1 | 120 |
| 391 | 4 | 105 |
| 392 | 11 | 105 |
| 393 | 10 | 101 |
| 394 | 7 | 94 |
| 395 | 32 | 78 |
| 396 | 78 | 52 |
| 397 | 32 | 76 |
| 398 | 9 | 84 |
| 399 | 6 | 95 |
| 400 | 98 | 88 |
| 401 | 9 | 99 |
| 402 | 10 | 103 |
| 403 | 20 | 93 |
| 404 | 10 | 96 |
| 405 | 98 | 97 |
| 406 | 100 | 54 |
| 407 | 92 | 70 |
| 408 | 99 | 69 |
| 409 | 96 | 63 |
| 410 | 100 | 55 |
| 411 | 171 | 45 |
| 412 | 78 | 56 |
| 413 | 3 | 98 |
| 414 | 64 | 84 |
| 415 | 148 | 41 |
| 416 | 112 | 50 |
| 417 | 33 | 66 |
| 418 | 35 | 75 |
| 419 | 31 | 81 |
| 420 | 65 | 60 |
| 421 | 95 | 85 |
| 422 | 22 | 88 |
| 423 | 3 | 112 |
| 424 | 26 | 80 |
| 425 | 12 | 79 |
| 426 | 9 | 84 |
| 427 | 19 | 92 |
| 428 | 10 | 123 |
| 429 | 23 | 84 |
| 430 | 24 | 80 |
| 431 | 94 | 60 |
| 432 | 9 | 99 |
| 433 | 11 | 95 |
| 434 | 8 | 95 |
| 435 | 12 | 94 |
| 436 | 1 | 117 |
| 437 | 11 | 96 |
| 438 | 34 | 86 |
| 439 | 5 | 104 |
| 440 | 21 | 88 |
| 441 | 37 | 74 |
| 442 | 74 | 54 |
| 443 | 7 | 98 |
| 444 | 62 | 69 |
| 445 | 10 | 105 |
| 446 | 6 | 101 |
| 447 | 1 | 131 |
| 448 | 10 | 95 |
| 449 | 28 | 84 |
| 450 | 20 | 89 |
| 451 | 12 | 95 |
| 452 | 39 | 74 |
| 453 | 12 | 90 |
| 454 | 6 | 89 |
| 455 | 1 | 104 |
| 456 | 1 | 99 |
| 457 | 10 | 96 |

TABLE 97

FAAH Inhibition

| Ex. No. | IC$_{50}$ (nM) | Inhibition Rate at 100 nM (%) |
|---|---|---|
| 458 | 1 | 120 |
| 459 | 9 | 108 |
| 460 | 11 | 108 |
| 461 | 10 | 107 |
| 462 | 10 | 113 |
| 463 | 10 | 136 |
| 464 | 25 | 76 |
| 465 | 10 | 96 |
| 466 | 52 | 72 |
| 467 | 52 | 69 |
| 468 | 32 | 69 |
| 469 | 40 | 82 |
| 470 | 2 | 103 |
| 471 | 32 | 80 |
| 472 | 3 | 119 |

TABLE 97-continued

| | FAAH Inhibition | |
|---|---|---|
| Ex. No. | IC$_{50}$ (nM) | Inhibition Rate at 100 nM (%) |
| 473 | 8 | 113 |
| 474 | 54 | 71 |
| 475 | 100 | 46 |
| 476 | 57 | 76 |
| 477 | 26 | 88 |
| 478 | 118 | 46 |
| 479 | 101 | 50 |
| 480 | 83 | 88 |
| 481 | 3 | 102 |
| 482 | 10 | 104 |
| 483 | 10 | 110 |
| 484 | 9 | 86 |
| 485 | 3 | 112 |
| 486 | 2 | 113 |
| 487 | 15 | 99 |
| 488 | 43 | 74 |
| 489 | 1 | 98 |
| 490 | 2 | 97 |
| 491 | 2 | 100 |
| 492 | 2 | 103 |
| 493 | 27 | 79 |
| 494 | 11 | 98 |
| 495 | 10 | 100 |
| 496 | 15 | 86 |
| 497 | 25 | 94 |
| 498 | 24 | 93 |
| 499 | 28 | 91 |
| 500 | 10 | 104 |
| 501 | 10 | 103 |
| 502 | 10 | 104 |
| 503 | 10 | 101 |
| 504 | 6 | 100 |
| 505 | 9 | 99 |
| 506 | 28 | 94 |
| 507 | 24 | 95 |
| 508 | 5 | 100 |
| 509 | 10 | 99 |
| 510 | 11 | 102 |
| 511 | 13 | 95 |
| 512 | 10 | 102 |
| 513 | 10 | 103 |
| 514 | 10 | 102 |
| 515 | 10 | 100 |
| 516 | 10 | 100 |
| 517 | 10 | 98 |
| 518 | 9 | 107 |
| 519 | 6 | 84 |
| 520 | 4 | 96 |
| 521 | 13 | 85 |
| 522 | 23 | 75 |
| 523 | 11 | 101 |
| 524 | 94 | 80 |
| 525 | 99 | 78 |
| 526 | >100 | 27 |
| 527 | 28 | 95 |

TABLE 98

| | FAAH Inhibition | |
|---|---|---|
| Ex. No. | IC$_{50}$ (nM) | Inhibition Rate at 100 nM (%) |
| 528 | 55 | 72 |
| 529 | 100 | 58 |
| 530 | 52 | 66 |
| 531 | 30 | 80 |
| 532 | 13 | 96 |
| 533 | 99 | 53 |
| 534 | 131 | 47 |
| 535 | 75 | 61 |
| 536 | 131 | 41 |
| 537 | 153 | 41 |
| 538 | 100 | 51 |
| 539 | 17 | 92 |
| 540 | 17 | 88 |
| 541 | 47 | 69 |
| 542 | 10 | 100 |
| 543 | 67 | 70 |
| 544 | 11 | 122 |
| 545 | 10 | 100 |
| 546 | 28 | 86 |
| 547 | 55 | 64 |
| 548 | 27 | 79 |
| 549 | 22 | 77 |
| 550 | 20 | 87 |
| 551 | 104 | 40 |
| 552 | 15 | 98 |
| 553 | 9 | 97 |
| 554 | 100 | 43 |
| 555 | 106 | 48 |
| 556 | 44 | 78 |
| 557 | 67 | 66 |
| 558 | 23 | 83 |
| 559 | 10 | 97 |
| 560 | 14 | 91 |
| 561 | 10 | 99 |
| 562 | 10 | 101 |
| 563 | 7 | 100 |
| 564 | 9 | 98 |
| 565 | 10 | 99 |
| 566 | 10 | 96 |
| 567 | 10 | 93 |
| 568 | 10 | 93 |
| 569 | 10 | 98 |
| 570 | 98 | 88 |
| 571 | 10 | 97 |
| 572 | 99 | 83 |
| 573 | 16 | 99 |
| 574 | 29 | 90 |
| 575 | 10 | 102 |
| 576 | 10 | 110 |
| 577 | 98 | 86 |
| 578 | 27 | 88 |
| 579 | 25 | 96 |
| 580 | 25 | 81 |
| 581 | 39 | 80 |
| 582 | 95 | 69 |
| 583 | 94 | 87 |
| 584 | 37 | 84 |
| 585 | 37 | 87 |
| 586 | 10 | 106 |
| 587 | 51 | 68 |
| 588 | 128 | 40 |
| 589 | 29 | 79 |
| 590 | 7 | 109 |
| 591 | 75 | 57 |
| 592 | >100 | 26 |
| 593 | 59 | 58 |
| 594 | 21 | 84 |
| 595 | 7 | 100 |
| 596 | 4 | 125 |
| 597 | 10 | 92 |

TABLE 99

| | FAAH Inhibition | |
|---|---|---|
| Ex. No. | IC$_{50}$ (nM) | Inhibition Rate at 100 nM (%) |
| 598 | 20 | 84 |
| 599 | 8 | 98 |
| 600 | 38 | 71 |

TABLE 99-continued

| | FAAH Inhibition | |
|---|---|---|
| Ex. No. | $IC_{50}$ (nM) | Inhibition Rate at 100 nM (%) |
| 601 | 28 | 83 |
| 602 | 34 | 83 |
| 603 | 14 | 90 |
| 604 | 15 | 92 |
| 605 | 14 | 97 |
| 606 | 5 | 105 |
| 607 | 6 | 94 |
| 608 | 6 | 101 |
| 609 | 4 | 108 |
| 610 | 8 | 103 |
| 611 | 22 | 91 |
| 612 | 9 | 96 |
| 613 | 12 | 95 |
| 614 | 28 | 81 |
| 615 | 10 | 96 |
| 616 | 10 | 99 |
| 617 | 6 | 93 |
| 618 | 10 | 101 |
| 619 | 9 | 103 |
| 620 | 88 | 87 |
| 621 | 10 | 78 |
| 622 | 1 | 116 |
| 623 | 3 | 87 |
| 624 | 18 | 97 |
| 625 | 7 | 104 |
| 626 | 4 | 128 |
| 627 | 4 | 107 |
| 628 | 10 | 90 |
| 629 | 105 | 48 |
| 630 | 10 | 102 |
| 631 | 36 | 77 |
| 632 | 31 | 84 |
| 633 | 19 | 82 |
| 634 | 98 | 95 |
| 635 | 44 | 88 |
| 636 | 78 | 94 |
| 637 | 7 | 102 |
| 638 | 12 | 95 |
| 639 | 27 | 76 |
| 640 | 12 | 95 |
| 641 | 8 | 105 |
| 642 | 9 | 89 |
| 643 | 16 | 97 |
| 644 | 10 | 95 |
| 645 | 20 | 98 |
| 646 | 13 | 117 |
| 647 | 10 | 100 |
| 648 | 27 | 87 |
| 649 | 17 | 90 |
| 650 | 10 | 96 |
| 651 | 9 | 100 |
| 652 | 31 | 60 |
| 653 | 11 | 108 |
| 654 | 11 | 110 |
| 655 | 10 | 102 |
| 656 | 10 | 115 |
| 657 | 9 | 119 |
| 658 | 15 | 86 |
| 659 | 6 | 112 |
| 660 | 10 | 121 |
| 661 | 36 | 82 |
| 662 | 8 | 97 |
| 663 | 24 | 88 |
| 664 | 10 | 102 |
| 665 | 7 | 99 |

INDUSTRIAL APPLICABILITY

The present compound and a pharmaceutically acceptable salt thereof show strong FAAH inhibitory activity, and can be thus used as a medicament, a pharmaceutical composition useful for treatment or prophylaxis of FAAH-related diseases such as depression, anxiety disorder or pains, as well as in a use and a method for treatment or prophylaxis thereof.

The invention claimed is:
1. A compound represented by the below-mentioned formula (1):

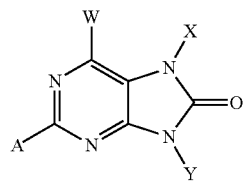

wherein,
W represents:
  a hydrogen atom,
  a halogen atom,
  a $C_{1-6}$ alkyl group optionally substituted with halogen atom or a $C_{1-6}$ alkyloxy group optionally substituted with halogen atom;
A represents:
  a hydrogen atom,
  a $C_{1-6}$ alkyl group,
  a $C_{2-6}$ alkenyl group,
  a $C_{2-6}$ alkynyl group, wherein said $C_{1-6}$ alkyl group, $C_{2-6}$ alkenyl group and $C_{2-6}$ alkynyl group each maybe optionally substituted at an optional substitutable position with one or two or more substituents selected from the group consisting of halogen atom, optionally substituted $C_{3-8}$ cycloalkyl group, optionally substituted $C_{4-10}$ cycloalkenyl group, optionally substituted 3 to 10 membered heterocycloalkyl group, optionally substituted 4 to 10 membered heterocycloalkenyl group, optionally substituted $C_{6-10}$ aryl group, optionally substituted 5 to 10 membered heteroaryl group, hydroxy group, optionally substituted amino group, optionally substituted $C_{1-6}$ alkyloxy group, optionally substituted $C_{3-8}$ cycloalkyloxy group, optionally substituted 3 to 10 membered heterocycloalkyloxy group, optionally substituted $C_{6-10}$ aryloxy group, optionally substituted 5 to 10 membered heteroaryloxy group, substituted $C_{3-8}$ cycloalkyl($C_{1-6}$ alkyl)oxy group, substituted 3 to 10 membered heterocycloalkyl($C_{1-6}$ alkyl)oxy group, substituted $C_{6-10}$ aryl($C_{1-6}$ alkyl)oxy group, substituted 5 to 10 membered heteroaryl($C_{1-6}$ alkyl)oxy group and optionally substituted $C_{1-6}$ alkyloxycarbonyl group,
  an optionally substituted $C_{3-8}$ cycloalkyl group, an optionally substituted $C_{4-10}$ cycloalkenyl group,
  an optionally substituted $C_{6-10}$ aryl group,
  an optionally substituted 5 to 10 membered heteroaryl group,
  an optionally substituted 3 to 10 membered heterocycloalkyl group, or
  an optionally substituted 4 to 10 membered heterocycloalkenyl group,
  provided that said optionally substituted 5 to 10 membered heteroaryl group, optionally substituted 3 to 10 membered heterocycloalkyl group and optionally substituted 4 to 10 membered heterocycloalkenyl group each binds at the carbon atom on each ring to a pyrimidine ring of the compound represented by the above-mentioned formula (1);

one of X and Y represents a group represented by the formula Q: —CONR$^1$R$^2$ and the other represents:
a hydrogen atom,
an optionally substituted C$_{1-6}$ alkylcarbonyl group,
a C$_{1-6}$ alkyl group, wherein said C$_{1-6}$ alkyl group may be optionally substituted at an optional substitutable position with one or two or more substituents selected from the group consisting of halogen atom, hydroxy group, optionally substituted C$_{3-8}$ cycloalkyl group, optionally substituted C$_{1-6}$ alkyloxy group, optionally substituted C$_{6-10}$ aryl group, optionally substituted 5 to 10 membered heteroaryl group and optionally substituted amino group,
or an optionally substituted C$_{3-8}$ cycloalkyl group;
R$^1$ represents:
a C$_{1-6}$ alkyl group, wherein said C$_{1-6}$ alkyl group may be optionally substituted at an optional substitutable position with one or two or more substituents selected from the group consisting of halogen atom, optionally substituted C$_{3-8}$ cycloalkyl group, optionally substituted C$_{4-10}$ cycloalkenyl group, optionally substituted 3 to 10 membered heterocycloalkyl group, optionally substituted 4 to 10 membered heterocycloalkenyl group, optionally substituted C$_{6-10}$ aryl group, optionally substituted 5 to 10 membered heteroaryl group, hydroxy group, optionally substituted C$_{1-6}$ alkyloxy group, optionally substituted C$_{3-8}$ cycloalkyloxy group, optionally substituted C$_{6-10}$ aryloxy group, optionally substituted 5 to 10 membered heteroaryloxy group, substituted C$_{6-10}$ aryl(C$_{1-6}$ alkyl)oxy group, substituted 5 to 10 membered heteroaryl(C$_{1-6}$ alkyl)oxy group; optionally substituted amino group, optionally substituted C$_{1-6}$ alkyloxycarbonyl group and optionally substituted aminocarbonyl group,
an optionally substituted C$_{3-8}$ cycloalkyl group,
an optionally substituted C$_{6-10}$ aryl group,
an optionally substituted 5 to 10 membered heteroaryl group,
an optionally substituted 3 to 10 membered heterocycloalkyl group, or
an optionally substituted 4 to 10 membered heterocycloalkenyl group;
R$^2$ represents:
a C$_{1-6}$ alkyl group, wherein said C$_{1-6}$ alkyl group may be optionally substituted at an optional substitutable position with one or two or more substituents selected from the group consisting of halogen atom, hydroxy group and optionally substituted C$_{1-6}$ alkyloxy group, or an optionally substituted C$_{3-8}$ cycloalkyl group,
or R$^1$ and R$^2$ combine together with the nitrogen atom to which R$^1$ and R$^2$ both bind to represent a cyclic group represented by the below-mentioned formula (2):

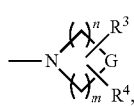

(2)

wherein
G represents —CH$_2$—, —CH=CH—, —NR$^5$—, —C(=CHR$^6$)—, an oxygen atom or a single bond (provided when G represents —CH$_2$— or —CH=CH—, then R$^3$ and R$^4$ can bind to the optional carbon atom of the —CH$_2$— or —CH=CH— instead of a hydrogen atom),
n and m are the same as or different from each other and:
represent 2 or 3 when G is —NR$^5$— or an oxygen atom, or represent an integer of 1 to 3 when G is —CH$_2$—, —CH=CH— or —C(=CHR$^6$)—, or
both represent 1 when G is a single bond;
R$^3$ and R$^4$ bind to the carbon atom on the cyclic group represented by the above-mentioned formula (2), and are the same as or different from each other and represent:
a hydrogen atom,
a halogen atom,
an optionally substituted C$_{3-8}$ cycloalkyl group,
an optionally substituted C$_{4-10}$ cycloalkenyl group,
a hydroxy group,
an optionally substituted C$_{1-6}$ alkyloxy group,
an optionally substituted C$_{3-8}$ cycloalkyloxy group,
an optionally substituted C$_{1-6}$ alkyloxycarbonyl group,
an optionally substituted aminocarbonyl group,
an optionally substituted C$_{6-10}$ aryl group,
an optionally substituted 5 to 10 membered heteroaryl group,
an optionally substituted C$_{6-10}$ aryloxy group,
an optionally substituted 5 to 10 membered heteroaryloxy group,
a C$_{1-6}$ alkyl group, wherein said C$_{1-6}$ alkyl group may be optionally substituted at an optional substitutable position with one or two or more substituents selected from the group consisting of halogen atom, optionally substituted C$_{3-8}$ cycloalkyl group, hydroxy group, optionally substituted C$_{1-6}$ alkyloxy group, optionally substituted C$_{3-8}$ cycloalkyloxy group, optionally substituted C$_{1-6}$ alkyloxycarbonyl group, optionally substituted aminocarbonyl group, optionally substituted C$_{6-10}$ aryl group, optionally substituted 5 to 10 membered heteroaryl group, optionally substituted C$_{6-10}$ aryloxy group, optionally substituted 5 to 10 membered heteroaryloxy group, substituted C$_{6-10}$ aryl(C$_{1-6}$ alkyl)oxy group, substituted 5 to 10 membered heteroaryl(C$_{1-6}$ alkyl)oxy group, optionally substituted 3 to 10 membered heterocycloalkyl group and optionally substituted 3 to 10 membered heterocycloalkyloxy group,
a C$_{2-6}$ alkenyl group,
a C$_{2-6}$ alkynyl group,
wherein said C$_{2-6}$ alkenyl group and C$_{2-6}$ alkynyl group may be optionally substituted at an optional substitutable position with one or two or more substituents selected from the group consisting of optionally substituted C$_{6-10}$ aryl group and optionally substituted 5 to 10 membered heteroaryl group,
an optionally substituted 3 to 10 membered heterocycloalkyl group, or
an optionally substituted 4 to 10 membered heterocycloalkenyl group;
R$^5$ represents:
a C$_{1-6}$ alkyl group, wherein said C$_{1-6}$ alkyl group may be optionally substituted at an optional substitutable position with one or two or more substituents selected from the group consisting of halogen atom, optionally substituted C$_{3-8}$ cycloalkyl group, optionally substituted C$_{6-10}$ aryl group, and optionally substituted 5 to 10 membered heteroaryl group,
an optionally substituted C$_{3-8}$ cycloalkyl group,
an optionally substituted C$_{6-10}$ aryl group, or
an optionally substituted 5 to 10 membered heteroaryl group; and $R^6$ represents:
an optionally substituted $C_{6-10}$ aryl group, or
an optionally substituted 5 to 10 membered heteroaryl group;
or a pharmaceutically acceptable salt thereof.

2. The compound according to claim 1 or a pharmaceutically acceptable salt thereof wherein one of X or Y represents:
an optionally substituted $C_{1-6}$ alkylcarbonyl group,
a $C_{1-6}$ alkyl group, wherein said $C_{1-6}$ alkyl group may be optionally substituted at an optional substitutable position with one or two or more substituents selected from the group consisting of halogen atom, hydroxy group, optionally substituted $C_{3-8}$ cycloalkyl group, optionally substituted $C_{1-6}$ alkyloxy group, optionally substituted $C_{6-10}$ aryl group, optionally substituted 5 to 10 membered heteroaryl group and optionally substituted amino group, or
an optionally substituted $C_{3-8}$ cycloalkyl group.

3. The compound according to claim 2 or a pharmaceutically acceptable salt thereof, wherein one of X or Y represents a $C_{1-6}$ alkyl group, wherein said $C_{1-6}$ alkyl group may be optionally substituted at an optional substitutable position with one or two or more substituents selected from the group consisting of halogen atom, hydroxy group, optionally substituted $C_{3-8}$ cycloalkyl group and optionally substituted $C_{1-6}$ alkyloxy group.

4. The compound of any one of claims 1 to 3 or a pharmaceutically acceptable salt thereof wherein A represents:
a $C_{1-6}$ alkyl group,
a $C_{2-6}$ alkenyl group, wherein said $C_{1-6}$ alkyl group and $C_{2-6}$ alkenyl group may be optionally substituted at an optional substitutable position with one or two or more substituents selected from the group consisting of halogen atom, optionally substituted $C_{3-8}$ cycloalkyl group, optionally substituted $C_{4-10}$ cycloalkenyl group, optionally substituted 3 to 10 membered heterocycloalkyl group, optionally substituted $C_{6-10}$ aryl group, optionally substituted 5 to 10 membered heteroaryl group, hydroxy group, optionally substituted amino group and optionally substituted $C_{1-6}$ alkyloxy group,
an optionally substituted $C_{3-8}$ cycloalkyl group,
an optionally substituted $C_{6-10}$ aryl group,
an optionally substituted 5 to 10 membered heteroaryl group, or
an optionally substituted 3 to 10 membered heterocycloalkyl group.

5. The compound according to claim 4 or a pharmaceutically acceptable salt thereof wherein A represents:
a $C_{1-6}$ alkyl group,
a $C_{2-6}$ alkenyl group, wherein said $C_{1-6}$ alkyl group and $C_{2-6}$ alkenyl group may be optionally substituted at an optional substitutable position with one or two or more substituents selected from the group consisting of optionally substituted $C_{6-10}$ aryl group, optionally substituted amino group and optionally substituted $C_{1-6}$ alkyloxy group,
an optionally substituted $C_{3-8}$ cycloalkyl group,
an optionally substituted $C_{6-10}$ aryl group, or
an optionally substituted 5 to 10 membered heteroaryl group.

6. The compound according to claim 1 or a pharmaceutically acceptable salt thereof wherein $R^1$ represents:
a $C_{1-6}$ alkyl group, wherein said $C_{1-6}$ alkyl group may be optionally substituted at an optional substitutable position with one or two or more substituents selected from the group consisting of halogen atom, optionally substituted $C_{3-8}$ cycloalkyl group, optionally substituted $C_{4-10}$ cycloalkenyl group, optionally substituted $C_{6-10}$ aryl group, optionally substituted 5 to 10 membered heteroaryl group, hydroxy group, optionally substituted $C_{1-6}$ alkyloxy group, optionally substituted $C_{3-8}$ cycloalkyloxy group, optionally substituted $C_{6-10}$ aryloxy group, and optionally substituted 5 to 10 membered heteroaryloxy group,
an optionally substituted $C_{6-10}$ aryl group, or
an optionally substituted 5 to 10 membered heteroaryl group.

7. The compound according to claim 6 or a pharmaceutically acceptable salt thereof wherein $R^1$ represents a $C_{1-6}$ alkyl group, wherein said $C_{1-6}$ alkyl group may be optionally substituted at an optional substitutable position with one or two or more substituents selected from the group consisting of halogen atom, optionally substituted $C_{3-8}$ cycloalkyl group, optionally substituted $C_{4-10}$ cycloalkenyl group, optionally substituted $C_{6-10}$ aryl group, optionally substituted $C_{1-6}$ alkyloxy group and optionally substituted $C_{6-10}$ aryloxy group.

8. The compound according to claim 1 represented by the below-mentioned formula (1-2a) or (1-2b):

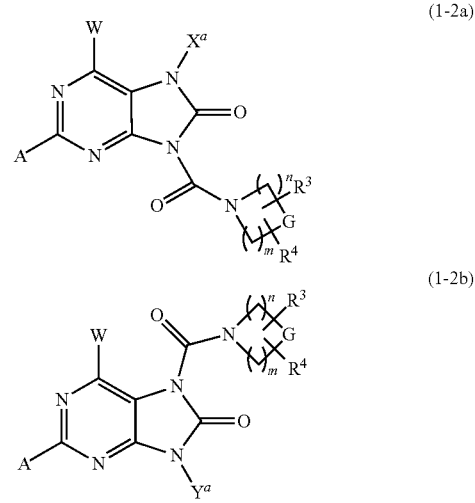

or a pharmaceutically acceptable salt thereof,
wherein $X^a$ and $Y^a$ represent:
an optionally substituted $C_{1-6}$ alkylcarbonyl group,
a $C_{1-6}$ alkyl group, wherein said $C_{1-6}$ alkyl group may be optionally substituted at an optional substitutable position with one or two or more sustituents selected from the group consisting of halogen atom, hydroxy group, optionally substituted $C_{3-8}$ cycloalkyl group, optionally substituted $C_{1-6}$ alkyloxy group, optionally substituted $C_{6-10}$ aryl group, optionally substituted 5 to 10 membered heteroaryl group and optionally substituted amino group, or
an optionally substituted $C_{3-8}$ cycloalkyl group, and
A, W, n, m, G, $R^3$ and $R^4$ are the same as defined in claim 1.

9. The compound according to claim 8 or a pharmaceutically acceptable salt thereof, wherein $R^3$ and $R^4$ are the same as or different from each other and represent:
a hydrogen atom,
a halogen atom,
an optionally substituted $C_{6-10}$ aryl group, an optionally substituted 5 to 10 membered heteroaryl group, or a $C_{1-6}$ alkyl group, wherein said $C_{1-6}$ alkyl group may be optionally substituted at an optional substitutable position with one or two or more substituents selected from the group consisting of halogen atom, optionally substituted $C_{3-8}$ cycloalkyl group, optionally substituted $C_{1-6}$ alkyloxy group, optionally substituted $C_{3-8}$ cycloalkyloxy group, optionally substituted $C_{6-10}$ aryl group, optionally substituted 5 to 10 membered heteroaryl group, optionally substituted $C_{6-10}$ aryloxy group, optionally substituted 5 to 10 membered heteroaryloxy group, substituted $C_{6-10}$ aryl($C_{1-6}$ alkyl)oxy group and substituted 5 to 10 membered heteroaryl($C_{1-6}$ alkyl)oxy group.

10. The compound according to claim 9 or a pharmaceutically acceptable salt thereof, wherein $R^3$ and $R^4$ are the same as or different from each other and represent:
a hydrogen atom,
a halogen atom,
an optionally substituted $C_{6-10}$ aryl group, or
a $C_{1-6}$ alkyl group, wherein said $C_{1-6}$ alkyl group may be optionally substituted at an optional substitutable position with one or two or more substituents selected from the group consisting of optionally substituted $C_{6-10}$ aryl group, optionally substituted 5 to 10 membered heteroaryl group, optionally substituted $C_{6-10}$ aryloxy group and optionally substituted 5 to 10 membered heteroaryloxy group.

11. The compound according to any one of claims 8 to 10 or a pharmaceutically acceptable salt thereof, wherein G represents —$CH_2$— and then n and m are the same as or different from each other and represent 1 or 2, or G is —$NR^5$—, and $R^5$ represents:
a $C_{1-6}$ alkyl group, wherein said $C_{1-6}$ alkyl group may be optionally substituted at an optional substitutable position with one or two or more substituents selected from the group consisting of halogen atom, optionally substituted $C_{6-10}$ aryl group and optionally substituted 5 to 10 membered heteroaryl group, and then n and m are the same as or different from each other and represent 2 or 3, or
an optionally substituted $C_{6-10}$ aryl group, and then n and m are the same as or different from each other and represent 2 or 3.

12. The compound according to claim 1 or a pharmaceutically acceptable salt thereof wherein W represents a hydrogen atom.

13. The compound according to claim 1 selected from the group consisting of the compounds:
N,9-Dimethyl-8-oxo-2-phenyl-N-(4-phenylbutyl)-8,9-dihydro-7H-purine-7-carboxamide;
N-Ethyl-2-(3-m ethoxyphenyl)-N,9-dimethyl-8-oxo-8,9-dihydro-7H-purine-7-carboxamide;
2-(3-Methoxyphenyl)-N,9-dimethyl-8-oxo-N-(2-phenylethyl)-8,9-dihydro-7H-purine-7-carboxamide;
2-(3-Methoxyphenyl)-N,9-dimethyl-8-oxo-N-(2-phenoxyethyl)-8,9-dihydro-7H-purine-7-carboxamide;
7-({4-[2-(4-Chlorophenyl)ethyl]piperidin-1-yl}carbonyl)-2-(3-methoxyphenyl)-9-methyl-7,9-dihydro-8H-purine-8-one;
N-[2-(4-Chlorophenyl)ethyl]-2-(3-methoxyphenyl)-N,9-dimethyl-8-oxo-8,9-dihydro-7H-purine-7-carboxamide;
N-(4-Fluorobenzyl)-2-(3-methoxyphenyl)-N,9-dimethyl-8-oxo-8,9-dihydro-7H-purine-7-carboxamide;
N-[2-(4-Fluorophenyl)ethyl]-2-(3-methoxyphenyl)-N,9-dimethyl-8-oxo-8,9-dihydro-7H-purine-7-carboxamide;
N-[2-(3-Fluorophenyl)ethyl]-2-(3-methoxyphenyl)-N,9-dimethyl-8-oxo-8,9-dihydro-7H-purine-7-carboxamide;
N-[2-(3-Chlorophenyl)ethyl]-2-(3-methoxyphenyl)-N,9-dimethyl-8-oxo-8,9-dihydro-7H-purine-7-carboxamide;
N-[2-(4-Chlorophenoxy)ethyl]-2-(3-methoxyphenyl)-N,9-dimethyl-8-oxo-8,9-dihydro-7H-purine-7-carboxamide;
N-(4-Chlorobenzyl)-2-(3-methoxyphenyl)-N,9-dimethyl-8-oxo-8,9-dihydro-7H-purine-7-carboxamide;
2-(3-Methoxyphenyl)-N,9-dimethyl-8-oxo-N-[4-(trifluoromethyl)benzyl]-8,9-dihydro-7H-purine-7-carboxamide;
2-(3-Methoxyphenyl)-N,9-dimethyl-8-oxo-N-[4-(trifluoromethoxy)benzyl]-8,9-dihydro-7H-purine-7-carboxamide;
N-[2-(3-Chlorophenoxy)ethyl]-2-(3-methoxyphenyl)-N,9-dimethyl-8-oxo-8,9-dihydro-7H-purine-7-carboxamide;
N-[2-(4-Fluorophenoxy)ethyl]-2-(3-methoxyphenyl)-N,9-dimethyl-8-oxo-8,9-dihydro-7H-purine-7-carboxamide;
2-(3-Methoxyphenyl)-N,9-dimethyl-8-oxo-N-{2-[4-(trifluoromethyphenyl]ethyl}-8,9-dihydro-7H-purine-7-carboxamide;
2-(3-Methoxyphenyl)-N-[2-(4-methoxyphenyl)ethyl]-N,9-dimethyl-8-oxo-8,9-dihydro-7H-purine-7-carboxamide;
7-({4-[(E)-2-(4-Chlorophenyl)ethenyl]-3,6-dihydropyridin-1(2H)-yl}carbonyl)-2-(3-methoxyphenyl)-9-methyl-7,9-dihydro-8H-purine-8-one;
7-({4-[(E)-2-(4-Fluorophenyl)ethenyl]-3,6-dihydropyridin-1(2H)-yl}carbonyl)-2-(3-methoxyphenyl)-9-methyl-7,9-dihydro-8H-purine-8-one;
7-({4-[2-(4-Fluorophenyl)ethyl]piperidin-1-yl}carbonyl)-2-(3-methoxyphenyl)-9-methyl-7,9-dihydro-8H-purine-8-one;
2-(3-Methoxyphenyl)-N,9-dimethyl-8-oxo-N-[2-(3-phenyl-1,2,4-oxadiazol-5-yl)ethyl]-8,9-dihydro-7H-purine-7-carboxamide;
N-[2-(3,4-Dichlorophenyl)ethyl]-2-(3-methoxyphenyl)-N,9-dimethyl-8-oxo-8,9-dihydro-7H-purine-7-carboxamide;
N-[2-(Cyclohex-1-en-1-yl)ethyl]-2-(3-methoxyphenyl)-N,9-dimethyl-8-oxo-8,9-dihydro-7H-purine-7-carboxamide;
N-(2-Cyclohexylethyl)-2-(3-methoxyphenyl)-N,9-dimethyl-8-oxo-8,9-dihydro-7H-purine-7-carboxamide;
N-[2-(2,4-Dichlorophenyl)ethyl]-2-(3-methoxyphenyl)-N,9-dimethyl-8-oxo-8,9-dihydro-7H-purine-7-carboxamide;
7-({4-[(E)-2-(4-Chlorophenyl)ethenyl]piperidin-1-yl}carbonyl)-2-(3-methoxyphenyl)-9-methyl-7,9-dihydro-8H-purine-8-one;
N-{2-[4-(Dimethylamino)phenyl]ethyl}-2-(3-methoxyphenyl)-N,9-dimethyl-8-oxo-8,9-dihydro-7H-purine-7-carboxamide;
N-[2-(Cyclopropylmethoxy)ethyl]-2-(3-methoxyphenyl)-N,9-dimethyl-8-oxo-8,9-dihydro-7H-purine-7-carboxamide;
2-(3-Methoxyphenyl)-7-({4-[2-(4-methoxyphenyl)ethyl]piperidin-1-yl}carbonyl)-9-methyl-7,9-dihydro-8H-purine-8-one;

7-{[4-(4-Methoxyphenyl)piperazin-1-yl]carbonyl}-9-methyl-2-phenyl-7,9-dihydro-8H-purine-8-one;
7-{[4-(4-Ethoxyphenyl)piperazin-1-yl]carbonyl}2-(3-methoxyphenyl)-9-methyl-7,9-dihydro-8H-purine-8-one;
7-{[4-(4-Chlorophenyl)piperazin-1-yl]carbonyl}-2-(3-methoxyphenyl)-9-methyl-7,9-dihydro-8H-purine-8-one;
7-{[4-(4-Ethoxyphenyl)piperazin-1-yl]carbonyl}-9-methyl-2-(pyridin-3-yl)-7,9-dihydro-8H-purine-8-one;
N-[2-(4-Chlorophenyl)ethyl]-N,9-dimethyl-8-oxo-2-(pyridin-3-yl)-8,9-dihydro-7H-purine-7-carboxamide;
N-[2-(4-Chlorophenoxy)ethyl]-N,9-dimethyl-8-oxo-2-(pyridin-3-yl)-8,9-dihydro-7H-purine-7-carboxamide;
7-({4-[2-(4-Chlorophenyl)ethyl]piperidin-1-yl}carbonyl)-9-methyl-2-(pyridin-3-yl)-7,9-dihydro-8H-purine-8-one;
N,N,9-Trimethyl-8-oxo-2-(pyridin-4-yl)-8,9-dihydro-7H-purine-7-carboxamide;
7-{[4-(4-Ethoxyphenyl)piperazin-1-yl]carbonyl}-9-methyl-2-(pyridin-4-yl)-7,9-dihydro-8H-purine-8-one;
N-[2-(4-Chlorophenyl)ethyl]-N,9-dimethyl-8-oxo-2-(pyridin-4-yl)-8,9-dihydro-7H-purine-7-carboxamide;
N-[2-(4-Chlorophenoxy)ethyl]-N,9-dimethyl-8-oxo-2-(pyridin-4-yl)-8,9-dihydro-7H-purine-7-carboxamide;
7-({4-[2-(4-Chlorophenyl)ethyl]piperidin-1-yl}carbonyl)-9-methyl-2-(pyridin-4-yl)-7,9-dihydro-8H-purine-8-one;
N-[2-(4-Chlorophenyl)ethyl]-N,9-dimethyl-8-oxo-2-propyl-8,9-dihydro-7H-purine-7-carboxamide;
2-Butyl-N-[2-(4-chlorophenyl)ethyl]-N,9-dimethyl-8-oxo-8,9-dihydro-7H-purine-7-carboxamide;
2-Benzyl-N-[2-(4-chlorophenyl)ethyl]-N,9-dimethyl-8-oxo-8,9-dihydro-7H-purine-7-carboxamide;
9-(Azetidin-1-ylcarbonyl)-2-[2-(3-fluorophenyl)ethyl]-7-methyl-7,9-dihydro-8H-purine-8-one;
2-[2-(3-Fluorophenyl)ethyl]-N,N,7-trimethyl-8-oxo-7,8-dihydro-9H-purine-9-carboxamide;
2-(2-Fluoropyridin-4-yl)-9-methyl-7-(pyrrolidin-1-ylcarbonyl)-7,9-dihydro-8H-purine-8-one;
N-Ethyl-N,9-dimethyl-8-oxo-2-(pyridin-4-yl)-8,9-dihydro-7H-purine-7-carboxamide;
N-Ethyl-2-(2-fluoropyridin-4-yl)-N,9-dimethyl-8-oxo-8,9-dihydro-7H-purine-7-carboxamide;
N-[2-(4-Chlorophenyl)ethyl]-2-(2-fluoropyridin-4-yl)-N,9-dimethyl-8-oxo-8,9-dihydro-7H-purine-7-carboxamide;
N-(2-Cyclohexylethyl)-N,9-dimethyl-8-oxo-2-(pyridin-4-yl)-8,9-dihydro-7H-purine-7-carboxamide;
N-Ethyl-2-(3-methoxybenzyl)-N,9-dimethyl-8-oxo-8,9-dihydro-7H-purine-7-carboxamide;
7-Methyl-9-(pyrrolidin-1-ylcarbonyl)-2-{2-[4-(trifluoromethyl)phenyl]ethyl}-7,9-dihydro-8H-purine-8-one;
7-Methyl-9-(pyrrolidin-1-ylcarbonyl)-2-{2-[3-(trifluoromethyl)phenyl]ethyl}-7,9-dihydro-8H-purine-8-one;
N,N,7-Trimethyl-8-oxo-2-[4-(trifluoromethyl)phenyl]-7,8-dihydro-9H-purine-9-carboxamide;
2-[2-Fluoro-4-(trifluoromethyl)phenyl]-N,N,7-trimethyl-8-oxo-7,8-dihydro-9H-purine-9-carboxamide;
2-[2-Chloro-4-(trifluoromethyl)phenyl]-N,N,7-trimethyl-8-oxo-7,8-dihydro-9H-purine-9-carboxamide;
9-(Azetidin-1-ylcarbonyl)-2-[3-(4-fluorophenoxy)propyl]-7-methyl-7,9-dihydro-8H-purine-8-one;
2-(Methoxymethyl)-9-methyl-7-[(3-phenylazetidin-1-yl)carbonyl]-7,9-dihydro-8H-purine-8-one;
7-{[3-(4-Fluorophenyl)azetidin-1-yl]carbonyl}-2-(methoxymethyl)-9-methyl-7,9-dihydro-8H-purine-8-one;
7-{[3-(3-Fluorophenyl)azetidin-1-yl]carbonyl}-2-(methoxymethyl)-9-methyl-7,9-dihydro-8H-purine-8-one;
7-{[3-(2-Fluorophenyl)azetidin-1-yl]carbonyl}-2-(methoxymethyl)-9-methyl-7,9-dihydro-8H-purine-8-one;
2-(Methoxymethyl)-9-methyl-7-({[3-(3-trifluoromethyl)phenyl]azetidin-1-yl}carbonyl)-7,9-dihydro-8H-purine-8-one;
7-{[3-(2-Chlorophenyl)azetidin-1-yl]carbonyl}-2-(methoxymethyl)-9-methyl-7,9-dihydro-8H-purine-8-one;
7-({3-[4-(Benzyloxy)phenyl]azetidin-1-yl}carbonyl)-2-(methoxymethyl)-9-methyl-7,9-dihydro-8H-purine-8-one;
2-(Methoxymethyl)-9-methyl-7-({3-[4-(trifluoromethoxy)phenyl]azetidin-1-yl}carbonyl)-7,9-dihydro-8H-purine-8-one;
7-{[(3R)-3-(4-Fluorophenoxy)pyrrolidin-1-yl]carbonly}-2-(methoxymethyl)-9-methyl-7,9-dihydro-8H-purine-8-one;
7-{[(3S)-3-(3-Fluorophenoxy)pyrrolidin-1-yl]carbonyl}-2-(methoxymethyl)-9-methyl-7,9-dihydro-8H-purine-8-one;
7-{[(3S)-3-(2-Fluorophenoxy)pyrrolidin-1-yl]carbonyl}-2-(methoxymethyl)-9-methyl-7,9-dihydro-8H-purine-8-one;
2-(Methoxymethyl)-9-methyl-7-{[(3S)-3-(4-methylphenoxy)pyrrolidin-1-yl]carbonyl}-7,9-dihydro-8H-purine-8-one;
2-(Methoxymethyl)-9-methyl-7-{[(3S)-3-(3-methylphenoxy)pytTolidin-1-yl]carbonyl}-7,9-dihydro-8H-purine-8-one;
2-(Methoxymethyl)-9-methyl-7-{[(3 S)-3-(2-methylphenoxy)pyrrolidin-1-yl]carbonyl}-7,9-dihydro-8H-purine-8-one;
7-{[(3R)-3-(3-Chlorophenoxy)pyrrolidin-1-yl]carbonyl}-2-(methoxymethyl)-9-methyl-7,9-dihydro-8H-purine-8-one;
7-{[(3S)-3-(4-Chlorophenoxy)pyrrolidin-1-yl]carbonyl}-2-(methoxymethyl)-9-methyl-7,9 -dihydro-8H-purine-8-one;
7-{[(3S)-3-(3-Chlorophenoxy)pyrrolidin-1-yl]carbonyl}-2-(methoxymethyl)-9-methyl-7,9-dihydro-8H-purine-8-one;
7-{[(3S)-3-(2-Chlorophenoxy)pyrrolidin-1-yl]carbonyl}-2-(methoxymethyl)-9-methyl-7,9-dihydro-8H-purine-8-one;
2-[2-(3,5-Difluorophenyl)ethyl]-N,N,7-trimethyl-8-oxo-7,8-dihydro-9H-purine-9-carboxamide;
2-[2-(4-Fluorophenyl)ethyl]-N,N,7-trimethyl-8-oxo-7,8-dihydro-9H-purine-9-carboxamide;
2-{2-[4-(2,2-Difluoroethoxy)phenyl]ethyl}-N,N,7-trimethyl-8-oxo-7,8-dihydro-9H-purine-9 -carboxamide;
9-(Azetidin-1-ylcarbonyl)-2-[2-(4-fluorophenyl)ethyl]-7-methyl-7,9-dihydro-8H-purine-8-one;
2-[243 -Chlorophenoxy)ethyl]-N,N,7-trimethyl-8-oxo-7,8-dihydro-9H-purine-9-carboxamide;
7-Ethyl-2-[2-(3-fluorophenyl)ethyl]-N,N-dimethyl-8-oxo-7,8-dihydro-9H-purine-9-carboxamide;
7-Ethyl-2-[2-(4-fluorophenyl)ethyl]-N,N-dimethyl-8-oxo-7,8-dihydro-9H-purine-9-carboxamide;
2-[2-(2-Fluorophenypethyl]-N,N-dimethyl-8-oxo-7-propyl-7,8-dihydro-9H-purine-9-carboxamide;
2-[2-(3-Fluorophenyl)ethyl]-N,N-dimethyl-8-oxo-7-propyl-7,8-dihydro-9H-purine-9-carboxamide;
2-[2-(4-Fluorophenyl)ethyl]-N,N-dimethyl-8-oxo-7-propyl-7,8-dihydro-9H-purine-9-carboxamide;

7-{[3-(3-Fluorophenyl)azetidin-1-yl]carbonyl}-2-(methoxymethyl)-9-propyl-7,9-dihydro-8H-purine-8-one; and 2-(Methoxymethyl)-9-propyl-7-({3 -[3-(trifluoromethyl)phenyl]azetidin-1-yl}carbonyl)-7,9-dihydro-8H-purine-8 -one; or a pharmaceutically acceptable salt of said compound.

14. The compound according to claim 1 selected from of the group consisting of the following compounds:

N,9-Dimethyl-8-oxo-2-phenyl-N-(4-phenylbutyl)-8,9-dihydro-7H-purine-7-carboxamide;

2-(3-Methoxyphenyl)-N,9-dimethyl-8-oxo-N-(2-phenylethyl)-8,9-dihydro-7H-purine-7-carboxamide;

2-(3-Methoxyphenyl)-N,9-dimethyl-8-oxo-N-(2-phenoxyethyl)-8,9-dihydro-7H-purine-7-carboxamide;

7-({4-[2-(4-Chlorophenyl)ethyl]piperidin-1-yl}carbonyl)-2-(3-methoxyphenyl)-9-methyl-7,9-dihydro-8H-purine-8-one;

N-[2-(4-Chlorophenyl)ethyl]-2-(3-methoxyphenyl)-N,9-dimethyl-8-oxo-8,9-dihydro-7H-purine-7-carboxamide;

N-[2-(4-Fluorophenyl)ethyl]-2-(3-methoxyphenyl)-N,9-dimethyl-8-oxo-8,9-dihydro-7H-purine-7-carboxamide;

N-[2-(3-Fluorophenyl)ethyl]-2-(3-methoxyphenyl)-N,9-dimethyl-8-oxo-8,9-dihydro-7H-purine-7-carboxamide;

N-[2-(3-Chlorophenyl)ethyl]-2-(3-methoxyphenyl)-N,9-dimethyl-8-oxo-8,9-dihydro-7H-purine-7-carboxamide;

N-[2-(4-Chlorophenoxy)ethyl]-2-(3-methoxyphenyl)-N,9-dimethyl-8-oxo-8,9-dihydro-7H-purine-7-carboxamide;

N-(4-Chlorobenzyl)-2-(3-methoxyphenyl)-N,9-dimethyl-8-oxo-8,9-dihydro-7H-purine-7-carboxamide;

2-(3-Methoxyphenyl)-N,9-dimethyl-8-oxo-N[4-(trifluoromethoxy)benzyl]-8,9-dihydro-7H-purine-7-carboxamide;

N-[2-(3-Chlorophenoxy)ethyl]-2-(3-methoxyphenyl)-N,9-dimethyl-8-oxo-8,9-dihydro-7H-purine-7-carboxamide;

N-[2-(4-Fluorophenoxy)ethyl]-2-(3-methoxyphenyl)-N,9-dimethyl-8-oxo-8,9-dihydro-7H-purine-7-carboxamide;

2-(3-Methoxyphenyl)-N,9-dimethyl-8-oxo-N-{2-[4-(trifluoromethyl)phenyl]ethyl}-8,9-dihydro-7H-purine-7-carboxamide;

2-(3-Methoxyphenyl)-N-[2-(4-methoxyphenyl)ethyl]-N,9-dimethyl-8-oxo-8,9-dihydro-7H-purine-7-carboxamide;

7-({4-[(E)-2-(4-Chlorophenyl)ethenyl]-3,6-dihydropyridin-1(2H)-yl}carbonyl)-2-(3-methoxyphenyl)-9-methyl-7,9-dihydro-8H-purine-8-one;

7-({4-[(E)-2-(4-Fluorophenyl)ethenyl]-3,6-dihydropyridin-1(2H)-yl}carbonyl)-2-(3-methoxyphenyl)-9-methyl-7,9-dihydro-8H-purine-8-one;

2-(3-Methoxyphenyl)-N,9-dimethyl-8-oxo-N-[2-(3-phenyl-1,2,4-oxadiazol-5-yl)ethyl]-8,9-dihydro-7H-purine-7-carboxamide;

N-[2-(3,4-Dichlorophenyl)ethyl]-2-(3-methoxyphenyl)-N,9-dimethyl-8-oxo-8,9-dihydro-7H-purine-7-carboxamide;

N-[2-(Cyclohex-1-en-1-yl)ethyl]-2-(3-methoxyphenyl)-N,9-dimethyl-8-oxo-8,9-dihydro-7H-purine-7-carboxamide;

N-(2-Cyclohexylethyl)-2-(3-methoxyphenyl)-N,9-dimethyl-8-oxo-8,9-dihydro-7H-purine-7-carboxamide;

N-[2-(2,4-Dichlorophenyl)ethyl]-2-(3-methoxyphenyl)-N,9-dimethyl-8-oxo-8,9-dihydro-7H-purine-7-carboxamide;

7-({4-[(E)-2-(4-Chlorophenyl)ethenyl]piperidin-1-yl}carbonyl)-2-(3-methoxyphenyl)-9-methyl-7,9-dihydro-8H-purine-8-one;

N-{2-[4-(Dimethylamino)phenyl]ethyl}-2-(3-methoxyphenyl)-N,9-dimethyl-8-oxo-8,9-dihydro-7H-purine-7-carboxamide;

N-[2-(Cyclopropylmethoxy)ethyl]-2-(3-methoxyphenyl)-N,9-dimethyl-8-oxo-8,9-dihydro-7H-purine-7-carboxamide;

2-(3-Methoxyphenyl)-7-({4-[2-(4-methoxyphenyl)ethyl]piperidin-1-yl}carbonyl)-9-methyl-7,9-dihydro-8H-purine-8-one;

7-{[4-(4-Ethoxyphenyl)piperazin-1-yl]carbonyl}-9-methyl-2-(pyridine-3-yl)-7,9-dihydro-8H-purine-8-one;

N-[2-(4-Chlorophenyl)ethyl]-N,9-dimethyl-8-oxo-2-(pyridin-3-yl)-8,9-dihydro-7H-purine-7-carboxamide;

N-[2-(4-Chlorophenoxy)ethyl]-N,9-dimethyl-8-oxo-2-(pyridin-3-yl)-8,9-dihydro-7H-purine-7-carboxamide;

7-({4-[2-(4-Chlorophenyl)ethyl]piperidin-1-yl}carbonyl)-9-methyl-2-(pyridin-3-yl)-7,9-dihydro-8H-purine-8-one;

N-[2-(4-Chlorophenyl)ethyl]-N,9-dimethyl-8-oxo-2-(pyridin-4-yl)-8,9-dihydro-7H-purine-7-carboxamide;

N-[2-(4-Chlorophenoxy)ethyl]-N,9-dimethyl-8-oxo-2-(pyridin-4-yl)-8,9-dihydro-7H-purine-7-carboxamide;

7-({4-[2-(4-Chlorophenyl)ethyl]piperidin-1-yl}carbonyl)-9-methyl-2-(pyridin-4-yl)-7,9-dihydro-8H-purine-8-one;

2-Butyl-N-[2-(4-chlorophenyl)ethyl]-N,9-dimethyl-8-oxo-8,9-dihydro-7H-purine-7-carboxamide, 2-Benzyl-N-[2-(4-chlorophenyl)ethyl]-N,9-dimethyl-8-oxo-8,9-dihydro-7H-purine-7-carboxamide;

2-[2-(3-Fluorophenyl)ethyl]-N,N,7-trimethyl-8-oxo-7,8-dihydro-9H-purine-9-carboxamide;

N-Ethyl-N,9-dimethyl-8-oxo-2-(pyridin-4-yl)-8,9-dihydro-7H-purine-7-carboxamide;

N-Ethyl-2-(2-fluoropyridin-4-yl)-N,9-dimethyl-8-oxo-8,9-dihydro-7H-purine-7-carboxamide;

N-[2-(4-Chlorophenyl)ethyl]-2-(2-fluoropyridin-4-yl)-N,9-dimethyl-8-oxo-8,9-dihydro-7H-purine-7-carboxamide;

N-(2-Cyclohexylethyl)-N,9-dimethyl-8-oxo-2-(pyridin-4-yl)-8,9-dihydro-7H-purine-7-carboxamide;

N,N,7-Trimethyl-8-oxo-2-[4-(trifluoromethyl)phenyl]-7,8-dihydro-9H-purine-9-carboxamide;

2-[2-Fluoro-4-(trifluoromethyl)phenyl]-N,N,7-trimethyl-8-oxo-7,8-dihydro-9H-purine-9-carboxamide;

2-[2-Chloro-4-(trifluoromethyl)phenyl]-N,N,7-trimethyl-8-oxo-7,8-dihydro-9H-purine-9-carboxamide;

9-(Azetidin-1-ylcarbonyl)-2-[3-(4-fluorophenoxy)propyl]-7-methyl-7,9-dihydro-8H-purine-8-one;

2-(Methoxymethyl)-9-methyl-7-[(3-phenylazetidin-1-yl)carbonyl]-7,9-dihydro-8H-purine-8-one;

7-{[3-(4-Fluorophenyl)azetidin-1-yl]carbonyl}-2-(methoxymethyl)-9-methyl-7,9-dihydro-8H-purine-8-one;

7-{[3-(3-Fluorophenypazetidin-1-yl]carbonyl}-2-(methoxymethyl)-9-methyl-7,9-dihydro-8H-purine-8-one;

7-{[3-(2-Fluorophenyl)azetidin-1-yl]carbonyl}-2-(methoxymethyl)-9-methyl-7,9-dihydro-8H-purine-8-one;

2-(Methoxymethyl)-9-methyl-7-({ [3-(3-trifluoromethyl)phenyl]azetidin-1-yl}carbonyl)-7,9-dihydro-8H-purine-8-one;

7-{[3-(2-Chlorophenyl)azetidin-1-yl]carbonyl}-2-(methoxymethyl)-9-methyl-7,9-dihydro-8H-purine-8-one;

7-({3-[4-(Benzyloxy)phenyl]azetidin-1-yl}carbonyl)-2-(methoxymethyl)-9-methyl-7,9-dihydro-8H-purine-8-one;

2-(Methoxymethyl)-9-methyl-7-({3-[4(trifluoromethoxy)phenyl]azetidin-1-yl}carbonyl)-7,9-dihydro-8H-purine-8-one;

7-{[(3R)-3-(4-Fluorophenoxy)pyrrolidin-1-yl]carbonyl}-2-(methoxymethyl)-9-methyl-7,9-dihydro-8H-purine-8-one;

7-{[(3S)-3-(3-Fluorophenoxy)pyrrolidin-1-yl]carbonyl}-2-(methoxymethyl)-9-methyl-7,9-dihydro-8H-purine-8-one;

7-{[(3S)-3-(2-Fluorophenoxy)pyrrolidin-1-yl]carbonyl}-2-(methoxymethyl)-9-methyl-7,9-dihydro-8H-purine-8-one;

2-(Methoxymethyl)-9-methyl-7-{[(3S)-3-(4-methylphenoxy)pyrrolidin-1-yl]carbonyl}-7,9-dihydro-8H-purine-8-one;

2-(Methoxymethyl)-9-methyl-7-{[(3S)-3-(3-methylphenoxy)pyrrolidin-1-yl]carbonyl}-7,9-dihydro-8H-purine-8-one;

2-(Methoxymethyl)-9-methyl-7-{[(3S)-3-(2-methylphenoxy)pyrrolidin-1-yl]carbonyl}-7,9-dihydro-8H-purine-8-one;

7-{[(3R)-3-(3-Chlorophenoxy)pyrrolidin-1-yl]carbonyl}-2-(methoxymethyl)-9-methyl-7,9-dihydro-8H-purine-8-one;

7-{[(3S)-3-(4-Chlorophenoxy)pyrrolidin-1-yl]carbonyl}-2-(methoxymethyl)-9-methyl-7,9-dihydro-8H-purine-8-one;

7-{[(3S)-3-(3-Chlorophenoxy)pyrrolidin-1-yl]carbonyl}-2-(methoxymethyl)-9-methyl-7,9-dihydro-8H-purine-8-one;

7-{[(3S)-3-(2-Chlorophenoxy)pyrrolidin-1-yl]carbonyl}-2-(methoxymethyl)-9-methyl-7,9-dihydro-8H-purine-8-one;

2-[2-(3,5-Difluorophenyl)ethyl]-N,N,7-trimethyl-8-oxo-7,8-dihydro-9H-purine-9-carboxamide;

2-[2-(4-Fluorophenyl)ethyl]-N,N,7-trimethyl-8-oxo-7,8-dihydro-9H-purine-9-carboxamide;

2-{2-[4-(2,2-Difluorethoxy)phenyl]ethyl}-N,N,7-trimethyl-8-oxo-7,8-dihydro-9H-purine-9-carboxamide;

9-(Azetidin-1-ylcarbonyl)-2-[2-(4-fluorophenyl)ethyl]-7-methyl-7,9-dihydro-8H-purine-8-one;

2-[2-(3-Chlorophenoxy)ethyl]-N,N,7-trimethyl-8-oxo-7,8-dihydro-9H-purine-9-carboxamide;

7-Ethyl-2-[2-(3-fluorophenyl)ethyl]-N,N-dimethyl-8-oxo-7,8-dihydro-9H-purine-9-carboxamide;

7-Ethyl-2-[2-(4-fluorophenyl)ethyl]-N,N-dimethyl-8-oxo-7,8-dihydro-9H-purine-9-carboxamide;

2-[2-(2-Fluorophenyl)ethyl]-N,N-dimethyl-8-oxo-7-propyl-7,8-dihydro-9H-purine-9-carboxamide;

2-[2-(3-Fluorophenyl)ethyl]-N,N-dimethyl-8-oxo-7-propyl-7,8-dihydro-9H-purine-9-carboxamide;

2-[2-(4-Fluorophenyl)ethyl]-N,N-dimethyl-8-oxo-7-propyl-7,8-dihydro-9H-purine-9-carboxamide; and 7-{[3-(3-Fluorophenyl)azetidin-1-yl]carbonyl}-2-(methoxymethyl)-9-propyl-7,9-dihydro-8H-purine-8-one;

2-(Methoxymethyl)-9-propyl-7-({3-[3-(trifluoromethyl)phenyl]azetidin-1-yl}carbonyl)-7,9-dihydro-8H-purine-8-one; or a pharmaceutically acceptable salt of said compound.

15. A pharmaceutical composition comprising as an active ingredient the compound according to claim 1 or a pharmaceutically acceptable salt thereof and a pharmaceutically acceptable carrier.

16. A method for treatment of depression, anxiety disorder or pains comprising administering a therapeutically effective amount of the compound according to claim 1 or a pharmaceutically acceptable salt thereof to a patient in need thereof.

* * * * *